(12) United States Patent
Gray et al.

(10) Patent No.: US 10,385,019 B2
(45) Date of Patent: Aug. 20, 2019

(54) INHIBITORS OF EGFR AND METHODS OF USE THEREOF

(71) Applicant: Dana-Farber Cancer Institute, Inc., Boston, MA (US)

(72) Inventors: Nathanael S. Gray, Boston, MA (US); Michael Eck, Brookline, MA (US); Pasi Janne, Needham, MA (US); Hwan Geun Choi, Daegu (KR); Jaebong Jang, Brookline, MA (US); Kwok-Kin Wong, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/580,088

(22) PCT Filed: Jun. 30, 2016

(86) PCT No.: PCT/US2016/040421
§ 371 (c)(1),
(2) Date: Dec. 6, 2017

(87) PCT Pub. No.: WO2017/004383
PCT Pub. Date: Jan. 5, 2017

(65) Prior Publication Data
US 2018/0290975 A1 Oct. 11, 2018

Related U.S. Application Data

(60) Provisional application No. 62/259,895, filed on Nov. 25, 2015, provisional application No. 62/186,563, filed on Jun. 30, 2015.

(51) Int. Cl.
| | |
|---|---|
| A61P 35/00 | (2006.01) |
| C07D 209/46 | (2006.01) |
| C07D 277/46 | (2006.01) |
| C07D 401/12 | (2006.01) |
| C07D 403/14 | (2006.01) |
| C07D 413/12 | (2006.01) |
| C07D 413/14 | (2006.01) |
| C07D 417/12 | (2006.01) |
| C07D 417/14 | (2006.01) |
| C07D 471/04 | (2006.01) |
| C07D 487/04 | (2006.01) |
| C07D 513/04 | (2006.01) |
| C07D 403/12 | (2006.01) |

(52) U.S. Cl.
CPC ........... *C07D 209/46* (2013.01); *A61P 35/00* (2018.01); *C07D 277/46* (2013.01); *C07D 401/12* (2013.01); *C07D 403/12* (2013.01); *C07D 403/14* (2013.01); *C07D 413/12* (2013.01); *C07D 413/14* (2013.01); *C07D 417/12* (2013.01); *C07D 417/14* (2013.01); *C07D 471/04* (2013.01); *C07D 487/04* (2013.01); *C07D 513/04* (2013.01)

(58) Field of Classification Search
CPC .. C07D 209/46; C07D 401/12; C07D 417/12; C07D 417/14; C07D 403/12; C07D 413/14; C07D 403/14; C07D 413/12; C07D 471/04; C07D 487/04; C07D 277/46; C07D 513/04; A61P 35/00
See application file for complete search history.

(56) References Cited

U.S. PATENT DOCUMENTS

2007/0003539 A1 1/2007 Zhang et al.
2007/0281942 A1 12/2007 Cao et al.

FOREIGN PATENT DOCUMENTS

| WO | WO 2005/021519 A2 | 3/2005 |
|---|---|---|
| WO | WO 2007/025709 A2 | 3/2007 |
| WO | WO 2009/080694 A1 | 7/2009 |
| WO | WO 2010/039534 A2 | 4/2010 |

(Continued)

OTHER PUBLICATIONS

CAS RN 1217776-85-6 (Apr. 9, 2010).
(Continued)

*Primary Examiner* — Shirley V Gembeh
(74) *Attorney, Agent, or Firm* — Cooley LLP; Heidi A. Erlacher; Chen Chen

(57) ABSTRACT

The disclosure relates to a compound having Formula (I'):

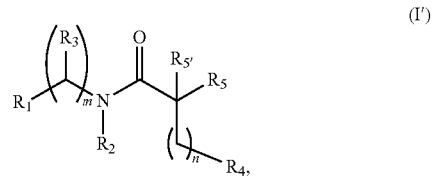

and
in particular, Compound I-126:

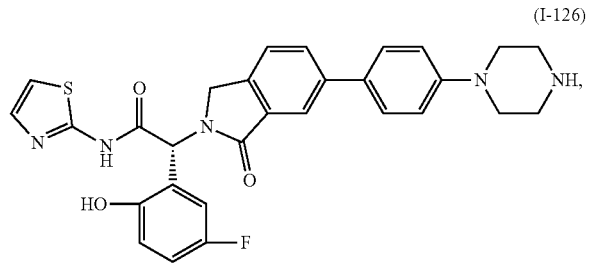

which modulates the activity of EGFR, a pharmaceutical composition comprising the compound, and a method of treating or preventing a disease in which EGFR plays a role.

21 Claims, 5 Drawing Sheets

(56) References Cited

FOREIGN PATENT DOCUMENTS

| WO | WO 2012/129562 A2 | 9/2012 |
|---|---|---|
| WO | WO 2013/184757 A1 | 12/2013 |

OTHER PUBLICATIONS

CAS RN 1214866-72-4 (Mar. 26, 2010).

Arteaga, C. L. "The Epidermal Growth Factor Receptor: From Mutant Oncogene in Nonhuman Cancers to Therapeutic Target in Human Neoplasia", Journal of Clinical Oncology, 2001, vol. 19, No. 18s (Sep. 15 Supplement), p. 32s-40s.

Beard, C et al. "Efficient method to generate single-copy transgenic mice by site-specific integration in embryonic stem cells," Genesis, 2006, vol. 44, p. 23-28.

Brewer, M. R. et al. "Mechanism for activation of mutated epidermal growth factor receptors in lung cancer", PNAS, 2013, vol. 110, No. 50, p. 3595-3604.

Cho, J. et al, "Cetuximab response of lung cancer-derived EGF receptor mutants is associated with asymmetric dimerization," Cancer Research, 2013, vol. 73, No. 22, p. 6770-6779.

Goldstein, N. I. et al. "Biological efficacy of a chimeric antibody to the epidermal growth factor receptor in a human tumor xenograft model," Clinical Cancer Research, 1995, vol. 1, p. 1311-1318.

Li, S. et al., "Structural basis for inhibition of the epidermal growth factor receptor by cetuximab," Cancer Cell, 2005, vol. 7, p. 301-311.

Li, D. et al., "Bronchial and peripheral murine lung carcinomas induced by T790M-L858R mutant EGFR respond to HKI-272 and rapamycin combination therapy," Cancer Cell, 2007, vol. 12, p. 81-93.

Lynch, T. J. et al. "Activating Mutations in the Epidermal Growth Factor Receptor Underlying Responsiveness of Non-Small-Cell Lung Cancer to Gefitinib", The New England Journal of Medicine, 2004, vol. 350, No. 21, p. 2129-2139.

Maemondo, M. et al. "Gefitinib or Chemotherapy for Non-Small-Cell Lung Cancer with Mutated EGFR", The New England Journal of Medicine, 2010, 362, p. 2380-2388.

Miller V.A. et al. "Afatinib versus placebo for patients with advanced, metastatic non-small-cell lung cancer after failure of erlotinib, gefitinib, or both, and one or two lines of chemotherapy (LUX-Lung 1): a phase 2b/3 randomised trial", Lancet Oncol., 2012, vol. 13, p. 528-538.

Mitsudomi T. et al. "Gefi tinib versus cisplatin plus docetaxel in patients with non-small-cell lung cancer harbouring mutations of the epidermal growth factor receptor (WJTOG3405): an open label, randomised phase 3 trial", Lancet Oncol., 2010, vol. 11, p. 121-128.

Mok, T.S. et al. "Gefitinib or Carboplatin-Paclitaxel in Pulmonary Adenocarcinoma", The New England Journal of Medicine, 2009, vol. 361, No. 10, p. 947-957.

Paez J.G. et al. "*EGFR* Mutations in Lung Cancer: Correlation with Clinical Response to Gefitinib Therapy", Science, 2004, vol. 304, p. 1497-1500.

Raymond E. et al. "Epidermal Growth Factor Receptor Tyrosine Kinase as a Target for Anticancer Therapy", Drugs 2000, vol. 60, Suppl. 1, p. 15-23.

Robinson et al. "Discovery of the Hemifumarate and (r-L-Alanyloxy)methyl Ether as Prodrugs of an Antirheumatic Oxindole: Prodrugs for the Enolic OH Group", J. Med. Chem. 1996, vol. 39, p. 10-18.

Rosell R. et al. "Erlotinib versus standard chemotherapy as first-line treatment for European patients with advanced EGFR mutation-positive non-small-cell lung cancer (EURTAC): a multicentre, open-label, randomised phase 3 trial", Lancet Oncol., 2012, vol. 13, p. 239-246.

Salomon et al. "Epidermal growth factor-related peptides and their receptors in human malignancies", Critical Reviews in Oncology/Hematology, 1995, vol. 19, p. 183-232.

Sequist L.V. et al. "Phase III Study of Afatinib or Cisplatin Plus Pemetrexed in Patients With Metastatic Lung Adenocarcinoma With *EGFR* Mutations", Journal of Clinical Onocology, 2013, vol. 31, p. 3327-3334.

Seymour L. K., "Epidermal Growth Factor Receptor as a Target: Recent Developments in the Search for Effective New Anti-Cancer Agents", Current Drug Targets, 2001, vol. 2, p. 117-133.

Shan, Y. et al. "Oncogenic mutations counteract intrinsic disorder in the EGFR kinase and promote receptor dimerization" Cell, 2012, vol. 149, p. 860-870.

Tsou, H. R. et al. "Optimization of 6, 7-disubstituted-4-(arylamino)quinoline-3-carbonitriles as orally active, irreversible inhibitors of human epidermal growth factor receptor-2 kinase activity" Journal of Medicinal Chemistry, 2005, vol. 48, p. 1107-1131.

Voldborg et al. "Epidermal growth factor receptor (EGFR) and EGFR mutations, function and possible role in clinical trials", Annals of Oncology, 1997, vol. 8, p. 1197-1206.

Walter A.O. et al. "Discovery of a Mutant-Selective Covalent Inhibitor of EGFR that Overcomes T790MMediated Resistance in NSCLC", Cancer Discovery, 2013, vol. 3, p. 1404-1415.

Wood, E. R. et al. "A unique structure for epidermal growth factor receptor bound toGW572016 (Lapatinib): relationships among protein conformation, inhibitor off-rate, and receptor activity in tumor cells", Cancer Research, 2004, vol. 64, p. 6652-6659.

Wu, Y.L. et al. "Afatinib versus cisplatin plus gemcitabine for first-line treatment of Asian patients with advanced non-small-cell lung cancer harbouring *EGFR* mutations (LUX-Lung 6): an open-label, randomised phase 3 trial", Lancet Oncology, 2014, vol. 15, p. 213-222.

Zhang X. et al. "An allosteric mechanism for activation of the kinase domain of epidermal growth factor receptor," Cell, 2006, vol. 125, p. 1137-1149.

Zhao, Y. et al. "The clinical development of MEK inhibitors" Nature Reviews, Clinical Oncology, 2014, vol. 11, p. 385-400.

Zhou, C. et al. "Erlotinib versus chemotherapy as first-line treatment for patients with advanced *EGFR* mutation-positive non-small-cell lung cancer (OPTIMAL, CTONG-0802): a multicentre, open-label, randomised, phase 3 study", Lancet Oncology, 2011, vol. 12, p. 735-742.

Zhou, W. et al. "Novel mutant-selective EGFR kinase inhibitors against EGFR T790M", Nature, 2009, vol. 462, p. 1070-1074.

Yu, H.A. et al. "Analysis of Tumor Specimens at the Time of Acquired Resistance to EGFR-TKI Therapy in 155 Patients with EGFR-Mutant Lung Cancers", Clinical Cancer Research, 2013, vol. 19, p. 2240-2247.

Yun C.H. et al. "The T790M mutation in EGFR kinase causes drug resistance by increasing the affinity for ATP", PNAS 2008, vol. 105, No. 6, p. 2070-2075.

Yun, C.H. et al. "Structures of lung cancer-derived EGFR mutants and inhibitor complexes: mechanism of activation and insights into differential inhibitor sensitivity", Cancer Cell, 2007, vol. 11, p. 217-227.

Dadiboyena, S. & Nefzi, A., "Parallel Synthesis of Aminobenzimidazole-Tethered Thiazoles," Synthesis 44:215-218 (2012).

Huang, X.-C. et al., "Synthesis and antitumor activities of novel dipeptide derivatives derived from dehydroabietic acid," Bioorg. Med. Chem. Lett. 24(6):1511-1518 (2014).

Li, S.-N. & Li, H.-Q., "Epidermal growth factor receptor inhibitors: a patent review (2010-present)," Expert Opin. Ther. Patents 24(3):309-321 (2014).

Zhang, L. et al., "Discovery of novel dual-action antidiabetic agents that inhibit glycogen phosphorylase and activate glucokinase," European Journal of Medicinal Chemistry 58:624-639 (2012).

Zhang, X. et al., "Design and Synthesis of Phenylpyrrolidine Phenylglycinamides as Highly Potent and Selective TF-FVIIa Inhibitors," ACS Med. Chem. Lett. 5(2):188-192 (2014).

INHIBITORS OF EGFR AND METHODS OF USE THEREOF

RELATED APPLICATIONS

This application is a U.S. National Phase application, filed under 35 U.S.C. § 371, of International Application No. PCT/US2016/040421, filed on Jun. 30, 2016, which claims the benefit of, and priority to, U.S. provisional application No. 62/186,563, filed on Jun. 30, 2015, and 62/259,895, filed on Nov. 25, 2015, the entire contents of each of which are incorporated herein by reference in their entireties.

GOVERNMENT SUPPORT

The work described herein was supported by the National Institutes of Health, NIH Grant No. P01 CA154303. The U.S. Government has certain rights to the claimed invention.

BACKGROUND OF THE DISCLOSURE

The epidermal growth factor receptor (EGFR, Erb-B1) belongs to a family of proteins, involved in the proliferation of normal and malignant cells (Arteaga, C. L., *J. Clin. Oncol.* 19, 2001, 32-40). Overexpression of Epidermal Growth Factor Receptor (EGFR) is present in at least 70% of human cancers (Seymour, L. K., *Curr. Drug Targets* 2, 2001, 117-133) such as, non-small cell lung carcinomas (NSCLC), breast cancers, gliomas, squamous cell carcinoma of the head and neck, and prostate cancer (Raymond et al., *Drugs* 60 Suppl. 1, 2000, discussion 41-2; Salomon et al., *Crit. Rev. Oneal. Hematol.* 19, 1995, 183-232; Voldborg et al., *Ann. Oneal.* 8, 1997, 1197-1206). The EGFR-TK is therefore widely recognized as an attractive target for the design and development of compounds that can specifically bind and inhibit the tyrosine kinase activity and its signal transduction pathway in cancer cells, and thus can serve as either diagnostic or therapeutic agents. For example, the EGFR tyrosine kinase (EGFR-TK) reversible inhibitor, TARCEVA®, is approved by the FDA for treatment of NSCLC and advanced pancreatic cancer. Other anti-EGFR targeted molecules have also been approved including LAPATINIB® and IRESSA®.

Epidermal growth factor receptor (EGFR) tyrosine kinase inhibitors (TKIs) are effective clinical therapies for EGFR mutant advanced non-small cell lung cancer (NSCLC) patients (Mok, T. S., et al., *N. Engl. J. Med.* 361, 2009, 947-57; Paez, J. G., et al., *Science.* 304, 2004, 1497-500; Lynch, T. J., et al., *N. Engl. J Med.* 350, 2004, 2129-39; Rosell, R., et al., *Lancet Oncol.* 13, 2012, 239-46). Several randomized clinical trials have demonstrated that EGFR TKIs are more effective, as measured by response rate (RR) and progression free survival (PFS), than chemotherapy when used as initial systemic treatment for advanced EGFR mutant NSCLC (Mok, T. S., et al., *N. Engl. J. Med.* 361, 2009, 947-57; Rosell, R., et al., *Lancet Oncol.* 13, 2012, 239-46; Sequist, L. V. et al., *J. Clin. Oncol.* 31, 2013, 3327-34; Wu, Y. L., et al., *Lancet Oncol.* 15, 2014, 213-22; Maemondo, M., et al. *N. Engl. J. Med.* 362, 2010, 2380-8; Zhou, C., et al., *Lancet Oncol.* 12, 2011, 735-42; Mitsudomi, T., et al., *Lancet Oncol.* 11, 2010, 121-8). However, the vast majority of patients will develop disease progression following successful treatment with an EGFR TKI. The most common mechanism of acquired resistance, detected in 60% of patients, is a secondary mutation in EGFR at position T790 (T790M) (Yu, H. A., et al., *Clin. Cancer Res.* 19, 2013, 2240-7). This mutation, leads to an increase in ATP affinity, thus making it more difficult for reversible EGFR TKIs gefitinib and erlotinib to bind the EGFR TKI domain (Yun C. H., et al., *Proc. Natl. Acad. Sci. USA.* 105, 2008, 2070-5).

Covalent EGFR inhibitors have emerged as strategies to inhibit EGFR T790M containing cancers. However, in lung cancer patients, afatinib is only effective in EGFR TKI naive EGFR mutant cancers and has a RR of <10% in patients with NSCLC that have developed resistance to gefitinib or erlotinib (Miller V. A., et al., *Lancet Oncol.* 13, 2012, 528-38). Afatinib is a potent inhibitor of both mutant and wild type (WT) EGFR. Inhibition of WT EGFR leads to toxicities, including skin rash and diarrhea, which limits the ability to escalate afatinib doses in patients to those necessary to inhibit EGFR T790M. Irreversible pyrimidine EGFR inhibitors, including the tool compound WZ4002 and clinical compounds CO-1686 and AZD9291, overcome many of the limitations of afatinib (Zhou, W., et al., *Nature* 462, 2009, 1070-4; Walter, A. O., et al., *Cancer Discov.* 3, 2013, 1404-15; Cross, D. A., et al., *Cancer Discov.* 2014). They are not only more potent on EGFR T790M, but also selectively inhibit mutant over WT EGFR and hence should lead to increased clinical efficacy and less toxicity compared with afatinib (Zhou, W., et al.; Walter, A. O., et al; Cross, D. A., et al.).

However, all current EGFR TKIs target the ATP site, and while third generation irreversible inhibitors can overcome T790M, they are all rendered impotent by the C797S mutation, which is already arising in treated patients. Cetuximab, an anti-EGFR antibody that blocks receptor dimerization is not effective in EGFR-mutant NSCLC, because mutational activation of the kinase is effectively "downstream" of receptor dimerization. Hence, alternative strategies to inhibit EGFR are needed. At present, suitable compounds with alternative mechanisms of action targeting mutant EGFR are not available. Thus, there is a need for novel and potent small molecule EGFR inhibitors with alternative mechanisms of action targeting mutant EGFR.

SUMMARY OF THE DISCLOSURE

The present disclosure relates to compounds of Formula (I'), as defined herein, that are capable of modulating EGFR activity. The disclosure features methods of treating or preventing a disease in which EGFR plays a role in a subject in need thereof by administering to the subject a therapeutically effective amount of a compound of Formula (I'), or a pharmaceutically acceptable salt, hydrate, solvate, prodrug, stereoisomer, or tautomer thereof, as defined herein. The methods of the disclosure can be used to treat diseases in which EGFR plays a role by inhibiting the kinase activity of EGFR.

A first aspect of the disclosure relates to compounds of Formula (I'):

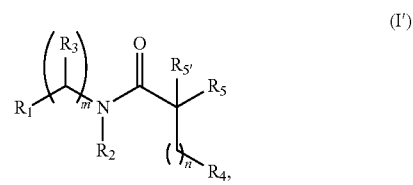

or pharmaceutically acceptable salts, hydrates, solvates, prodrugs, stereoisomers, or tautomers thereof, wherein $R_1$, $R_2$, $R_3$, $R_4$, $R_5$, $R_{5'}$, m, and n are described herein in detail below.

Another aspect of the present disclosure relates to a pharmaceutical composition comprising a compound of Formula (I'), or a pharmaceutically acceptable salt, hydrate, solvate, prodrug, stereoisomer, or tautomer thereof, and a pharmaceutically acceptable carrier. In another aspect, the pharmaceutical composition further comprises a second agent wherein said second agent prevents EGFR dimer formation, and a pharmaceutically acceptable carrier.

Another aspect of the present disclosure relates to a method of inhibiting a kinase. The method comprises administering to a subject in need thereof an effective amount of a compound of Formula (I'), or a pharmaceutically acceptable salt, hydrate, solvate, prodrug, stereoisomer, or tautomer thereof. In one aspect, the method further comprises administering to the subject a second agent wherein said second agent prevents EGFR dimer formation.

Another aspect of the present disclosure relates to a method of inhibiting epidermal growth factor receptor (EGFR). The method comprises administering to a subject in need thereof an effective amount of a compound that binds to an allosteric site in EGFR, or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of inhibiting epidermal growth factor receptor (EGFR). The method comprises administering to a subject in need thereof an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing a disease. The method comprises administering to a subject in need thereof an effective amount of a compound that binds to an allosteric site in EGFR, or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing a disease. The method comprises administering to a subject in need thereof an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing a kinase mediated disorder. The method comprises administering to a subject in need thereof an effective amount of a compound that binds to an allosteric site in EGFR, or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing a kinase mediated disorder. The method comprises administering to a subject in need thereof an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing a disease, wherein the disease is resistant to an EGFR targeted therapy, such as a therapy with gefitinib, erlotinib, AZD9291, CO-1686 or WZ4002. The method comprises administering to a subject in need thereof an effective amount of a compound that binds to an allosteric site in EGFR, or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing a disease, wherein the disease is resistant to an EGFR targeted therapy, such as a therapy with gefitinib, erlotinib, AZD9291, CO-1686 or WZ4002. The method comprises administering to a subject in need thereof an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing cancer, wherein the cancer cell comprises an activated EGFR. The method comprises administering to a subject in need thereof an effective amount of a compound that binds to an allosteric site in EGFR, or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing cancer, wherein the cancer cell comprises an activated EGFR. The method comprises administering to a subject in need thereof an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing cancer in a subject, wherein the subject is identified as being in need of EGFR inhibition for the treatment or prevention of cancer. The method comprises administering to the subject an effective amount of a compound that binds to an allosteric site in EGFR, or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing cancer in a subject, wherein the subject is identified as being in need of EGFR inhibition for the treatment or prevention of cancer. The method comprises administering to the subject an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents EGFR dimer formation.

Another aspect of the present disclosure relates to a method of treating or preventing cancer, wherein the cancer cell comprises an activated ERBB2. The method comprises administering to a subject in need thereof an effective amount of a compound that binds to an allosteric site in ERBB2, or a pharmaceutically acceptable salt, hydrate, solvate, prodrug, stereoisomer, or tautomer thereof. In another aspect, the method further comprises administering to the subject a second agent wherein said second agent prevents ERBB2 dimer formation.

Another aspect of the present disclosure relates to a method of treating or preventing cancer, wherein the cancer cell comprises an activated ERBB2. The method comprises administering to a subject in need thereof an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents ERBB2 dimer formation.

Another aspect of the present disclosure relates to a method of treating or preventing cancer in a subject, wherein the subject is identified as being in need of ERBB2 inhibition for the treatment of cancer. The method comprises administering to the subject an effective amount of a compound that binds to an allosteric site in ERBB2, or a pharmaceutically acceptable salt, hydrate, solvate, prodrug, stereoisomer, or tautomer thereof. In another aspect, the method further comprises administering to the subject a second agent wherein said second agent prevents ERBB2 dimer formation.

Another aspect of the present disclosure relates to a method of treating or preventing cancer in a subject, wherein the subject is identified as being in need of ERBB2 inhibition for the treatment of cancer. The method comprises administering to the subject an effective amount of a compound of Formula (I'), or a pharmaceutically acceptable salt, hydrate, solvate, prodrug, stereoisomer, or tautomer thereof. In another aspect, the method further comprises administering to the subject a second agent wherein said second agent prevents ERBB2 dimer formation.

Another aspect of the present disclosure relates to a kit comprising a compound capable of inhibiting EGFR activity selected from a compound of Formula (I'), or a pharmaceutically acceptable salt, hydrate, solvate, prodrug, stereoisomer, or tautomer thereof. In another aspect, the kit further comprises a second agent wherein said second agent prevents EGFR dimer formation.

Another aspect of the present disclosure relates to a compound that binds to an allosteric site in EGFR, or a pharmaceutically acceptable salt, hydrate, solvate, prodrug, stereoisomer, or tautomer thereof, for use in the manufacture of a medicament for treating or preventing a disease in which EGFR plays a role. In another aspect, the present disclosure relates to a compound that binds to an allosteric site in EGFR, or a pharmaceutically acceptable salt, hydrate, solvate, prodrug, stereoisomer, or tautomer thereof, and a second agent wherein said second agent prevents EGFR dimer formation for use in the manufacture of a medicament for treating or preventing a disease in which EGFR plays a role.

Another aspect of the present disclosure relates to a compound of Formula (I'), or a pharmaceutically acceptable salt, hydrate, solvate, prodrug, stereoisomer, or tautomer thereof, for use in the manufacture of a medicament for treating or preventing a disease in which EGFR plays a role. In another aspect, the present disclosure relates to a compound of Formula (I'), or a pharmaceutically acceptable salt, hydrate, solvate, prodrug, stereoisomer, or tautomer thereof, and a second agent wherein said second agent prevents EGFR dimer formation for use in the manufacture of a medicament for treating or preventing a disease in which EGFR plays a role.

Another aspect of the present disclosure relates to the use of a compound that binds to an allosteric site in EGFR, or a pharmaceutically acceptable salt, hydrate, solvate, prodrug, stereoisomer, or tautomer thereof, in the treatment or prevention of a disease in which EGFR plays a role. In another aspect, the present disclosure relates to the use of a compound that binds to an allosteric site in EGFR, or a pharmaceutically acceptable salt, hydrate, solvate, prodrug, stereoisomer, or tautomer thereof, and a second agent wherein said second agent prevents EGFR dimer formation in the treatment or prevention of a disease in which EGFR plays a role.

Another aspect of the present disclosure relates to the use of a compound of Formula (I'), or a pharmaceutically acceptable salt, hydrate, solvate, prodrug, stereoisomer, or tautomer thereof, in the treatment or prevention of a disease in which EGFR plays a role. In another aspect, the present disclosure relates to the use of a compound of Formula (I'), or a pharmaceutically acceptable salt, hydrate, solvate, prodrug, stereoisomer, or tautomer thereof, and a second agent wherein said second agent prevents EGFR dimer formation in the treatment or prevention of a disease in which EGFR plays a role.

In one embodiment, in any of the above aspects, a compound of Formula (I') is Compound I-126:

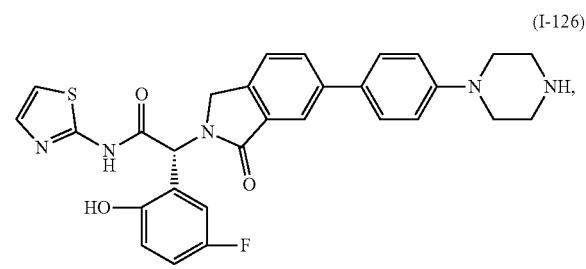 [SMILES: O=C(Nc1nccs1)[C@@H](c1cc(F)ccc1O)N1Cc2ccc(-c3ccc(N4CCNCC4)cc3)cc2C1=O]

(I-126)

or pharmaceutically acceptable salts, hydrates, solvates, prodrugs, stereoisomers, or tautomers thereof. In one embodiment, Compound I-126 is administered in any of the above methods without a second agent which prevents EGFR dimer formation. In one embodiment, Compound I-126 is for use in the manufacture of medicament as described above, without a second agent which prevents EGFR dimer formation. In one embodiment, Compound I-126 is for use in the treatment or prevention as described above, without a second agent which prevents EGFR dimer formation The present disclosure provides inhibitors of EGFR, such as EGFR containing one or more mutations, that are therapeutic agents in the treatment or prevention of diseases such as cancer and metastasis.

The present disclosure further provides compounds and compositions with an improved efficacy and/or safety profile relative to known EGFR inhibitors. The present disclosure also provides agents with novel mechanisms of action toward EGFR kinases in the treatment of various types of diseases including cancer and metastasis.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

DETAILED DESCRIPTION OF THE DISCLOSURE

Compounds of the Disclosure

Figure 1:
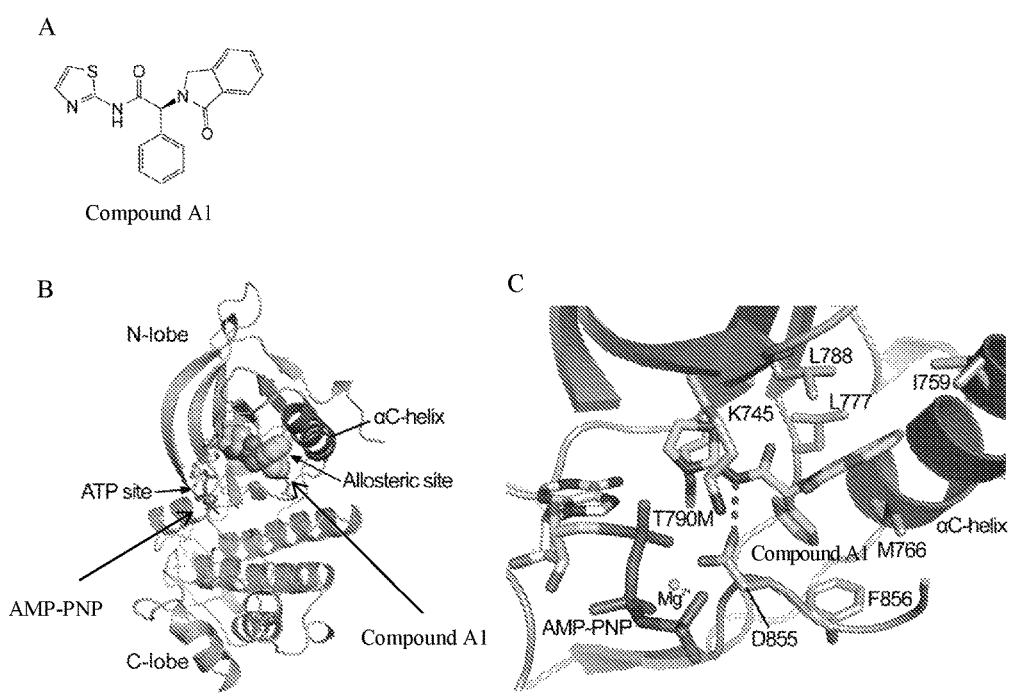
FIG. 1A shows the chemical structure of Compound A1.
FIG. 1B shows an overall view of the crystal structure of Compound A1 bound to T790M-mutant EGFR. Compound A1 is shown in CPK form with carbon atoms and the ATP analog AMP-PNP is shown in stick form. The kinase adopts an inactive conformation, and Compound A1 occupies an allosteric site created by outward displacement of the C-helix.
FIG. 1C shows the detailed view of interactions of Compound A1 with EGFR in the crystal structure of Compound A1 bound to T790M-mutant EGFR. The compound forms a hydrogen bond with Asp855 in the "DFG" segment of the kinase (dashed line), and the aminothiazole group extends between active site residue Lys745 and the mutant gatekeeper Met790. A number of hydrophobic residues contact the phenyl and oxindole "blades" of the compound.
Figure 2:
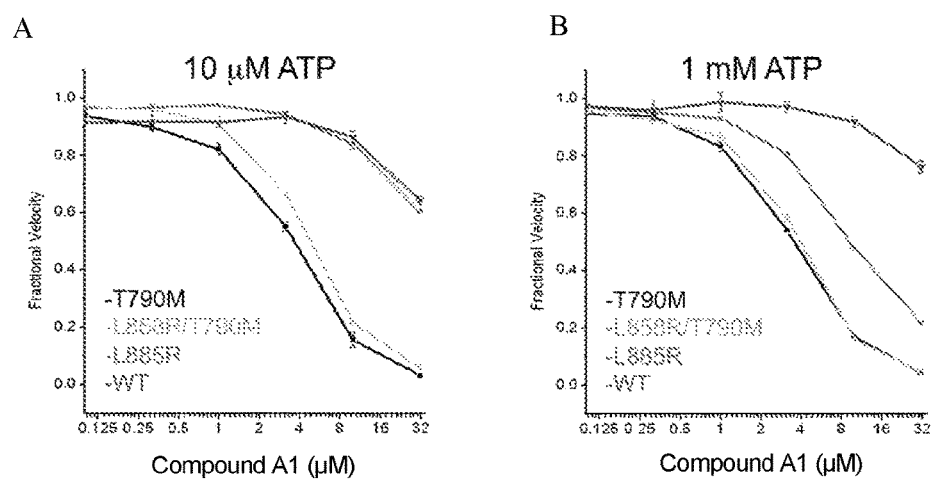
FIG. 2A is a graph showing EGFR activity in wild type and mutant EGFR kinases when treated with various concentrations of Compound A1 using 10 μM ATP and 0.5 μM EGFR kinase (wild type, L858R, T790M, or L858R/T790M) and 1.25 mM poly[Glu$_4$Tyr] as a peptide substrate.
FIG. 2B is a graph showing EGFR activity in wild type and mutant EGFR kinases when treated with various concentrations of Compound A1 using 1 mM ATP and 0.5 LM EGFR kinase (wild type, L858R, T790M, or L858R/T790M) and 1.25 mM poly[Glu$_4$Tyr] as a peptide substrate.

A first aspect of the disclosure relates to compounds of Formula (I'):

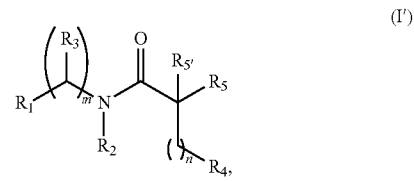

or pharmaceutically acceptable salts, hydrates, solvates, prodrugs, stereoisomers, or tautomers thereof, wherein:

$R_1$ is ($C_6$-$C_{10}$) aryl, or heteroaryl comprising one or two 5- to 7-membered rings and 1-4 heteroatoms selected from N, O, and S, wherein the aryl and heteroaryl are each optionally substituted with one or more $R_{11}$;

each $R_{11}$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, C(O)$R_{13}$, C(O)O$R_{13}$, C(O)$NR_{13}R_{14}$, $NR_{13}R_{14}$, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the alkyl, cycloalkyl, heterocyclyl, aryl, and heteroaryl are each optionally substituted with one or more $R_{12}$;

each $R_{12}$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the aryl and heteroaryl are each optionally substituted with one or more substituents independently selected from ($C_1$-$C_4$) alkyl, ($C_1$-$C_4$) alkoxy, ($C_1$-$C_4$) haloalkyl, ($C_1$-$C_4$) haloalkoxy, halogen, $NH_2$, NH($C_1$-$C_4$) alkyl, N(($C_1$-$C_4$) alkyl)$_2$, ($C_3$-$C_7$) cycloalkyl, and heterocyclyl comprising a 5- to 7-membered ring and 1-3 heteroatoms selected from N, O, and S;

each $R_{13}$ is independently selected from H, ($C_1$-$C_4$) alkyl, ($C_3$-$C_7$) cycloalkyl, and heterocyclyl comprising a 5- to 7-membered ring and 1-3 heteroatoms selected from N, O, and S, wherein the alkyl, cycloalkyl, and heterocyclyl are each optionally substituted with one or more substituents independently selected from ($C_1$-$C_4$) alkyl, halogen, OH, $NH_2$, NH($C_1$-$C_4$) alkyl, N(($C_1$-$C_4$) alkyl)$_2$, and heterocyclyl comprising a 5- to 7-membered ring and 1-3 heteroatoms selected from N, O, and S;

each $R_{14}$ is independently H or ($C_1$-$C_3$) alkyl;
$R_2$ is H or ($C_1$-$C_3$) alkyl;
$R_3$ is H or ($C_1$-$C_3$) alkyl;
$R_4$ is ($C_1$-$C_3$) alkyl or

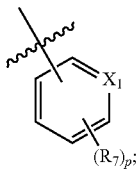

$X_1$ is N or $CR_6$;
$R_6$ is H, ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, $(CH_2)_qOH$, $S(O)_rR_{23}$, or CN;
each $R_7$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, $NH_2$, $(CH_2)_qOH$, $S(O)_rR_{23}$, and CN;
$R_5$ is $NR_{15}R_{16}$;
$R_{5'}$ is H or ($C_1$-$C_4$) alkyl;
$R_{15}$ is H or ($C_1$-$C_3$) alkyl; $R_{16}$ is ($C_6$-$C_{10}$) aryl, or heteroaryl comprising a 5- to 7-membered ring and 1-3 heteroatoms selected from N, O, and S, wherein the aryl and heteroaryl are each optionally substituted with one or more $R_{18}$; or
$R_{15}$ and $R_{16}$ together with the nitrogen atom to which they are attached form a 5- or 6-membered heterocyclyl optionally comprising 1 or 2 additional heteroatoms selected from N, O, and S and optionally substituted with one or more oxo groups, wherein the heterocyclyl is fused with a phenyl ring which is optionally substituted with one or more $R_{19}$;
each $R_{18}$ is independently selected from ($C_1$-$C_4$) alkyl, ($C_1$-$C_4$) alkoxy, ($C_1$-$C_4$) haloalkyl, ($C_1$-$C_4$) haloalkoxy, halogen, $C(O)O(C_1$-$C_4$) alkyl, $NO_2$, $C(O)NH(C_1$-$C_4$) alkyl, $NH_2$, $NH(C_1$-$C_4$) alkyl, and $N((C_1$-$C_4$) alkyl)$_2$, wherein the alkyl is optionally substituted with one or more substituents independently selected from halogen, OH, $NH_2$, $NH(C_1$-$C_4$) alkyl, and $N((C_1$-$C_4$) alkyl)$_2$;
each $R_{19}$ is independently selected from halogen, O$(CH_2)_{1-3}$—OH, ($C_3$-$C_7$) cycloalkyl, ($C_4$-$C_7$) cycloalkenyl, ($C_6$-$C_{10}$) aryl, NH—($C_6$-$C_{10}$) aryl, and heteroaryl comprising one or two 5- to 7-membered ring and 1-4 heteroatoms selected from N, O, and S, wherein the aryl and heteroaryl are each optionally substituted with one or more $R_{20}$; or
two $R_{19}$ together with the atoms to which they are attached form a ($C_6$-$C_{10}$) aryl optionally substituted with one or more $R_{20}$;
each $R_{20}$ is independently selected from ($C_1$-$C_4$) alkyl, ($C_1$-$C_4$) alkoxy, ($C_1$-$C_4$) haloalkyl, ($C_1$-$C_4$) haloalkoxy, halogen, C(O)OH, $C(O)O(C_1$-$C_4$) alkyl, $C(O)NR_{21}R_{22}$, $O(CH_2)_{1-3}$—OH, $NH_2$, OH, CN, $O(CH_2)_{0-3}$—($C_6$-$C_{10}$) aryl, and $(CH_2)_{0-3}$-heterocyclyl which comprises a 5- to 7-membered ring and 1-3 heteroatoms selected from N, O, and S, wherein the heterocyclyl is optionally substituted with one or more substituents independently selected from ($C_1$-$C_4$) alkyl, ($C_1$-$C_4$) alkoxy, ($C_1$-$C_4$) haloalkyl, ($C_1$-$C_4$) haloalkoxy, halogen, $NH_2$, $NH(C_1$-$C_4$) alkyl, $N((C_1$-$C_4$) alkyl)$_2$, $S(O)_2NH_2$, $(CH_2)_sOH$, $C(O)(CH_2)_sOH$, and C(O)O ($C_1$-$C_4$) alkyl);
$R_{21}$ is H or ($C_1$-$C_3$) alkyl;
$R_{22}$ is H or ($C_1$-$C_4$) alkyl optionally substituted with one or more substituents independently selected from $NH_2$, $NH(C_1$-$C_4$) alkyl, $N((C_1$-$C_4$) alkyl)$_2$, and heterocyclyl comprising a 5- to 7-membered ring and 1-3 heteroatoms selected from N, O, and S; or
$R_{21}$ and $R_{22}$ together with the nitrogen atom to which they are attached form a 5- or 6-membered heterocyclyl optionally containing 1-2 additional heteroatoms selected from N, O, and S;
$R_{23}$ is H or $NH_2$;
m and n are each independently 0 or 1;
each r and each q are independently 0, 1, or 2;
each s is 1 or 2; and
p is 0, 1, 2, 3 or 4;
provided that when m is 0, n is 0, p is 0, $R_{15}$ and $R_{16}$ together with the nitrogen atom to which they are attached form an unsubstituted isoindolinone, and $R_6$ is H, then $R_1$ is not

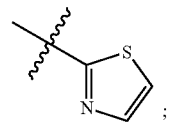 [SMILES: *c1nccs1]

and
provided that $R_4$ is not 4-fluoro-2-hydroxyphenyl.
(1a) In some embodiments of Formula (I'), $R_2$ is H.
(1b) In some embodiments of Formula (I'), $R_2$ is ($C_1$-$C_3$) alkyl (e.g., methyl, ethyl, propyl, or i-propyl). In other embodiments, $R_2$ is methyl. In other embodiments, $R_2$ is ethyl.
(2a) In some embodiments of Formula (I'), $R_3$ is H.
(2b) In some embodiments of Formula (I'), $R_3$ is ($C_1$-$C_3$) alkyl (e.g., methyl, ethyl, propyl, or i-propyl). In other embodiments, $R_3$ is methyl. In other embodiments, $R_3$ is ethyl.
(3a) In some embodiments of Formula (I'), $R_4$ is ($C_1$-$C_3$) alkyl (e.g., methyl, ethyl, propyl, or i-propyl). In other embodiments, $R_4$ is methyl. In other embodiments, $R_4$ is ethyl.
(3b) In some embodiments of Formula (I'), $R_4$ is

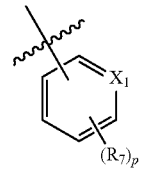

(e.g., phenyl, 2-pyridinyl, 3-pyridinyl, or 4-pyridinyl).
(4a) In some embodiments of Formula (I'), $X_1$ is N.
(4b) In some embodiments of Formula (I'), $X_1$ is $CR_6$.
(5a) In some embodiments of Formula (I'), $R_6$ is H.
(5b) In some embodiments of Formula (I'), $R_6$ is ($C_1$-$C_4$) alkyl (e.g., methyl, ethyl, propyl, i-propyl, or butyl).
(5c) In some embodiments of Formula (I'), $R_6$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$).
(5d) In some embodiments of Formula (I'), $R_6$ is ($C_1$-$C_4$) alkoxy (e.g., methoxy, ethoxy, propoxy, or butoxy).
(5e) In some embodiments of Formula (I'), $R_6$ is halogen (e.g., F, Cl, Br or I). In other embodiments, $R_6$ is F or Cl. In further embodiments, $R_6$ is F.
(5f) In some embodiments of Formula (I'), $R_6$ is $NO_2$, $NH_2$, $(CH_2)_qOH$, $S(O)_rR_{23}$, or CN. In further embodiments, $R_6$ is $(CH_2)_qOH$, $S(O)_rR_{23}$, $NO_2$, or $NH_2$.

(6a) In some embodiments of Formula (I'), at least one $R_7$ is $(C_1-C_4)$ alkyl (e.g., methyl, ethyl, propyl, i-propyl, or butyl).

(6b) In some embodiments of Formula (I'), at least one $R_7$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$).

(6c) In some embodiments of Formula (I'), at least one $R_7$ is $(C_1-C_4)$ alkoxy (e.g., methoxy, ethoxy, propoxy, or butoxy).

(6d) In some embodiments of Formula (I'), at least one $R_7$ is halogen (e.g., F, Cl, Br or I). In other embodiments, at least one $R_7$ is F or Cl. In further embodiments, at least one $R_7$ is F.

(6e) In some embodiments of Formula (I'), at least one $R_7$ is $NO_2$, $NH_2$, $(CH_2)_qOH$, $S(O)_rR_{23}$, or CN. In further embodiments, at least one $R_7$ is $(CH_2)_qOH$, $S(O)_rR_{23}$, $NO_2$, or $NH_2$.

(6f) In some embodiments of Formula (I'), at least one $R_7$ is halogen (e.g., F, Cl, Br or I) and at least one $R_7$ is OH.

(6g) In some embodiments of Formula (I'), one $R_7$ is halogen (e.g., F, Cl, Br or I) and one $R_7$ is OH.

(7a) In some embodiments of Formula (I'), $R_5$ is $NR_{15}R_{16}$.

(7b) In some embodiments of Formula (I'), $R_5$ is N(H)-phenyl.

(8a) In some embodiments of Formula (I'), $R_{15}$ is H.

(8b) In some embodiments of Formula (I'), $R_{15}$ is $(C_1-C_3)$ alkyl (e.g., methyl, ethyl, propyl, or i-propyl). In other embodiments, $R_{15}$ is methyl. In other embodiments, $R_{15}$ is ethyl.

(9a) In some embodiments of Formula (I'), $R_{16}$ is $(C_6-C_{10})$ aryl optionally substituted with one or more $R_{18}$. In other embodiments, $R_{16}$ is phenyl optionally substituted with one or more $R_{18}$. In further embodiments, $R_{16}$ is phenyl optionally substituted with one to three $R_{18}$.

(9b) In some embodiments of Formula (I'), $R_{16}$ is heteroaryl comprising a 5- to 7-membered ring and 1-3 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, etc.) optionally substituted with one or more $R_{18}$. In further embodiments, $R_{16}$ is 2-pyridinyl, 3-pyridinyl, or 4-pyridinyl optionally substituted with one or more $R_{18}$.

(9c) In some embodiments of Formula (I'), $R_{15}$ and $R_{16}$ together with the nitrogen atom to which they are attached form a 5- or 6-membered heterocyclyl optionally comprising 1 or 2 additional heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, etc.) and optionally substituted with one or more oxo groups. In other embodiments, $R_{15}$ and $R_{16}$ together with the nitrogen atom to which they are attached form

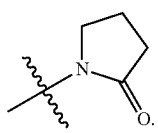

(10a) In some embodiments of Formula (I'), at least one $R_{18}$ is $(C_1-C_4)$ alkyl (e.g., methyl, ethyl, propyl, i-propyl, or butyl) optionally substituted with one or more substituents independently selected from halogen (e.g., F, Cl, Br or I), OH, $NH_2$, $NH(C_1-C_4)$ alkyl (e.g., methylamino, ethylamino, propylamino, or butylamino), and $N((C_1-C_4)$ alkyl$)_2$ (e.g., dimethylamino, diethylamino, dipropylamino, or dibutylamino). In other embodiments, at least one $R_{18}$ is methyl or ethyl optionally substituted with one or more substituents independently selected from halogen (e.g., F, Cl, Br or I), OH, $NH_2$, $NH(C_1-C_4)$ alkyl (e.g., methylamino, ethylamino, propylamino, or butylamino), and $N((C_1-C_4)$ alkyl$)_2$ (e.g., dimethylamino, diethylamino, dipropylamino, or dibutylamino). In other embodiments, at least one $R_{18}$ is methyl or ethyl.

(10b) In some embodiments of Formula (I'), at least one $R_{18}$ is $(C_1-C_4)$ alkoxy (e.g., methoxy, ethoxy, propoxy, or butoxy).

(10c) In some embodiments of Formula (I'), at least one $R_{18}$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$).

(10d) In some embodiments of Formula (I'), at least one $R_{18}$ is halogen (e.g., F, Cl, Br or I). In other embodiments, at least one $R_{18}$ is F or Br.

(10e) In some embodiments of Formula (I'), at least one $R_{18}$ is $C(O)O(C_1-C_4)$ alkyl or $C(O)NH(C_1-C_4)$ alkyl, wherein the alkyl is optionally substituted with one or more substituents independently selected from halogen (e.g., F, Cl, Br or I), OH, $NH_2$, $NH(C_1-C_4)$ alkyl (e.g., methylamino, ethylamino, propylamino, or butylamino), and $N((C_1-C_4)$ alkyl$)_2$ (e.g., dimethylamino, diethylamino, dipropylamino, or dibutylamino). In other embodiments, at least one $R_{18}$ is $C(O)O(C_1-C_4)$ alkyl. In other embodiments, at least one $R_{18}$ is $C(O)NH(C_1-C_4)$ alkyl optionally substituted with one or more OH. In other embodiments, at least one $R_{18}$ is $C(O)OCH_3$. In other embodiments, at least one $R_{18}$ is $C(O)N(H)CH_2CH(OH)CH_2OH$.

(10f) In some embodiments of Formula (I'), at least one $R_{18}$ is $NO_2$, $NH_2$, $NH(C_1-C_4)$ alkyl (e.g., methylamino, ethylamino, propylamino, or butylamino), or $N((C_1-C_4)$ alkyl$)_2$ (e.g., dimethylamino, diethylamino, dipropylamino, or dibutylamino), wherein the alkyl is optionally substituted with one or more substituents independently selected from halogen (e.g., F, Cl, Br or I), OH, $NH_2$, $NH(C_1-C_4)$ alkyl (e.g., methylamino, ethylamino, propylamino, or butylamino), and $N((C_1-C_4)$ alkyl$)_2$ (e.g., dimethylamino, diethylamino, dipropylamino, or dibutylamino). In other embodiments, at least one $R_{18}$ is $NO_2$.

(11a) In some embodiments of Formula (I'), at least one $R_{19}$ is halogen (e.g., F, Cl, Br or I). In other embodiments, at least one $R_{19}$ is F, Cl, or Br. In other embodiments, at least one $R_{19}$ is F. In other embodiments, at least one $R_{19}$ is Cl. In other embodiments, at least one $R_{19}$ is Br.

(11b) In some embodiments of Formula (I'), at least one $R_{19}$ is $(C_3-C_7)$ cycloalkyl (e.g., cyclopropyl, cyclobutyl, cyclopentyl, cyclohexyl, or cycloheptyl).

(11c) In some embodiments of Formula (I'), at least one $R_{19}$ is $(C_4-C_7)$ cycloalkenyl (e.g., cyclobutenyl, cyclopentenyl, cyclohexenyl, or cycloheptenyl). In other embodiments, at least one $R_{19}$ is cyclohexenyl.

(11d) In some embodiments of Formula (I'), at least one $R_{19}$ is $(C_6-C_{10})$ aryl optionally substituted with one or more $R_{20}$. In other embodiments, at least one $R_{19}$ is phenyl optionally substituted with one or more $R_{20}$. In other embodiments, at least one $R_{19}$ is phenyl optionally substituted with one to three $R_{20}$. In other embodiments, at least one $R_{19}$ is phenyl.

(11e) In some embodiments of Formula (I'), at least one $R_{19}$ is $NH-(C_6-C_{10})$ aryl optionally substituted with one or more $R_{20}$. In other embodiments, at least one $R_{19}$ is NH-phenyl optionally substituted with one or more $R_{20}$. In other embodiments, at least one $R_{19}$ is NH-phenyl optionally substituted with one to three $R_{20}$. In other embodiments, at least one $R_{19}$ is NH-phenyl.

(11f) In some embodiments of Formula (I'), at least one $R_{19}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, indolyl, indazolyl, quinolinyl, isoquinolinyl, benzothiazolyl, benzoimidazolyl, benzooxazolyl, thiazolopyridinyl, pyrrolopyridinyl, pyrazolopyrimidinyl, etc.) optionally substituted with one or more $R_{20}$. In other embodiments, at least one $R_{19}$ is pyrazolyl, thiophenyl, pyridinyl, pyrimidinyl, indolyl, or quinolinyl optionally substituted with one or more $R_{20}$.

(11g) In some embodiments of Formula (I'), at least one $R_{19}$ is $O(CH_2)_{1-3}$—OH. In other embodiments, at least one $R_{19}$ is $O(CH_2)$—OH. In other embodiments, at least one $R_{19}$ is $O(CH_2)_2$—OH. In other embodiments, at least one $R_{19}$ is $O(CH_2)_3$—OH.

(11h) In some embodiments of Formula (I'), two $R_{19}$ together with the atoms to which they are attached form a ($C_6$-$C_{10}$) aryl optionally substituted with one or more $R_{20}$. In other embodiments, two $R_{19}$ together with the atoms to which they are attached form a phenyl optionally substituted with one or more $R_{20}$. In other embodiments, two $R_{19}$ together with the atoms to which they are attached form a phenyl.

(12a) In some embodiments of Formula (I'), at least one $R_{20}$ is ($C_1$-$C_4$) alkyl (e.g., methyl, ethyl, propyl, i-propyl, or butyl). In further embodiments, at least one $R_{20}$ is methyl or ethyl.

(12b) In some embodiments of Formula (I'), at least one $R_{20}$ is ($C_1$-$C_4$) alkoxy (e.g., methoxy, ethoxy, propoxy, or butoxy). In further embodiments, at least one $R_{20}$ is methoxy.

(12c) In some embodiments of Formula (I'), at least one $R_{20}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$). In further embodiments, at least one $R_{20}$ is $CF_3$ or $OCF_3$.

(12d) In some embodiments of Formula (I'), at least one $R_{20}$ is halogen (e.g., F, Cl, Br or I). In further embodiments, at least one $R_{20}$ is F.

(12e) In some embodiments of Formula (I'), at least one $R_{20}$ is C(O)OH or C(O)O($C_1$-$C_4$) alkyl (e.g., methyl, ethyl, propyl, i-propyl, or butyl). In further embodiments, at least one $R_{20}$ is C(O)OH or C(O)OCH$_3$.

(12f) In some embodiments of Formula (I'), at least one $R_{20}$ is $NH_2$, OH, or CN.

(12g) In some embodiments of Formula (I'), at least one $R_{20}$ is C(O)NR$_{21}$R$_{22}$.

(12h) In some embodiments of Formula (I'), at least one $R_{20}$ is $O(CH_2)_{0-3}$—($C_6$-$C_{10}$) aryl. In further embodiments, at least one $R_{20}$ is $OCH_2$-phenyl.

(12i) In some embodiments of Formula (I'), at least one $R_{20}$ is $(CH_2)_{0-3}$-heterocyclyl which comprises a 5- to 7-membered ring and 1-3 heteroatoms selected from N, O, and S, wherein the heterocyclyl is selected from pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc., and is optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, NH($C_1$-$C_4$) alkyl (e.g., methylamino, ethylamino, propylamino, or butylamino), N(($C_1$-$C_4$) alkyl)$_2$ (e.g., dimethylamino, diethylamino, dipropylamino, or dibutylamino), S(O)$_2$NH$_2$, $(CH_2)_s$OH (e.g., $CH_2OH$, $CH_2CH_2OH$), C(O)$(CH_2)_s$OH (e.g., C(O)CH$_2$OH, C(O)CH$_2$CH$_2$OH), and C(O)O($C_1$-$C_4$) alkyl (e.g., methyl, ethyl, propyl, i-propyl, butyl, i-butyl, or t-butyl). In other embodiments, at least one $R_{20}$ is $(CH_2)_{0-1}$-heterocycle optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), and C(O)O($C_1$-$C_4$) alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl wherein the pyrrolidinyl, morpholinyl, and piperazinyl are each optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, NH($C_1$-$C_4$) alkyl (e.g., methylamino, ethylamino, propylamino, or butylamino), N(($C_1$-$C_4$) alkyl)$_2$ (e.g., dimethylamino, diethylamino, dipropylamino, or dibutylamino), S(O)$_2$NH$_2$, $(CH_2)_s$OH (e.g., $CH_2OH$, $CH_2CH_2OH$), C(O)$(CH_2)_s$OH (e.g., C(O)CH$_2$OH, C(O)CH$_2$CH$_2$OH), and C(O)O($C_1$-$C_4$) alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl, wherein the pyrrolidinyl, morpholinyl, and piperazinyl are each optionally substituted with one or more ($C_1$-$C_4$) alkyl (e.g., methyl, ethyl, propyl, i-propyl, or butyl), N(($C_1$-$C_4$) alkyl)$_2$ (e.g., dimethylamino, diethylamino, dipropylamino, or dibutylamino), S(O)$_2$NH$_2$, $(CH_2)_s$OH (e.g., $CH_2OH$, $CH_2CH_2OH$), C(O)$(CH_2)_s$OH (e.g., C(O)CH$_2$OH, C(O)CH$_2$CH$_2$OH), or C(O)O($C_1$-$C_4$)alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl, wherein the pyrrolidinyl, morpholinyl, and piperazinyl are each optionally substituted with one or more ($C_1$-$C_4$) alkyl (e.g., methyl, ethyl, propyl, i-propyl, or butyl) or C(O)O($C_1$-$C_4$)alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, morpholinyl, or piperazinyl, wherein the pyrrolidinyl, morpholinyl, and piperazinyl are optionally methyl, ethyl, N(methyl)$_2$, S(O)$_2$NH$_2$, $(CH_2)_2$OH, C(O)(CH$_2$)OH, or C(O)O-t-butyl. In other embodiments, at least one $R_{20}$ is $CH_2$-pyrrolidinyl, $CH_2$-piperazinyl, morpholinyl, or piperazinyl, wherein the pyrrolidinyl, morpholinyl, and piperazinyl are optionally methyl, ethyl, or C(O)O-t-butyl.

(12j) In some embodiments of Formula (I'), at least one $R_{20}$ is $O(CH_2)_{1-3}$—OH. In other embodiments, at least one $R_{20}$ is $O(CH_2)$—OH. In other embodiments, at least one $R_{20}$ is $O(CH_2)_2$—OH. In other embodiments, at least one $R_{20}$ is $O(CH_2)_3$—OH.

(13a) In some embodiments of Formula (I'), $R_{21}$ is H.

(13b) In some embodiments of Formula (I'), $R_{21}$ is ($C_1$-$C_3$) alkyl (e.g., methyl, ethyl, propyl, or i-propyl). In other embodiments, $R_{21}$ is methyl. In other embodiments, $R_{21}$ is ethyl.

(14a) In some embodiments of Formula (I'), $R_{22}$ is H.

(14b) In some embodiments of Formula (I'), $R_{22}$ is ($C_1$-$C_4$) alkyl (e.g., methyl, ethyl, propyl, i-propyl, or butyl) optionally substituted with one or more substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, etc.). In other embodiments, $R_{22}$ is ($C_1$-$C_4$) alkyl (e.g., methyl, ethyl, propyl, i-propyl, or butyl) optionally substituted with one to two substituents independently selected from $NH_2$, $NH(C_1$-$C_4)$ alkyl, $N((C_1$-$C_4)$ alkyl$)_2$, and 6-membered heterocycle comprising 1-3 heteroatoms selected from N, O, and S. In further embodiments, $R_{22}$ is ethyl, propyl, or butyl optionally substituted with dimethylamino, diethylamino, or morpholinyl.

(14c) In some embodiments of Formula (I'), $R_{21}$ and $R_{22}$ together with the nitrogen atom to which they are attached form a 5-membered heterocyclyl optionally containing 1-2 additional heteroatoms selected from N, O, and S. In other embodiments, $R_{21}$ and $R_{22}$ together with the nitrogen atom to which they are attached form a 6-membered heterocycle optionally containing 1-2 additional heteroatoms selected from N, O, and S. In further embodiments, $R_{21}$ and $R_{22}$ together with the nitrogen atom to which they are attached form a morpholinyl.

(15a) In some embodiments of Formula (I'), $R_1$ is ($C_6$-$C_{10}$) aryl optionally substituted with one or more $R_{11}$. In other embodiments, $R_1$ is phenyl optionally substituted with one or more $R_{11}$.

(15b) In some embodiments of Formula (I'), $R_1$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, thiazolopyridinyl, pyrazolopyrimidinyl, etc.) optionally substituted with one or more $R_{11}$. In other embodiments, $R_1$ is heteroaryl comprising a 5-membered ring and 1-3 heteroatoms selected from N, O, and S, optionally substituted with one or more $R_{11}$. In other embodiments, $R_1$ is heteroaryl comprising a 6-membered ring and 1-3 heteroatoms selected from N, O, and S, optionally substituted with one or more $R_{11}$. In other embodiments, $R_1$ is heteroaryl comprising a 5-membered ring fused with a 6-membered ring and 1-4 heteroatoms selected from N, O, and S, optionally substituted with one or more $R_{11}$. In other embodiments, $R_1$ is selected from:

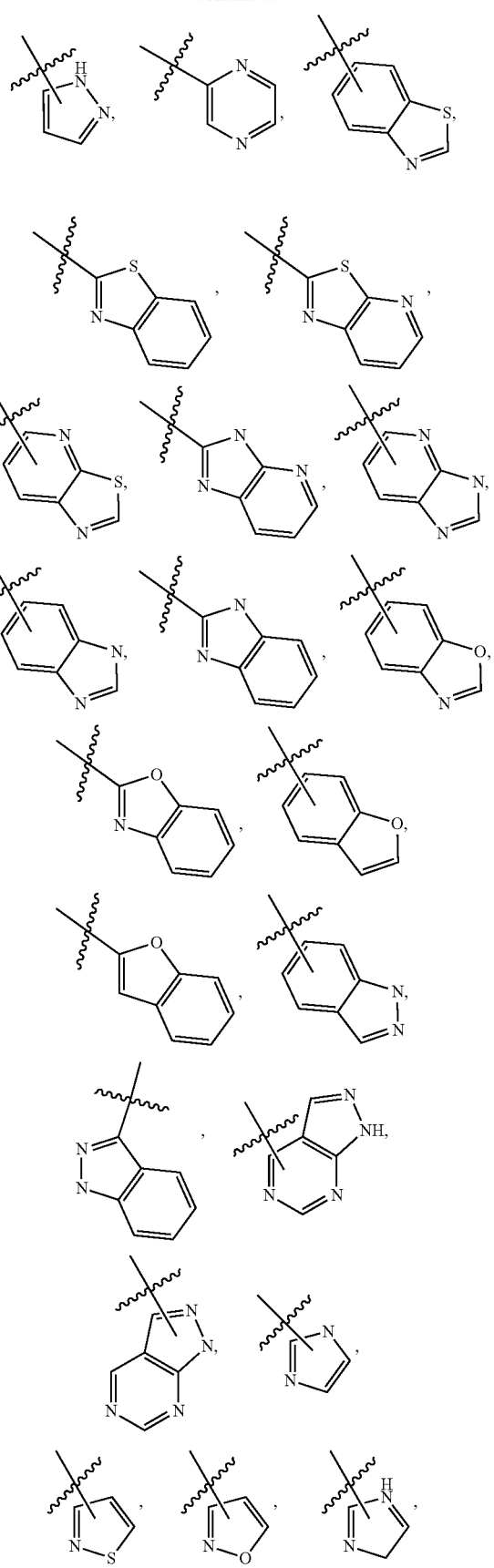

-continued

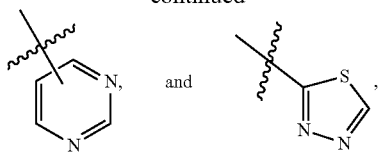

wherein each moiety is optionally substituted with one or more $R_{11}$. In other embodiments, $R_1$ is selected from:

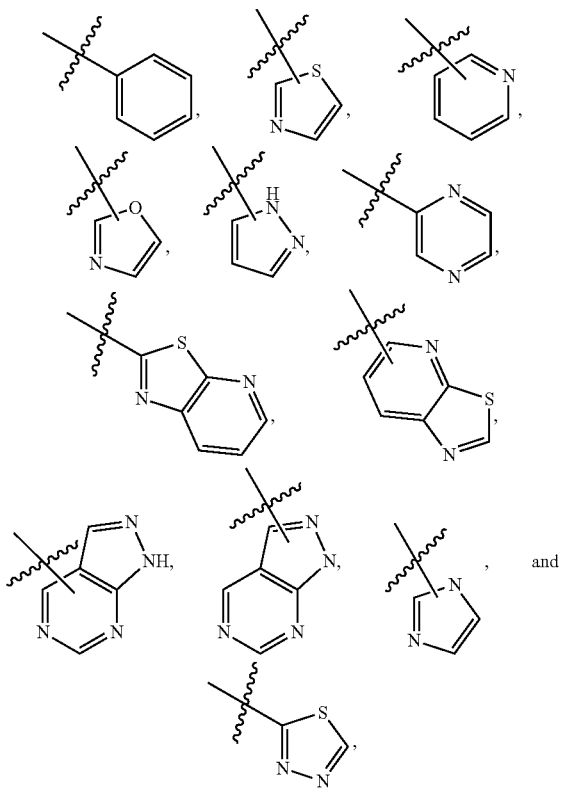

wherein each moiety is optionally substituted with one or more $R_{11}$. In other embodiments, $R_1$ is

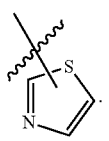

(16a) In some embodiments of Formula (I'), at least one $R_{11}$ is ($C_1$-$C_4$) alkyl (e.g., methyl, ethyl, propyl, i-propyl, or butyl) optionally substituted with one or more $R_{12}$. In other embodiments, at least one $R_{11}$ is methyl. In other embodiments, at least one $R_{11}$ is propyl optionally substituted with one to two $R_{12}$.

(16b) In some embodiments of Formula (I'), at least one $R_{11}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$). In further embodiments, at least one $R_{11}$ is $CF_3$.

(16c) In some embodiments of Formula (I'), at least one $R_{11}$ is ($C_1$-$C_4$) alkoxy (e.g., methoxy, ethoxy, propoxy, or butoxy).

(16d) In some embodiments of Formula (I'), at least one $R_{11}$ is halogen (e.g., F, Cl, Br or I). In other embodiments, at least one $R_{11}$ is F. In other embodiments, at least one $R_{11}$ is Cl. In other embodiments, at least one $R_{11}$ is Br.

(16e) In some embodiments of Formula (I'), at least one $R_{11}$ is $NO_2$, OH, or CN.

(16f) In some embodiments of Formula (I'), at least one $R_{11}$ is $C(O)R_{13}$ or $C(O)OR_{13}$. In other embodiments, at least one $R_{11}$ is $C(O)OCH_2CH_3$.

(16g) In some embodiments of Formula (I'), at least one $R_{11}$ is $C(O)NR_{13}R_{14}$ or $NR_{13}R_{14}$. In other embodiments, at least one $R_{11}$ is $C(O)NR_{13}R_{14}$ or $NH_2$.

(16h) In some embodiments of Formula (I'), at least one $R_{11}$ is ($C_3$-$C_7$) cycloalkyl (e.g., cyclopropyl, cyclobutyl, cyclopentyl, cyclohexyl, or cycloheptyl) optionally substituted with one or more $R_{12}$. In further embodiments, at least one $R_{11}$ is cyclopropyl.

(16i) In some embodiments of Formula (I'), at least one $R_{11}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more $R_{12}$.

(16j) In some embodiments of Formula (I'), at least one $R_{11}$ is ($C_6$-$C_{10}$) aryl optionally substituted with one or more $R_{12}$. In further embodiments, at least one $R_{11}$ is phenyl optionally substituted with one or more $R_{12}$.

(16k) In some embodiments of Formula (I'), at least one $R_{11}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) comprising 1-3 heteroatoms selected from N, O, and S, optionally substituted with one or more $R_{12}$. In other embodiments, at least one $R_{11}$ is heteroaryl comprising a 6-membered ring (e.g., pyridinyl, pyridazinyl, pyrimidinyl, triazinyl, etc.) optionally substituted with one or more $R_{12}$. In other embodiments, at least one $R_{11}$ is pyridinyl optionally substituted with one or more $R_{12}$. In further embodiments, at least one $R_{11}$ is pyridinyl.

(17a) In some embodiments of Formula (I'), at least one $R_{12}$ is ($C_1$-$C_4$) alkyl (e.g., methyl, ethyl, propyl, i-propyl, or butyl).

(17b) In some embodiments of Formula (I'), at least one $R_{12}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$).

(17c) In some embodiments of Formula (I'), at least one $R_{12}$ is ($C_1$-$C_4$) alkoxy (e.g., methoxy, ethoxy, propoxy, or butoxy).

(17d) In some embodiments of Formula (I'), at least one $R_{12}$ is halogen (e.g., F, Cl, Br or I).

(17e) In some embodiments of Formula (I'), at least one $R_{12}$ is $NO_2$, OH, or CN.

(17f) In some embodiments of Formula (I'), at least one $R_{12}$ is ($C_3$-$C_7$) cycloalkyl (e.g., cyclopropyl, cyclobutyl, cyclopentyl, cyclohexyl, or cycloheptyl).

(17g) In some embodiments of Formula (I'), at least one $R_{12}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) comprising 1-3 heteroatoms selected from N, O, and S. In other embodiments, at least one $R_{12}$ is piperidinyl, piperazinyl, or morpholinyl. In further embodiments, at least one $R_{12}$ is morpholinyl.

(17h) In some embodiments of Formula (I'), at least one $R_{12}$ is ($C_6$-$C_{10}$) aryl optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), ($C_3$-$C_7$) cycloalkyl (e.g., cyclopropyl, cyclobutyl, cyclopentyl, cyclohexyl, or cycloheptyl), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.).

(17i) In some embodiments of Formula (I'), $R_{12}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), ($C_3$-$C_7$) cycloalkyl (e.g., cyclopropyl, cyclobutyl, cyclopentyl, cyclohexyl, or cycloheptyl), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.). In other embodiments, at least one $R_{12}$ is heteroaryl comprising a 5-membered ring fused with a 6-membered ring and 1-4 heteroatoms selected from N, O, and S, optionally substituted with one or more substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and ($C_3$-$C_7$) cycloalkyl (e.g., cyclopropyl, cyclobutyl, cyclopentyl, cyclohexyl, or cycloheptyl).

(18a) In some embodiments of Formula (I'), at least one $R_{13}$ is H.

(18b) In some embodiments of Formula (I'), at least one $R_{13}$ is ($C_1$-$C_4$) alkyl (e.g., methyl, ethyl, propyl, i-propyl, or butyl) optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.). In other embodiments, at least one $R_{13}$ is methyl, ethyl, or propyl. In other embodiments, at least one $R_{13}$ is ethyl, propyl, or butyl, wherein the ethyl, propyl, and butyl are optionally substituted with one to two substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is ethyl, propyl, or butyl, wherein the ethyl, propyl, and butyl are optionally substituted with one to two substituents independently selected from $N((C_1$-$C_4)$ alkyl$)_2$ (e.g., dimethylamino, diethylamino, dipropylamino, or dibutylamino) and heterocycle comprising a 5- to 7-membered ring and 1-3 heteroatoms selected from N, O, and S. In other embodiments, at least one $R_{13}$ is ethyl, propyl, or butyl, wherein the ethyl, propyl, and butyl are optionally substituted with one to two substituents independently selected from dimethylamino and heterocycle comprising a 6-membered ring and 1-3 heteroatoms selected from N, O, and S. In other embodiments, at least one $R_{13}$ is ethyl, propyl, or butyl wherein the ethyl, propyl, and butyl are optionally substituted with one to two substituents independently selected from dimethylamino, morpholinyl, piperidinyl or piperazinyl. In further embodiments, at least one $R_{13}$ is ethyl, propyl, or butyl wherein the ethyl, propyl, and butyl are optionally substituted with dimethylamino or morpholinyl.

(18c) In some embodiments of Formula (I'), at least one $R_{13}$ is ($C_3$-$C_7$) cycloalkyl (e.g., cyclopropyl, cyclobutyl, cyclopentyl, cyclohexyl, or cycloheptyl).

(18d) In some embodiments of Formula (I'), at least one $R_{13}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is heterocycle comprising a 6-membered ring and 1-3 heteroatoms selected from N, O, and S, optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, NH($C_1$-$C_4$) alkyl (e.g., methylamino, ethylamino, propylamino, or butylamino), N(($C_1$-$C_4$) alkyl)$_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with ($C_1$-$C_4$) alkyl (e.g., methyl, ethyl, propyl, i-propyl, or butyl), halogen (e.g., F, Cl, Br or I), OH, $NH_2$, NH($C_1$-$C_4$) alkyl (e.g., methylamino, ethylamino, propylamino, or butylamino), N(($C_1$-$C_4$) alkyl)$_2$ (e.g., dimethylamino, diethylamino, dipropylamino, or dibutylamino), or heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with ($C_1$-$C_4$) alkyl (e.g., methyl, ethyl, propyl, i-propyl, or butyl), N(($C_1$-$C_4$) alkyl)$_2$ (e.g., dimethylamino, diethylamino, dipropylamino, or dibutylamino), or heterocycle comprising a 6-membered ring and 1-3 heteroatoms selected from N, O, and S. In further embodiments, at least one $R_{13}$ is morpholinyl, piperidinyl, or piperazinyl, wherein the morpholinyl, piperidinyl, and piperazinyl are optionally substituted with methyl, dimethylamino, or morpholinyl.

(19a) In some embodiments of Formula (I'), at least one $R_{14}$ is H.

(19b) In some embodiments of Formula (I'), at least one $R_{14}$ is ($C_1$-$C_3$) alkyl (e.g., methyl, ethyl, propyl, or i-propyl).

(20a) In some embodiments of Formula (I'), m is 0 or 1.

(20b) In some embodiments of Formula (I'), m is 0.

(20c) In some embodiments of Formula (I'), m is 1.

(21a) In some embodiments of Formula (I'), n is 0 or 1.

(21b) In some embodiments of Formula (I'), n is 0.

(21c) In some embodiments of Formula (I'), n is 1.

(22a) In some embodiments of Formula (I'), p is 0, 1, 2, 3, or 4. In other embodiments, p is 0, 1, 2, or 3. In other embodiments, p is 0, 1, or 2.

(22b) In some embodiments of Formula (I'), p is 0 or 1.

(22c) In some embodiments of Formula (I'), p is 1 or 2. In other embodiments, p is 2 or 3.

(22d) In some embodiments of Formula (I'), p is 0. In other embodiments, p is 1. In other embodiments, p is 2. In other embodiments, p is 3. In other embodiments, p is 4.

(23a) In some embodiments of Formula (I'), $R_5$ is H.

(23b) In some embodiments of Formula (I'), $R_{5'}$ is ($C_1$-$C_4$) alkyl (e.g., methyl, ethyl, propyl, i-propyl, butyl, i-butyl, or t-butyl).

(24a) In some embodiments of Formula (I'), $R_{23}$ is H.

(24b) In some embodiments of Formula (I'), $R_{23}$ is $NH_2$.

(25a) In some embodiments of Formula (I'), r is 0 or 1. In other embodiments, r is 1 or 2.

(25b) In some embodiments of Formula (I'), r is 0.

(25c) In some embodiments of Formula (I'), r is 1.

(25d) In some embodiments of Formula (I'), r is 2.

(26a) In some embodiments of Formula (I'), q is 0 or 1. In other embodiments, q is 1 or 2.

(26b) In some embodiments of Formula (I'), q is 0.

(26c) In some embodiments of Formula (I'), q is 1.

(26d) In some embodiments of Formula (I'), q is 2.

(27a) In some embodiments of Formula (I'), s is 1.

(27b) In some embodiments of Formula (I'), s is 2.

In some embodiments of Formula (I'), $R_5$ is

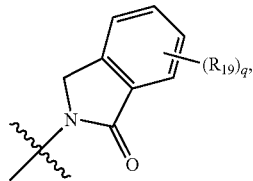

wherein q is 0, 1, 2, 3, or 4.

In some embodiments of Formula (I'), each of the substituents defined for any one of $X_1$, $R_1$, $R_2$, $R_3$, $R_4$, $R_5$, $R_{5'}$, $R_6$, $R_7$, $R_{11}$, $R_{12}$, $R_{13}$, $R_{14}$, $R_{15}$, $R_{16}$, $R_{18}$, $R_{19}$, $R_{20}$, $R_{21}$, $R_{22}$, $R_{23}$, m, n, p, q, r, and s can be combined with any of the substituents defined for the remainder of $X_1$, $R_1$, $R_2$, $R_3$, $R_4$, $R_5$, $R_{5'}$, $R_6$, $R_7$, $R_{11}$, $R_{12}$, $R_{13}$, $R_{14}$, $R_{15}$, $R_{16}$, $R_{18}$, $R_{19}$, $R_{20}$, $R_{21}$, $R_{22}$, $R_{23}$, m, n, p, q, r, and s.

(28) In some embodiments, $R_1$ is as defined in (15a).

(29) In some embodiments, $R_1$ is as defined in (15a) and m is as defined in (20b).

(30) In some embodiments, $R_1$ is as defined in (15a), m is as defined in (20b), and $R_2$ is as defined in (1a).

(31) In some embodiments, $R_1$ is as defined in (15a), m is as defined in (20b), $R_2$ is as defined in (1a), and n is as defined in (21b).

(32) In some embodiments, $R_1$ is as defined in (15a), m is as defined in (20b), $R_2$ is as defined in (1a), n is as defined in (21b), and $R_4$ is as defined in (3a).

(33) In some embodiments, $R_1$ is as defined in (15a), m is as defined in (20b), $R_2$ is as defined in (1a), n is as defined in (21b), $R_4$ is as defined in (3a), and $R_5$ is as defined in (7a).

(34) In some embodiments, $R_1$ is as defined in (15a), m is as defined in (20b), $R_2$ is as defined in (1a), n is as defined in (21b), and $R_4$ is as defined in (3b).

(35) In some embodiments, $R_1$ is as defined in (15a), m is as defined in (20b), $R_2$ is as defined in (1a), n is as defined in (21b), $R_4$ is as defined in (3b), and $R_5$ is as defined in (7a).

(36) In some embodiments, $R_1$ is as defined in (15a), m is as defined in (20b), $R_2$ is as defined in (1a), n is as defined in (21b), $R_4$ is as defined in (3b), $R_5$ is as defined in (7a), and $X_1$ is as defined in (4b).

(37) In some embodiments, $R_1$ is as defined in (15a), m is as defined in (20b), $R_2$ is as defined in (1a), n is as defined in (21b), $R_4$ is as defined in (3b), $R_5$ is as defined in (7a), $X_1$ is as defined in (4b), and $R_6$ is as defined in (5a).

(38) In some embodiments, $R_1$ is as defined in (15a), m is as defined in (20b), $R_2$ is as defined in (1a), and n is as defined in (21c).

(39) In some embodiments, $R_1$ is as defined in (15a), m is as defined in (20b), $R_2$ is as defined in (1a), n is as defined in (21c), and $R_4$ is as defined in (3a).

(40) In some embodiments, $R_1$ is as defined in (15a), m is as defined in (20b), $R_2$ is as defined in (1a), n is as defined in (21c), $R_4$ is as defined in (3a), and $R_5$ is as defined in (7a).

(41) In some embodiments, $R_1$ is as defined in (15a), m is as defined in (20b), $R_2$ is as defined in (1a), n is as defined in (21c), and $R_4$ is as defined in (3b).

(42) In some embodiments, $R_1$ is as defined in (15a), m is as defined in (20b), $R_2$ is as defined in (1a), n is as defined in (21c), $R_4$ is as defined in (3b), and $R_5$ is as defined in (7a).

(43) In some embodiments, $R_1$ is as defined in (15a), m is as defined in (20b), $R_2$ is as defined in (1a), n is as defined in (21c), $R_4$ is as defined in (3b), $R_5$ is as defined in (7a), and $X_1$ is as defined in (4b).

(44) In some embodiments, $R_1$ is as defined in (15a), m is as defined in (20b), $R_2$ is as defined in (1a), n is as defined in (21c), $R_4$ is as defined in (3b), $R_5$ is as defined in (7a), $X_1$ is as defined in (4b), and $R_6$ is as defined in (5a).

(45) In some embodiments, $R_1$ is as defined in (15a) and m is as defined in (20c).

(46) In some embodiments, $R_1$ is as defined in (15a), m is as defined in (20c), and $R_2$ is as defined in (1a).

(47) In some embodiments, $R_1$ is as defined in (15a), m is as defined in (20c), $R_2$ is as defined in (1a), and $R_3$ is as defined in (2a).

(48) In some embodiments, $R_1$ is as defined in (15a), m is as defined in (20c), $R_2$ is as defined in (1a), $R_3$ is as defined in (2a), and n is as defined in (21b).

(49) In some embodiments, $R_1$ is as defined in (15a), m is as defined in (20c), $R_2$ is as defined in (1a), $R_3$ is as defined in (2a), n is as defined in (21b), and $R_4$ is as defined in (3a).

(50) In some embodiments, $R_1$ is as defined in (15a), m is as defined in (20c), $R_2$ is as defined in (1a), $R_3$ is as defined in (2a), n is as defined in (21b), $R_4$ is as defined in (3a), and $R_5$ is as defined in (7a).

(51) In some embodiments, $R_1$ is as defined in (15a), m is as defined in (20c), $R_2$ is as defined in (1a), $R_3$ is as defined in (2a), n is as defined in (21b), and $R_4$ is as defined in (3b).

(52) In some embodiments, $R_1$ is as defined in (15a), m is as defined in (20c), $R_2$ is as defined in (1a), $R_3$ is as defined in (2a), n is as defined in (21b), $R_4$ is as defined in (3b), and $R_5$ is as defined in (7a).

(53) In some embodiments, $R_1$ is as defined in (15a), m is as defined in (20c), $R_2$ is as defined in (1a), $R_3$ is as defined in (2a), n is as defined in (21b), $R_4$ is as defined in (3b), $R_5$ is as defined in (7a), and $X_1$ is as defined in (4b).

(54) In some embodiments, $R_1$ is as defined in (15a), m is as defined in (20c), $R_2$ is as defined in (1a), $R_3$ is as defined in (2a), n is as defined in (21b), $R_4$ is as defined in (3b), $R_5$ is as defined in (7a), $X_1$ is as defined in (4b), and $R_6$ is as defined in (5a).

(55) In some embodiments, $R_1$ is as defined in (15a), m is as defined in (20c), $R_2$ is as defined in (1a), $R_3$ is as defined in (2a), and n is as defined in (21c).

(56) In some embodiments, $R_1$ is as defined in (15a), m is as defined in (20c), $R_2$ is as defined in (1a), $R_3$ is as defined in (2a), n is as defined in (21c), and $R_4$ is as defined in (3a).

(57) In some embodiments, $R_1$ is as defined in (15a), m is as defined in (20c), $R_2$ is as defined in (1a), $R_3$ is as defined in (2a), n is as defined in (21c), $R_4$ is as defined in (3a), and $R_5$ is as defined in (7a).

(58) In some embodiments, $R_1$ is as defined in (15a), m is as defined in (20c), $R_2$ is as defined in (1a), $R_3$ is as defined in (2a), n is as defined in (21c), and $R_4$ is as defined in (3b).

(59) In some embodiments, $R_1$ is as defined in (15a), m is as defined in (20c), $R_2$ is as defined in (1a), $R_3$ is as defined in (2a), n is as defined in (21c), $R_4$ is as defined in (3b), and $R_5$ is as defined in (7a).

(60) In some embodiments, $R_1$ is as defined in (15a), m is as defined in (20c), $R_2$ is as defined in (1a), $R_3$ is as defined in (2a), n is as defined in (21c), $R_4$ is as defined in (3b), $R_5$ is as defined in (7a), and $X_1$ is as defined in (4b).

(61) In some embodiments, $R_1$ is as defined in (15a), m is as defined in (20c), $R_2$ is as defined in (1a), $R_3$ is as defined in (2a), n is as defined in (21c), $R_4$ is as defined in (3b), $R_5$ is as defined in (7a), $X_1$ is as defined in (4b), and $R_6$ is as defined in (5a).

(62) In some embodiments, $R_1$ is as defined in (15b).

(63) In some embodiments, $R_1$ is as defined in (15b) and m is as defined in (20b).

(64) In some embodiments, $R_1$ is as defined in (15b), m is as defined in (20b), and $R_2$ is as defined in (1a).

(65) In some embodiments, $R_1$ is as defined in (15b), m is as defined in (20b), $R_2$ is as defined in (1a), and n is as defined in (21b).

(66) In some embodiments, $R_1$ is as defined in (15b), m is as defined in (20b), $R_2$ is as defined in (1a), n is as defined in (21b), and $R_4$ is as defined in (3a).

(67) In some embodiments, $R_1$ is as defined in (15b), m is as defined in (20b), $R_2$ is as defined in (1a), n is as defined in (21b), $R_4$ is as defined in (3a), and $R_5$ is as defined in (7a).

(68) In some embodiments, $R_1$ is as defined in (15b), m is as defined in (20b), $R_2$ is as defined in (1a), n is as defined in (21b), and $R_4$ is as defined in (3b).

(69) In some embodiments, $R_1$ is as defined in (15b), m is as defined in (20b), $R_2$ is as defined in (1a), n is as defined in (21b), $R_4$ is as defined in (3b), and $R_5$ is as defined in (7a).

(70) In some embodiments, $R_1$ is as defined in (15b), m is as defined in (20b), $R_2$ is as defined in (1a), n is as defined in (21b), $R_4$ is as defined in (3b), $R_5$ is as defined in (7a), and $X_1$ is as defined in (4b).

(71) In some embodiments, $R_1$ is as defined in (15b), m is as defined in (20b), $R_2$ is as defined in (1a), n is as defined in (21b), $R_4$ is as defined in (3b), $R_5$ is as defined in (7a), $X_1$ is as defined in (4b), and $R_6$ is as defined in (5a).

(72) In some embodiments, $R_1$ is as defined in (15b), m is as defined in (20b), $R_2$ is as defined in (1a), and n is as defined in (21c).

(73) In some embodiments, $R_1$ is as defined in (15b), m is as defined in (20b), $R_2$ is as defined in (1a), n is as defined in (21c), and $R_4$ is as defined in (3a).

(74) In some embodiments, $R_1$ is as defined in (15b), m is as defined in (20b), $R_2$ is as defined in (1a), n is as defined in (21c), $R_4$ is as defined in (3a), and $R_5$ is as defined in (7a).

(75) In some embodiments, $R_1$ is as defined in (15b), m is as defined in (20b), $R_2$ is as defined in (1a), n is as defined in (21c), and $R_4$ is as defined in (3b).

(76) In some embodiments, $R_1$ is as defined in (15b), m is as defined in (20b), $R_2$ is as defined in (1a), n is as defined in (21c), $R_4$ is as defined in (3b), and $R_5$ is as defined in (7a).

(77) In some embodiments, $R_1$ is as defined in (15b), m is as defined in (20b), $R_2$ is as defined in (1a), n is as defined in (21c), $R_4$ is as defined in (3b), $R_5$ is as defined in (7a), and $X_1$ is as defined in (4b).

(78) In some embodiments, $R_1$ is as defined in (15b), m is as defined in (20b), $R_2$ is as defined in (1a), n is as defined in (21c), $R_4$ is as defined in (3b), $R_5$ is as defined in (7a), $X_1$ is as defined in (4b), and $R_6$ is as defined in (5a).

(79) In some embodiments, $R_1$ is as defined in (15b), m is as defined in (20c).

(80) In some embodiments, $R_1$ is as defined in (15b), m is as defined in (20c), and $R_2$ is as defined in (1a).

(81) In some embodiments, $R_1$ is as defined in (15b), m is as defined in (20c), $R_2$ is as defined in (1a), and $R_3$ is as defined in (2a).

(82) In some embodiments, $R_1$ is as defined in (15b), m is as defined in (20c), $R_2$ is as defined in (1a), $R_3$ is as defined in (2a), and n is as defined in (21b).

(83) In some embodiments, $R_1$ is as defined in (15b), m is as defined in (20c), $R_2$ is as defined in (1a), $R_3$ is as defined in (2a), n is as defined in (21b), and $R_4$ is as defined in (3a).

(84) In some embodiments, $R_1$ is as defined in (15b), m is as defined in (20c), $R_2$ is as defined in (1a), $R_3$ is as defined in (2a), n is as defined in (21b), $R_4$ is as defined in (3a), and $R_5$ is as defined in (7a).

(85) In some embodiments, $R_1$ is as defined in (15b), m is as defined in (20c), $R_2$ is as defined in (1a), $R_3$ is as defined in (2a), n is as defined in (21b), and $R_4$ is as defined in (3b).

(86) In some embodiments, $R_1$ is as defined in (15b), m is as defined in (20c), $R_2$ is as defined in (1a), $R_3$ is as defined in (2a), n is as defined in (21b), $R_4$ is as defined in (3b), and $R_5$ is as defined in (7a).

(87) In some embodiments, $R_1$ is as defined in (15b), m is as defined in (20c), $R_2$ is as defined in (1a), $R_3$ is as defined in (2a), n is as defined in (21b), $R_4$ is as defined in (3b), $R_5$ is as defined in (7a), and $X_1$ is as defined in (4b).

(88) In some embodiments, $R_1$ is as defined in (15b), m is as defined in (20c), $R_2$ is as defined in (1a), $R_3$ is as defined in (2a), n is as defined in (21b), $R_4$ is as defined in (3b), $R_5$ is as defined in (7a), $X_1$ is as defined in (4b), and $R_6$ is as defined in (5a).

(89) In some embodiments, $R_1$ is as defined in (15b), m is as defined in (20c), $R_2$ is as defined in (1a), $R_3$ is as defined in (2a), and n is as defined in (21c).

(90) In some embodiments, $R_1$ is as defined in (15b), m is as defined in (20c), $R_2$ is as defined in (1a), $R_3$ is as defined in (2a), n is as defined in (21c), and $R_4$ is as defined in (3a).

(91) In some embodiments, $R_1$ is as defined in (15b), m is as defined in (20c), $R_2$ is as defined in (1a), $R_3$ is as defined in (2a), n is as defined in (21c), $R_4$ is as defined in (3a), and $R_5$ is as defined in (7a).

(92) In some embodiments, $R_1$ is as defined in (15b), m is as defined in (20c), $R_2$ is as defined in (1a), $R_3$ is as defined in (2a), n is as defined in (21c), and $R_4$ is as defined in (3b).

(93) In some embodiments, $R_1$ is as defined in (15b), m is as defined in (20c), $R_2$ is as defined in (1a), $R_3$ is as defined in (2a), n is as defined in (21c), $R_4$ is as defined in (3b), and $R_5$ is as defined in (7a).

(94) In some embodiments, $R_1$ is as defined in (15b), m is as defined in (20c), $R_2$ is as defined in (1a), $R_3$ is as defined in (2a), n is as defined in (21c), $R_4$ is as defined in (3b), $R_5$ is as defined in (7a), and $X_1$ is as defined in (4b).

(95) In some embodiments, $R_1$ is as defined in (15b), m is as defined in (20c), $R_2$ is as defined in (1a), $R_3$ is as defined in (2a), n is as defined in (21c), $R_4$ is as defined in (3b), $R_5$ is as defined in (7a), $X_1$ is as defined in (4b), and $R_6$ is as defined in (5a).

(96) In some embodiments, $R_1$ is as defined in (15b), m is as defined in (20b), $R_2$ is as defined in (1a), n is as defined in (21c), $R_4$ is as defined in (3b), $R_5$ is as defined in (7a), and $X_1$ is as defined in (4a).

(97) In some embodiments, $R_1$ is as defined in (15b), m is as defined in (20b), $R_2$ is as defined in (1a), n is as defined in (21b), $R_4$ is as defined in (3b), $R_5$ is as defined in (7a), $X_1$ is as defined in (4b), $R_6$ is as defined in (5a), and $R_{5'}$ is as defined in (23a).

(98) In some embodiments, $R_1$ is as defined in (15b), m is as defined in (20b), $R_2$ is as defined in (1a), n is as defined in (21b), $R_4$ is as defined in (3b), $R_5$ is as defined in (7a), $X_1$ is as defined in (4b), $R_6$ is as defined in (5a), and $R_{5'}$ is as defined in (23b).

In some embodiments, the compounds of Formula (I') have the structure of Formula (I):

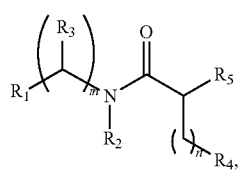

(I)

or pharmaceutically acceptable salts, hydrates, solvates, prodrugs, stereoisomers, or tautomers thereof, wherein:

$R_1$ is $(C_6-C_{10})$ aryl, or heteroaryl comprising one or two 5- to 7-membered rings and 1-4 heteroatoms selected from N, O, and S, wherein the aryl and heteroaryl are each optionally substituted with one or more $R_{11}$;

each $R_{11}$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, OH, CN, $C(O)R_{13}$, $C(O)OR_{13}$, $C(O)NR_{13}R_{14}$, $NR_{13}R_{14}$, $(C_3-C_7)$ cycloalkyl, heterocyclyl comprising a 5- to 7-membered ring and 1-3 heteroatoms selected from N, O, and S, $(C_6-C_{10})$ aryl, and heteroaryl comprising one or two 5- to 7-membered rings and 1-4 heteroatoms selected from N, O, and S, wherein the alkyl, cycloalkyl, heterocyclyl, aryl, and heteroaryl are each optionally substituted with one or more $R_{12}$;

each $R_{12}$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, OH, CN, $(C_3-C_7)$ cycloalkyl, heterocyclyl comprising a 5- to 7-membered ring and 1-3 heteroatoms selected from N, O, and S, $(C_6-C_{10})$ aryl, and heteroaryl comprising one or two 5- to 7-membered rings and 1-4 heteroatoms selected from N, O, and S, wherein the aryl and heteroaryl are each optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, halogen, $NH_2$, $NH(C_1-C_4)$ alkyl, $N((C_1-C_4)$ alkyl$)_2$, $(C_3-C_7)$ cycloalkyl, and heterocyclyl comprising a 5- to 7-membered ring and 1-3 heteroatoms selected from N, O, and S;

each $R_{13}$ is independently selected from H, $(C_1-C_4)$ alkyl, $(C_3-C_7)$ cycloalkyl, and heterocyclyl comprising a 5- to 7-membered ring and 1-3 heteroatoms selected from N, O, and S, wherein the alkyl, cycloalkyl, and heterocyclyl are each optionally substituted with one or more substituents independently selected from $(C_1-C_4)$ alkyl, halogen, OH, $NH_2$, $NH(C_1-C_4)$ alkyl, $N((C_1-C_4)$ alkyl$)_2$, and heterocyclyl comprising a 5- to 7-membered ring and 1-3 heteroatoms selected from N, O, and S;

each $R_{14}$ is independently H or $(C_1-C_3)$ alkyl;

$R_2$ is H or $(C_1-C_3)$ alkyl;

$R_3$ is H or $(C_1-C_3)$ alkyl;

$R_4$ is $(C_1-C_3)$ alkyl or

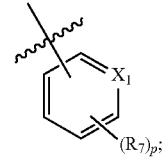

$X_1$ is N or $CR_6$;

$R_6$ is H, $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, OH, or CN;

each $R_7$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, OH, and CN;

$R_5$ is $NR_{15}R_{16}$;

$R_{15}$ is H or $(C_1-C_3)$ alkyl;

$R_{16}$ is $(C_6-C_{10})$ aryl, or heteroaryl comprising a 5- to 7-membered ring and 1-3 heteroatoms selected from N, O, and S, wherein the aryl and heteroaryl are each optionally substituted with one or more $R_{18}$; or $R_{15}$ and $R_{16}$ together with the nitrogen atom to which they are attached form a 5- or 6-membered heterocyclyl optionally comprising 1 or 2 additional heteroatoms selected from N, O, and S and optionally substituted with one or more oxo groups, wherein the heterocyclyl is fused with a phenyl ring which is optionally substituted with one or more $R_{19}$;

each $R_{18}$ is independently selected from $(C_1-C_4)$ alkyl, $(C_1-C_4)$ alkoxy, $(C_1-C_4)$ haloalkyl, $(C_1-C_4)$ haloalkoxy, halogen, $C(O)O(C_1-C_4)$ alkyl, $NO_2$, $C(O)NH(C_1-C_4)$ alkyl, $NH_2$, $NH(C_1-C_4)$ alkyl, and $N((C_1-C_4)$ alkyl$)_2$, wherein the alkyl is optionally substituted with one or more substituents independently selected from halogen, OH, $NH_2$, $NH(C_1-C_4)$ alkyl, and $N((C_1-C_4)$ alkyl$)_2$;

each $R_{19}$ is independently selected from halogen, $(C_3-C_7)$ cycloalkyl, $(C_4-C_7)$ cycloalkenyl, $(C_6-C_{10})$ aryl, $NH-(C_6-C_{10})$ aryl, and heteroaryl comprising one or two 5- to 7-membered ring and 1-4 heteroatoms selected from N, O, and S, wherein the aryl and heteroaryl are each optionally substituted with one or more $R_{20}$;

each $R_{20}$ is independently selected from $(C_1-C_4)$ alkyl, $(C_1-C_4)$ alkoxy, $(C_1-C_4)$ haloalkyl, $(C_1-C_4)$ haloalkoxy, halogen, $C(O)OH$, $C(O)O(C_1-C_4)$ alkyl, $C(O)NR_{21}R_{22}$, $NH_2$, OH, CN, $O(CH_2)_{0-3}-(C_6-C_{10})$ aryl, and $(CH_2)_{0-3}$-heterocyclyl which comprises a 5- to 7-membered ring and 1-3 heteroatoms selected from N, O, and S, wherein the heterocyclyl is optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, halogen, and $C(O)O(C_1-C_4)$ alkyl);

$R_{21}$ is H or $(C_1-C_3)$ alkyl;

$R_{22}$ is H or $(C_1-C_4)$ alkyl optionally substituted with one or more substituents independently selected from $NH_2$, $NH(C_1-C_4)$ alkyl, $N((C_1-C_4)$ alkyl$)_2$, and heterocyclyl comprising a 5- to 7-membered ring and 1-3 heteroatoms selected from N, O, and S; or $R_{21}$ and $R_{22}$ together with the nitrogen atom to which they are attached form a 5- or 6-membered heterocyclyl optionally containing 1-2 additional heteroatoms selected from N, O, and S;

m and n are each independently 0 or 1; and p is 0, 1, 2, 3 or 4;

provided that when m is 0, n is 0, p is 0, $R_{15}$ and $R_{16}$ together with the nitrogen atom to which they are attached form an unsubstituted isoindolinone, and $R_6$ is H, then $R_1$ is not

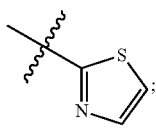 [SMILES: *c1nccs1]

and provided that $R_4$ is not 4-fluoro-2-hydroxyphenyl.

(1a) In some embodiments of Formula (I), $R_2$ is H.

(1b) In some embodiments of Formula (I), $R_2$ is $(C_1-C_3)$ alkyl (e.g., methyl, ethyl, propyl, or i-propyl). In other embodiments, $R_2$ is methyl. In other embodiments, $R_2$ is ethyl.

(2a) In some embodiments of Formula (I), $R_3$ is H.

(2b) In some embodiments of Formula (I), $R_3$ is $(C_1-C_3)$ alkyl (e.g., methyl, ethyl, propyl, or i-propyl). In other embodiments, $R_3$ is methyl. In other embodiments, $R_3$ is ethyl.

(3a) In some embodiments of Formula (I), $R_4$ is $(C_1-C_3)$ alkyl (e.g., methyl, ethyl, propyl, or i-propyl). In other embodiments, $R_4$ is methyl. In other embodiments, $R_4$ is ethyl.

(3b) In some embodiments of Formula (I), $R_4$ is

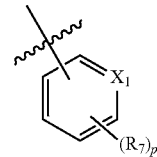

(e.g., phenyl, 2-pyridinyl, 3-pyridinyl, or 4-pyridinyl).

(4a) In some embodiments of Formula (I), $X_1$ is N.

(4b) In some embodiments of Formula (I), $X_1$ is $CR_6$.

(5a) In some embodiments of Formula (I), $R_6$ is H.

(5b) In some embodiments of Formula (I), $R_6$ is $(C_1-C_4)$ alkyl (e.g., methyl, ethyl, propyl, i-propyl, or butyl).

(5c) In some embodiments of Formula (I), $R_6$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$).

(5d) In some embodiments of Formula (I), $R_6$ is $(C_1-C_4)$ alkoxy (e.g., methoxy, ethoxy, propoxy, or butoxy).

(5e) In some embodiments of Formula (I), $R_6$ is halogen (e.g., F, Cl, Br or I). In other embodiments, $R_6$ is F or Cl. In further embodiments, $R_6$ is F.

(5f) In some embodiments of Formula (I), $R_6$ is $NO_2$, $NH_2$, OH, or CN. In further embodiments, $R_6$ is $NO_2$ or $NH_2$.

(6a) In some embodiments of Formula (I), at least one $R_7$ is $(C_1-C_4)$ alkyl (e.g., methyl, ethyl, propyl, i-propyl, or butyl).

(6b) In some embodiments of Formula (I), at least one $R_7$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$).

(6c) In some embodiments of Formula (I), at least one $R_7$ is $(C_1-C_4)$ alkoxy (e.g., methoxy, ethoxy, propoxy, or butoxy).

(6d) In some embodiments of Formula (I), at least one $R_7$ is halogen (e.g., F, Cl, Br or I). In other embodiments, at least one $R_7$ is F or Cl. In further embodiments, at least one $R_7$ is F.

(6e) In some embodiments of Formula (I), at least one $R_7$ is $NO_2$, $NH_2$, OH, or CN. In further embodiments, at least one $R_7$ is $NO_2$ or $NH_2$.

(6f) In some embodiments of Formula (I), at least one $R_7$ is halogen (e.g., F, Cl, Br or I) and at least one $R_7$ is OH.

(6g) In some embodiments of Formula (I), one $R_7$ is halogen (e.g., F, Cl, Br or I) and one $R_7$ is OH.

(7a) In some embodiments of Formula (I), $R_5$ is $NR_{15}R_{16}$.

(7b) In some embodiments of Formula (I), $R_5$ is $N(H)$-phenyl.

(8a) In some embodiments of Formula (I), $R_{15}$ is H.

(8b) In some embodiments of Formula (I), $R_{15}$ is $(C_1-C_3)$ alkyl (e.g., methyl, ethyl, propyl, or i-propyl). In other embodiments, $R_{15}$ is methyl. In other embodiments, $R_{15}$ is ethyl.

(9a) In some embodiments of Formula (I), $R_{16}$ is $(C_6-C_{10})$ aryl optionally substituted with one or more $R_{18}$. In other embodiments, $R_{16}$ is phenyl optionally substituted with one or more $R_{18}$. In further embodiments, $R_{16}$ is phenyl optionally substituted with one to three $R_{18}$.

(9b) In some embodiments of Formula (I), $R_{16}$ is heteroaryl comprising a 5- to 7-membered ring and 1-3 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, etc.) optionally substituted with one or more $R_{18}$. In further embodiments, $R_{16}$ is 2-pyridinyl, 3-pyridinyl, or 4-pyridinyl optionally substituted with one or more $R_{18}$.

(9c) In some embodiments of Formula (I), $R_{15}$ and $R_{16}$ together with the nitrogen atom to which they are attached form a 5- or 6-membered heterocyclyl optionally comprising 1 or 2 additional heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, etc.) and optionally substituted with one or more oxo groups. In other embodiments, $R_{15}$ and $R_{16}$ together with the nitrogen atom to which they are attached form

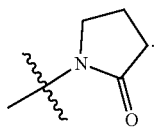

(10a) In some embodiments of Formula (I), at least one $R_{18}$ is ($C_1$-$C_4$) alkyl (e.g., methyl, ethyl, propyl, i-propyl, or butyl) optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), and $N((C_1$-$C_4)$ alkyl$)_2$ (e.g., dimethylamino, diethylamino, dipropylamino, or dibutylamino). In other embodiments, at least one $R_{18}$ is methyl or ethyl optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), and $N((C_1$-$C_4)$ alkyl$)_2$ (e.g., dimethylamino, diethylamino, dipropylamino, or dibutylamino). In other embodiments, at least one $R_{18}$ is methyl or ethyl.

(10b) In some embodiments of Formula (I), at least one $R_{18}$ is ($C_1$-$C_4$) alkoxy (e.g., methoxy, ethoxy, propoxy, or butoxy).

(10c) In some embodiments of Formula (I), at least one $R_{18}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$).

(10d) In some embodiments of Formula (I), at least one $R_{18}$ is halogen (e.g., F, Cl, Br or I). In other embodiments, at least one $R_{18}$ is F or Br.

(10e) In some embodiments of Formula (I), at least one $R_{18}$ is $C(O)O(C_1$-$C_4)$ alkyl or $C(O)NH(C_1$-$C_4)$ alkyl, wherein the alkyl is optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), and $N((C_1$-$C_4)$ alkyl$)_2$ (e.g., dimethylamino, diethylamino, dipropylamino, or dibutylamino). In other embodiments, at least one $R_{18}$ is $C(O)O(C_1$-$C_4)$ alkyl. In other embodiments, at least one $R_{18}$ is $C(O)NH(C_1$-$C_4)$ alkyl optionally substituted with one or more OH. In other embodiments, at least one $R_{18}$ is $C(O)OCH_3$. In other embodiments, at least one $R_{18}$ is $C(O)N(H)CH_2CH(OH)CH_2OH$.

(10f) In some embodiments of Formula (I), at least one $R_{18}$ is $NO_2$, $NH_2$, $NH(C_1$-$C_4)$ alkyl (e.g., methylamino, ethylamino, propylamino, or butylamino), or $N((C_1$-$C_4)$ alkyl$)_2$ (e.g., dimethylamino, diethylamino, dipropylamino, or dibutylamino), wherein the alkyl is optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), and $N((C_1$-$C_4)$ alkyl$)_2$ (e.g., dimethylamino, diethylamino, dipropylamino, or dibutylamino). In other embodiments, at least one $R_{18}$ is $NO_2$.

(11a) In some embodiments of Formula (I), at least one $R_{19}$ is halogen (e.g., F, Cl, Br or I). In other embodiments, at least one $R_{19}$ is F, Cl, or Br. In other embodiments, at least one $R_{19}$ is F. In other embodiments, at least one $R_{19}$ is Cl. In other embodiments, at least one $R_{19}$ is Br.

(11b) In some embodiments of Formula (I), at least one $R_{19}$ is ($C_3$-$C_7$) cycloalkyl (e.g., cyclopropyl, cyclobutyl, cyclopentyl, cyclohexyl, or cycloheptyl).

(11c) In some embodiments of Formula (I), at least one $R_{19}$ is ($C_4$-$C_7$) cycloalkenyl (e.g., cyclobutenyl, cyclopentenyl, cyclohexenyl, or cycloheptenyl). In other embodiments, at least one $R_{19}$ is cyclohexenyl.

(11d) In some embodiments of Formula (I), at least one $R_{19}$ is ($C_6$-$C_{10}$) aryl optionally substituted with one or more $R_{20}$. In other embodiments, at least one $R_{19}$ is phenyl optionally substituted with one or more $R_{20}$. In other embodiments, at least one $R_{19}$ is phenyl optionally substituted with one to three $R_{20}$. In other embodiments, at least one $R_{19}$ is phenyl.

(11e) In some embodiments of Formula (I), at least one $R_{19}$ is NH—($C_6$-$C_{10}$) aryl optionally substituted with one or more $R_{20}$. In other embodiments, at least one $R_{19}$ is NH-phenyl optionally substituted with one or more $R_{20}$. In other embodiments, at least one $R_{19}$ is NH-phenyl optionally substituted with one to three $R_{20}$. In other embodiments, at least one $R_{19}$ is NH-phenyl.

(11f) In some embodiments of Formula (I), at least one $R_{19}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, indolyl, quinolinyl, isoquinolinyl, benzothiazolyl, benzoimidazolyl, benzooxazolyl, thiazolopyridinyl, pyrazolopyrimidinyl, etc.) optionally substituted with one or more $R_{20}$. In other embodiments, at least one $R_{19}$ is pyrazolyl, thiophenyl, pyridinyl, pyrimidinyl, indolyl, or quinolinyl optionally substituted with one or more $R_{20}$.

(12a) In some embodiments of Formula (I), at least one $R_{20}$ is ($C_1$-$C_4$) alkyl (e.g., methyl, ethyl, propyl, i-propyl, or butyl). In further embodiments, at least one $R_{20}$ is methyl or ethyl.

(12b) In some embodiments of Formula (I), at least one $R_{20}$ is ($C_1$-$C_4$) alkoxy (e.g., methoxy, ethoxy, propoxy, or butoxy). In further embodiments, at least one $R_{20}$ is methoxy.

(12c) In some embodiments of Formula (I), at least one $R_{20}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$). In further embodiments, at least one $R_{20}$ is $CF_3$ or $OCF_3$.

(12d) In some embodiments of Formula (I), at least one $R_{20}$ is halogen (e.g., F, Cl, Br or I). In further embodiments, at least one $R_{20}$ is F.

(12e) In some embodiments of Formula (I), at least one $R_{20}$ is $C(O)OH$ or $C(O)O(C_1$-$C_4)$ alkyl (e.g., methyl, ethyl, propyl, i-propyl, or butyl). In further embodiments, at least one $R_{20}$ is $C(O)OH$ or $C(O)OCH_3$.

(12f) In some embodiments of Formula (I), at least one $R_{20}$ is $NH_2$, OH, or CN.

(12g) In some embodiments of Formula (I), at least one $R_{20}$ is $C(O)NR_{21}R_{22}$.

(12h) In some embodiments of Formula (I), at least one $R_{20}$ is $O(CH_2)_{0-3}$—$(C_6-C_{10})$ aryl. In further embodiments, at least one $R_{20}$ is $OCH_2$-phenyl.

(12i) In some embodiments of Formula (I), at least one $R_{20}$ is $(CH_2)_{0-3}$-heterocyclyl which comprises a 5- to 7-membered ring and 1-3 heteroatoms selected from N, O, and S, wherein the heterocyclyl is selected from pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc., and is optionally substituted with one or more substituents independently selected from $(C_1-C_4)$ alkyl (e.g., methyl, ethyl, propyl, i-propyl, or butyl), $(C_1-C_4)$ alkoxy (e.g., methoxy, ethoxy, propoxy, or butoxy), $(C_1-C_4)$ haloalkyl (e.g., $CH_2F$, $CHF_2$, or $CF_3$), $(C_1-C_4)$ haloalkoxy (e.g., $OCH_2F$, $OCHF_2$, or $OCF_3$), halogen (e.g., F, Cl, Br or I), and $C(O)O(C_1-C_4)$ alkyl (e.g., methyl, ethyl, propyl, i-propyl, butyl, i-butyl, or t-butyl). In other embodiments, at least one $R_{20}$ is $(CH_2)_{0-1}$-heterocycle optionally substituted with one or more substituents independently selected from $(C_1-C_4)$ alkyl (e.g., methyl, ethyl, propyl, i-propyl, or butyl), $(C_1-C_4)$ alkoxy (e.g., methoxy, ethoxy, propoxy, or butoxy), $(C_1-C_4)$ haloalkyl (e.g., $CH_2F$, $CHF_2$, or $CF_3$), $(C_1-C_4)$ haloalkoxy (e.g., $OCH_2F$, $OCHF_2$, or $OCF_3$), halogen (e.g., F, Cl, Br or I), and $C(O)O(C_1-C_4)$ alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl wherein the pyrrolidinyl, morpholinyl, and piperazinyl are each optionally substituted with one or more substituents independently selected from $(C_1-C_4)$ alkyl (e.g., methyl, ethyl, propyl, i-propyl, or butyl), $(C_1-C_4)$ alkoxy (e.g., methoxy, ethoxy, propoxy, or butoxy), $(C_1-C_4)$ haloalkyl (e.g., $CH_2F$, $CHF_2$, or $CF_3$), $(C_1-C_4)$ haloalkoxy (e.g., $OCH_2F$, $OCHF_2$, or $OCF_3$), halogen (e.g., F, Cl, Br or I), and $C(O)O(C_1-C_4)$ alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl, wherein the pyrrolidinyl, morpholinyl, and piperazinyl are each optionally substituted with one or more $(C_1-C_4)$ alkyl (e.g., methyl, ethyl, propyl, i-propyl, or butyl), or $C(O)O(C_1-C_4)$alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, morpholinyl, or piperazinyl, wherein the pyrrolidinyl, morpholinyl, and piperazinyl are optionally methyl, ethyl, or $C(O)O$-t-butyl.

(13a) In some embodiments of Formula (I), $R_{21}$ is H.

(13b) In some embodiments of Formula (I), $R_{21}$ is $(C_1-C_3)$ alkyl (e.g., methyl, ethyl, propyl, or i-propyl). In other embodiments, $R_{21}$ is methyl. In other embodiments, $R_{21}$ is ethyl.

(14a) In some embodiments of Formula (I), $R_{22}$ is H.

(14b) In some embodiments of Formula (I), $R_{22}$ is $(C_1-C_4)$ alkyl (e.g., methyl, ethyl, propyl, i-propyl, or butyl) optionally substituted with one or more substituents independently selected from $NH_2$, $NH(C_1-C_4)$ alkyl (e.g., methylamino, ethylamino, propylamino, or butylamino), $N((C_1-C_4)$ alkyl$)_2$ (e.g., dimethylamino, diethylamino, dipropylamino, or dibutylamino), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, etc.). In other embodiments, $R_{22}$ is $(C_1-C_4)$ alkyl (e.g., methyl, ethyl, propyl, i-propyl, or butyl) optionally substituted with one to two substituents independently selected from $NH_2$, $NH(C_1-C_4)$ alkyl, $N((C_1-C_4)$ alkyl$)_2$, and 6-membered heterocycle comprising 1-3 heteroatoms selected from N, O, and S. In further embodiments, $R_{22}$ is ethyl, propyl, or butyl optionally substituted with dimethylamino, diethylamino, or morpholinyl.

(14c) In some embodiments of Formula (I), $R_{21}$ and $R_{22}$ together with the nitrogen atom to which they are attached form a 5-membered heterocyclyl optionally containing 1-2 additional heteroatoms selected from N, O, and S. In other embodiments, $R_{21}$ and $R_{22}$ together with the nitrogen atom to which they are attached form a 6-membered heterocycle optionally containing 1-2 additional heteroatoms selected from N, O, and S. In further embodiments, $R_{21}$ and $R_{22}$ together with the nitrogen atom to which they are attached form a morpholinyl.

(15a) In some embodiments of Formula (I), $R_1$ is $(C_6-C_{10})$ aryl optionally substituted with one or more $R_{11}$. In other embodiments, $R_1$ is phenyl optionally substituted with one or more $R_{11}$.

(15b) In some embodiments of Formula (I), $R_1$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, thiazolopyridinyl, pyrazolopyrimidinyl, etc.) optionally substituted with one or more $R_{11}$. In other embodiments, $R_1$ is heteroaryl comprising a 5-membered ring and 1-3 heteroatoms selected from N, O, and S, optionally substituted with one or more $R_{11}$. In other embodiments, $R_1$ is heteroaryl comprising a 6-membered ring and 1-3 heteroatoms selected from N, O, and S, optionally substituted with one or more $R_{11}$. In other embodiments, $R_1$ is heteroaryl comprising a 5-membered ring fused with a 6-membered ring and 1-4 heteroatoms selected from N, O, and S, optionally substituted with one or more $R_{11}$. In other embodiments, $R_1$ is selected from:

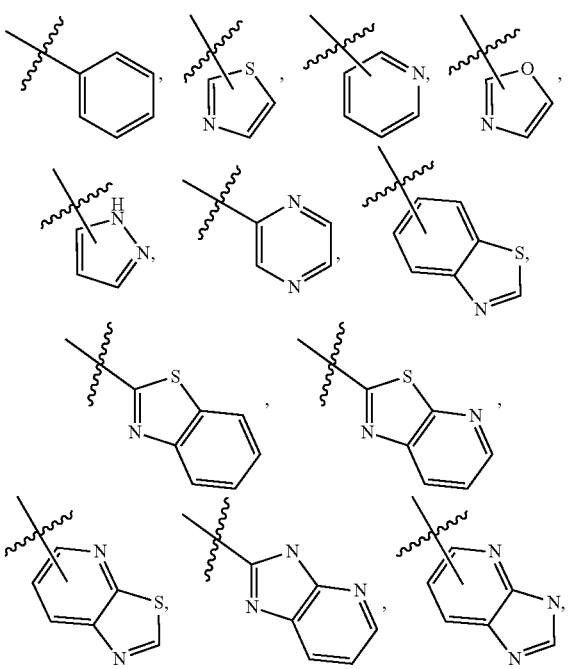

-continued

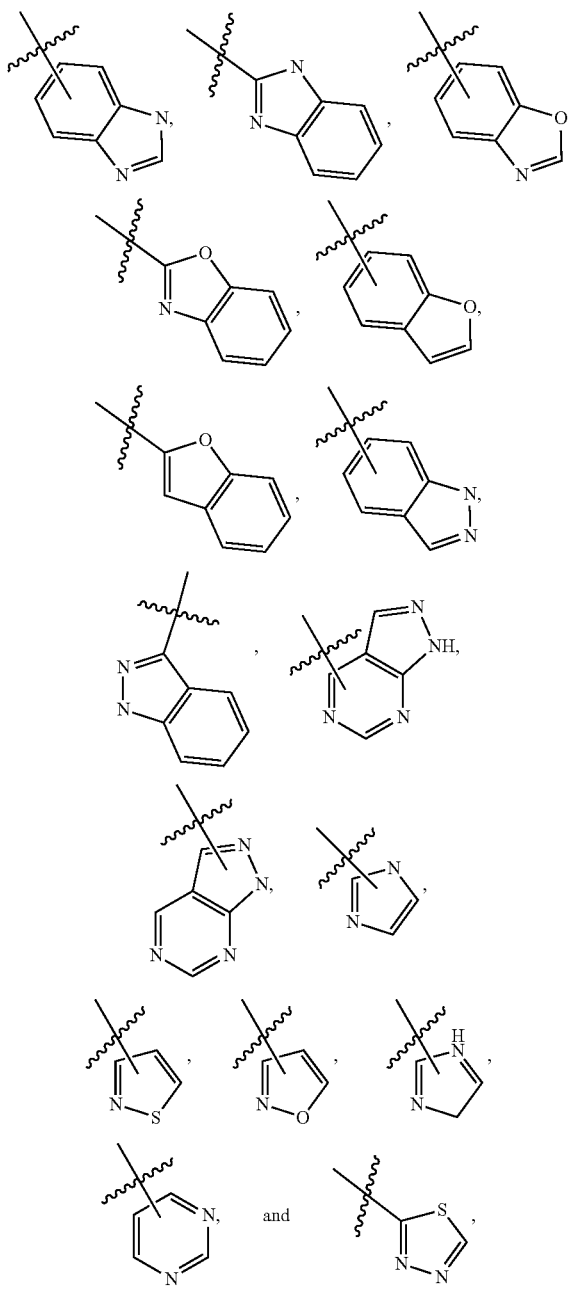

wherein each moiety is optionally substituted with one or more $R_{11}$. In other embodiments, $R_1$ is selected from:

-continued

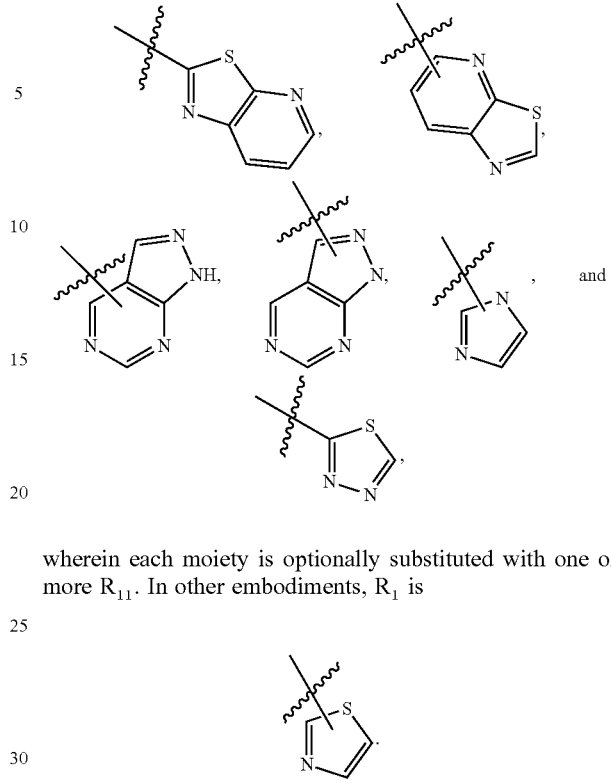

wherein each moiety is optionally substituted with one or more $R_{11}$. In other embodiments, $R_1$ is (16a) In some embodiments of Formula (I), at least one $R_{11}$ is ($C_1$-$C_4$) alkyl (e.g., methyl, ethyl, propyl, i-propyl, or butyl) optionally substituted with one or more $R_{12}$. In other embodiments, at least one $R_{11}$ is methyl. In other embodiments, at least one $R_{11}$ is propyl optionally substituted with one to two $R_{12}$.

(16b) In some embodiments of Formula (I), at least one $R_{11}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$). In further embodiments, at least one $R_{11}$ is $CF_3$.

(16c) In some embodiments of Formula (I), at least one $R_{11}$ is ($C_1$-$C_4$) alkoxy (e.g., methoxy, ethoxy, propoxy, or butoxy).

(16d) In some embodiments of Formula (I), at least one $R_{11}$ is halogen (e.g., F, Cl, Br or I). In other embodiments, at least one $R_{11}$ is F. In other embodiments, at least one $R_{11}$ is Cl. In other embodiments, at least one $R_{11}$ is Br.

(16e) In some embodiments of Formula (I), at least one $R_{11}$ is $NO_2$, OH, or CN.

(16f) In some embodiments of Formula (I), at least one $R_{11}$ is $C(O)R_{13}$ or $C(O)OR_{13}$. In other embodiments, at least one $R_{11}$ is $C(O)OCH_2CH_3$.

(16g) In some embodiments of Formula (I), at least one $R_{11}$ is $C(O)NR_{13}R_{14}$ or $NR_{13}R_{14}$. In other embodiments, at least one $R_{11}$ is $C(O)NR_{13}R_{14}$ or $NH_2$.

(16h) In some embodiments of Formula (I), at least one $R_{11}$ is ($C_3$-$C_7$) cycloalkyl (e.g., cyclopropyl, cyclobutyl, cyclopentyl, cyclohexyl, or cycloheptyl) optionally substituted with one or more $R_{12}$. In further embodiments, at least one $R_{11}$ is cyclopropyl.

(16i) In some embodiments of Formula (I), at least one $R_{11}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more $R_{12}$.

(16j) In some embodiments of Formula (I), at least one $R_{11}$ is ($C_6$-$C_{10}$) aryl optionally substituted with one or more $R_{12}$. In further embodiments, at least one $R_{11}$ is phenyl optionally substituted with one or more $R_{12}$.

(16k) In some embodiments of Formula (I), at least one $R_{11}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) comprising 1-3 heteroatoms selected from N, O, and S, optionally substituted with one or more $R_{12}$. In other embodiments, at least one $R_{11}$ is heteroaryl comprising a 6-membered ring (e.g., pyridinyl, pyridazinyl, pyrimidinyl, triazinyl, etc.) optionally substituted with one or more $R_{12}$. In other embodiments, at least one $R_{11}$ is pyridinyl optionally substituted with one or more $R_{12}$. In further embodiments, at least one $R_{11}$ is pyridinyl.

(17a) In some embodiments of Formula (I), at least one $R_{12}$ is ($C_1$-$C_4$) alkyl (e.g., methyl, ethyl, propyl, i-propyl, or butyl).

(17b) In some embodiments of Formula (I), at least one $R_{12}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$).

(17c) In some embodiments of Formula (I), at least one $R_{12}$ is ($C_1$-$C_4$) alkoxy (e.g., methoxy, ethoxy, propoxy, or butoxy).

(17d) In some embodiments of Formula (I), at least one $R_{12}$ is halogen (e.g., F, Cl, Br or I).

(17e) In some embodiments of Formula (I), at least one $R_{12}$ is $NO_2$, OH, or CN.

(17f) In some embodiments of Formula (I), at least one $R_{12}$ is ($C_3$-$C_7$) cycloalkyl (e.g., cyclopropyl, cyclobutyl, cyclopentyl, cyclohexyl, or cycloheptyl).

(17g) In some embodiments of Formula (I), at least one $R_{12}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) comprising 1-3 heteroatoms selected from N, O, and S. In other embodiments, at least one $R_{12}$ is piperidinyl, piperazinyl, or morpholinyl. In further embodiments, at least one $R_{12}$ is morpholinyl.

(17h) In some embodiments of Formula (I), at least one $R_{12}$ is ($C_6$-$C_{10}$) aryl optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), ($C_3$-$C_7$) cycloalkyl (e.g., cyclopropyl, cyclobutyl, cyclopentyl, cyclohexyl, or cycloheptyl), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.).

(17i) In some embodiments of Formula (I), $R_{12}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), ($C_3$-$C_7$) cycloalkyl (e.g., cyclopropyl, cyclobutyl, cyclopentyl, cyclohexyl, or cycloheptyl), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.). In other embodiments, at least one $R_{12}$ is heteroaryl comprising a 5-membered ring fused with a 6-membered ring and 1-4 heteroatoms selected from N, O, and S, optionally substituted with one or more substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and ($C_3$-$C_7$) cycloalkyl (e.g., cyclopropyl, cyclobutyl, cyclopentyl, cyclohexyl, or cycloheptyl).

(18a) In some embodiments of Formula (I), at least one $R_{13}$ is H.

(18b) In some embodiments of Formula (I), at least one $R_{13}$ is ($C_1$-$C_4$) alkyl (e.g., methyl, ethyl, propyl, i-propyl, or butyl) optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.). In other embodiments, at least one $R_{13}$ is methyl, ethyl, or propyl. In other embodiments, at least one $R_{13}$ is ethyl, propyl, or butyl, wherein the ethyl, propyl, and butyl are optionally substituted with one to two substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is ethyl, propyl, or butyl, wherein the ethyl, propyl, and butyl are optionally substituted with one to two substituents independently selected from $N((C_1$-$C_4)$ alkyl$)_2$ (e.g., dimethylamino, diethylamino, dipropylamino, or dibutylamino) and heterocycle comprising a 5- to 7-membered ring and 1-3 heteroatoms selected from N, O, and S. In other embodiments, at least one $R_{13}$ is ethyl, propyl, or butyl, wherein the ethyl, propyl, and butyl are optionally substituted with one to two substituents independently selected from dimethylamino and heterocycle comprising a 6-membered ring and 1-3 heteroatoms selected from N, O, and S. In other embodiments, at least one $R_{13}$ is ethyl, propyl, or butyl wherein the ethyl, propyl, and butyl are optionally substituted with one to two substituents independently selected from dimethylamino, morpholinyl, piperidinyl or piperazinyl. In further embodiments, at least one $R_{13}$ is ethyl, propyl, or butyl wherein the ethyl, propyl, and butyl are optionally substituted with dimethylamino or morpholinyl.

(18c) In some embodiments of Formula (I), at least one $R_{13}$ is ($C_3$-$C_7$) cycloalkyl (e.g., cyclopropyl, cyclobutyl, cyclopentyl, cyclohexyl, or cycloheptyl).

(18d) In some embodiments of Formula (I), at least one $R_{13}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is heterocycle comprising a 6-membered ring and 1-3 heteroatoms selected from N, O, and S, optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), or heterocycle comprising a 6-membered ring and 1-3 heteroatoms selected from N, O, and S. In further embodiments, at least one $R_{13}$ is morpholinyl, piperidinyl, or piperazinyl, wherein the morpholinyl, piperidinyl, and piperazinyl are optionally substituted with methyl, dimethylamino, or morpholinyl.

(19a) In some embodiments of Formula (I), at least one $R_{14}$ is H.

(19b) In some embodiments of Formula (I), at least one $R_{14}$ is ($C_1$-$C_3$) alkyl (e.g., methyl, ethyl, propyl, or i-propyl).

(20a) In some embodiments of Formula (I), m is 0 or 1.
(20b) In some embodiments of Formula (I), m is 0.
(20c) In some embodiments of Formula (I), m is 1.
(21a) In some embodiments of Formula (I), n is 0 or 1.
(21b) In some embodiments of Formula (I), n is 0.
(21c) In some embodiments of Formula (I), n is 1.
(22a) In some embodiments of Formula (I), p is 0, 1, 2, 3, or 4. In other embodiments, p is 0, 1, 2, or 3. In other embodiments, p is 0, 1, or 2.
(22b) In some embodiments of Formula (I), p is 0 or 1.
(22c) In some embodiments of Formula (I), p is 1 or 2. In other embodiments, p is 2 or 3.
(22d) In some embodiments of Formula (I), p is 0. In other embodiments, p is 1. In other embodiments, p is 2. In other embodiments, p is 3. In other embodiments, p is 4.

In some embodiments of Formula (I), $R_5$ is

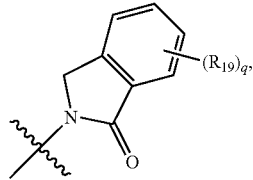

wherein q is 0, 1, 2, 3, or 4.

In some embodiments of Formula (I), each of the substituents defined for any one of $X_1$, $R_1$, $R_2$, $R_3$, $R_4$, $R_5$, $R_6$, $R_7$, $R_{11}$, $R_{12}$, $R_{13}$, $R_{14}$, $R_{15}$, $R_{16}$, $R_{18}$, $R_{19}$, $R_{20}$, $R_{21}$, $R_{22}$, m, n, p, and q can be combined with any of the substituents defined for the remainder of $X_1$, $R_1$, $R_2$, $R_3$, $R_4$, $R_5$, $R_6$, $R_7$, $R_{11}$, $R_{12}$, $R_{13}$, $R_{14}$, $R_{15}$, $R_{16}$, $R_{18}$, $R_{19}$, $R_{20}$, $R_{21}$, $R_{22}$, m, n, p, and q.

(23) In some embodiments, $R_1$ is as defined in (15a).
(24) In some embodiments, $R_1$ is as defined in (15a) and m is as defined in (20b).
(25) In some embodiments, $R_1$ is as defined in (15a), m is as defined in (20b), and $R_2$ is as defined in (1a).
(26) In some embodiments, $R_1$ is as defined in (15a), m is as defined in (20b), $R_2$ is as defined in (1a), and n is as defined in (21b).
(27) In some embodiments, $R_1$ is as defined in (15a), m is as defined in (20b), $R_2$ is as defined in (1a), n is as defined in (21b), and $R_4$ is as defined in (3a).
(28) In some embodiments, $R_1$ is as defined in (15a), m is as defined in (20b), $R_2$ is as defined in (1a), n is as defined in (21b), $R_4$ is as defined in (3a), and $R_5$ is as defined in (7a).
(29) In some embodiments, $R_1$ is as defined in (15a), m is as defined in (20b), $R_2$ is as defined in (1a), n is as defined in (21b), and $R_4$ is as defined in (3b).
(30) In some embodiments, $R_1$ is as defined in (15a), m is as defined in (20b), $R_2$ is as defined in (1a), n is as defined in (21b), $R_4$ is as defined in (3b), and $R_5$ is as defined in (7a).
(31) In some embodiments, $R_1$ is as defined in (15a), m is as defined in (20b), $R_2$ is as defined in (1a), n is as defined in (21b), $R_4$ is as defined in (3b), $R_5$ is as defined in (7a), and $X_1$ is as defined in (4b).

(32) In some embodiments, $R_1$ is as defined in (15a), m is as defined in (20b), $R_2$ is as defined in (1a), n is as defined in (21b), $R_4$ is as defined in (3b), $R_5$ is as defined in (7a), $X_1$ is as defined in (4b), and R % is as defined in (5a).

(33) In some embodiments, $R_1$ is as defined in (15a), m is as defined in (20b), $R_2$ is as defined in (1a), and n is as defined in (21c).

(34) In some embodiments, $R_1$ is as defined in (15a), m is as defined in (20b), $R_2$ is as defined in (1a), n is as defined in (21c), and $R_4$ is as defined in (3a).

(35) In some embodiments, $R_1$ is as defined in (15a), m is as defined in (20b), $R_2$ is as defined in (1a), n is as defined in (21c), $R_4$ is as defined in (3a), and $R_5$ is as defined in (7a).

(36) In some embodiments, $R_1$ is as defined in (15a), m is as defined in (20b), $R_2$ is as defined in (1a), n is as defined in (21c), and $R_4$ is as defined in (3b).

(37) In some embodiments, $R_1$ is as defined in (15a), m is as defined in (20b), $R_2$ is as defined in (1a), n is as defined in (21c), $R_4$ is as defined in (3b), and $R_5$ is as defined in (7a).

(38) In some embodiments, $R_1$ is as defined in (15a), m is as defined in (20b), $R_2$ is as defined in (1a), n is as defined in (21c), $R_4$ is as defined in (3b), $R_5$ is as defined in (7a), and $X_1$ is as defined in (4b).

(39) In some embodiments, $R_1$ is as defined in (15a), m is as defined in (20b), $R_2$ is as defined in (1a), n is as defined in (21c), $R_4$ is as defined in (3b), $R_5$ is as defined in (7a), $X_1$ is as defined in (4b), and R % is as defined in (5a).

(40) In some embodiments, $R_1$ is as defined in (15a) and m is as defined in (20c).

(41) In some embodiments, $R_1$ is as defined in (15a), m is as defined in (20c), and $R_2$ is as defined in (1a).

(42) In some embodiments, $R_1$ is as defined in (15a), m is as defined in (20c), $R_2$ is as defined in (1a), and $R_3$ is as defined in (2a).

(43) In some embodiments, $R_1$ is as defined in (15a), m is as defined in (20c), $R_2$ is as defined in (1a), $R_3$ is as defined in (2a), and n is as defined in (21b).

(44) In some embodiments, $R_1$ is as defined in (15a), m is as defined in (20c), $R_2$ is as defined in (1a), $R_3$ is as defined in (2a), n is as defined in (21b), and $R_4$ is as defined in (3a).

(45) In some embodiments, $R_1$ is as defined in (15a), m is as defined in (20c), $R_2$ is as defined in (1a), $R_3$ is as defined in (2a), n is as defined in (21b), $R_4$ is as defined in (3a), and $R_5$ is as defined in (7a).

(46) In some embodiments, $R_1$ is as defined in (15a), m is as defined in (20c), $R_2$ is as defined in (1a), $R_3$ is as defined in (2a), n is as defined in (21b), and $R_4$ is as defined in (3b).

(47) In some embodiments, $R_1$ is as defined in (15a), m is as defined in (20c), $R_2$ is as defined in (1a), $R_3$ is as defined in (2a), n is as defined in (21b), $R_4$ is as defined in (3b), and $R_5$ is as defined in (7a).

(48) In some embodiments, $R_1$ is as defined in (15a), m is as defined in (20c), $R_2$ is as defined in (1a), $R_3$ is as defined in (2a), n is as defined in (21b), $R_4$ is as defined in (3b), $R_5$ is as defined in (7a), and $X_1$ is as defined in (4b).

(49) In some embodiments, $R_1$ is as defined in (15a), m is as defined in (20c), $R_2$ is as defined in (1a), $R_3$ is as defined in (2a), n is as defined in (21b), $R_4$ is as defined in (3b), $R_5$ is as defined in (7a), $X_1$ is as defined in (4b), and $R_6$ is as defined in (5a).

(50) In some embodiments, $R_1$ is as defined in (15a), m is as defined in (20c), $R_2$ is as defined in (1a), $R_3$ is as defined in (2a), and n is as defined in (21c).

(51) In some embodiments, $R_1$ is as defined in (15a), m is as defined in (20c), $R_2$ is as defined in (1a), $R_3$ is as defined in (2a), n is as defined in (21c), and $R_4$ is as defined in (3a).

(52) In some embodiments, $R_1$ is as defined in (15a), m is as defined in (20c), $R_2$ is as defined in (1a), $R_3$ is as defined in (2a), n is as defined in (21c), $R_4$ is as defined in (3a), and $R_5$ is as defined in (7a).

(53) In some embodiments, $R_1$ is as defined in (15a), m is as defined in (20c), $R_2$ is as defined in (1a), $R_3$ is as defined in (2a), n is as defined in (21c), and $R_4$ is as defined in (3b).

(54) In some embodiments, $R_1$ is as defined in (15a), m is as defined in (20c), $R_2$ is as defined in (1a), $R_3$ is as defined in (2a), n is as defined in (21c), $R_4$ is as defined in (3b), and $R_5$ is as defined in (7a).

(55) In some embodiments, $R_1$ is as defined in (15a), m is as defined in (20c), $R_2$ is as defined in (1a), $R_3$ is as defined in (2a), n is as defined in (21c), $R_4$ is as defined in (3b), $R_5$ is as defined in (7a), and $X_1$ is as defined in (4b).

(56) In some embodiments, $R_1$ is as defined in (15a), m is as defined in (20c), $R_2$ is as defined in (1a), $R_3$ is as defined in (2a), n is as defined in (21c), $R_4$ is as defined in (3b), $R_5$ is as defined in (7a), $X_1$ is as defined in (4b), and $R_6$ is as defined in (5a).

(57) In some embodiments, $R_1$ is as defined in (15b).

(58) In some embodiments, $R_1$ is as defined in (15b) and m is as defined in (20b).

(59) In some embodiments, $R_1$ is as defined in (15b), m is as defined in (20b), and $R_2$ is as defined in (1a).

(60) In some embodiments, $R_1$ is as defined in (15b), m is as defined in (20b), $R_2$ is as defined in (1a), and n is as defined in (21b).

(61) In some embodiments, $R_1$ is as defined in (15b), m is as defined in (20b), $R_2$ is as defined in (1a), n is as defined in (21b), and $R_4$ is as defined in (3a).

(62) In some embodiments, $R_1$ is as defined in (15b), m is as defined in (20b), $R_2$ is as defined in (1a), n is as defined in (21b), $R_4$ is as defined in (3a), and $R_5$ is as defined in (7a).

(63) In some embodiments, $R_1$ is as defined in (15b), m is as defined in (20b), $R_2$ is as defined in (1a), n is as defined in (21b), and $R_4$ is as defined in (3b).

(64) In some embodiments, $R_1$ is as defined in (15b), m is as defined in (20b), $R_2$ is as defined in (1a), n is as defined in (21b), $R_4$ is as defined in (3b), and $R_5$ is as defined in (7a).

(65) In some embodiments, $R_1$ is as defined in (15b), m is as defined in (20b), $R_2$ is as defined in (1a), n is as defined in (21b), $R_4$ is as defined in (3b), $R_5$ is as defined in (7a), and $X_1$ is as defined in (4b).

(66) In some embodiments, $R_1$ is as defined in (15b), m is as defined in (20b), $R_2$ is as defined in (1a), n is as defined in (21b), $R_4$ is as defined in (3b), $R_5$ is as defined in (7a), $X_1$ is as defined in (4b), and $R_6$ is as defined in (5a).

(67) In some embodiments, $R_1$ is as defined in (15b), m is as defined in (20b), $R_2$ is as defined in (1a), and n is as defined in (21c).

(68) In some embodiments, $R_1$ is as defined in (15b), m is as defined in (20b), $R_2$ is as defined in (1a), n is as defined in (21c), and $R_4$ is as defined in (3a).

(69) In some embodiments, $R_1$ is as defined in (15b), m is as defined in (20b), $R_2$ is as defined in (1a), n is as defined in (21c), $R_4$ is as defined in (3a), and $R_5$ is as defined in (7a).

(70) In some embodiments, $R_1$ is as defined in (15b), m is as defined in (20b), $R_2$ is as defined in (1a), n is as defined in (21c), and $R_4$ is as defined in (3b).

(71) In some embodiments, $R_1$ is as defined in (15b), m is as defined in (20b), $R_2$ is as defined in (1a), n is as defined in (21c), $R_4$ is as defined in (3b), and $R_5$ is as defined in (7a).

(72) In some embodiments, $R_1$ is as defined in (15b), m is as defined in (20b), $R_2$ is as defined in (1a), n is as defined in (21c), $R_4$ is as defined in (3b), $R_5$ is as defined in (7a), and $X_1$ is as defined in (4b).

(73) In some embodiments, $R_1$ is as defined in (15b), m is as defined in (20b), $R_2$ is as defined in (1a), n is as defined in (21c), $R_4$ is as defined in (3b), $R_5$ is as defined in (7a), $X_1$ is as defined in (4b), and $R_6$ is as defined in (5a).

(74) In some embodiments, $R_1$ is as defined in (15b), m is as defined in (20c).

(75) In some embodiments, $R_1$ is as defined in (15b), m is as defined in (20c), and $R_2$ is as defined in (1a).

(76) In some embodiments, $R_1$ is as defined in (15b), m is as defined in (20c), $R_2$ is as defined in (1a), and $R_3$ is as defined in (2a).

(77) In some embodiments, $R_1$ is as defined in (15b), m is as defined in (20c), $R_2$ is as defined in (1a), $R_3$ is as defined in (2a), and n is as defined in (21b).

(78) In some embodiments, $R_1$ is as defined in (15b), m is as defined in (20c), $R_2$ is as defined in (1a), $R_3$ is as defined in (2a), n is as defined in (21b), and $R_4$ is as defined in (3a).

(79) In some embodiments, $R_1$ is as defined in (15b), m is as defined in (20c), $R_2$ is as defined in (1a), $R_3$ is as defined in (2a), n is as defined in (21b), $R_4$ is as defined in (3a), and $R_5$ is as defined in (7a).

(80) In some embodiments, $R_1$ is as defined in (15b), m is as defined in (20c), $R_2$ is as defined in (1a), $R_3$ is as defined in (2a), n is as defined in (21b), and $R_4$ is as defined in (3b).

(81) In some embodiments, $R_1$ is as defined in (15b), m is as defined in (20c), $R_2$ is as defined in (1a), $R_3$ is as defined in (2a), n is as defined in (21b), $R_4$ is as defined in (3b), and $R_5$ is as defined in (7a).

(82) In some embodiments, $R_1$ is as defined in (15b), m is as defined in (20c), $R_2$ is as defined in (1a), $R_3$ is as defined in (2a), n is as defined in (21b), $R_4$ is as defined in (3b), $R_5$ is as defined in (7a), and $X_1$ is as defined in (4b).

(83) In some embodiments, $R_1$ is as defined in (15b), m is as defined in (20c), $R_2$ is as defined in (1a), $R_3$ is as defined in (2a), n is as defined in (21b), $R_4$ is as defined in (3b), $R_5$ is as defined in (7a), $X_1$ is as defined in (4b), and $R_6$ is as defined in (5a).

(84) In some embodiments, $R_1$ is as defined in (15b), m is as defined in (20c), $R_2$ is as defined in (1a), $R_3$ is as defined in (2a), and n is as defined in (21c).

(85) In some embodiments, $R_1$ is as defined in (15b), m is as defined in (20c), $R_2$ is as defined in (1a), $R_3$ is as defined in (2a), n is as defined in (21c), and $R_4$ is as defined in (3a).

(86) In some embodiments, $R_1$ is as defined in (15b), m is as defined in (20c), $R_2$ is as defined in (1a), $R_3$ is as defined in (2a), n is as defined in (21c), $R_4$ is as defined in (3a), and $R_5$ is as defined in (7a).

(87) In some embodiments, $R_1$ is as defined in (15b), m is as defined in (20c), $R_2$ is as defined in (1a), $R_3$ is as defined in (2a), n is as defined in (21c), and $R_4$ is as defined in (3b).

(88) In some embodiments, $R_1$ is as defined in (15b), m is as defined in (20c), $R_2$ is as defined in (1a), $R_3$ is as defined in (2a), n is as defined in (21c), $R_4$ is as defined in (3b), and $R_5$ is as defined in (7a).

(89) In some embodiments, $R_1$ is as defined in (15b), m is as defined in (20c), $R_2$ is as defined in (1a), $R_3$ is as defined in (2a), n is as defined in (21c), $R_4$ is as defined in (3b), $R_5$ is as defined in (7a), and $X_1$ is as defined in (4b).

(90) In some embodiments, $R_1$ is as defined in (15b), m is as defined in (20c), $R_2$ is as defined in (1a), $R_3$ is as defined in (2a), n is as defined in (21c), $R_4$ is as defined in (3b), $R_5$ is as defined in (7a), $X_1$ is as defined in (4b), and $R_6$ is as defined in (5a).

In other embodiments, the compounds of Formula (I') have the structure of Formula (Ia) or (Ib):

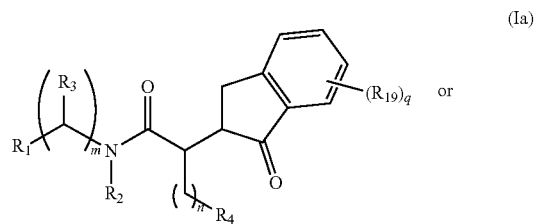

(Ia)

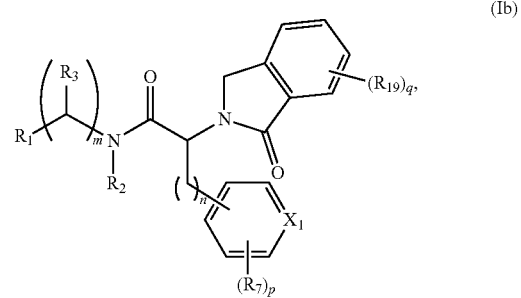

(Ib)

or pharmaceutically acceptable salts, hydrates, solvates, prodrugs, stereoisomers, or tautomers thereof, wherein:

$R_1$ is ($C_6$-$C_{10}$) aryl, or heteroaryl comprising one or two 5- to 7-membered rings and 1-4 heteroatoms selected from N, O, and S, wherein the aryl and heteroaryl are each optionally substituted with one or more $R_{11}$;

each $R_{11}$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, C(O)$R_{13}$, C(O)O$R_{13}$, C(O)N$R_{13}R_{14}$, $NR_{13}R_{14}$, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the alkyl, cycloalkyl, heterocyclyl, aryl, and heteroaryl are each optionally substituted with one or more $R_{12}$;

each $R_{12}$ is independently selected from ($C_1$-$C_4$) alkyl, ($C_1$-$C_4$) haloalkyl, ($C_1$-$C_4$) alkoxy, ($C_1$-$C_4$) haloalkoxy, halogen, $NO_2$, OH, CN, ($C_3$-$C_7$) cycloalkyl, heterocyclyl comprising a 5- to 7-membered ring and 1-3 heteroatoms selected from N, O, and S, ($C_6$-$C_{10}$) aryl, and heteroaryl comprising one or two 5- to 7-membered rings and 1-4 heteroatoms selected from N, O, and S, wherein the aryl and heteroaryl are each optionally substituted with one or more substituents independently selected from ($C_1$-$C_4$) alkyl, ($C_1$-$C_4$) alkoxy, ($C_1$-$C_4$) haloalkyl, ($C_1$-$C_4$) haloalkoxy, halogen, $NH_2$, NH($C_1$-$C_4$) alkyl, N(($C_1$-$C_4$) alkyl)$_2$, ($C_3$-$C_7$) cycloalkyl, and heterocyclyl comprising a 5- to 7-membered ring and 1-3 heteroatoms selected from N, O, and S;

each $R_{13}$ is independently selected from H, ($C_1$-$C_4$) alkyl, ($C_3$-$C_7$) cycloalkyl, and heterocyclyl comprising a 5- to 7-membered ring and 1-3 heteroatoms selected from N, O, and S, wherein the alkyl, cycloalkyl, and heterocyclyl are each optionally substituted with one or more substituents independently selected from ($C_1$-$C_4$) alkyl, halogen, OH, $NH_2$, NH($C_1$-$C_4$) alkyl, N(($C_1$-$C_4$) alkyl)$_2$, and heterocyclyl comprising a 5- to 7-membered ring and 1-3 heteroatoms selected from N, O, and S;

each $R_{14}$ is independently H or ($C_1$-$C_3$) alkyl;

$R_2$ is H or ($C_1$-$C_3$) alkyl;

$R_3$ is H or ($C_1$-$C_3$) alkyl;

$R_4$ is ($C_1$-$C_3$) alkyl or

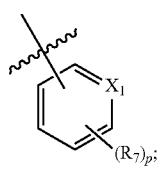

$X_1$ is N or $CR_6$;

$R_6$ is H, $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, OH, or CN;

each $R_7$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, OH, and CN;

each $R_{19}$ is independently selected from halogen, $(C_3-C_7)$ cycloalkyl, $(C_4-C_7)$ cycloalkenyl, $(C_6-C_{10})$ aryl, NH—$(C_6-C_{10})$ aryl, and heteroaryl comprising one or two 5- to 7-membered ring and 1-4 heteroatoms selected from N, O, and S, wherein the aryl and heteroaryl are each optionally substituted with one or more $R_{20}$;

each $R_{20}$ is independently selected from $(C_1-C_4)$ alkyl, $(C_1-C_4)$ alkoxy, $(C_1-C_4)$ haloalkyl, $(C_1-C_4)$ haloalkoxy, halogen, C(O)OH, $C(O)O(C_1-C_4)$ alkyl, $C(O)NR_{21}R_{22}$, $NH_2$, OH, CN, $O(CH_2)_{0-3}$—$(C_6-C_{10})$ aryl, and $(CH_2)_{0-3}$-heterocyclyl which comprises a 5- to 7-membered ring and 1-3 heteroatoms selected from N, O, and S, wherein the heterocyclyl is optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, halogen, and $C(O)O(C_1-C_4)$ alkyl);

$R_{21}$ is H or $(C_1-C_3)$ alkyl;

$R_{22}$ is H or $(C_1-C_4)$ alkyl optionally substituted with one or more substituents independently selected from $NH_2$, $NH(C_1-C_4)$ alkyl, $N((C_1-C_4)$ alkyl$)_2$, and heterocyclyl comprising a 5- to 7-membered ring and 1-3 heteroatoms selected from N, O, and S; or $R_{21}$ and $R_{22}$ together with the nitrogen atom to which they are attached form a 5- or 6-membered heterocyclyl optionally containing 1-2 additional heteroatoms selected from N, O, and S;

m and n are each independently 0 or 1; and p and q are each independently 0, 1, 2, 3 or 4;

provided that when m is 0, n is 0, p is 0, $R_{15}$ and $R_{16}$ together with the nitrogen atom to which they are attached form an unsubstituted isoindolinone, and $R_6$ is H, then $R_1$ is not

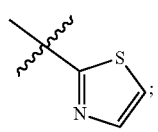

and provided that $R_4$ is not 4-fluoro-2-hydroxyphenyl.

(101a) In some embodiments of Formula (Ia) or (Ib), $R_2$ is H.

(101b) In some embodiments of Formula (Ia) or (Ib), $R_2$ is $(C_1-C_3)$ alkyl (e.g., methyl, ethyl, propyl, or i-propyl). In other embodiments, $R_2$ is methyl. In other embodiments, $R_2$ is ethyl.

(102a) In some embodiments of Formula (Ia) or (Ib), $R_3$ is H.

(102b) In some embodiments of Formula (Ia) or (Ib), $R_3$ is $(C_1-C_3)$ alkyl (e.g., methyl, ethyl, propyl, or i-propyl). In other embodiments, $R_3$ is methyl. In other embodiments, $R_3$ is ethyl.

(103a) In some embodiments of Formula (Ia) or (Ib), $R_4$ is $(C_1-C_3)$ alkyl (e.g., methyl, ethyl, propyl, or i-propyl). In other embodiments, $R_4$ is methyl. In other embodiments, $R_4$ is ethyl.

(103b) In some embodiments of Formula (Ia) or (Ib), $R_4$ is

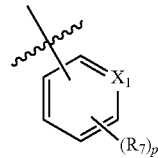

(e.g., phenyl, 2-pyridinyl, 3-pyridinyl, or 4-pyridinyl).

(104a) In some embodiments of Formula (Ia) or (Ib), $X_1$ is N.

(104b) In some embodiments of Formula (Ia) or (Ib), $X_1$ is $CR_6$.

(105a) In some embodiments of Formula (Ia) or (Ib), $R_6$ is H.

(105b) In some embodiments of Formula (Ia) or (Ib), $R_6$ is $(C_1-C_4)$ alkyl (e.g., methyl, ethyl, propyl, i-propyl, or butyl).

(105c) In some embodiments of Formula (Ia) or (Ib), $R_6$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$).

(105d) In some embodiments of Formula (Ia) or (Ib), $R_6$ is $(C_1-C_4)$ alkoxy (e.g., methoxy, ethoxy, propoxy, or butoxy).

(105e) In some embodiments of Formula (Ia) or (Ib), $R_6$ is halogen (e.g., F, Cl, Br or I). In other embodiments, $R_6$ is F or Cl. In further embodiments, $R_6$ is F.

(105f) In some embodiments of Formula (Ia) or (Ib), $R_6$ is $NO_2$, $NH_2$, OH, or CN. In further embodiments, $R_6$ is $NO_2$ or $NH_2$.

(106a) In some embodiments of Formula (Ia) or (Ib), at least one $R_7$ is $(C_1-C_4)$ alkyl (e.g., methyl, ethyl, propyl, i-propyl, or butyl).

(106b) In some embodiments of Formula (Ia) or (Ib), at least one $R_7$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$).

(106c) In some embodiments of Formula (Ia) or (Ib), at least one $R_7$ is $(C_1-C_4)$ alkoxy (e.g., methoxy, ethoxy, propoxy, or butoxy).

(106d) In some embodiments of Formula (Ia) or (Ib), at least one $R_7$ is halogen (e.g., F, Cl, Br or I). In other embodiments, at least one $R_7$ is F or Cl. In further embodiments, at least one $R_7$ is F.

(106e) In some embodiments of Formula (Ia) or (Ib), at least one $R_7$ is $NO_2$, $NH_2$, OH, or CN. In further embodiments, at least one $R_7$ is $NO_2$ or $NH_2$.

(106f) In some embodiments of Formula (Ia) or (Ib), at least one $R_7$ is halogen (e.g., F, Cl, Br or I) and at least one $R_7$ is OH.

(106g) In some embodiments of Formula (Ia) or (Ib), one $R_7$ is halogen (e.g., F, Cl, Br or I) and one $R_7$ is OH.

(111a) In some embodiments of Formula (Ia) or (Ib), at least one $R_{19}$ is halogen (e.g., F, Cl, Br or I). In other embodiments, at least one $R_{19}$ is F, Cl, or Br. In other embodiments, at least one $R_{19}$ is F. In other embodiments, at least one $R_{19}$ is Cl. In other embodiments, at least one $R_{19}$ is Br.

(111b) In some embodiments of Formula (Ia) or (Ib), at least one $R_{19}$ is $(C_3-C_7)$ cycloalkyl (e.g., cyclopropyl, cyclobutyl, cyclopentyl, cyclohexyl, or cycloheptyl).

(111c) In some embodiments of Formula (Ia) or (Ib), at least one $R_{19}$ is $(C_4-C_7)$ cycloalkenyl (e.g., cyclobutenyl, cyclopentenyl, cyclohexenyl, or cycloheptenyl). In other embodiments, at least one $R_{19}$ is cyclohexenyl.

(111d) In some embodiments of Formula (Ia) or (Ib), at least one $R_{19}$ is $(C_6-C_{10})$ aryl optionally substituted with one or more $R_{20}$. In other embodiments, at least one $R_{19}$ is phenyl optionally substituted with one or more $R_{20}$. In other embodiments, at least one $R_{19}$ is phenyl optionally substituted with one to three $R_{20}$. In other embodiments, at least one $R_{19}$ is phenyl.

(111e) In some embodiments of Formula (Ia) or (Ib), at least one $R_{19}$ is NH—$(C_6-C_{10})$ aryl optionally substituted with one or more $R_{20}$. In other embodiments, at least one $R_{19}$ is NH-phenyl optionally substituted with one or more $R_{20}$. In other embodiments, at least one $R_{19}$ is NH-phenyl optionally substituted with one to three $R_{20}$. In other embodiments, at least one $R_{19}$ is NH-phenyl.

(111f) In some embodiments of Formula (Ia) or (Ib), at least one $R_{19}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, indolyl, quinolinyl, isoquinolinyl, benzothiazolyl, benzoimidazolyl, benzooxazolyl, thiazolopyridinyl, pyrazolopyrimidinyl, etc.) optionally substituted with one or more $R_{20}$. In other embodiments, at least one $R_{19}$ is pyrazolyl, thiophenyl, pyridinyl, pyrimidinyl, indolyl, or quinolinyl optionally substituted with one or more $R_{20}$.

(112a) In some embodiments of Formula (Ia) or (Ib), at least one $R_{20}$ is $(C_1-C_4)$ alkyl (e.g., methyl, ethyl, propyl, i-propyl, or butyl). In further embodiments, at least one $R_{20}$ is methyl or ethyl.

(112b) In some embodiments of Formula (Ia) or (Ib), at least one $R_{20}$ is $(C_1-C_4)$ alkoxy (e.g., methoxy, ethoxy, propoxy, or butoxy). In further embodiments, at least one $R_{20}$ is methoxy.

(112c) In some embodiments of Formula (Ia) or (Ib), at least one $R_{20}$ is $(C_1-C_4)$ haloalkyl (e.g., $CH_2F$, $CHF_2$, or $CF_3$) or $(C_1-C_4)$ haloalkoxy (e.g., $OCH_2F$, $OCHF_2$, or $OCF_3$). In further embodiments, at least one $R_{20}$ is $CF_3$ or $OCF_3$.

(112d) In some embodiments of Formula (Ia) or (Ib), at least one $R_{20}$ is halogen (e.g., F, Cl, Br or I). In further embodiments, at least one $R_{20}$ is F.

(112e) In some embodiments of Formula (Ia) or (Ib), at least one $R_{20}$ is C(O)OH or $C(O)O(C_1-C_4)$ alkyl (e.g., methyl, ethyl, propyl, i-propyl, or butyl). In further embodiments, at least one $R_{20}$ is C(O)OH or $C(O)OCH_3$.

(112f) In some embodiments of Formula (Ia) or (Ib), at least one $R_{20}$ is $NH_2$, OH, or CN.

(112g) In some embodiments of Formula (Ia) or (Ib), at least one $R_{20}$ is $C(O)NR_{21}R_{22}$.

(112h) In some embodiments of Formula (Ia) or (Ib), at least one $R_{20}$ is $O(CH_2)_{0-3}$—$(C_6-C_{10})$ aryl. In further embodiments, at least one $R_{20}$ is $OCH_2$-phenyl.

(112i) In some embodiments of Formula (Ia) or (Ib), at least one $R_{20}$ is $(CH_2)_{0-3}$-heterocyclyl which comprises a 5- to 7-membered ring and 1-3 heteroatoms selected from N, O, and S, wherein the heterocyclyl is selected from pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc., and is optionally substituted with one or more substituents independently selected from $(C_1-C_4)$ alkyl (e.g., methyl, ethyl, propyl, i-propyl, or butyl), $(C_1-C_4)$ alkoxy (e.g., methoxy, ethoxy, propoxy, or butoxy), $(C_1-C_4)$ haloalkyl (e.g., $CH_2F$, $CHF_2$, or $CF_3$), $(C_1-C_4)$ haloalkoxy (e.g., $OCH_2F$, $OCHF_2$, or $OCF_3$), halogen (e.g., F, Cl, Br or I), and $C(O)O(C_1-C_4)$ alkyl (e.g., methyl, ethyl, propyl, i-propyl, butyl, i-butyl, or t-butyl). In other embodiments, at least one $R_{20}$ is $(CH_2)_{0-1}$-heterocycle optionally substituted with one or more substituents independently selected from $(C_1-C_4)$ alkyl (e.g., methyl, ethyl, propyl, i-propyl, or butyl), $(C_1-C_4)$ alkoxy (e.g., methoxy, ethoxy, propoxy, or butoxy), $(C_1-C_4)$ haloalkyl (e.g., $CH_2F$, $CHF_2$, or $CF_3$), $(C_1-C_4)$ haloalkoxy (e.g., $OCH_2F$, $OCHF_2$, or $OCF_3$), halogen (e.g., F, Cl, Br or I), and $C(O)O(C_1-C_4)$ alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl wherein the pyrrolidinyl, morpholinyl, and piperazinyl are each optionally substituted with one or more substituents independently selected from $(C_1-C_4)$ alkyl (e.g., methyl, ethyl, propyl, i-propyl, or butyl), $(C_1-C_4)$ alkoxy (e.g., methoxy, ethoxy, propoxy, or butoxy), $(C_1-C_4)$ haloalkyl (e.g., $CH_2F$, $CHF_2$, or $CF_3$), $(C_1-C_4)$ haloalkoxy (e.g., $OCH_2F$, $OCHF_2$, or $OCF_3$), halogen (e.g., F, Cl, Br or I), and $C(O)O(C_1-C_4)$ alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, pyrrolidinyl, morpholinyl, or piperazinyl, wherein the pyrrolidinyl, morpholinyl, and piperazinyl are each optionally substituted with one or more $(C_1-C_4)$ alkyl (e.g., methyl, ethyl, propyl, i-propyl, or butyl), or $C(O)O(C_1-C_4)$alkyl (e.g., methyl, ethyl, propyl, i-propyl, butyl, i-butyl, or t-butyl). In other embodiments, at least one $R_{20}$ is $CH_2$-pyrrolidinyl, $CH_2$-piperazinyl, morpholinyl, or piperazinyl, wherein the pyrrolidinyl, morpholinyl, and piperazinyl are optionally methyl, ethyl, or C(O)O-t-butyl.

(113a) In some embodiments of Formula (Ia) or (Ib), $R_{21}$ is H.

(113b) In some embodiments of Formula (Ia) or (Ib), $R_{21}$ is $(C_1-C_3)$ alkyl (e.g., methyl, ethyl, propyl, or i-propyl). In other embodiments, $R_{21}$ is methyl. In other embodiments, $R_{21}$ is ethyl.

(114a) In some embodiments of Formula (Ia) or (Ib), $R_{22}$ is H.

(114b) In some embodiments of Formula (Ia) or (Ib), $R_{22}$ is $(C_1-C_4)$ alkyl (e.g., methyl, ethyl, propyl, i-propyl, or butyl) optionally substituted with one or more substituents independently selected from $NH_2$, $NH(C_1-C_4)$ alkyl (e.g., methylamino, ethylamino, propylamino, or butylamino), $N((C_1-C_4)$ alkyl$)_2$ (e.g., dimethylamino, diethylamino, dipropylamino, or dibutylamino), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, etc.). In other embodiments, $R_{22}$ is $(C_1-C_4)$ alkyl (e.g., methyl, ethyl, propyl, i-propyl, or butyl) optionally substituted with one to two substituents independently selected from $NH_2$, $NH(C_1-C_4)$ alkyl, $N((C_1-C_4)$ alkyl$)_2$, and 6-membered heterocycle comprising 1-3 heteroatoms selected from N, O, and S. In further embodiments, $R_{22}$ is ethyl, propyl, or butyl optionally substituted with dimethylamino, diethylamino, or morpholinyl.

(114c) In some embodiments of Formula (Ia) or (Ib), $R_{21}$ and $R_{22}$ together with the nitrogen atom to which they are attached form a 5-membered heterocyclyl optionally containing 1-2 additional heteroatoms selected from N, O, and S. In other embodiments, $R_{21}$ and $R_{22}$ together with the nitrogen atom to which they are attached form a 6-membered heterocycle optionally containing 1-2 additional heteroatoms selected from N, O, and S. In further embodiments, $R_{21}$ and $R_{22}$ together with the nitrogen atom to which they are attached form a morpholinyl.

(115a) In some embodiments of Formula (Ia) or (Ib), $R_1$ is ($C_6$-$C_{10}$) aryl optionally substituted with one or more $R_{11}$. In other embodiments, $R_1$ is phenyl optionally substituted with one or more $R_{11}$.

(115b) In some embodiments of Formula (Ia) or (Ib), $R_1$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, thiazolopyridinyl, pyrazolopyrimidinyl, etc.) optionally substituted with one or more $R_{11}$. In other embodiments, $R_1$ is heteroaryl comprising a 5-membered ring and 1-3 heteroatoms selected from N, O, and S, optionally substituted with one or more $R_{11}$. In other embodiments, $R_1$ is heteroaryl comprising a 6-membered ring and 1-3 heteroatoms selected from N, O, and S, optionally substituted with one or more $R_{11}$. In other embodiments, $R_1$ is heteroaryl comprising a 5-membered ring fused with a 6-membered ring and 1-4 heteroatoms selected from N, O, and S, optionally substituted with one or more $R_{11}$. In other embodiments, $R_1$ is selected from:

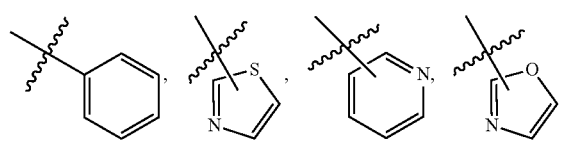

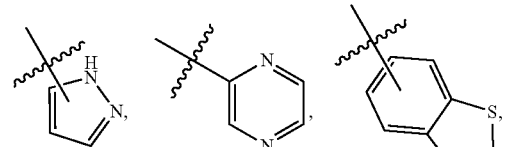

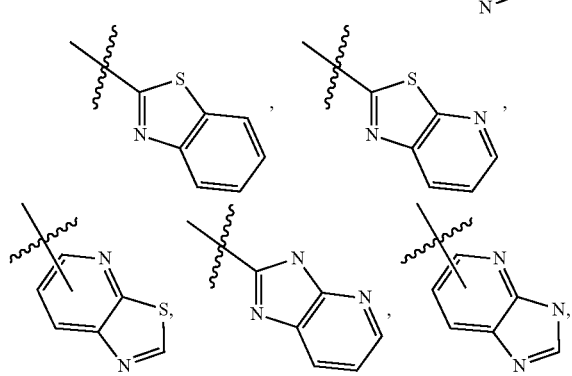

wherein each moiety is optionally substituted with one or more $R_{11}$. In other embodiments, $R_1$ is selected from:

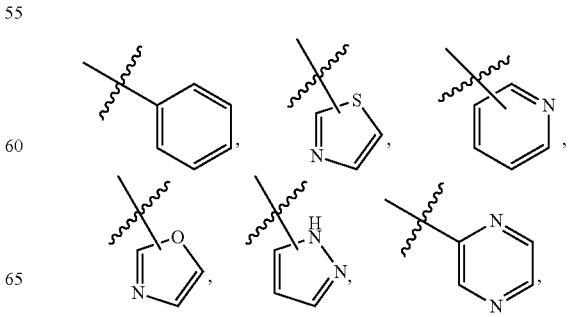

-continued

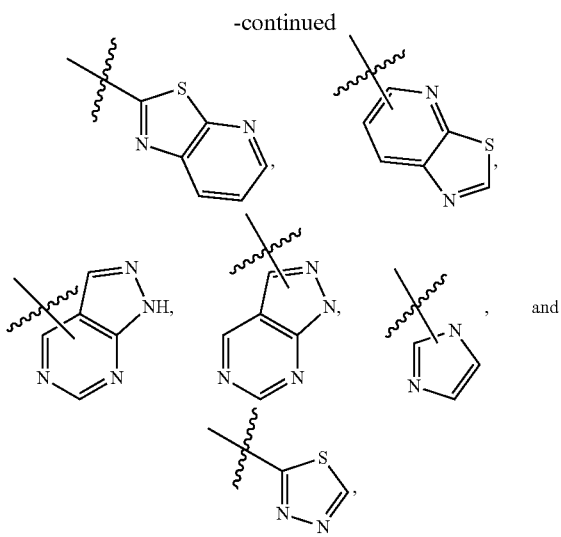

wherein each moiety is optionally substituted with one or more $R_{11}$. In other embodiments, $R_1$ is

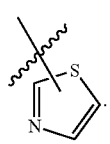

(116a) In some embodiments of Formula (Ia) or (Ib), at least one $R_{11}$ is ($C_1$-$C_4$) alkyl (e.g., methyl, ethyl, propyl, i-propyl, or butyl) optionally substituted with one or more $R_{12}$. In other embodiments, at least one $R_{11}$ is methyl. In other embodiments, at least one $R_{11}$ is propyl optionally substituted with one to two $R_{12}$.

(116b) In some embodiments of Formula (Ia) or (Ib), at least one $R_{11}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$). In further embodiments, at least one $R_{11}$ is $CF_3$.

(116c) In some embodiments of Formula (Ia) or (Ib), at least one $R_{11}$ is ($C_1$-$C_4$) alkoxy (e.g., methoxy, ethoxy, propoxy, or butoxy).

(116d) In some embodiments of Formula (Ia) or (Ib), at least one $R_{11}$ is halogen (e.g., F, Cl, Br or I). In other embodiments, at least one $R_{11}$ is F. In other embodiments, at least one $R_{11}$ is Cl. In other embodiments, at least one $R_{11}$ is Br.

(116e) In some embodiments of Formula (Ia) or (Ib), at least one $R_{11}$ is $NO_2$, OH, or CN.

(116f) In some embodiments of Formula (Ia) or (Ib), at least one $R_{11}$ is $C(O)R_{13}$ or $C(O)OR_{13}$. In other embodiments, at least one $R_{11}$ is $C(O)OCH_2CH_3$.

(116g) In some embodiments of Formula (Ia) or (Ib), at least one $R_{11}$ is $C(O)NR_{13}R_{14}$ or $NR_{13}R_{14}$. In other embodiments, at least one $R_{11}$ is $C(O)NR_{13}R_{14}$ or $NH_2$.

(116h) In some embodiments of Formula (Ia) or (Ib), at least one $R_{11}$ is ($C_3$-$C_7$) cycloalkyl (e.g., cyclopropyl, cyclobutyl, cyclopentyl, cyclohexyl, or cycloheptyl) optionally substituted with one or more $R_{12}$. In further embodiments, at least one $R_{11}$ is cyclopropyl.

(116i) In some embodiments of Formula (Ia) or (Ib), at least one $R_{11}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more $R_{12}$.

(116j) In some embodiments of Formula (Ia) or (Ib), at least one $R_{11}$ is ($C_6$-$C_{10}$) aryl optionally substituted with one or more $R_{12}$. In further embodiments, at least one $R_{11}$ is phenyl optionally substituted with one or more $R_{12}$.

(116k) In some embodiments of Formula (Ia) or (Ib), at least one $R_{11}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) comprising 1-3 heteroatoms selected from N, O, and S, optionally substituted with one or more $R_{12}$. In other embodiments, at least one $R_{11}$ is heteroaryl comprising a 6-membered ring (e.g., pyridinyl, pyridazinyl, pyrimidinyl, triazinyl, etc.) optionally substituted with one or more $R_{12}$. In other embodiments, at least one $R_{11}$ is pyridinyl optionally substituted with one or more $R_{12}$. In further embodiments, at least one $R_{11}$ is pyridinyl.

(117a) In some embodiments of Formula (Ia) or (Ib), at least one $R_{12}$ is ($C_1$-$C_4$) alkyl (e.g., methyl, ethyl, propyl, i-propyl, or butyl).

(117b) In some embodiments of Formula (Ia) or (Ib), at least one $R_{12}$ is ($C_1$-$C_4$) haloalkyl (e.g., $CH_2F$, $CHF_2$, or $CF_3$) or ($C_1$-$C_4$) haloalkoxy (e.g., $OCH_2F$, $OCHF_2$, or $OCF_3$).

(117c) In some embodiments of Formula (Ia) or (Ib), at least one $R_{12}$ is ($C_1$-$C_4$) alkoxy (e.g., methoxy, ethoxy, propoxy, or butoxy).

(117d) In some embodiments of Formula (Ia) or (Ib), at least one $R_{12}$ is halogen (e.g., F, Cl, Br or I).

(117e) In some embodiments of Formula (Ia) or (Ib), at least one $R_{12}$ is $NO_2$, OH, or CN.

(117f) In some embodiments of Formula (Ia) or (Ib), at least one $R_{12}$ is ($C_3$-$C_7$) cycloalkyl (e.g., cyclopropyl, cyclobutyl, cyclopentyl, cyclohexyl, or cycloheptyl).

(117g) In some embodiments of Formula (Ia) or (Ib), at least one $R_{12}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) comprising 1-3 heteroatoms selected from N, O, and S. In other embodiments, at least one $R_{12}$ is piperidinyl, piperazinyl, or morpholinyl. In further embodiments, at least one $R_{12}$ is morpholinyl.

(117h) In some embodiments of Formula (Ia) or (Ib), at least one $R_{12}$ is ($C_6$-$C_{10}$) aryl optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, $NH(C_1$-$C_4$) alkyl (e.g., methylamino, ethylamino, propylamino, or butylamino), $N((C_1$-$C_4$) alkyl$)_2$ (e.g., dimethylamino, diethylamino, dipropylamino, or dibutylamino), ($C_3$-$C_7$) cycloalkyl (e.g., cyclopropyl, cyclobutyl, cyclopentyl, cyclohexyl, or cycloheptyl), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.).

(117i) In some embodiments of Formula (Ia) or (Ib), $R_{12}$ is heteroaryl comprising one or two 5- to 7-membered rings and 1-4 heteroatoms selected from N, O, and S (e.g., pyrrolyl, pyrazolyl, imidazolyl, triazolyl, oxazolyl, isoxazolyl, oxadiazolyl, dioxazolyl, thiazolyl, isothiazolyl, thiadiazolyl, dithiazolyl, thiophenyl, pyridinyl, pyridazinyl, pyrimidinyl, triazinyl, benzothiazolyl, benzoimidazolyl, benzooxazolyl, quinolinyl, etc.) optionally substituted with one or more substituents independently selected from ($C_1$-$C_4$) alkyl (e.g., methyl, ethyl, propyl, i-propyl, or butyl), ($C_1$-$C_4$) alkoxy (e.g., methoxy, ethoxy, propoxy, or butoxy), ($C_1$-$C_4$) haloalkyl (e.g., $CH_2F$, $CHF_2$, or $CF_3$), ($C_1$-$C_4$) haloalkoxy (e.g., $OCH_2F$, $OCHF_2$, or $OCF_3$), halogen (e.g., F, Cl, Br or I), $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), ($C_3$-$C_7$) cycloalkyl (e.g., cyclopropyl, cyclobutyl, cyclopentyl, cyclohexyl, or cycloheptyl), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.). In other embodiments, at least one $R_{12}$ is heteroaryl comprising a 5-membered ring fused with a 6-membered ring and 1-4 heteroatoms selected from N, O, and S, optionally substituted with one or more substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and ($C_3$-$C_7$) cycloalkyl (e.g., cyclopropyl, cyclobutyl, cyclopentyl, cyclohexyl, or cycloheptyl).

(118a) In some embodiments of Formula (Ia) or (Ib), at least one $R_{13}$ is H.

(118b) In some embodiments of Formula (Ia) or (Ib), at least one $R_{13}$ is ($C_1$-$C_4$) alkyl (e.g., methyl, ethyl, propyl, i-propyl, or butyl) optionally substituted with one or more substituents independently selected from halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.). In other embodiments, at least one $R_{13}$ is methyl, ethyl, or propyl. In other embodiments, at least one $R_{13}$ is ethyl, propyl, or butyl, wherein the ethyl, propyl, and butyl are optionally substituted with one to two substituents independently selected from $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is ethyl, propyl, or butyl, wherein the ethyl, propyl, and butyl are optionally substituted with one to two substituents independently selected from $N((C_1$-$C_4)$ alkyl$)_2$ (e.g., dimethylamino, diethylamino, dipropylamino, or dibutylamino) and heterocycle comprising a 5- to 7-membered ring and 1-3 heteroatoms selected from N, O, and S. In other embodiments, at least one $R_{13}$ is ethyl, propyl, or butyl, wherein the ethyl, propyl, and butyl are optionally substituted with one to two substituents independently selected from dimethylamino and heterocycle comprising a 6-membered ring and 1-3 heteroatoms selected from N, O, and S. In other embodiments, at least one $R_{13}$ is ethyl, propyl, or butyl wherein the ethyl, propyl, and butyl are optionally substituted with one to two substituents independently selected from dimethylamino, morpholinyl, piperidinyl or piperazinyl. In further embodiments, at least one $R_{13}$ is ethyl, propyl, or butyl wherein the ethyl, propyl, and butyl are optionally substituted with dimethylamino or morpholinyl.

(118c) In some embodiments of Formula (Ia) or (Ib), at least one $R_{13}$ is ($C_3$-$C_7$) cycloalkyl (e.g., cyclopropyl, cyclobutyl, cyclopentyl, cyclohexyl, or cycloheptyl).

(118d) In some embodiments of Formula (Ia) or (Ib), at least one $R_{13}$ is heterocyclyl comprising a 5- to 7-membered ring and 1-3 heteroatoms selected from N, O, and S (e.g., pyrrolidinyl, pyrazolidinyl, imidazolidinyl, triazolidinyl, oxazolidinyl, isoxazolidinyl, oxadiazolidinyl, dioxazolidinyl, thiazolidinyl, isothiazolidinyl, thiadiazolidinyl, dithiazolidinyl, piperidinyl, hexahydropyridazinyl, hexahydropyrimidinyl, morpholinyl, dioxanyl, azepinyl, diazepinyl, etc.) optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is heterocycle comprising a 6-membered ring and 1-3 heteroatoms selected from N, O, and S, optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with one or more substituents independently selected from ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), and heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with ($C_1$-$C_4$) alkyl (e.g., methyl, ethyl, propyl, i-propyl, or butyl), halogen (e.g., F, Cl, Br or I), OH, $NH_2$, $NH(C_1$-$C_4)$ alkyl (e.g., methylamino, ethylamino, propylamino, or butylamino), $N((C_1$-$C_4)$ alkyl$)_2$ (e.g., dimethylamino, diethylamino, dipropylamino, or dibutylamino), or heterocycle comprising a 5- to 7-membered ring and 1-3 heteroatoms selected from N, O, and S. In other embodiments, at least one $R_{13}$ is morpholinyl, piperidinyl, or piperazinyl, wherein the morpholinyl, piperidinyl, and piperazinyl are optionally substituted with ($C_1$-$C_4$) alkyl (e.g., methyl, ethyl, propyl, i-propyl, or butyl), $N(($C_1$-$C_4$) alkyl$)_2$ (e.g., dimethylamino, diethylamino, dipropylamino, or dibutylamino), or heterocycle comprising a 6-membered ring and 1-3 heteroatoms selected from N, O, and S. In further embodiments, at least one $R_{13}$ is morpholinyl, piperidinyl, or piperazinyl, wherein the morpholinyl, piperidinyl, and piperazinyl are optionally substituted with methyl, dimethylamino, or morpholinyl.

(119a) In some embodiments of Formula (Ia) or (Ib), at least one $R_{14}$ is H.

(119b) In some embodiments of Formula (Ia) or (Ib), at least one $R_{14}$ is ($C_1$-$C_3$) alkyl (e.g., methyl, ethyl, propyl, or i-propyl).

(120a) In some embodiments of Formula (Ia) or (Ib), m is 0 or 1.

(120b) In some embodiments of Formula (Ia) or (Ib), m is 0.

(120c) In some embodiments of Formula (Ia) or (Ib), m is 1.

(121a) In some embodiments of Formula (Ia) or (Ib), n is 0 or 1.

(121b) In some embodiments of Formula (Ia) or (Ib), n is 0.

(121c) In some embodiments of Formula (Ia) or (Ib), n is 1.

(122a) In some embodiments of Formula (Ia) or (Ib), p is 0, 1, 2, 3, or 4. In other embodiments, p is 0, 1, 2, or 3. In other embodiments, p is 0, 1, or 2.

(122b) In some embodiments of Formula (Ia) or (Ib), p is 0 or 1.

(122c) In some embodiments of Formula (Ia) or (Ib), p is 1 or 2. In other embodiments, p is 2 or 3.

(122d) In some embodiments of Formula (Ia) or (Ib), p is 0. In other embodiments, p is 1. In other embodiments, p is 2. In other embodiments, p is 3. In other embodiments, p is 4.

(123a) In some embodiments of Formula (Ia) or (Ib), q is 0, 1, 2, 3, or 4. In other embodiments, q is 0, 1, 2, or 3. In other embodiments, q is 0, 1, or 2.

(123b) In some embodiments of Formula (Ia) or (Ib), q is 0 or 1.

(123c) In some embodiments of Formula (Ia) or (Ib), q is 1 or 2. In other embodiments, q is 2 or 3.

(123d) In some embodiments of Formula (Ia) or (Ib), q is 0. In other embodiments, q is 1. In other embodiments, q is 2. In other embodiments, q is 3. In other embodiments, q is 4.

(123e) In some embodiments of Formula (Ia) or (Ib), q is 0.

In some embodiments of Formula (Ia) or (Ib), each of the substituents defined for any one of $X_1$, $R_1$, $R_2$, $R_3$, $R_4$, $R_6$, $R_7$, $R_{11}$, $R_{12}$, $R_{13}$, $R_{14}$, $R_{19}$, $R_{20}$, $R_{21}$, $R_{22}$, m, n, p, and q can be combined with any of the substituents defined for the remainder of $X_1$, $R_1$, $R_2$, $R_3$, $R_4$, $R_6$, $R_7$, $R_{11}$, $R_{12}$, $R_{13}$, $R_{14}$, $R_{15}$, $R_{16}$, $R_{18}$, $R_{19}$, $R_{20}$, $R_{21}$, $R_{22}$, m, n, p, and q.

(130) In some embodiments, $R_1$ is as defined in (115a).

(131) In some embodiments, $R_1$ is as defined in (115a) and m is as defined in (120b).

(132) In some embodiments, $R_1$ is as defined in (115a), m is as defined in (120b), and $R_2$ is as defined in (101a).

(133) In some embodiments, $R_1$ is as defined in (115a), m is as defined in (120b), $R_2$ is as defined in (101a), and n is as defined in (121b).

(134) In some embodiments, $R_1$ is as defined in (115a), m is as defined in (120b), $R_2$ is as defined in (101a), n is as defined in (121b), and $R_4$ is as defined in (103a).

(135) In some embodiments, $R_1$ is as defined in (115a), m is as defined in (120b), $R_2$ is as defined in (101a), n is as defined in (121b), and $R_4$ is as defined in (103b).

(136) In some embodiments, $R_1$ is as defined in (115a), m is as defined in (120b), $R_2$ is as defined in (101a), n is as defined in (121b), $R_4$ is as defined in (103b), and $X_1$ is as defined in (104b).

(137) In some embodiments, $R_1$ is as defined in (115a), m is as defined in (120b), $R_2$ is as defined in (101a), n is as defined in (121b), $R_4$ is as defined in (103b), $X_1$ is as defined in (104b), and $R_6$ is as defined in (105a).

(138) In some embodiments, $R_1$ is as defined in (115a), m is as defined in (120b), $R_2$ is as defined in (101a), and n is as defined in (121c).

(139) In some embodiments, $R_1$ is as defined in (115a), m is as defined in (120b), $R_2$ is as defined in (101a), n is as defined in (121c), and $R_4$ is as defined in (103a).

(140) In some embodiments, $R_1$ is as defined in (115a), m is as defined in (120b), $R_2$ is as defined in (101a), n is as defined in (121c), and $R_4$ is as defined in (103b).

(141) In some embodiments, $R_1$ is as defined in (115a), m is as defined in (120b), $R_2$ is as defined in (101a), n is as defined in (121c), $R_4$ is as defined in (103b), and $X_1$ is as defined in (104b).

(142) In some embodiments, $R_1$ is as defined in (115a), m is as defined in (120b), $R_2$ is as defined in (101a), n is as defined in (121c), $R_4$ is as defined in (103b), $X_1$ is as defined in (104b), and $R_6$ is as defined in (105a).

(143) In some embodiments, $R_1$ is as defined in (115a) and m is as defined in (120c).

(144) In some embodiments, $R_1$ is as defined in (115a), m is as defined in (120c), and $R_2$ is as defined in (101a).

(145) In some embodiments, $R_1$ is as defined in (115a), m is as defined in (120c), $R_2$ is as defined in (101a), and $R_3$ is as defined in (102a).

(146) In some embodiments, $R_1$ is as defined in (115a), m is as defined in (120c), $R_2$ is as defined in (101a), $R_3$ is as defined in (102a), and n is as defined in (121b).

(147) In some embodiments, $R_1$ is as defined in (115a), m is as defined in (120c), $R_2$ is as defined in (101a), $R_3$ is as defined in (102a), n is as defined in (121b), and $R_4$ is as defined in (103a).

(148) In some embodiments, $R_1$ is as defined in (115a), m is as defined in (120c), $R_2$ is as defined in (101a), $R_3$ is as defined in (102a), n is as defined in (121b), and $R_4$ is as defined in (103b).

(149) In some embodiments, $R_1$ is as defined in (115a), m is as defined in (120c), $R_2$ is as defined in (101a), $R_3$ is as defined in (102a), n is as defined in (121b), $R_4$ is as defined in (103b), and $X_1$ is as defined in (104b).

(150) In some embodiments, $R_1$ is as defined in (115a), m is as defined in (120c), $R_2$ is as defined in (101a), $R_3$ is as defined in (102a), n is as defined in (121b), $R_4$ is as defined in (103b), $X_1$ is as defined in (104b), and $R_6$ is as defined in (105a).

(151) In some embodiments, $R_1$ is as defined in (115a), m is as defined in (120c), $R_2$ is as defined in (101a), $R_3$ is as defined in (102a), and n is as defined in (121c).

(152) In some embodiments, $R_1$ is as defined in (115a), m is as defined in (120c), $R_2$ is as defined in (101a), $R_3$ is as defined in (102a), n is as defined in (121c), and $R_4$ is as defined in (103a).

(153) In some embodiments, $R_1$ is as defined in (115a), m is as defined in (120c), $R_2$ is as defined in (101a), $R_3$ is as defined in (102a), n is as defined in (121c), and $R_4$ is as defined in (103b).

(154) In some embodiments, $R_1$ is as defined in (115a), m is as defined in (120c), $R_2$ is as defined in (101a), $R_3$ is as defined in (102a), n is as defined in (121c), $R_4$ is as defined in (103b), and $X_1$ is as defined in (104b).

(155) In some embodiments, $R_1$ is as defined in (115a), m is as defined in (120c), $R_2$ is as defined in (101a), $R_3$ is as defined in (102a), n is as defined in (121c), $R_4$ is as defined in (103b), $X_1$ is as defined in (104b), and $R_6$ is as defined in (105a).

(156) In some embodiments, $R_1$ is as defined in (115b).

(157) In some embodiments, $R_1$ is as defined in (115b) and m is as defined in (120b).

(158) In some embodiments, $R_1$ is as defined in (115b), m is as defined in (120b), and $R_2$ is as defined in (101a).

(159) In some embodiments, $R_1$ is as defined in (115b), m is as defined in (120b), $R_2$ is as defined in (101a), and n is as defined in (121b).

(160) In some embodiments, $R_1$ is as defined in (115b), m is as defined in (120b), $R_2$ is as defined in (101a), n is as defined in (121b), and $R_4$ is as defined in (103a).

(161) In some embodiments, $R_1$ is as defined in (115b), m is as defined in (120b), $R_2$ is as defined in (101a), n is as defined in (121b), and $R_4$ is as defined in (103b).

(162) In some embodiments, $R_1$ is as defined in (115b), m is as defined in (120b), $R_2$ is as defined in (101a), n is as defined in (121b), $R_4$ is as defined in (103b), and $X_1$ is as defined in (104b).

(163) In some embodiments, $R_1$ is as defined in (115b), m is as defined in (120b), $R_2$ is as defined in (101a), n is as defined in (121b), $R_4$ is as defined in (103b), $X_1$ is as defined in (104b), and $R_6$ is as defined in (105a).

(164) In some embodiments, $R_1$ is as defined in (115b), m is as defined in (120b), $R_2$ is as defined in (101a), and n is as defined in (121c).

(165) In some embodiments, $R_1$ is as defined in (115b), m is as defined in (120b), $R_2$ is as defined in (101a), n is as defined in (121c), and $R_4$ is as defined in (103a).

(166) In some embodiments, $R_1$ is as defined in (115b), m is as defined in (120b), $R_2$ is as defined in (101a), n is as defined in (121c), and $R_4$ is as defined in (103b).

(167) In some embodiments, $R_1$ is as defined in (115b), m is as defined in (120b), $R_2$ is as defined in (101a), n is as defined in (121c), $R_4$ is as defined in (103b), and $X_1$ is as defined in (104b).

(168) In some embodiments, $R_1$ is as defined in (115b), m is as defined in (120b), $R_2$ is as defined in (101a), n is as defined in (121c), $R_4$ is as defined in (103b), $X_1$ is as defined in (104b), and $R_6$ is as defined in (105a).

(169) In some embodiments, $R_1$ is as defined in (115b) and m is as defined in (120c).

(170) In some embodiments, $R_1$ is as defined in (115b), m is as defined in (120c), and $R_2$ is as defined in (101a).

(171) In some embodiments, $R_1$ is as defined in (115b), m is as defined in (120c), $R_2$ is as defined in (101a), and $R_3$ is as defined in (102a).

(172) In some embodiments, $R_1$ is as defined in (115b), m is as defined in (120c), $R_2$ is as defined in (101a), $R_3$ is as defined in (102a), and n is as defined in (121b).

(173) In some embodiments, $R_1$ is as defined in (115b), m is as defined in (120c), $R_2$ is as defined in (101a), $R_3$ is as defined in (102a), n is as defined in (121b), and $R_4$ is as defined in (103a).

(174) In some embodiments, $R_1$ is as defined in (115b), m is as defined in (120c), $R_2$ is as defined in (101a), $R_3$ is as defined in (102a), n is as defined in (121b), and $R_4$ is as defined in (103b).

(175) In some embodiments, $R_1$ is as defined in (115b), m is as defined in (120c), $R_2$ is as defined in (101a), $R_3$ is as defined in (102a), n is as defined in (121b), $R_4$ is as defined in (103b), and $X_1$ is as defined in (104b).

(176) In some embodiments, $R_1$ is as defined in (115b), m is as defined in (120c), $R_2$ is as defined in (101a), $R_3$ is as defined in (102a), n is as defined in (121b), $R_4$ is as defined in (103b), $X_1$ is as defined in (104b), and $R_6$ is as defined in (105a).

(177) In some embodiments, $R_1$ is as defined in (115b), m is as defined in (120c), $R_2$ is as defined in (101a), $R_3$ is as defined in (102a), and n is as defined in (121c).

(178) In some embodiments, $R_1$ is as defined in (115b), m is as defined in (120c), $R_2$ is as defined in (101a), $R_3$ is as defined in (102a), n is as defined in (121c), and $R_4$ is as defined in (103a).

(179) In some embodiments, $R_1$ is as defined in (115b), m is as defined in (120c), $R_2$ is as defined in (101a), $R_3$ is as defined in (102a), n is as defined in (121c), and $R_4$ is as defined in (103b).

(180) In some embodiments, $R_1$ is as defined in (115b), m is as defined in (120c), $R_2$ is as defined in (101a), $R_3$ is as defined in (102a), n is as defined in (121c), $R_4$ is as defined in (103b), and $X_1$ is as defined in (104b).

(181) In some embodiments, $R_1$ is as defined in (115b), m is as defined in (120c), $R_2$ is as defined in (101a), $R_3$ is as defined in (102a), n is as defined in (121c), $R_4$ is as defined in (103b), $X_1$ is as defined in (104b), and $R_6$ is as defined in (105a).

(182) In some embodiments, $R_1$, $R_2$, $R_3$, $R_4$, $R_6$, $X_1$, m, and/or n are as defined in any of (130)-(181), and q is as defined in (123b).

(183) In some embodiments, $R_1$, $R_2$, $R_3$, $R_4$, $R_6$, $X_1$, m, and/or n are as defined in any of (130)-(181), and q is as defined in (123e).

(184) In some embodiments, $R_1$, $R_2$, $R_3$, $R_4$, $R_6$, $X_1$, m, and/or n are as defined in any of (134)-(137), and q is as defined in (123b).

(185) In some embodiments, $R_1$, $R_2$, $R_3$, $R_4$, $R_6$, $X_1$, m, and/or n are as defined in any of (134)-(137), and q is as defined in (123e).

(186) In some embodiments, $R_1$, $R_2$, $R_3$, $R_4$, $R_6$, $X_1$, m, and/or n are as defined in any of (139)-(142), and q is as defined in (123b).

(187) In some embodiments, $R_1$, $R_2$, $R_3$, $R_4$, $R_6$, $X_1$, m, and/or n are as defined in any of (139)-(142), and q is as defined in (123e).

(188) In some embodiments, $R_1$, $R_2$, $R_3$, $R_4$, $R_6$, $X_1$, m, and/or n are as defined in (137) or (142), and q is as defined in (123b).

(189) In some embodiments, $R_1$, $R_2$, $R_3$, $R_4$, $R_6$, $X_1$, m, and/or n are as defined in (137) or (142), and q is as defined in (123e).

(190) In some embodiments, $R_1$, $R_2$, $R_3$, $R_4$, $R_6$, $X_1$, m, and/or n are as defined in any of (147)-(150), and q is as defined in (123b).

(191) In some embodiments, $R_1$, $R_2$, $R_3$, $R_4$, $R_6$, $X_1$, m, and/or n are as defined in any of (147)-(150), and q is as defined in (123e).

(192) In some embodiments, $R_1$, $R_2$, $R_3$, $R_4$, $R_6$, $X_1$, m, and/or n are as defined in any of (152)-(155), and q is as defined in (123b).

(193) In some embodiments, $R_1$, $R_2$, $R_3$, $R_4$, $R_6$, $X_1$, m, and/or n are as defined in any of (152)-(155), and q is as defined in (123e).

(194) In some embodiments, $R_1$, $R_2$, $R_3$, $R_4$, $R_6$, $X_1$, m, and/or n are as defined in (150) or (155), and q is as defined in (123b).

(195) In some embodiments, $R_1$, $R_2$, $R_3$, $R_4$, $R_6$, $X_1$, m, and/or n are as defined in (150) or (155), and q is as defined in (123e).

(196) In some embodiments, $R_1$, $R_2$, $R_3$, $R_4$, $R_6$, $X_1$, m, and/or n are as defined in any of (160)-(163), and q is as defined in (123b).

(197) In some embodiments, $R_1$, $R_2$, $R_3$, $R_4$, $R_6$, $X_1$, m, and/or n are as defined in any of (160)-(163), and q is as defined in (123e).

(198) In some embodiments, $R_1$, $R_2$, $R_3$, $R_4$, $R_6$, $X_1$, m, and/or n are as defined in any of (165)-(168), and q is as defined in (123b).

(199) In some embodiments, $R_1$, $R_2$, $R_3$, $R_4$, $R_6$, $X_1$, m, and/or n are as defined in any of (165)-(168), and q is as defined in (123e).

(200) In some embodiments, $R_1$, $R_2$, $R_3$, $R_4$, $R_6$, $X_1$, m, and/or n are as defined in (163) or (168), and q is as defined in (123b).

(201) In some embodiments, $R_1$, $R_2$, $R_3$, $R_4$, $R_6$, $X_1$, m, and/or n are as defined in (163) or (168), and q is as defined in (123e).

(202) In some embodiments, $R_1$, $R_2$, $R_3$, $R_4$, $R_6$, $X_1$, m, and/or n are as defined in any of (173)-(176), and q is as defined in (123b).

(203) In some embodiments, $R_1$, $R_2$, $R_3$, $R_4$, $R_6$, $X_1$, m, and/or n are as defined in any of (173)-(176), and q is as defined in (123e).

(204) In some embodiments, $R_1$, $R_2$, $R_3$, $R_4$, $R_6$, $X_1$, m, and/or n are as defined in any of (178)-(181), and q is as defined in (123b).

(205) In some embodiments, $R_1$, $R_2$, $R_3$, $R_4$, $R_6$, $X_1$, m, and/or n are as defined in any of (178)-(181), and q is as defined in (123e).

(206) In some embodiments, $R_1$, $R_2$, $R_3$, $R_4$, $R_6$, $X_1$, m, and/or n are as defined in (176) or (181), and q is as defined in (123b).

(207) In some embodiments, $R_1$, $R_2$, $R_3$, $R_4$, $R_6$, $X_1$, m, and/or n are as defined in (176) or (181), and q is as defined in (123e).

Non-limiting illustrative compounds of the disclosure include:

| Compound Number | Structure | Compound Name |
| --- | --- | --- |
| I-1 | 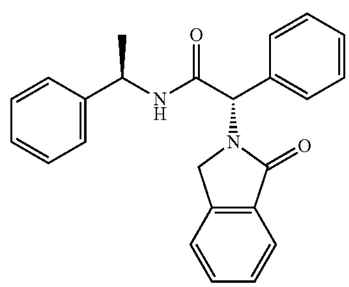 [SMILES: C[C@@H](NC(=O)[C@H](c1ccccc1)N1Cc2ccccc2C1=O)c1ccccc1] | (S)-2-(1-oxoisoindolin-2-yl)-2-phenyl-N-((R)-1-phenylethyl)acetamide |
| I-2 | 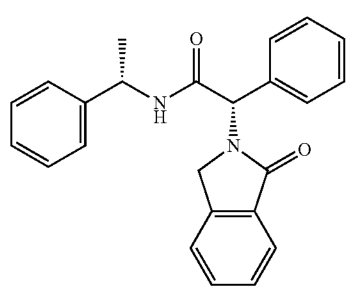 [SMILES: C[C@H](NC(=O)[C@H](c1ccccc1)N1Cc2ccccc2C1=O)c1ccccc1] | (S)-2-(1-oxoisoindolin-2-yl)-2-phenyl-N-((S)-1-phenylethyl)acetamide |
| I-3 | 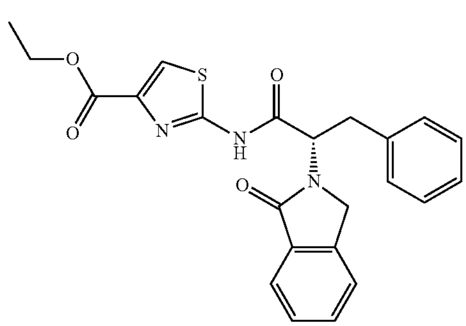 [SMILES: CCOC(=O)c1csc(NC(=O)[C@H](Cc2ccccc2)N2Cc3ccccc3C2=O)n1] | ethyl (S)-2-(2-(1-oxoisoindolin-2-yl)-3-phenylpropanamido)thiazole-4-carboxylate |

-continued

| Compound Number | Structure | Compound Name |
| --- | --- | --- |
| I-4 | 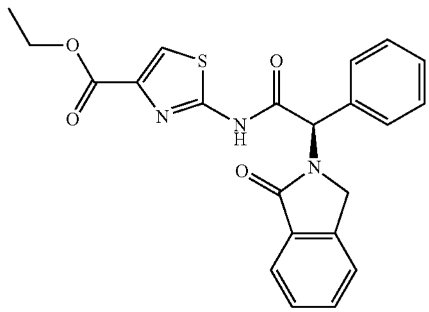 [SMILES: CCOC(=O)c1csc(NC(=O)[C@@H](c2ccccc2)N2Cc3ccccc3C2=O)n1] | ethyl (R)-2-(2-(1-oxoisoindolin-2-yl)-2-phenylacetamido)thiazole-4-carboxylate |
| I-5 | 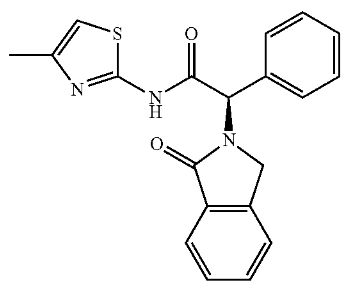 [SMILES: Cc1csc(NC(=O)[C@@H](c2ccccc2)N2Cc3ccccc3C2=O)n1] | (R)-N-(4-methylthiazol-2-yl)-2-(1-oxoisoindolin-2-yl)-2-phenylacetamide |
| I-6 | 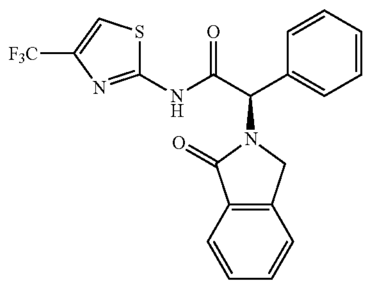 [SMILES: O=C(Nc1nc(C(F)(F)F)cs1)[C@@H](c1ccccc1)N1Cc2ccccc2C1=O] | (R)-2-(1-oxoisoindolin-2-yl)-2-phenyl-N-(4-(trifluoromethyl)thiazol-2-yl)acetamide |
| I-7 | 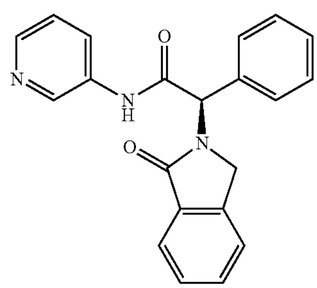 [SMILES: O=C(Nc1cccnc1)[C@@H](c1ccccc1)N1Cc2ccccc2C1=O] | (R)-2-(1-oxoisoindolin-2-yl)-2-phenyl-N-(pyridin-3-yl)acetamide |
| I-8 | 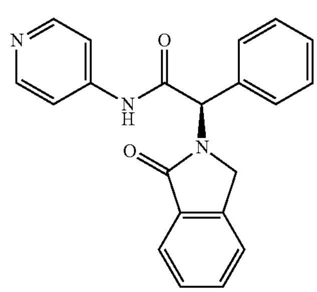 [SMILES: O=C(Nc1ccncc1)[C@@H](c1ccccc1)N1Cc2ccccc2C1=O] | (R)-2-(1-oxoisoindolin-2-yl)-2-phenyl-N-(pyridin-4-yl)acetamide |

-continued

| Compound Number | Structure | Compound Name |
|---|---|---|
| I-9 | 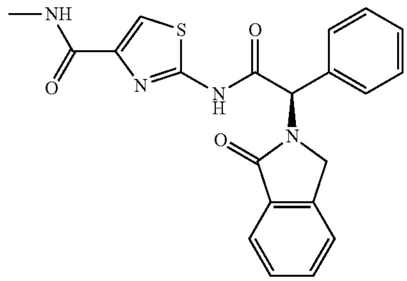 [SMILES: CNC(=O)c1csc(NC(=O)[C@@H](c2ccccc2)N2Cc3ccccc3C2=O)n1] | (R)-N-methyl-2-(2-(1-oxoisoindolin-2-yl)-2-phenylacetamido)thiazole-4-carboxamide |
| I-10 | 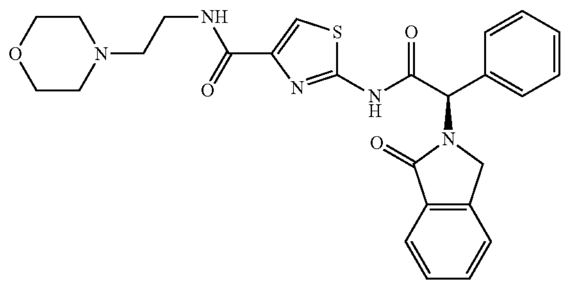 [SMILES: O=C(NCCN1CCOCC1)c1csc(NC(=O)[C@@H](c2ccccc2)N2Cc3ccccc3C2=O)n1] | (R)-N-(2-morpholinoethyl)-2-(2-(1-oxoisoindolin-2-yl)-2-phenylacetamido)thiazole-4-carboxamide |
| I-11 | 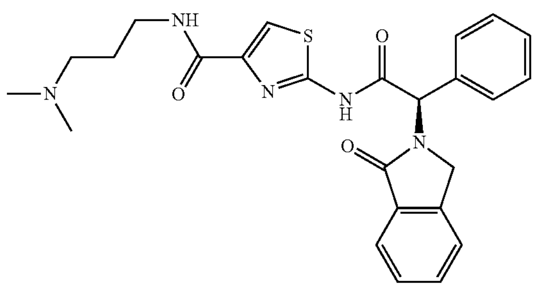 [SMILES: CN(C)CCCNC(=O)c1csc(NC(=O)[C@@H](c2ccccc2)N2Cc3ccccc3C2=O)n1] | (R)-N-(3-(dimethylamino)propyl)-2-(2-(1-oxoisoindolin-2-yl)-2-phenylacetamido)thiazole-4-carboxamide |
| I-12 | 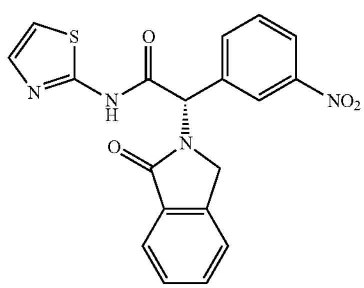 [SMILES: O=C(Nc1nccs1)[C@H](c1cccc([N+](=O)[O-])c1)N1Cc2ccccc2C1=O] | (S)-2-(3-nitrophenyl)-2-(1-oxoisoindolin-2-yl)-N-(thiazol-2-yl)acetamide |
| I-13 | 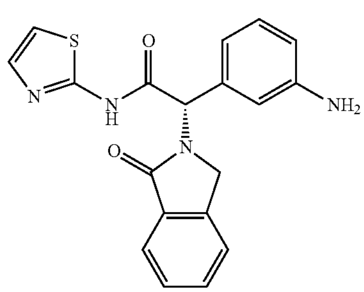 | (S)-2-(3-aminophenyl)-2-(1-oxoisoindolin-2-yl)-N-(thiazol-2-yl)acetamide |

-continued

| Compound Number | Structure | Compound Name |
|---|---|---|
| I-14 | 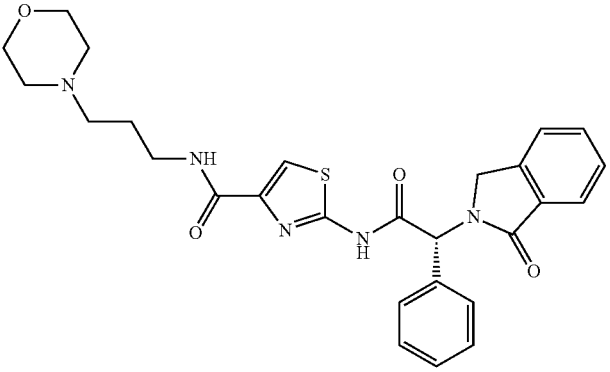 [SMILES: O=C(NCCCN1CCOCC1)c1csc(NC(=O)[C@@H](c2ccccc2)N2Cc3ccccc3C2=O)n1] | (R)-N-(3-morpholinopropyl)-2-(2-(1-oxoisoindolin-2-yl)-2-phenylacetamido)thiazole-4-carboxamide |
| I-15 | 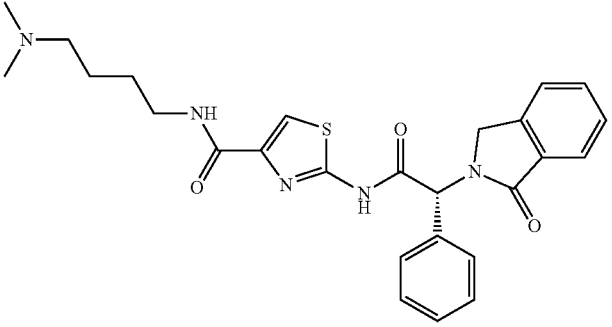 [SMILES: CN(C)CCCCNC(=O)c1csc(NC(=O)[C@@H](c2ccccc2)N2Cc3ccccc3C2=O)n1] | (R)-N-(4-(dimethylamino)butyl)-2-(2-(1-oxoisoindolin-2-yl)-2-phenylacetamido)thiazole-4-carboxamide |
| I-16 | 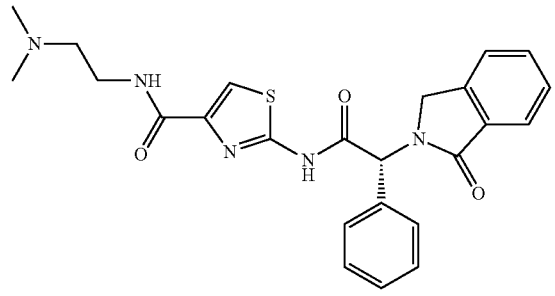 [SMILES: CN(C)CCNC(=O)c1csc(NC(=O)[C@@H](c2ccccc2)N2Cc3ccccc3C2=O)n1] | (R)-N-(2-(dimethylamino)ethyl)-2-(2-(1-oxoisoindolin-2-yl)-2-phenylacetamido)thiazole-4-carboxamide |
| I-17 | 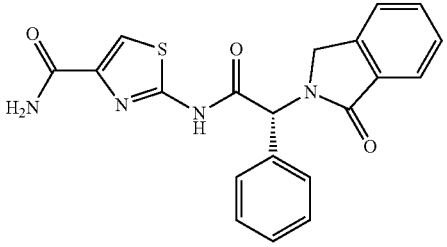 [SMILES: NC(=O)c1csc(NC(=O)[C@@H](c2ccccc2)N2Cc3ccccc3C2=O)n1] | (R)-2-(2-(1-oxoisoindolin-2-yl)-2-phenylacetamido)thiazole-4-carboxamide |
| I-18 | 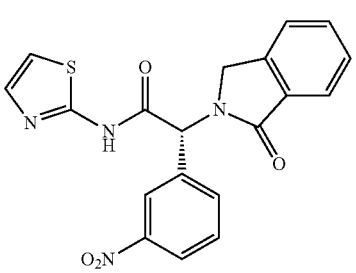 | (R)-2-(3-nitrophenyl)-2-(1-oxoisoindolin-2-yl)-N-(thiazol-2-yl)acetamide |

-continued

| Compound Number | Structure | Compound Name |
| --- | --- | --- |
| I-19 | 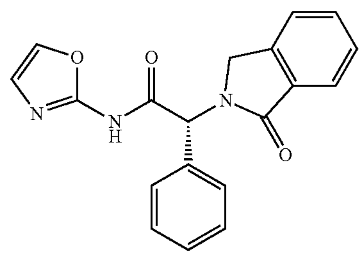 [SMILES: O=C(Nc1ncco1)[C@@H](c1ccccc1)N1Cc2ccccc2C1=O] | (R)-N-(oxazol-2-yl)-2-(1-oxoisoindolin-2-yl)-2-phenylacetamide |
| I-20 | 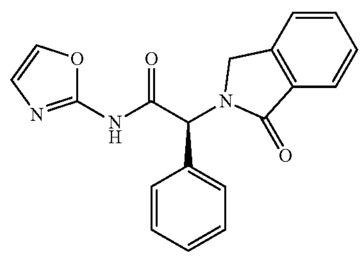 [SMILES: O=C(Nc1ncco1)[C@H](c1ccccc1)N1Cc2ccccc2C1=O] | (S)-N-(oxazol-2-yl)-2-(1-oxoisoindolin-2-yl)-2-phenylacetamide |
| I-21 | 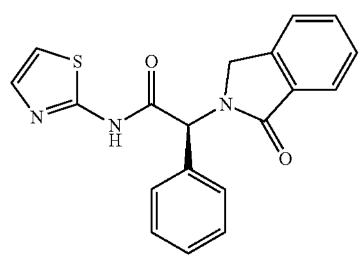 | (S)-2-(1-oxoisoindolin-2-yl)-2-phenyl-N-(thiazol-2-yl)acetamide |
| I-22 | 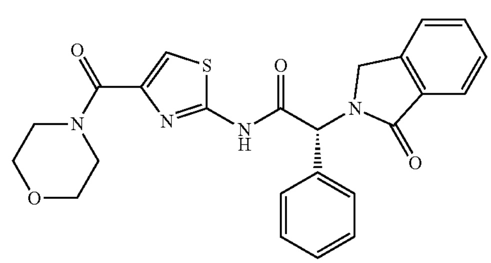 | (R)-N-(4-(morpholine-4-carbonyl)thiazol-2-yl)-2-(1-oxoisoindolin-2-yl)-2-phenylacetamide |
| I-23 | 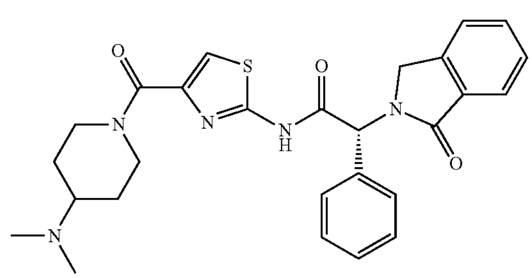 [SMILES: CN(C)C1CCN(C(=O)c2csc(NC(=O)[C@@H](c3ccccc3)N3Cc4ccccc4C3=O)n2)CC1] | (R)-N-(4-(4-(dimethylamino)piperidine-1-carbonyl)thiazol-2-yl)-2-(1-oxoisoindolin-2-yl)-2-phenylacetamide |

| Compound Number | Structure | Compound Name |
|---|---|---|
| I-24 | 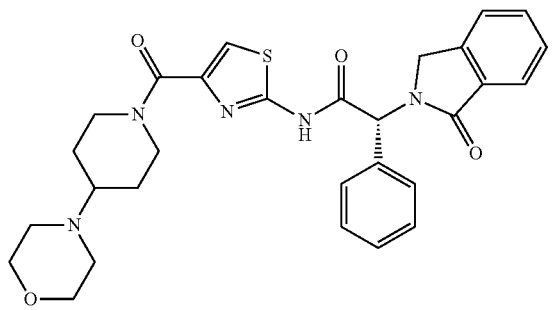 [SMILES: O=C(Nc1nc(C(=O)N2CCC(N3CCOCC3)CC2)cs1)[C@@H](c1ccccc1)N1Cc2ccccc2C1=O] | (R)-N-(4-(4-morpholinopiperidine-1-carbonyl)thiazol-2-yl)-2-(1-oxoisoindolin-2-yl)-2-phenylacetamide |
| I-25 | 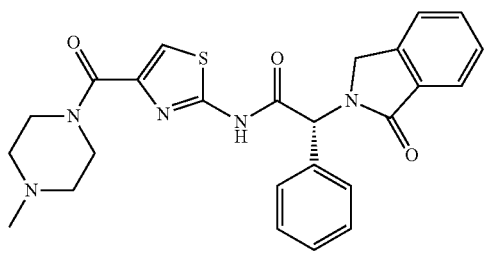 [SMILES: CN1CCN(C(=O)c2csc(NC(=O)[C@@H](c3ccccc3)N3Cc4ccccc4C3=O)n2)CC1] | (R)-N-(4-(4-methylpiperazine-1-carbonyl)thiazol-2-yl)-2-(1-oxoisoindolin-2-yl)-2-phenylacetamide |
| I-26 | 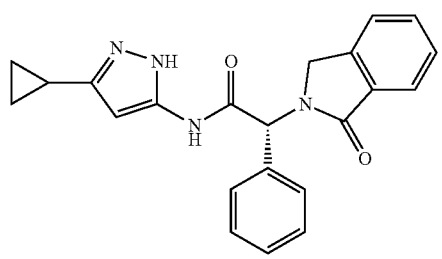 [SMILES: O=C(Nc1cc(C2CC2)n[nH]1)[C@@H](c1ccccc1)N1Cc2ccccc2C1=O] | (R)-N-(3-cyclopropyl-1H-pyrazol-5-yl)-2-(1-oxoisoindolin-2-yl)-2-phenylacetamide |
| I-27 | 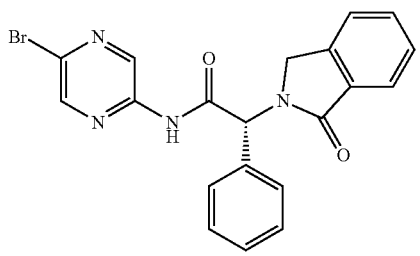 [SMILES: O=C(Nc1cnc(Br)cn1)[C@@H](c1ccccc1)N1Cc2ccccc2C1=O] | (R)-N-(5-bromopyrazin-2-yl)-2-(1-oxoisoindolin-2-yl)-2-phenylacetamide |
| I-28 | 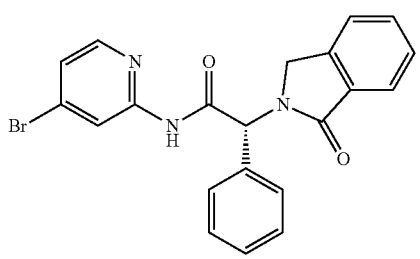 [SMILES: O=C(Nc1cc(Br)ccn1)[C@@H](c1ccccc1)N1Cc2ccccc2C1=O] | (R)-N-(4-bromopyridin-2-yl)-2-(1-oxoisoindolin-2-yl)-2-phenylacetamide |

| Compound Number | Structure | Compound Name |
|---|---|---|
| I-29 | 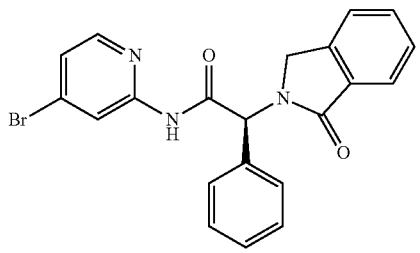 [SMILES: O=C(Nc1cc(Br)ccn1)[C@H](c1ccccc1)N1Cc2ccccc2C1=O] | (S)-N-(4-bromopyridin-2-yl)-2-(1-oxoisoindolin-2-yl)-2-phenylacetamide |
| I-30 | 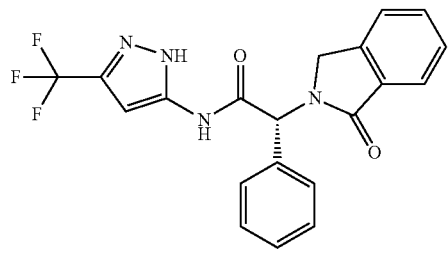 [SMILES: O=C(Nc1cc(C(F)(F)F)n[nH]1)[C@@H](c1ccccc1)N1Cc2ccccc2C1=O] | (R)-2-(1-oxoisoindolin-2-yl)-2-phenyl-N-(3-(trifluoromethyl)-1H-pyrazol-5-yl)acetamide |
| I-31 | 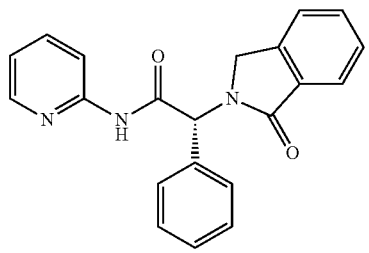 [SMILES: O=C(Nc1ccccn1)[C@@H](c1ccccc1)N1Cc2ccccc2C1=O] | (R)-2-(1-oxoisoindolin-2-yl)-2-phenyl-N-(pyridin-2-yl)acetamide |
| I-32 | 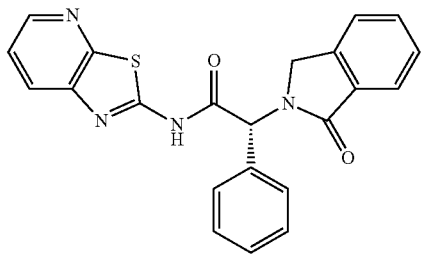 [SMILES: O=C(Nc1nc2cccnc2s1)[C@@H](c1ccccc1)N1Cc2ccccc2C1=O] | (R)-2-(1-oxoisoindolin-2-yl)-2-phenyl-N-(thiazolo[5,4-b]pyridin-2-yl)acetamide |
| I-33 | 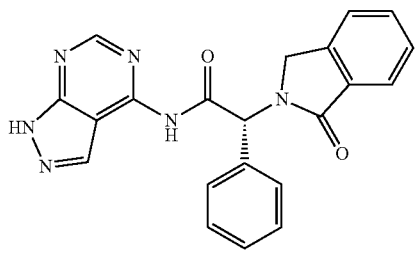 [SMILES: O=C(Nc1ncnc2[nH]ncc12)[C@@H](c1ccccc1)N1Cc2ccccc2C1=O] | (R)-2-(1-oxoisoindolin-2-yl)-2-phenyl-N-(1H-pyrazolo[3,4-d]pyrimidin-4-yl)acetamide |

-continued
| Compound Number | Structure | Compound Name |
|---|---|---|
| I-34 | 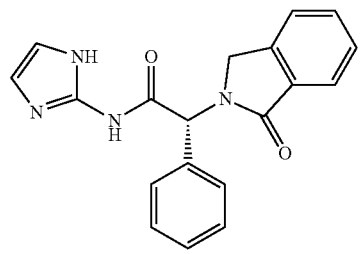 [SMILES: O=C(Nc1ncc[nH]1)[C@@H](c1ccccc1)N1Cc2ccccc2C1=O] | (R)-N-(1H-imidazol-2-yl)-2-(1-oxoisoindolin-2-yl)-2-phenylacetamide |
| I-35 | 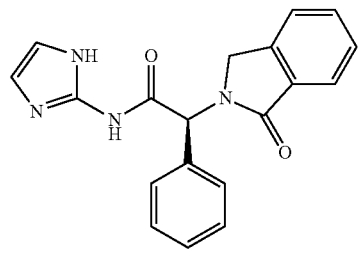 | (S)-N-(1H-imidazol-2-yl)-2-(1-oxoisoindolin-2-yl)-2-phenylacetamide |
| I-36 | 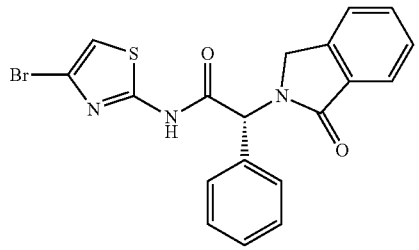 [SMILES: O=C(Nc1nc(Br)cs1)[C@@H](c1ccccc1)N1Cc2ccccc2C1=O] | (R)-N-(4-bromothiazol-2-yl)-2-(1-oxoisoindolin-2-yl)-2-phenylacetamide |
| I-37 | 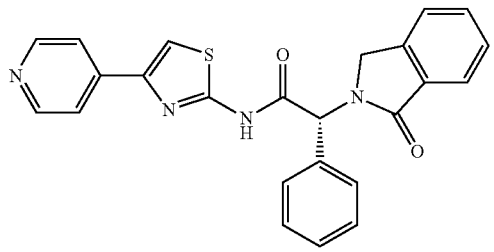 [SMILES: O=C(Nc1nc(-c2ccncc2)cs1)[C@@H](c1ccccc1)N1Cc2ccccc2C1=O] | (R)-2-(1-oxoisoindolin-2-yl)-2-phenyl-N-(4-(pyridin-4-yl)thiazol-2-yl)acetamide |
| I-38 | 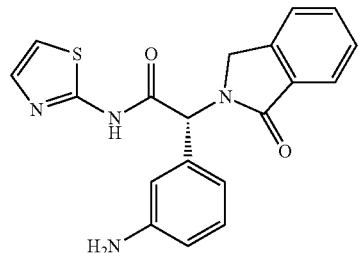 | (R)-2-(3-aminophenyl)-2-(1-oxoisoindolin-2-yl)-N-(thiazol-2-yl)acetamide |

| Compound Number | Structure | Compound Name |
|---|---|---|
| I-39 | 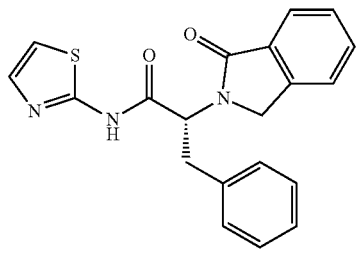 [SMILES: O=C(Nc1nccs1)[C@@H](Cc1ccccc1)N1Cc2ccccc2C1=O] | (R)-2-(1-oxoisoindolin-2-yl)-3-phenyl-N-(thiazol-2-yl)propanamide |
| I-40 | 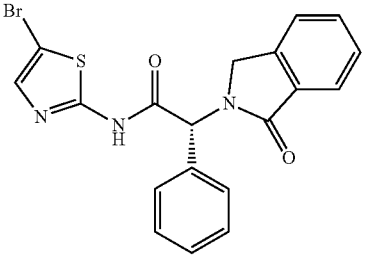 [SMILES: O=C(Nc1ncc(Br)s1)[C@@H](c1ccccc1)N1Cc2ccccc2C1=O] | (R)-N-(5-bromothiazol-2-yl)-2-(1-oxoisoindolin-2-yl)-2-phenylacetamide |
| I-41 | 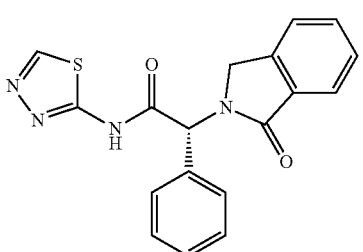 | (R)-2-(1-oxoisoindolin-2-yl)-2-phenyl-N-(1,3,4-thiadiazol-2-yl)acetamide |
| I-42 | 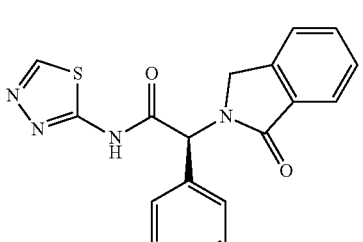 | (S)-2-(1-oxoisoindolin-2-yl)-2-phenyl-N-(1,3,4-thiadiazol-2-yl)acetamide |
| I-43 | 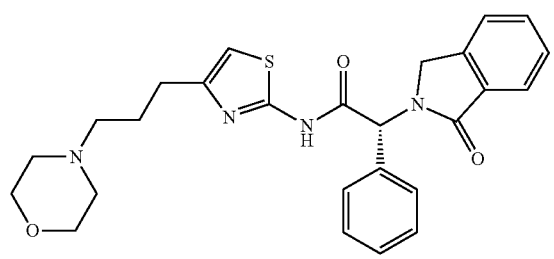 [SMILES: O=C(Nc1nc(CCCN2CCOCC2)cs1)[C@@H](c1ccccc1)N1Cc2ccccc2C1=O] | (R)-N-(4-(3-morpholinopropyl)thiazol-2-yl)-2-(1-oxoisoindolin-2-yl)-2-phenylacetamide |

| Compound Number | Structure | Compound Name |
|---|---|---|
| I-44 | 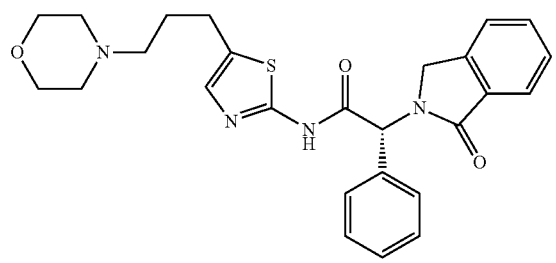 [SMILES: O=C(Nc1ncc(CCCN2CCOCC2)s1)[C@@H](c1ccccc1)N1Cc2ccccc2C1=O] | (R)-N-(5-(3-morpholinopropyl)thiazol-2-yl)-2-(1-oxoisoindolin-2-yl)-2-phenylacetamide |
| I-45 | 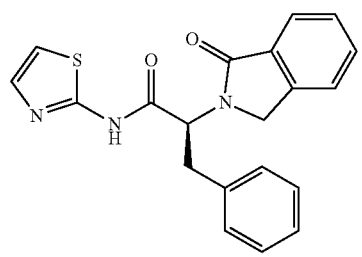 [SMILES: O=C(Nc1nccs1)[C@H](Cc1ccccc1)N1Cc2ccccc2C1=O] | (S)-2-(1-oxoisoindolin-2-yl)-3-phenyl-N-(thiazol-2-yl)propanamide |
| I-46 | 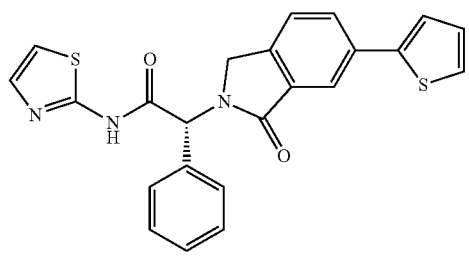 [SMILES: O=C(Nc1nccs1)[C@@H](c1ccccc1)N1Cc2ccc(-c3cccs3)cc2C1=O] | (R)-2-(1-oxo-6-(thiophen-2-yl)isoindolin-2-yl)-2-phenyl-N-(thiazol-2-yl)acetamide |
| I-47 | 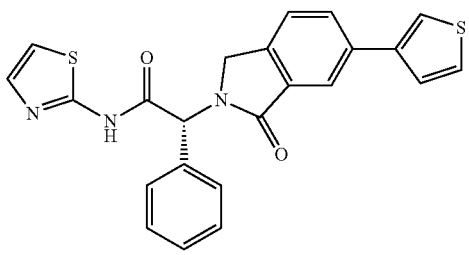 [SMILES: O=C(Nc1nccs1)[C@@H](c1ccccc1)N1Cc2ccc(-c3ccsc3)cc2C1=O] | (R)-2-(1-oxo-6-(thiophen-3-yl)isoindolin-2-yl)-2-phenyl-N-(thiazol-2-yl)acetamide |
| I-48 | 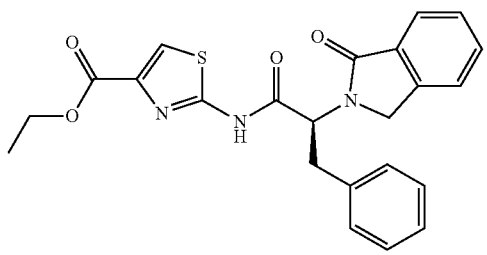 [SMILES: CCOC(=O)c1csc(NC(=O)[C@H](Cc2ccccc2)N2Cc3ccccc3C2=O)n1] | ethyl (S)-2-(2-(1-oxoisoindolin-2-yl)-3-phenylpropanamido)thiazole-4-carboxylate |

-continued
| Compound Number | Structure | Compound Name |
|---|---|---|
| I-49 | 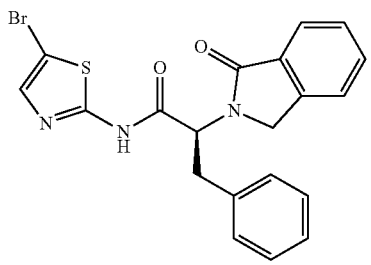 [SMILES: O=C(Nc1ncc(Br)s1)[C@H](Cc1ccccc1)N1Cc2ccccc2C1=O] | (S)-N-(5-bromothiazol-2-yl)-2-(1-oxoisoindolin-2-yl)-3-phenylpropanamide |
| I-50 | 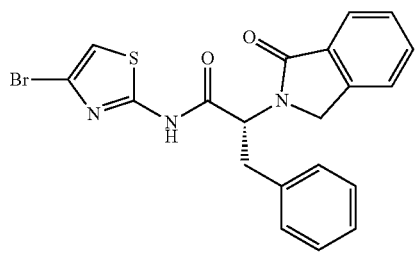 [SMILES: O=C(Nc1nc(Br)cs1)[C@@H](Cc1ccccc1)N1Cc2ccccc2C1=O] | (R)-N-(4-bromothiazol-2-yl)-2-(1-oxoisoindolin-2-yl)-3-phenylpropanamide |
| I-51 | 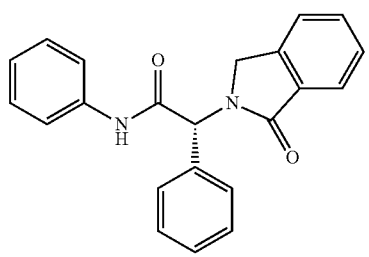 [SMILES: O=C(Nc1ccccc1)[C@@H](c1ccccc1)N1Cc2ccccc2C1=O] | (R)-2-(1-oxoisoindolin-2-yl)-N,2-diphenylacetamide |
| I-52 | 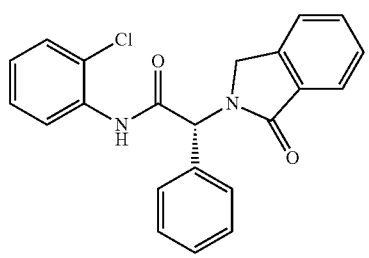 [SMILES: O=C(Nc1ccccc1Cl)[C@@H](c1ccccc1)N1Cc2ccccc2C1=O] | (R)-N-(2-chlorophenyl)-2-(1-oxoisoindolin-2-yl)-2-phenylacetamide |
| I-53 | 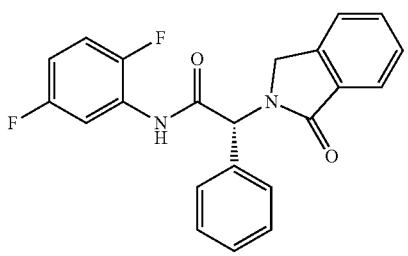 [SMILES: O=C(Nc1cc(F)ccc1F)[C@@H](c1ccccc1)N1Cc2ccccc2C1=O] | (R)-N-(2,5-difluorophenyl)-2-(1-oxoisoindolin-2-yl)-2-phenylacetamide |

-continued

| Compound Number | Structure | Compound Name |
|---|---|---|
| I-54 | 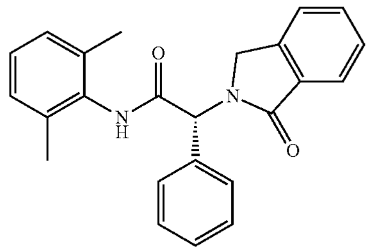 [SMILES: Cc1cccc(C)c1NC(=O)[C@@H](c1ccccc1)N1Cc2ccccc2C1=O] | (R)-N-(2,6-dimethylphenyl)-2-(1-oxoisoindolin-2-yl)-2-phenylacetamide |
| I-55 | 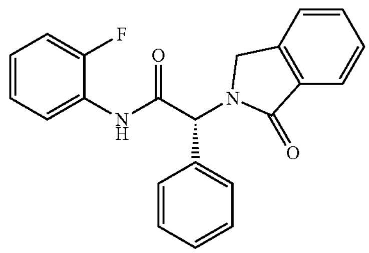 [SMILES: O=C(Nc1ccccc1F)[C@@H](c1ccccc1)N1Cc2ccccc2C1=O] | (R)-N-(2-fluorophenyl)-2-(1-oxoisoindolin-2-yl)-2-phenylacetamide |
| I-56 | 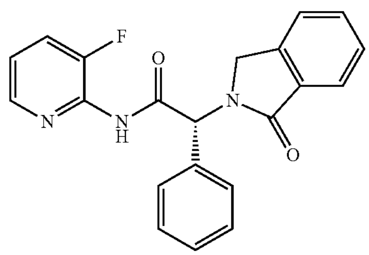 [SMILES: O=C(Nc1ncccc1F)[C@@H](c1ccccc1)N1Cc2ccccc2C1=O] | (R)-N-(3-fluoropyridin-2-yl)-2-(1-oxoisoindolin-2-yl)-2-phenylacetamide |
| I-57 | 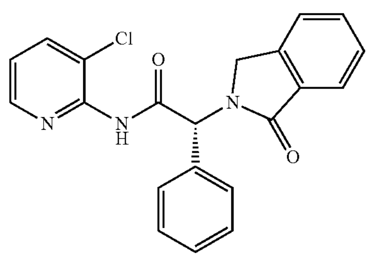 | (R)-N-(3-chloropyridin-2-yl)-2-(1-oxoisoindolin-2-yl)-2-phenylacetamide |
| I-58 | 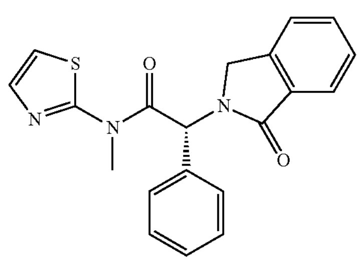 [SMILES: CN(C(=O)[C@@H](c1ccccc1)N1Cc2ccccc2C1=O)c1nccs1] | (R)-N-methyl-2-(1-oxoisoindolin-2-yl)-2-phenyl-N-(thiazol-2-yl)acetamide |
| I-59 | 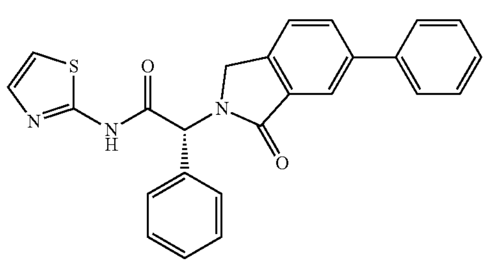 [SMILES: O=C(Nc1nccs1)[C@@H](c1ccccc1)N1Cc2ccc(-c3ccccc3)cc2C1=O] | (R)-2-(1-oxo-6-phenylisoindolin-2-yl)-2-phenyl-N-(thiazol-2-yl)acetamide |

| Compound Number | Structure | Compound Name |
|---|---|---|
| I-60 | 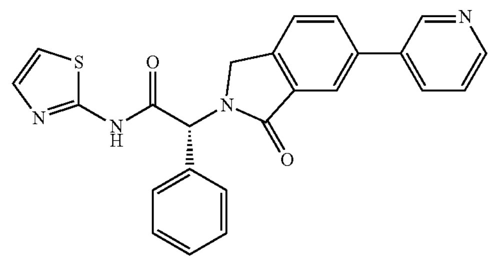 [SMILES: O=C(Nc1nccs1)[C@@H](c1ccccc1)N1Cc2ccc(-c3cccnc3)cc2C1=O] | (R)-2-(1-oxo-6-(pyridin-3-yl)isoindolin-2-yl)-2-phenyl-N-(thiazol-2-yl)acetamide |
| I-61 | 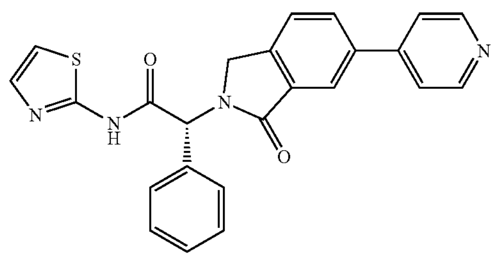 [SMILES: O=C(Nc1nccs1)[C@@H](c1ccccc1)N1Cc2ccc(-c3ccncc3)cc2C1=O] | (R)-2-(1-oxo-6-(pyridin-4-yl)isoindolin-2-yl)-2-phenyl-N-(thiazol-2-yl)acetamide |
| I-62 | 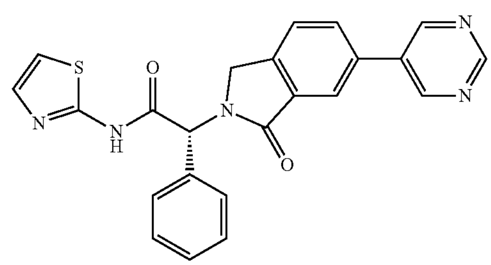 [SMILES: O=C(Nc1nccs1)[C@@H](c1ccccc1)N1Cc2ccc(-c3cncnc3)cc2C1=O] | (R)-2-(1-oxo-6-(pyrimidin-5-yl)isoindolin-2-yl)-2-phenyl-N-(thiazol-2-yl)acetamide |
| I-63 | 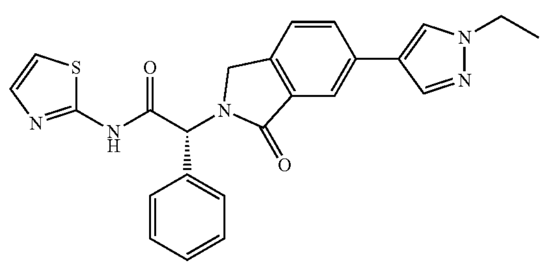 [SMILES: CCn1cc(-c2ccc3c(c2)C(=O)N([C@@H](C(=O)Nc2nccs2)c2ccccc2)C3)cn1] | (R)-2-(6-(1-ethyl-1H-pyrazol-4-yl)-1-oxoisoindolin-2-yl)-2-phenyl-N-(thiazol-2-yl)acetamide |
| I-64 | 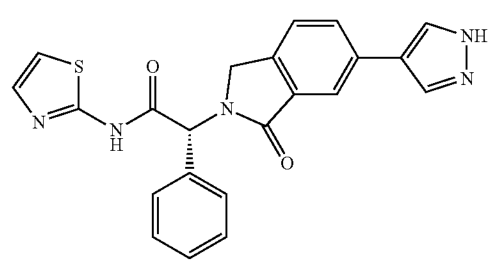 [SMILES: O=C(Nc1nccs1)[C@@H](c1ccccc1)N1Cc2ccc(-c3cn[nH]c3)cc2C1=O] | (R)-2-(1-oxo-6-(1H-pyrazol-4-yl)isoindolin-2-yl)-2-phenyl-N-(thiazol-2-yl)acetamide |

-continued

| Compound Number | Structure | Compound Name |
|---|---|---|
| I-65 | 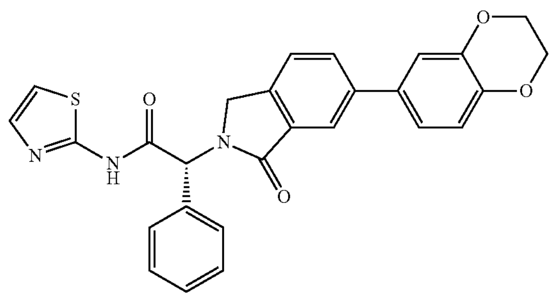 [SMILES: O=C(Nc1nccs1)[C@@H](c1ccccc1)N1Cc2ccc(-c3ccc4c(c3)OCCO4)cc2C1=O] | (R)-2-(6-(2,3-dihydrobenzo[b][1,4]dioxin-6-yl)-1-oxoisoindolin-2-yl)-2-phenyl-N-(thiazol-2-yl)acetamide |
| I-66 | 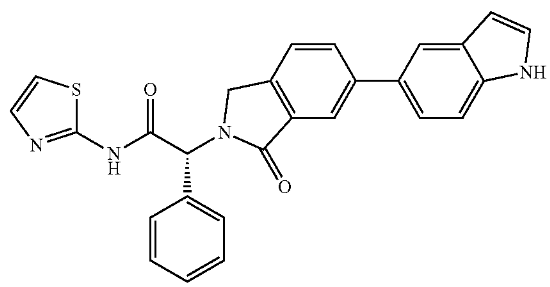 [SMILES: O=C(Nc1nccs1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-2-phenyl-N-(thiazol-2-yl)acetamide |
| I-67 | 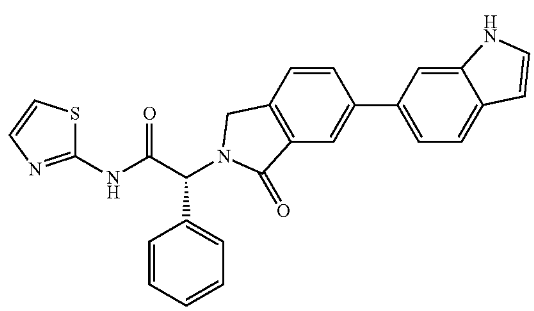 [SMILES: O=C(Nc1nccs1)[C@@H](c1ccccc1)N1Cc2ccc(-c3ccc4cc[nH]c4c3)cc2C1=O] | (R)-2-(6-(1H-indol-6-yl)-1-oxoisoindolin-2-yl)-2-phenyl-N-(thiazol-2-yl)acetamide |
| I-68 | 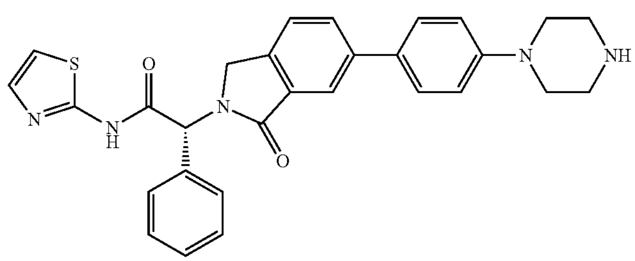 [SMILES: O=C(Nc1nccs1)[C@@H](c1ccccc1)N1Cc2ccc(-c3ccc(N4CCNCC4)cc3)cc2C1=O] | (R)-2-(1-oxo-6-(4-(piperazin-1-yl)phenyl)isoindolin-2-yl)-2-phenyl-N-(thiazol-2-yl)acetamide |
| I-69 | 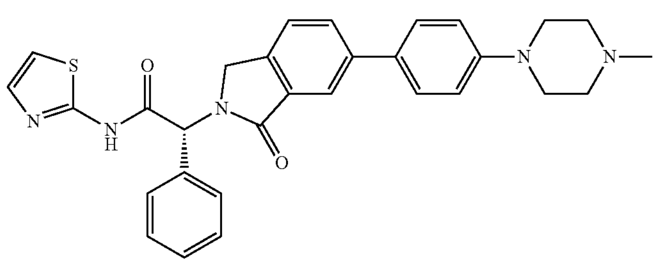 [SMILES: CN1CCN(c2ccc(-c3ccc4c(c3)C(=O)N([C@@H](C(=O)Nc3nccs3)c3ccccc3)C4)cc2)CC1] | (R)-2-(6-(4-(4-methylpiperazin-1-yl)phenyl)-1-oxoisoindolin-2-yl)-2-phenyl-N-(thiazol-2-yl)acetamide |

| Compound Number | Structure | Compound Name |
|---|---|---|
| I-70 | 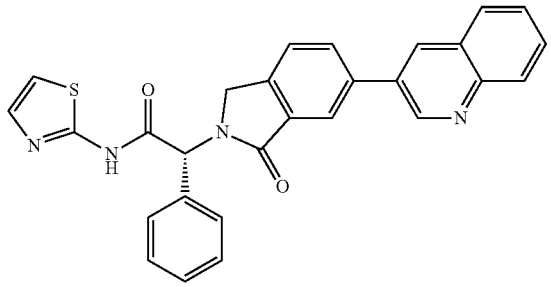 [SMILES: O=C(Nc1nccs1)[C@@H](c1ccccc1)N1Cc2ccc(-c3cnc4ccccc4c3)cc2C1=O] | (R)-2-(1-oxo-6-(quinolin-3-yl)isoindolin-2-yl)-2-phenyl-N-(thiazol-2-yl)acetamide |
| I-71 | 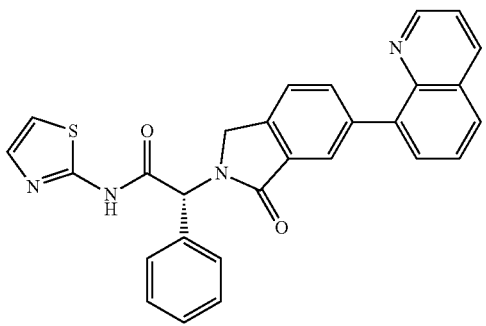 [SMILES: O=C(Nc1nccs1)[C@@H](c1ccccc1)N1Cc2ccc(-c3cccc4cccnc34)cc2C1=O] | (R)-2-(1-oxo-6-(quinolin-8-yl)isoindolin-2-yl)-2-phenyl-N-(thiazol-2-yl)acetamide |
| I-72 | 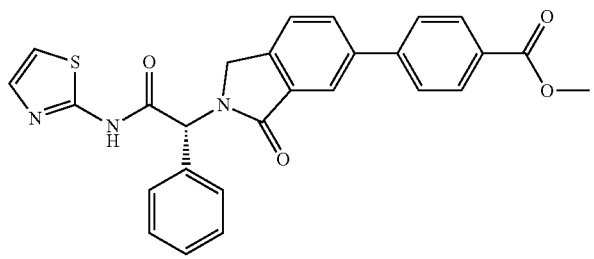 [SMILES: COC(=O)c1ccc(-c2ccc3c(c2)C(=O)N([C@@H](C(=O)Nc2nccs2)c2ccccc2)C3)cc1] | methyl (R)-4-(3-oxo-2-(2-oxo-1-phenyl-2-(thiazol-2-ylamino)ethyl)isoindolin-5-yl)benzoate |
| I-73 | 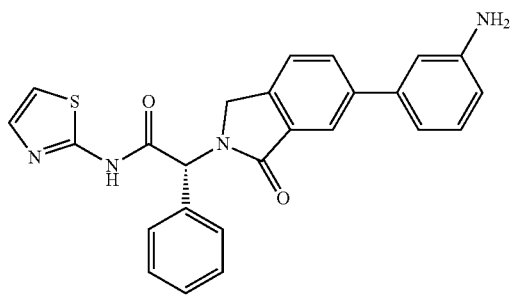 [SMILES: Nc1cccc(-c2ccc3c(c2)C(=O)N([C@@H](C(=O)Nc2nccs2)c2ccccc2)C3)c1] | (R)-2-(6-(3-aminophenyl)-1-oxoisoindolin-2-yl)-2-phenyl-N-(thiazol-2-yl)acetamide |
| I-74 | 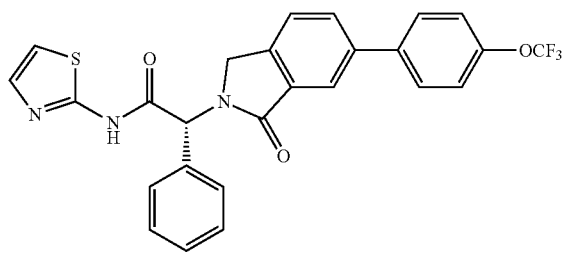 [SMILES: O=C(Nc1nccs1)[C@@H](c1ccccc1)N1Cc2ccc(-c3ccc(OC(F)(F)F)cc3)cc2C1=O] | (R)-2-(1-oxo-6-(4-(trifluoromethoxy)phenyl)isoindolin-2-yl)-2-phenyl-N-(thiazol-2-yl)acetamide |

| Compound Number | Structure | Compound Name |
|---|---|---|
| I-75 | 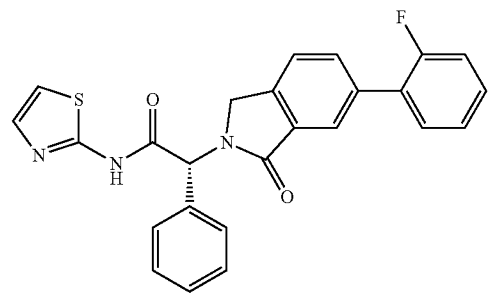 [SMILES: O=C(Nc1nccs1)[C@@H](c1ccccc1)N1Cc2ccc(-c3ccccc3F)cc2C1=O] | (R)-2-(6-(2-fluorophenyl)-1-oxoisoindolin-2-yl)-2-phenyl-N-(thiazol-2-yl)acetamide |
| I-76 | 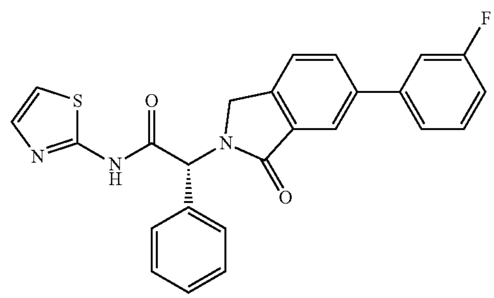 [SMILES: O=C(Nc1nccs1)[C@@H](c1ccccc1)N1Cc2ccc(-c3cccc(F)c3)cc2C1=O] | (R)-2-(6-(3-fluorophenyl)-1-oxoisoindolin-2-yl)-2-phenyl-N-(thiazol-2-yl)acetamide |
| I-77 | 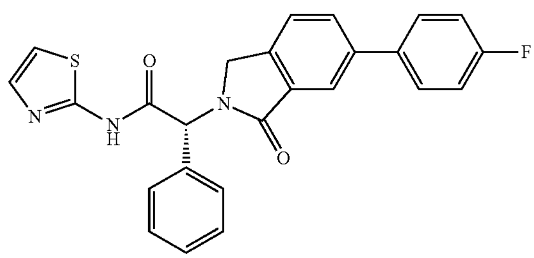 [SMILES: O=C(Nc1nccs1)[C@@H](c1ccccc1)N1Cc2ccc(-c3ccc(F)cc3)cc2C1=O] | (R)-2-(6-(4-fluorophenyl)-1-oxoisoindolin-2-yl)-2-phenyl-N-(thiazol-2-yl)acetamide |
| I-78 | 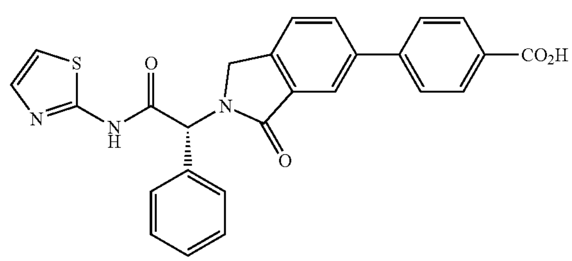 [SMILES: O=C(O)c1ccc(-c2ccc3c(c2)C(=O)N([C@@H](C(=O)Nc2nccs2)c2ccccc2)C3)cc1] | (R)-4-(3-oxo-2-(2-oxo-1-phenyl-2-(thiazol-2-ylamino)ethyl)isoindolin-5-yl)benzoic acid |
| I-79 | 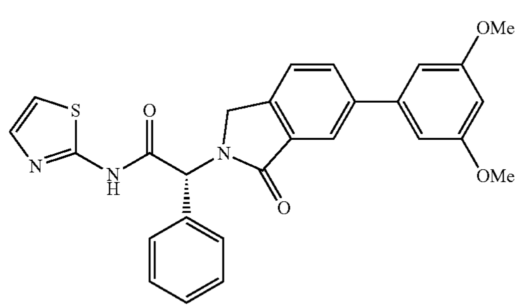 [SMILES: COc1cc(OC)cc(-c2ccc3c(c2)C(=O)N([C@@H](C(=O)Nc2nccs2)c2ccccc2)C3)c1] | (R)-2-(6-(3,5-dimethoxyphenyl)-1-oxoisoindolin-2-yl)-2-phenyl-N-(thiazol-2-yl)acetamide |

| Compound Number | Structure | Compound Name |
|---|---|---|
| I-80 | 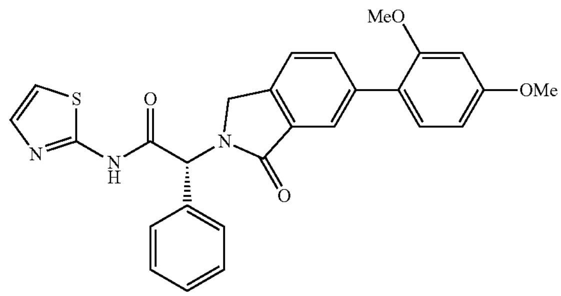 [SMILES: COc1ccc(-c2ccc3c(c2)C(=O)N([C@@H](C(=O)Nc2nccs2)c2ccccc2)C3)c(OC)c1] | (R)-2-(6-(2,4-dimethoxyphenyl)-1-oxoisoindolin-2-yl)-2-phenyl-N-(thiazol-2-yl)acetamide |
| I-81 | 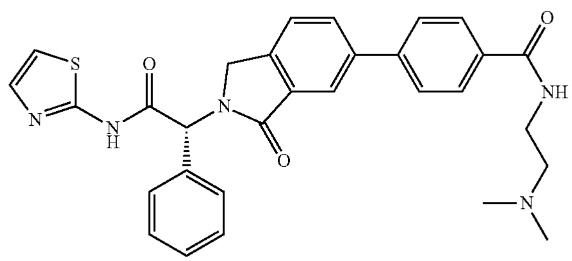 [SMILES: CN(C)CCNC(=O)c1ccc(-c2ccc3c(c2)C(=O)N([C@@H](C(=O)Nc2nccs2)c2ccccc2)C3)cc1] | (R)-N-(2-(dimethylamino)ethyl)-4-(3-oxo-2-(2-oxo-1-phenyl-2-(thiazol-2-ylamino)ethyl)isoindolin-5-yl)benzamide |
| I-82 | 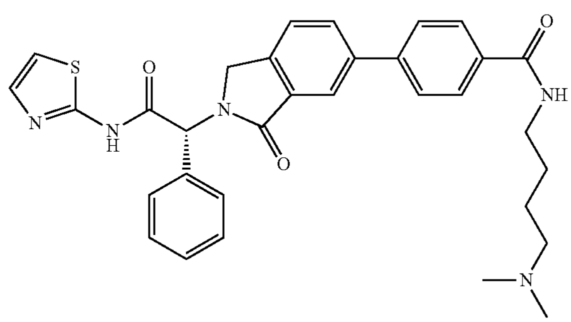 [SMILES: CN(C)CCCCNC(=O)c1ccc(-c2ccc3c(c2)C(=O)N([C@@H](C(=O)Nc2nccs2)c2ccccc2)C3)cc1] | (R)-N-(4-(dimethylamino)butyl)-4-(3-oxo-2-(2-oxo-1-phenyl-2-(thiazol-2-ylamino)ethyl)isoindolin-5-yl)benzamide |
| I-83 | 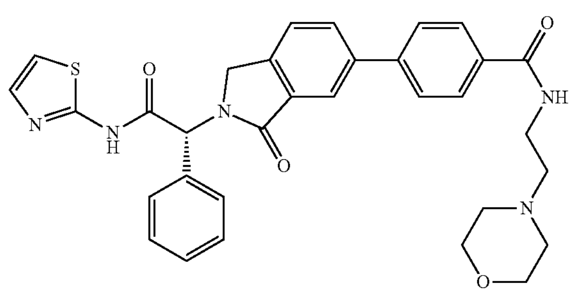 [SMILES: O=C(NCCN1CCOCC1)c1ccc(-c2ccc3c(c2)C(=O)N([C@@H](C(=O)Nc2nccs2)c2ccccc2)C3)cc1] | (R)-N-(2-morpholinoethyl)-4-(3-oxo-2-(2-oxo-1-phenyl-2-(thiazol-2-ylamino)ethyl)isoindolin-5-yl)benzamide |
| I-84 | 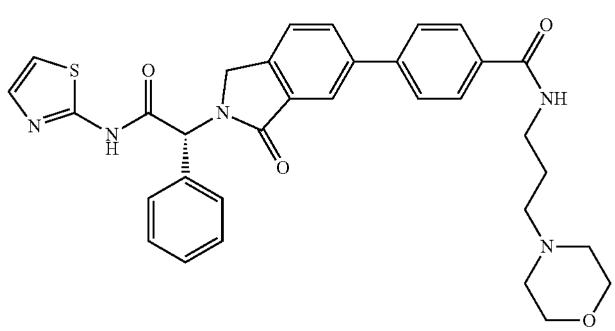 [SMILES: O=C(NCCCN1CCOCC1)c1ccc(-c2ccc3c(c2)C(=O)N([C@@H](C(=O)Nc2nccs2)c2ccccc2)C3)cc1] | (R)-N-(3-morpholinopropyl)-4-(3-oxo-2-(2-oxo-1-phenyl-2-(thiazol-2-ylamino)ethyl)isoindolin-5-yl)benzamide |

| Compound Number | Structure | Compound Name |
|---|---|---|
| I-85 | 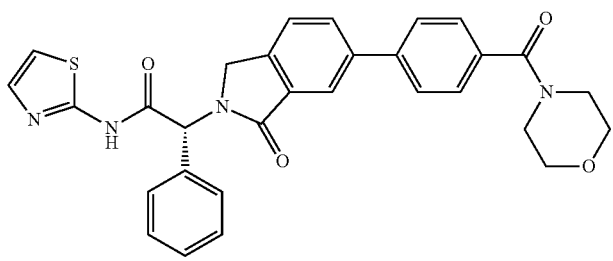 [SMILES: O=C(Nc1nccs1)[C@@H](c1ccccc1)N1Cc2ccc(-c3ccc(C(=O)N4CCOCC4)cc3)cc2C1=O] | (R)-2-(6-(4-(morpholine-4-carbonyl)phenyl)-1-oxoisoindolin-2-yl)-2-phenyl-N-(thiazol-2-yl)acetamide |
| I-86 | 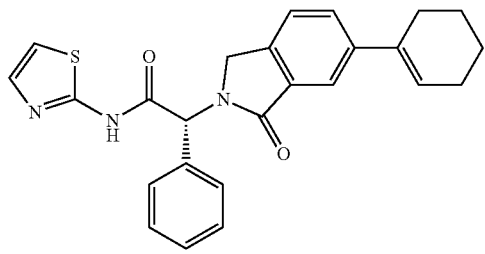 [SMILES: O=C(Nc1nccs1)[C@@H](c1ccccc1)N1Cc2ccc(C3=CCCCC3)cc2C1=O] | (R)-2-(6-(cyclohex-1-en-1-yl)-1-oxoisoindolin-2-yl)-2-phenyl-N-(thiazol-2-yl)acetamide |
| I-87 | 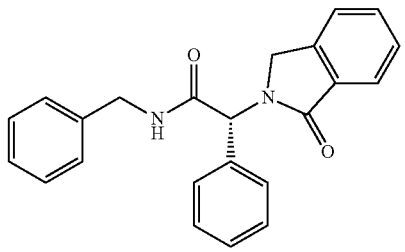 [SMILES: O=C(NCc1ccccc1)[C@@H](c1ccccc1)N1Cc2ccccc2C1=O] | (R)-N-benzyl-2-(1-oxoisoindolin-2-yl)-2-phenylacetamide |
| I-88 | 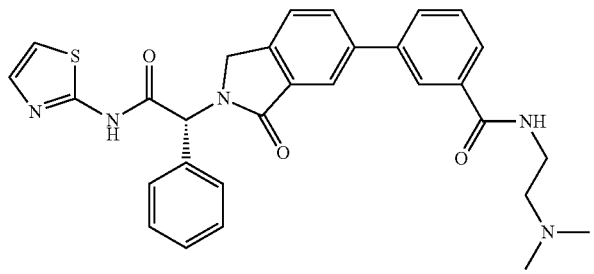 [SMILES: CN(C)CCNC(=O)c1cccc(-c2ccc3c(c2)C(=O)N([C@@H](C(=O)Nc2nccs2)c2ccccc2)C3)c1] | (R)-N-(2-(dimethylamino)ethyl)-3-(3-oxo-2-(2-oxo-1-phenyl-2-(thiazol-2-ylamino)ethyl)isoindolin-5-yl)benzamide |
| I-89 | 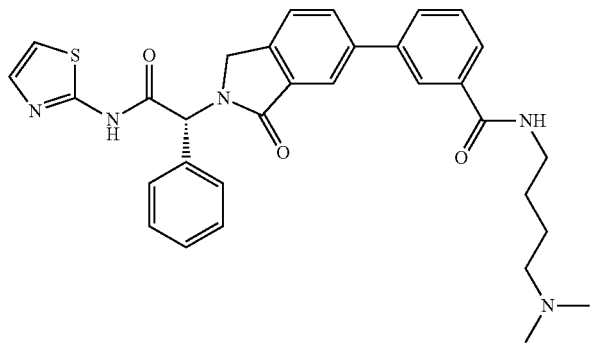 [SMILES: CN(C)CCCCNC(=O)c1cccc(-c2ccc3c(c2)C(=O)N([C@@H](C(=O)Nc2nccs2)c2ccccc2)C3)c1] | (R)-N-(4-(dimethylamino)butyl)-(3-oxo-2-(2-oxo-1-phenyl-2-(thiazol-2-ylamino)ethyl)isoindolin-5-yl)benzamide |

| Compound Number | Structure | Compound Name |
|---|---|---|
| I-90 | 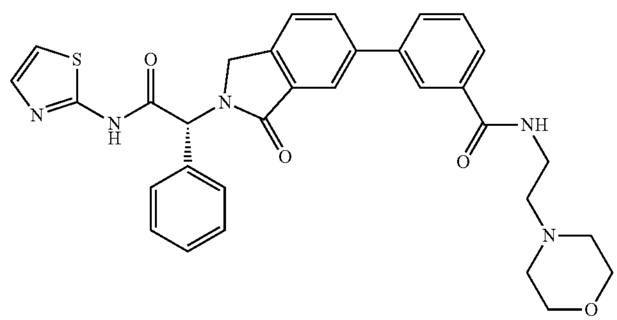 [SMILES: O=C(NCCN1CCOCC1)c1cccc(-c2ccc3c(c2)C(=O)N([C@@H](C(=O)Nc2nccs2)c2ccccc2)C3)c1] | (R)-N-(2-morpholinoethyl)-3-(3-oxo-2-(2-oxo-1-phenyl-2-(thiazol-2-ylamino)ethyl)isoindolin-5-yl)benzamide |
| I-91 | 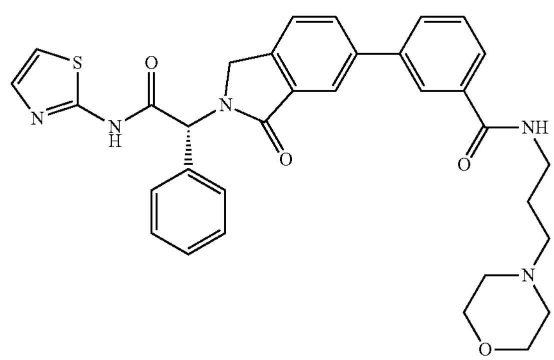 [SMILES: O=C(NCCCN1CCOCC1)c1cccc(-c2ccc3c(c2)C(=O)N([C@@H](C(=O)Nc2nccs2)c2ccccc2)C3)c1] | (R)-N-(3-morpholinopropyl)-3-(3-oxo-2-(2-oxo-1-phenyl-2-(thiazol-2-ylamino)ethyl)isoindolin-5-yl)benzamide |
| I-92 | 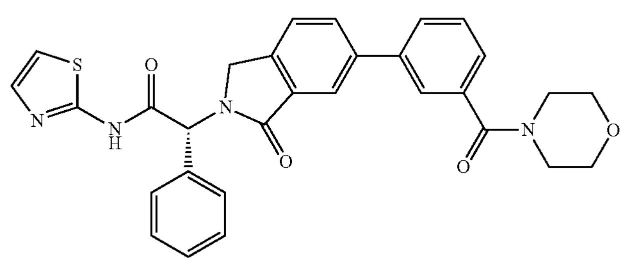 [SMILES: O=C(Nc1nccs1)[C@@H](c1ccccc1)N1Cc2ccc(-c3cccc(C(=O)N4CCOCC4)c3)cc2C1=O] | (R)-2-(6-(3-(morpholine-4-carbonyl)phenyl)-1-oxoisoindolin-2-yl)-2-phenyl-N-(thiazol-2-yl)acetamide |
| I-93 | 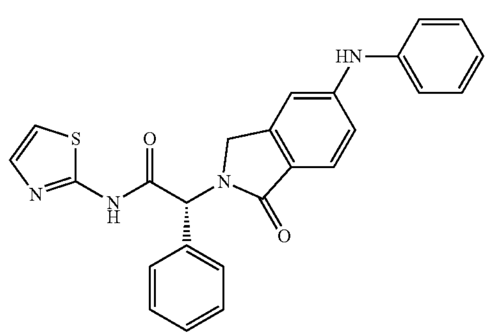 [SMILES: O=C(Nc1nccs1)[C@@H](c1ccccc1)N1Cc2cc(Nc3ccccc3)ccc2C1=O] | (R)-2-(1-oxo-5-(phenylamino)isoindolin-2-yl)-2-phenyl-N-(thiazol-2-yl)acetamide |

| Compound Number | Structure | Compound Name |
|---|---|---|
| I-94 | 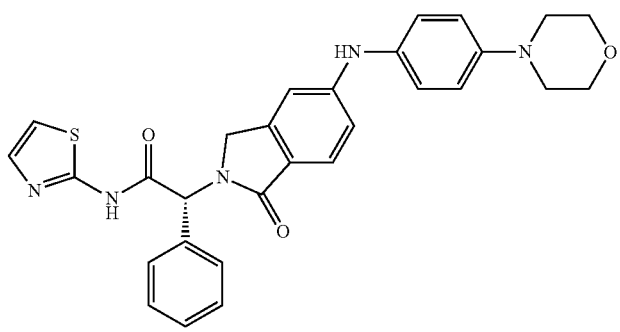 [SMILES: O=C(Nc1nccs1)[C@@H](c1ccccc1)N1Cc2cc(Nc3ccc(N4CCOCC4)cc3)ccc2C1=O] | (R)-2-(5-((4-morpholinophenyl)amino)-1-oxoisoindolin-2-yl)-2-phenyl-(thiazol-2-yl)acetamide |
| I-95 | 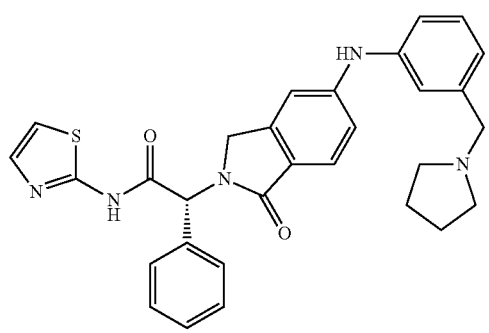 [SMILES: O=C(Nc1nccs1)[C@@H](c1ccccc1)N1Cc2cc(Nc3cccc(CN4CCCC4)c3)ccc2C1=O] | (R)-2-(1-oxo-5-((3-(pyrrolidin-1-ylmethyl)phenyl)amino)isoindolin-2-yl)-2-phenyl-N-(thiazol-2-yl)acetamide |
| I-96 | 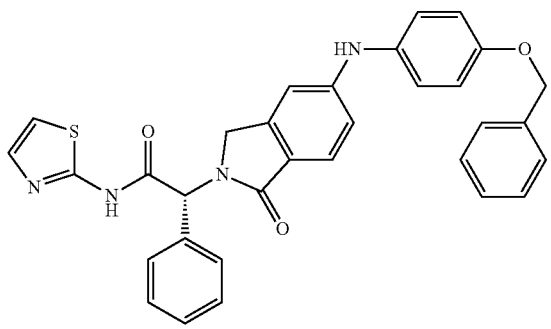 [SMILES: O=C(Nc1nccs1)[C@@H](c1ccccc1)N1Cc2cc(Nc3ccc(OCc4ccccc4)cc3)ccc2C1=O] | (R)-2-(5-((4-(benzyloxy)phenyl)amino)-1-oxoisoindolin-2-yl)-2-phenyl-N-(thiazol-2-yl)acetamide |
| I-97 | 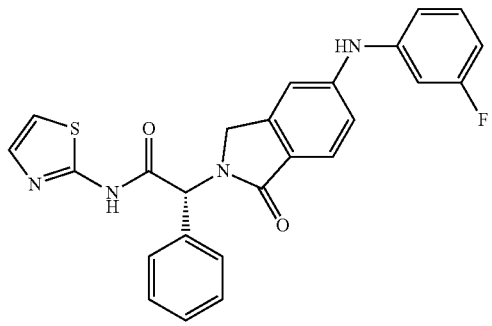 [SMILES: O=C(Nc1nccs1)[C@@H](c1ccccc1)N1Cc2cc(Nc3cccc(F)c3)ccc2C1=O] | (R)-2-(5-((3-fluorophenyl)amino)-1-oxoisoindolin-2-yl)-2-phenyl-N-(thiazol-2-yl)acetamide |

-continued

| Compound Number | Structure | Compound Name |
|---|---|---|
| I-98 | 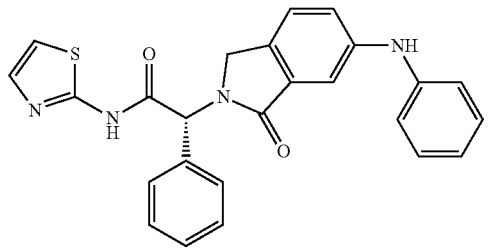 [SMILES: O=C(Nc1nccs1)[C@@H](c1ccccc1)N1Cc2ccc(Nc3ccccc3)cc2C1=O] | (R)-2-(1-oxo-6-(phenylamino)isoindolin-2-yl)-2-phenyl-N-(thiazol-2-yl)acetamide |
| I-99 | 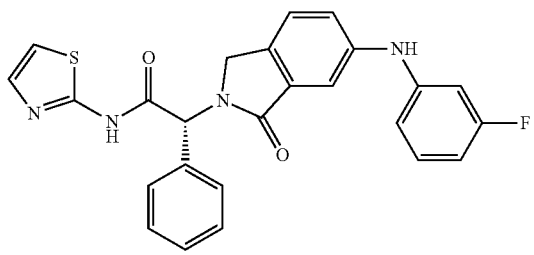 [SMILES: O=C(Nc1nccs1)[C@@H](c1ccccc1)N1Cc2ccc(Nc3cccc(F)c3)cc2C1=O] | (R)-2-(6-((3-fluorophenyl)amino)-1-oxoisoindolin-2-yl)-2-phenyl-N-(thiazol-2-yl)acetamide |
| I-100 | 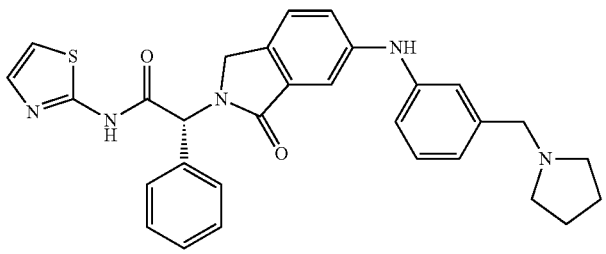 [SMILES: O=C(Nc1nccs1)[C@@H](c1ccccc1)N1Cc2ccc(Nc3cccc(CN4CCCC4)c3)cc2C1=O] | (R)-2-(1-oxo-6-((3-(pyrrolidin-1-ylmethyl)phenyl)amino)isoindolin-2-yl)-2-phenyl-N-(thiazol-2-yl)acetamide |
| I-101 | 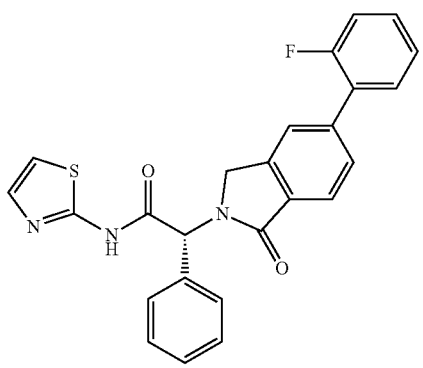 [SMILES: O=C(Nc1nccs1)[C@@H](c1ccccc1)N1Cc2cc(-c3ccccc3F)ccc2C1=O] | (R)-2-(5-(2-fluorophenyl)-1-oxoisoindolin-2-yl)-2-phenyl-N-(thiazol-2-yl)acetamide |
| I-102 | 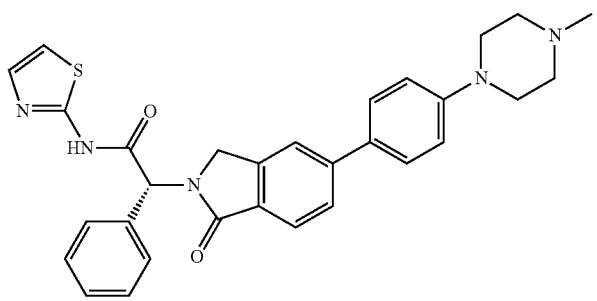 [SMILES: CN1CCN(c2ccc(-c3ccc4c(c3)CN([C@@H](C(=O)Nc3nccs3)c3ccccc3)C4=O)cc2)CC1] | (R)-2-(5-(4-(4-methylpiperazin-1-yl)phenyl)-1-oxoisoindolin-2-yl)-2-phenyl-N-(thiazol-2-yl)acetamide |

| Compound Number | Structure | Compound Name |
|---|---|---|
| I-103 | 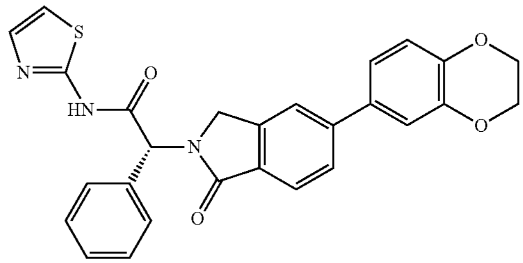 [SMILES: O=C(Nc1nccs1)[C@@H](c1ccccc1)N1Cc2cc(-c3ccc4c(c3)OCCO4)ccc2C1=O] | (R)-2-(5-(2,3-dihydrobenzo[b][1,4]dioxin-6-yl)-1-oxoisoindolin-2-yl)-2-phenyl-N-(thiazol-2-yl)acetamide |
| I-104 | 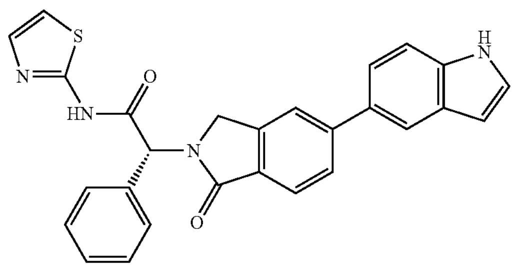 [SMILES: O=C(Nc1nccs1)[C@@H](c1ccccc1)N1Cc2cc(-c3ccc4[nH]ccc4c3)ccc2C1=O] | (R)-2-(5-(1H-indol-5-yl)-1-oxoisoindolin-2-yl)-2-phenyl-N-(thiazol-2-yl)acetamide |
| I-105 | 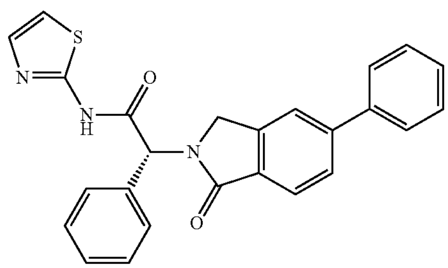 [SMILES: O=C(Nc1nccs1)[C@@H](c1ccccc1)N1Cc2cc(-c3ccccc3)ccc2C1=O] | (R)-2-(1-oxo-5-phenylisoindolin-2-yl)-2-phenyl-N-(thiazol-2-yl)acetamide |
| I-106 | 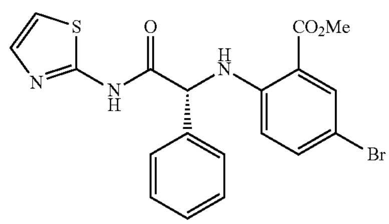 [SMILES: COC(=O)c1cc(Br)ccc1N[C@@H](C(=O)Nc1nccs1)c1ccccc1] | methyl (R)-5-bromo-2-((2-oxo-1-phenyl-2-(thiazol-2-ylamino)ethyl)amino)benzoate |
| I-107 | 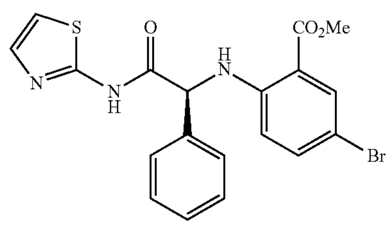 [SMILES: COC(=O)c1cc(Br)ccc1N[C@H](C(=O)Nc1nccs1)c1ccccc1] | methyl (S)-5-bromo-2-((2-oxo-1-phenyl-2-(thiazol-2-ylamino)ethyl)amino)benzoate |
| I-108 | 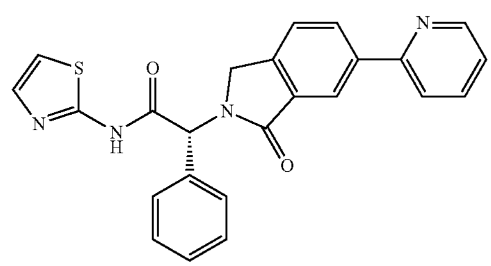 [SMILES: O=C(Nc1nccs1)[C@@H](c1ccccc1)N1Cc2ccc(-c3ccccn3)cc2C1=O] | (R)-2-(1-oxo-6-(pyridin-2-yl)isoindolin-2-yl)-2-phenyl-N-(thiazol-2-yl)acetamide |

| Compound Number | Structure | Compound Name |
|---|---|---|
| I-109 | 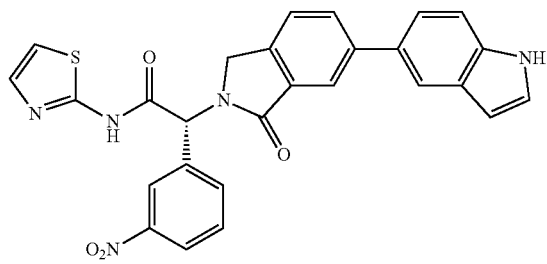 [SMILES: O=C(Nc1nccs1)[C@@H](c1cccc([N+](=O)[O-])c1)N1Cc2ccc(-c3ccc4[nH]ccc4c3)cc2C1=O] | (R)-2-(6-(1H-indol-5-yl)-1-oxoisoindolin-2-yl)-2-(3-nitrophenyl)-N-(thiazol-2-yl)acetamide |
| I-110 | 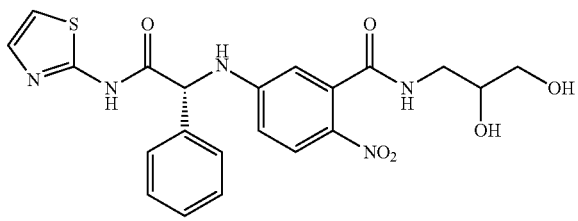 [SMILES: O=C(NCC(O)CO)c1cc(N[C@@H](C(=O)Nc2nccs2)c2ccccc2)ccc1[N+](=O)[O-]] | N-(2,3-dihydroxypropyl)-2-nitro-5-(((R)-2-oxo-1-phenyl-2-(thiazol-2-ylamino)ethyl)amino)benzamide |
| I-111 | 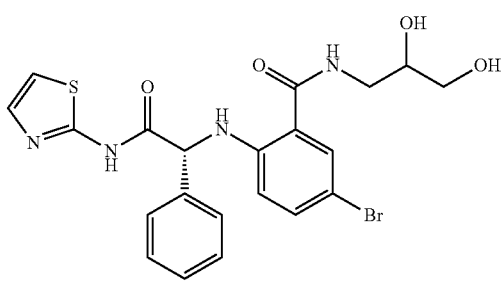 [SMILES: O=C(NCC(O)CO)c1cc(Br)ccc1N[C@@H](C(=O)Nc1nccs1)c1ccccc1] | 5-bromo-N-(2,3-dihydroxypropyl)-2-(((R)-2-oxo-1-phenyl-2-(thiazol-2-ylamino)ethyl)amino)benzamide |
| I-112 | 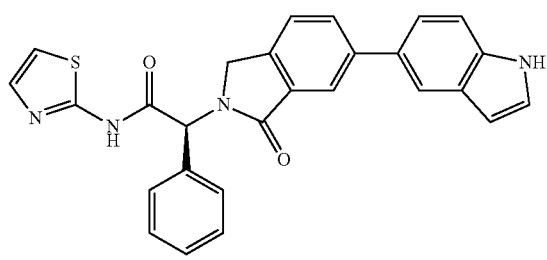 [SMILES: O=C(Nc1nccs1)[C@H](c1ccccc1)N1Cc2ccc(-c3ccc4[nH]ccc4c3)cc2C1=O] | (S)-2-(6-(1H-indol-5-yl)-1-oxoisoindolin-2-yl)-2-phenyl-N-(thiazol-2-yl)acetamide |
| I-113 | 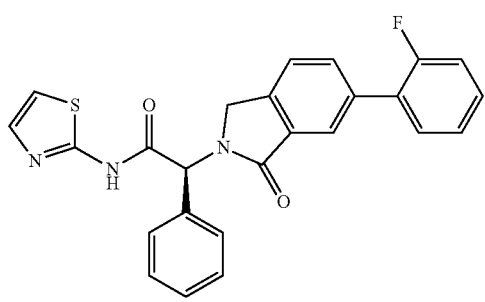 [SMILES: O=C(Nc1nccs1)[C@H](c1ccccc1)N1Cc2ccc(-c3ccccc3F)cc2C1=O] | (S)-2-(6-(2-fluorophenyl)-1-oxoisoindolin-2-yl)-2-phenyl-N-(thiazol-2-yl)acetamide |

| Compound Number | Structure | Compound Name |
|---|---|---|
| I-114 | 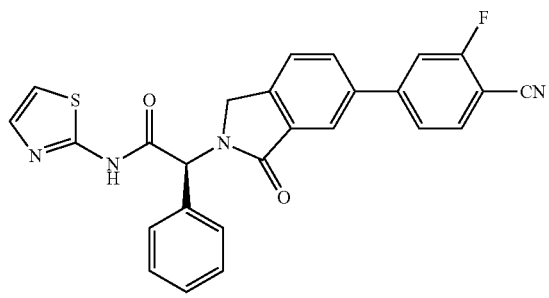 [SMILES: N#Cc1ccc(-c2ccc3c(c2)C(=O)N([C@H](C(=O)Nc2nccs2)c2ccccc2)C3)cc1F] | (S)-2-(6-(4-cyano-3-fluorophenyl)-1-oxoisoindolin-2-yl)-2-phenyl-N-(thiazol-2-yl)acetamide |
| I-115 | 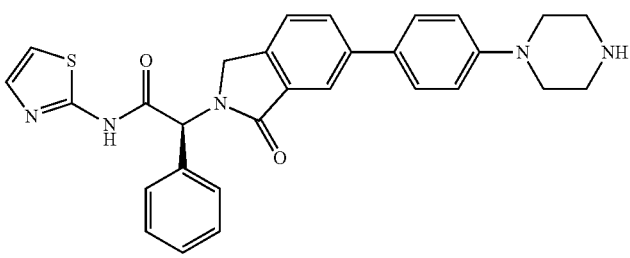 [SMILES: O=C(Nc1nccs1)[C@H](c1ccccc1)N1Cc2ccc(-c3ccc(N4CCNCC4)cc3)cc2C1=O] | (S)-2-(1-oxo-6-(4-(piperazin-1-yl)phenyl)isoindolin-2-yl)-2-phenyl-N-(thiazol-2-yl)acetamide |
| I-116 | 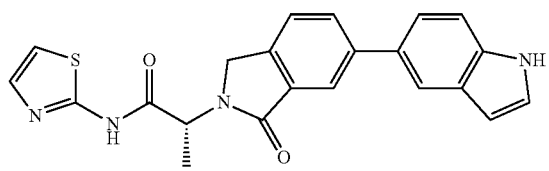 [SMILES: C[C@H](C(=O)Nc1nccs1)N1Cc2ccc(-c3ccc4[nH]ccc4c3)cc2C1=O] | (R)-2-(6-(1H-indol-5-yl)-1-oxoisoindolin-2-yl)-N-(thiazol-2-yl)propanamide |
| I-117 | 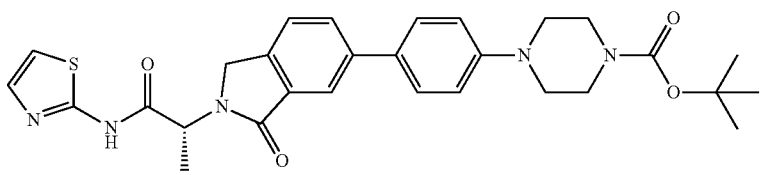 [SMILES: C[C@H](C(=O)Nc1nccs1)N1Cc2ccc(-c3ccc(N4CCN(C(=O)OC(C)(C)C)CC4)cc3)cc2C1=O] | tert-butyl (R)-4-(4-(3-oxo-2-(1-oxo-1-(thiazol-2-ylamino)propan-2-yl)isoindolin-5-yl)phenyl)piperazine-1-carboxylate |
| I-118 | 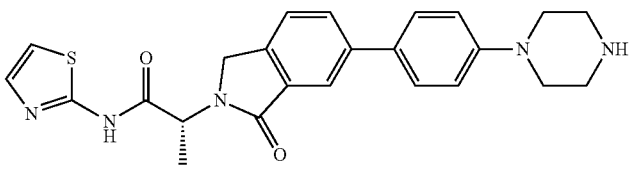 [SMILES: C[C@H](C(=O)Nc1nccs1)N1Cc2ccc(-c3ccc(N4CCNCC4)cc3)cc2C1=O] | (R)-2-(1-oxo-6-(4-(piperazin-1-yl)phenyl)isoindolin-2-yl)-N-(thiazol-2-yl)propanamide |
| I-119 | 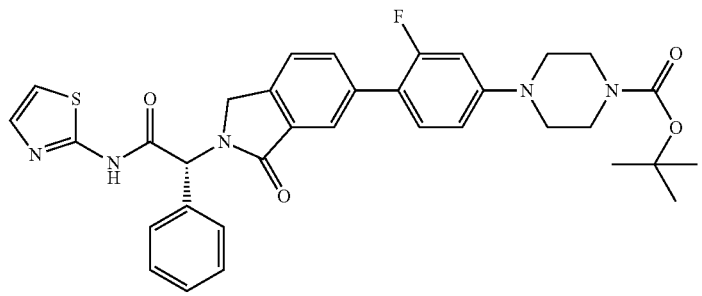 [SMILES: CC(C)(C)OC(=O)N1CCN(c2ccc(-c3ccc4c(c3)C(=O)N([C@@H](C(=O)Nc3nccs3)c3ccccc3)C4)c(F)c2)CC1] | tert-butyl (R)-4-(3-fluoro-4-(3-oxo-2-(2-oxo-1-phenyl-2-(thiazol-2-ylamino)ethyl)isoindolin-5-yl)phenyl)piperazine-1-carboxylate |

| Compound Number | Structure | Compound Name |
|---|---|---|
| I-120 | 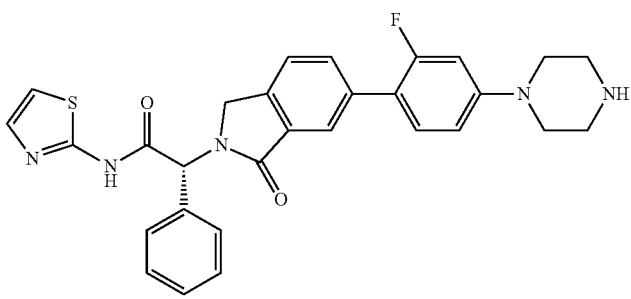 [SMILES: O=C(Nc1nccs1)[C@@H](c1ccccc1)N1Cc2ccc(-c3ccc(N4CCNCC4)cc3F)cc2C1=O] | (R)-2-(6-(2-fluoro-4-(piperazin-1-yl)phenyl)-1-oxoisoindolin-2-yl)-2-phenyl-N-(thiazol-2-yl)acetamide |
| I-121 | 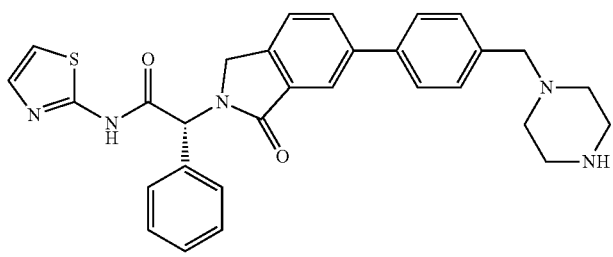 [SMILES: O=C(Nc1nccs1)[C@@H](c1ccccc1)N1Cc2ccc(-c3ccc(CN4CCNCC4)cc3)cc2C1=O] | (R)-2-(1-oxo-6-(4-(piperazin-1-ylmethyl)phenyl)isoindolin-2-yl)-2-phenyl-N-(thiazol-2-yl)acetamide |
| I-122 | 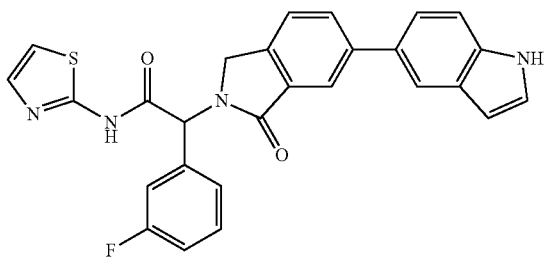 [SMILES: O=C(Nc1nccs1)C(c1cccc(F)c1)N1Cc2ccc(-c3ccc4[nH]ccc4c3)cc2C1=O] | 2-(6-(1H-indol-5-yl)-1-oxoisoindolin-2-yl)-2-(3-fluorophenyl)-N-(thiazol-2-yl)acetamide |
| I-123 | 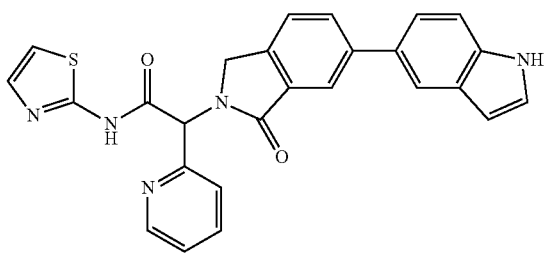 [SMILES: O=C(Nc1nccs1)C(c1ccccn1)N1Cc2ccc(-c3ccc4[nH]ccc4c3)cc2C1=O] | 2-(6-(1H-indol-5-yl)-1-oxoisoindolin-2-yl)-2-(pyridin-2-yl)-N-(thiazol-2-yl)acetamide |
| I-124 | 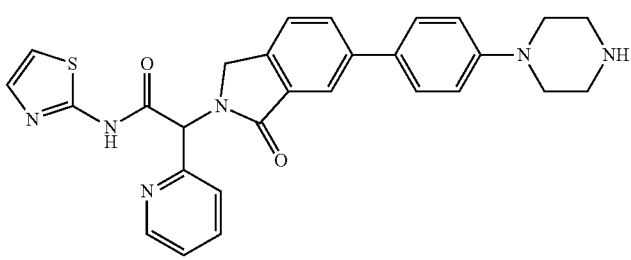 [SMILES: O=C(Nc1nccs1)C(c1ccccn1)N1Cc2ccc(-c3ccc(N4CCNCC4)cc3)cc2C1=O] | 2-(1-oxo-6-(4-(piperazin-1-yl)phenyl)isoindolin-2-yl)-2-(pyridin-2-yl)-N-(thiazol-2-yl)acetamide |

-continued

| Compound Number | Structure | Compound Name |
|---|---|---|
| I-125 | 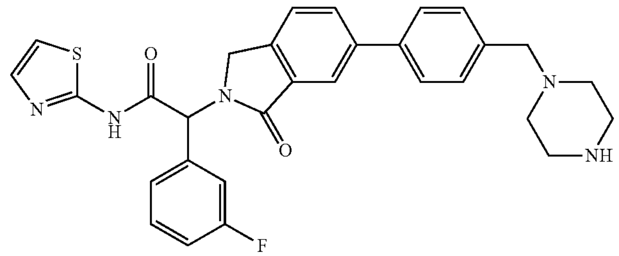 [SMILES: O=C(Nc1nccs1)C(c1cccc(F)c1)N1Cc2ccc(-c3ccc(CN4CCNCC4)cc3)cc2C1=O] | 2-(3-fluorophenyl)-2-(1-oxo-6-(4-(piperazin-1-ylmethyl)phenyl)isoindolin-2-yl)-N-(thiazol-2-yl)acetamide |
| I-126 | 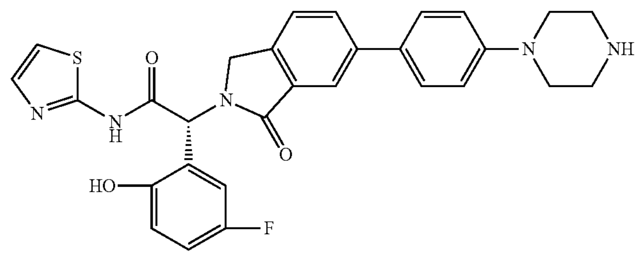 [SMILES: O=C(Nc1nccs1)[C@@H](c1cc(F)ccc1O)N1Cc2ccc(-c3ccc(N4CCNCC4)cc3)cc2C1=O] | (R)-2-(5-fluoro-2-hydroxyphenyl)-2-(1-oxo-6-(4-(piperazin-1-yl)phenyl)isoindolin-2-yl)-N-(thiazol-2-yl)acetamide |
| I-127 | 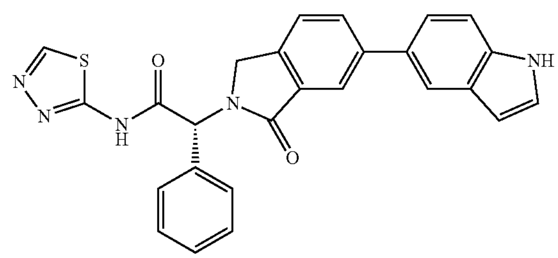 [SMILES: O=C(Nc1nncs1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-2-phenyl-N-(1,3,4-thiadiazol-2-yl)acetamide |
| I-128 | 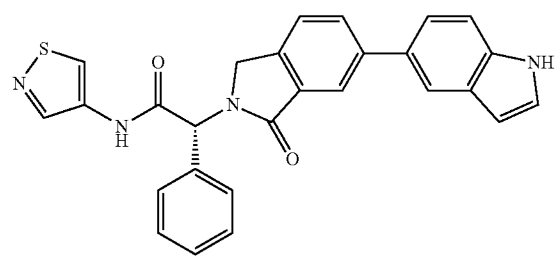 | (R)-2-(6-(1H-indol-5-yl)-1-oxoisoindolin-2-yl)-N-(isothiazol-4-yl)-2-phenylacetamide |
| I-129 | 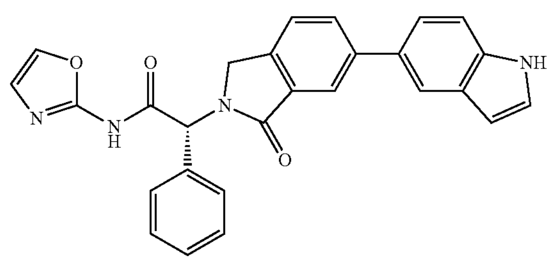 [SMILES: O=C(Nc1ncco1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-N-(oxazol-2-yl)-2-phenylacetamide |
| I-130 | 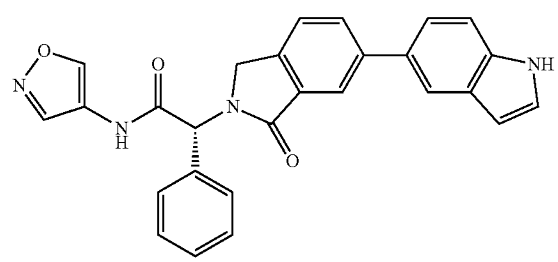 [SMILES: O=C(Nc1cnoc1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-N-(isoxazol-4-yl)-2-phenylacetamide |

| Compound Number | Structure | Compound Name |
|---|---|---|
| I-131 | 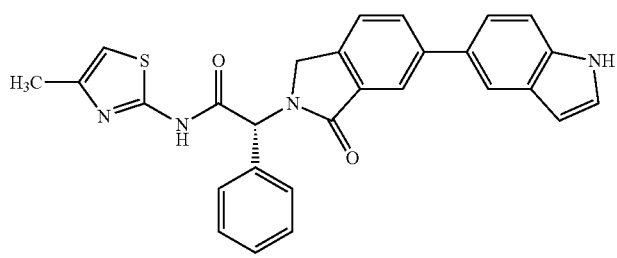 [SMILES: Cc1csc(NC(=O)[C@@H](c2ccccc2)N2Cc3ccc(-c4ccc5[nH]ccc5c4)cc3C2=O)n1] | (R)-2-(6-(1H-indol-5-yl)-1-oxoisoindolin-2-yl)-N-(4-methylthiazol-2-yl)-2-phenylacetamide |
| I-132 | 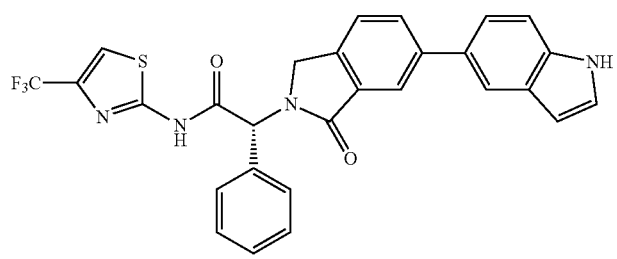 [SMILES: O=C(Nc1nc(C(F)(F)F)cs1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-2-phenyl-N-(4-(trifluoromethyl)thiazol-2-yl)acetamide |
| I-133 | 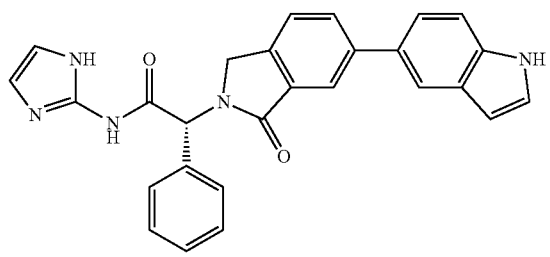 [SMILES: O=C(Nc1ncc[nH]1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-N-(1H-imidazol-2-yl)-2-phenylacetamide |
| I-134 | 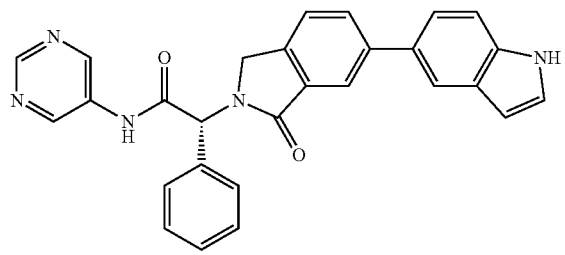 [SMILES: O=C(Nc1cncnc1)[C@@H](c1ccccc1)N1Cc2ccc(-c3ccc4[nH]ccc4c3)cc2C1=O] | (R)-2-(6-(1H-indol-5-yl)-1-oxoisoindolin-2-yl)-2-phenyl-N-(pyrimidin-5-yl)acetamide |
| I-135 | 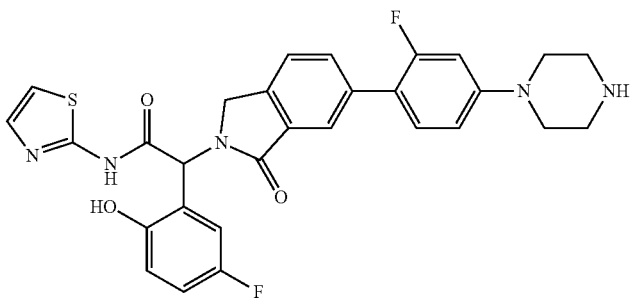 [SMILES: O=C(Nc1nccs1)C(c1cc(F)ccc1O)N1Cc2ccc(-c3ccc(N4CCNCC4)cc3F)cc2C1=O] | 2-(5-fluoro-2-hydroxyphenyl)-2-(6-(2-fluoro-4-(piperazin-1-yl)phenyl)-1-oxoisoindolin-2-yl)-N-(thiazol-2-yl)acetamide |

| Compound Number | Structure | Compound Name |
|---|---|---|
| I-136 | 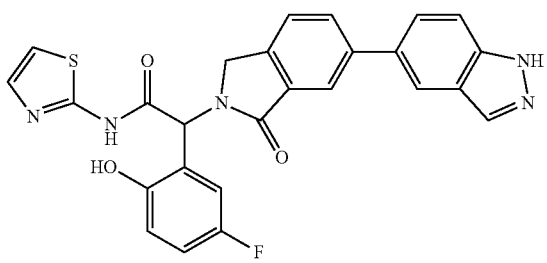 [SMILES: O=C(Nc1nccs1)C(c1cc(F)ccc1O)N1Cc2ccc(-c3ccc4[nH]ncc4c3)cc2C1=O] | 2-(6-(1H-indazol-5-yl)-1-oxoisoindolin-2-yl)-2-(5-fluoro-2-hydroxyphenyl)-N-(thiazol-2-yl)acetamide |
| I-137 | 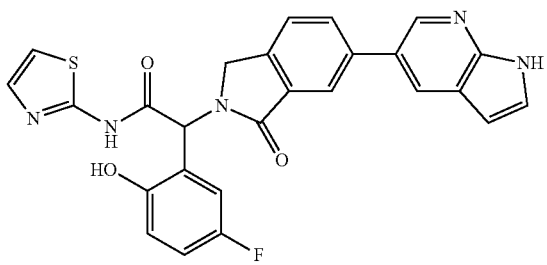 [SMILES: O=C(Nc1nccs1)C(c1cc(F)ccc1O)N1Cc2ccc(-c3cnc4[nH]ccc4c3)cc2C1=O] | 2-(5-fluoro-2-hydroxyphenyl)-2-(1-oxo-6-(1H-pyrrolo[2,3-b]pyridin-5-yl)isoindolin-2-yl)-N-(thiazol-2-yl)acetamide |
| I-138 | 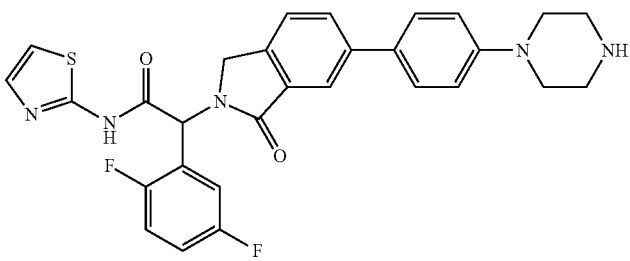 [SMILES: O=C(Nc1nccs1)C(c1cc(F)ccc1F)N1Cc2ccc(-c3ccc(N4CCNCC4)cc3)cc2C1=O] | 2-(2,5-difluorophenyl)-2-(1-oxo-6-(4-(piperazin-1-yl)phenyl)isoindolin-2-yl)-N-(thiazol-2-yl)acetamide |
| I-139 | 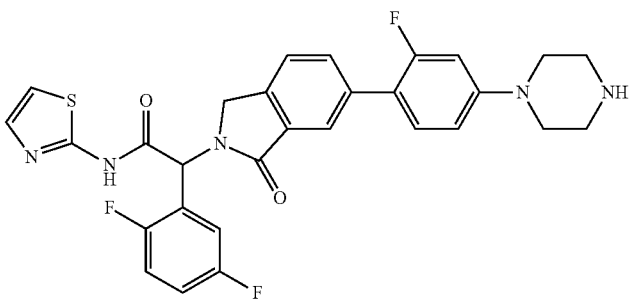 | 2-(2,5-difluorophenyl)-2-(6-(2-fluoro-4-(piperazin-1-yl)phenyl)-1-oxoisoindolin-2-yl)-N-(thiazol-2-yl)acetamide |
| I-140 | 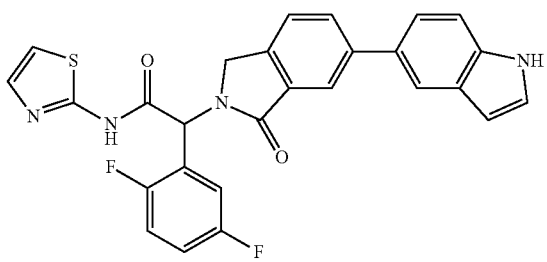 [SMILES: O=C(Nc1nccs1)C(c1cc(F)ccc1F)N1Cc2ccc(-c3ccc4[nH]ccc4c3)cc2C1=O] | 2-(6-(1H-indol-5-yl)-1-oxoisoindolin-2-yl)-2-(2,5-difluorophenyl)-N-(thiazol-2-yl)acetamide |

| Compound Number | Structure | Compound Name |
|---|---|---|
| I-141 | 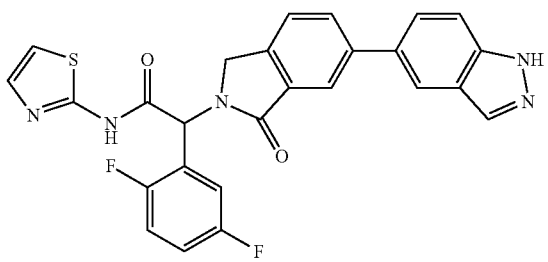 [SMILES: O=C(Nc1nccs1)C(c1cc(F)ccc1F)N1Cc2ccc(-c3ccc4[nH]ncc4c3)cc2C1=O] | 2-(6-(1H-indazol-5-yl)-1-oxoisoindolin-2-yl)-2-(2,5-difluorophenyl)-N-(thiazol-2-yl)acetamide |
| I-142 | 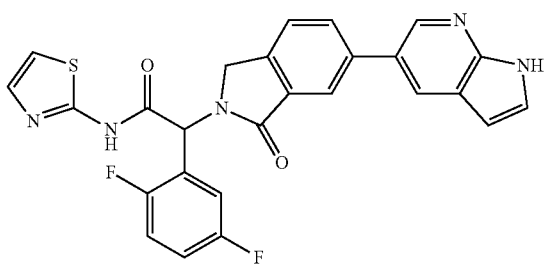 [SMILES: O=C(Nc1nccs1)C(c1cc(F)ccc1F)N1Cc2ccc(-c3cnc4[nH]ccc4c3)cc2C1=O] | 2-(2,5-difluorophenyl)-2-(1-oxo-6-(1H-pyrrolo[2,3-b]pyridin-5-yl)isoindolin-2-yl)-N-(thiazol-2-yl)acetamide |
| I-143 | 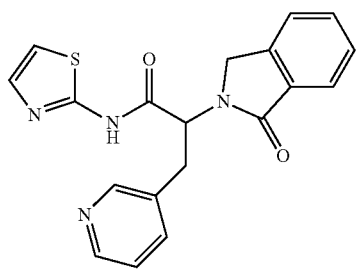 [SMILES: O=C(Nc1nccs1)C(Cc1cccnc1)N1Cc2ccccc2C1=O] | 2-(1-oxoisoindolin-2-yl)-3-(pyridin-3-yl)-N-(thiazol-2-yl)propanamide |
| I-144 | 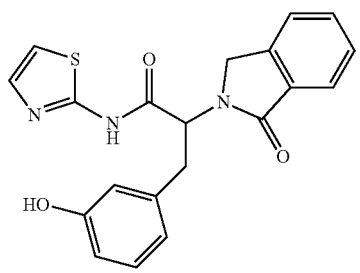 [SMILES: O=C(Nc1nccs1)C(Cc1cccc(O)c1)N1Cc2ccccc2C1=O] | 3-(3-hydroxyphenyl)-2-(1-oxoisoindolin-2-yl)-N-(thiazol-2-yl)propanamide |
| I-145 | 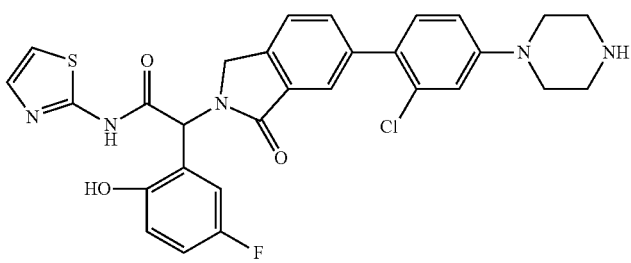 | 2-(6-(2-chloro-4-(piperazin-1-yl)phenyl)-1-oxoisoindolin-2-yl)-2-(5-fluoro-2-hydroxyphenyl)-N-(thiazol-2-yl)acetamide |

| Compound Number | Structure | Compound Name |
|---|---|---|
| I-146 | 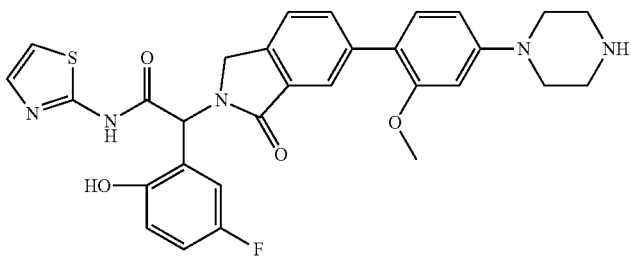 [SMILES: COc1cc(N2CCNCC2)ccc1-c1ccc2c(c1)C(=O)N(C(C(=O)Nc1nccs1)c1cc(F)ccc1O)C2] | 2-(5-fluoro-2-hydroxyphenyl)-2-(6-(2-methoxy-4-(piperazin-1-yl)phenyl)-1-oxoisoindolin-2-yl)-N-(thiazol-2-yl)acetamide |
| I-147 | 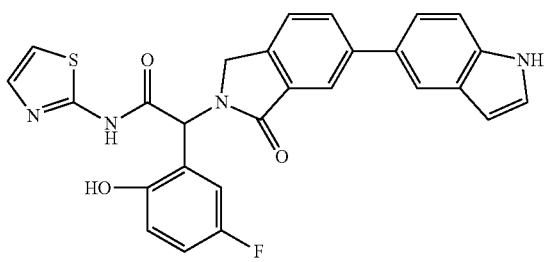 [SMILES: O=C(Nc1nccs1)C(c1cc(F)ccc1O)N1Cc2ccc(-c3ccc4[nH]ccc4c3)cc2C1=O] | 2-(6-(1H-indol-5-yl)-1-oxoisoindolin-2-yl)-2-(5-fluoro-hydroxyphenyl)-N-(thiazol-2-yl)acetamide |
| I-148 | 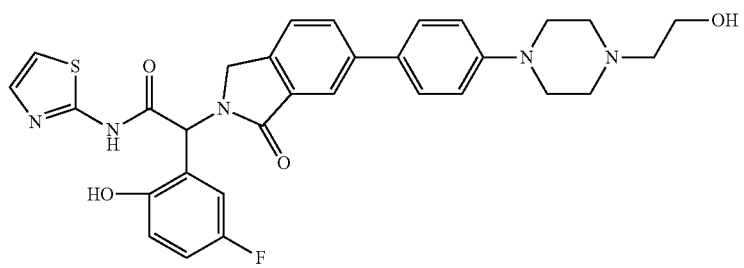 [SMILES: O=C(Nc1nccs1)C(c1cc(F)ccc1O)N1Cc2ccc(-c3ccc(N4CCN(CCO)CC4)cc3)cc2C1=O] | 2-(5-fluoro-2-hydroxyphenyl)-2-(6-(4-(4-(2-hydroxyethyl)piperazin-1-yl)phenyl)-1-oxoisoindolin-2-yl)-N-(thiazol-2-yl)acetamide |
| I-149 | 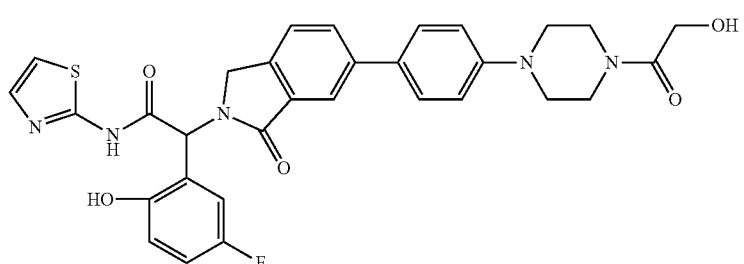 | 2-(5-fluoro-2-hydroxyphenyl)-2-(6-(4-(4-(2-hydroxyacetyl)piperazin-1-yl)phenyl)-1-oxoisoindolin-2-yl)-N-(thiazol-2-yl)acetamide |
| I-150 | 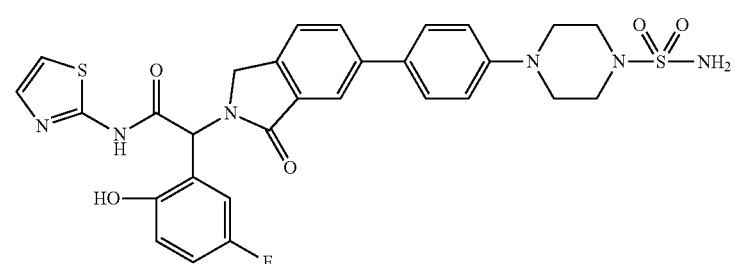 | 2-(5-fluoro-2-hydroxyphenyl)-2-(1-oxo-6-(4-(4-sulfamoylpiperazin-1-yl)phenyl)isoindolin-2-yl)-N-(thiazol-2-yl)acetamide |

| Compound Number | Structure | Compound Name |
|---|---|---|
| I-151 | 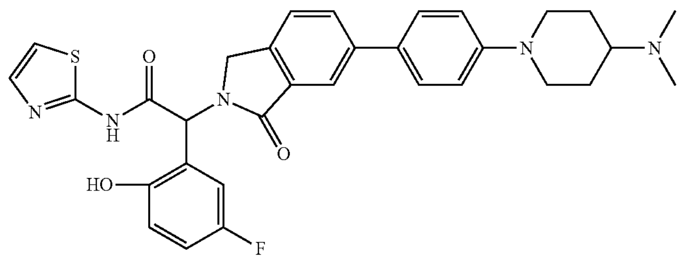 [SMILES: CN(C)C1CCN(c2ccc(-c3ccc4c(c3)C(=O)N(C(C(=O)Nc3nccs3)c3cc(F)ccc3O)C4)cc2)CC1] | 2-(6-(4-(4-(dimethylamino)piperidin-1-yl)phenyl)-1-oxoisoindolin-2-yl)-2-(5-fluoro-2-hydroxyphenyl)-N-(thiazol-2-yl)acetamide |
| I-152 | 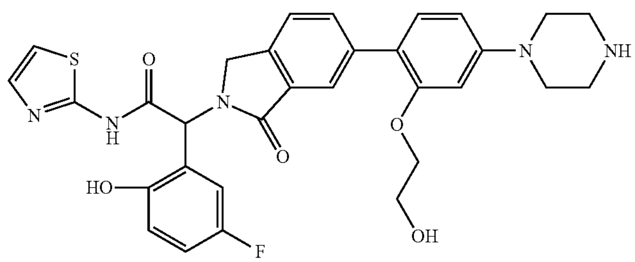 [SMILES: O=C(Nc1nccs1)C(c1cc(F)ccc1O)N1Cc2ccc(-c3ccc(N4CCNCC4)cc3OCCO)cc2C1=O] | 2-(5-fluoro-2-hydroxyphenyl)-2-(6-(2-(2-hydroxyethoxy)-4-(piperazin-1-yl)phenyl)-1-oxoisoindolin-2-yl)-N-(thiazol-2-yl)acetamide |
| I-153 | 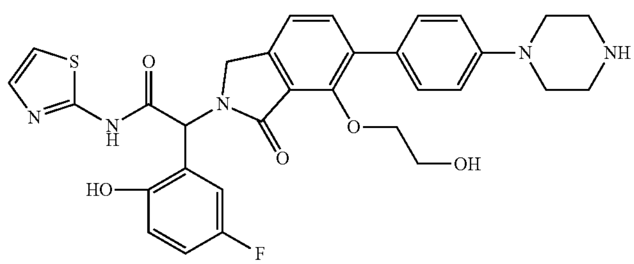 [SMILES: O=C(Nc1nccs1)C(c1cc(F)ccc1O)N1Cc2ccc(-c3ccc(N4CCNCC4)cc3)c(OCCO)c2C1=O] | 2-(5-fluoro-2-hydroxyphenyl)-2-(7-(2-hydroxyethoxy)-1-oxo-6-(4-(piperazin-1-yl)phenyl)isoindolin-2-yl)-N-(thiazol-2-yl)acetamide |
| I-154 | 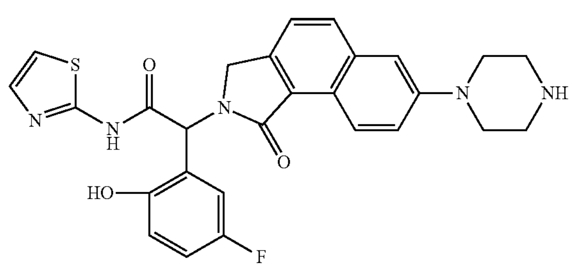 [SMILES: O=C(Nc1nccs1)C(c1cc(F)ccc1O)N1Cc2ccc3cc(N4CCNCC4)ccc3c2C1=O] | 2-(5-fluoro-2-hydroxyphenyl)-2-(1-oxo-7-(piperazin-1-yl)-1,3-dihydro-2H-benzo[e]isoindol-2-yl)-N-(thiazol-2-yl)acetamide |
| I-155 | 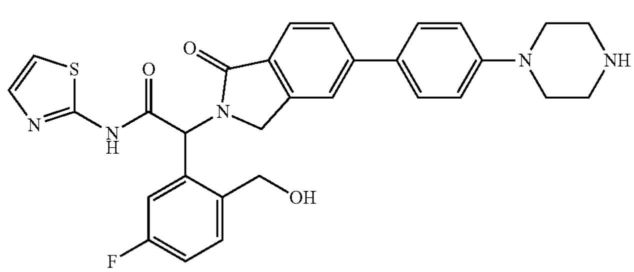 [SMILES: O=C(Nc1nccs1)C(c1cc(F)ccc1CO)N1Cc2cc(-c3ccc(N4CCNCC4)cc3)ccc2C1=O] | 2-(5-fluoro-2-(hydroxymethyl)phenyl)-2-(1-oxo-5-(4-(piperazin-1-yl)phenyl)isoindolin-2-yl)-N-(thiazol-2-yl)acetamide |

-continued

| Compound Number | Structure | Compound Name |
|---|---|---|
| I-156 | 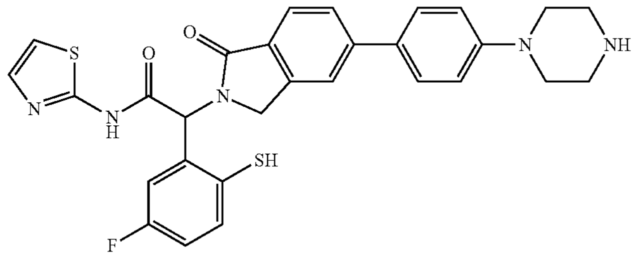 [SMILES: O=C(Nc1nccs1)C(c1cc(F)ccc1S)N1Cc2cc(-c3ccc(N4CCNCC4)cc3)ccc2C1=O] | 2-(5-fluoro-2-mercaptophenyl)-2-(1-oxo-5-(4-(piperazin-1-yl)phenyl)isoindolin-2-yl)-N-(thiazol-2-yl)acetamide |
| I-157 | 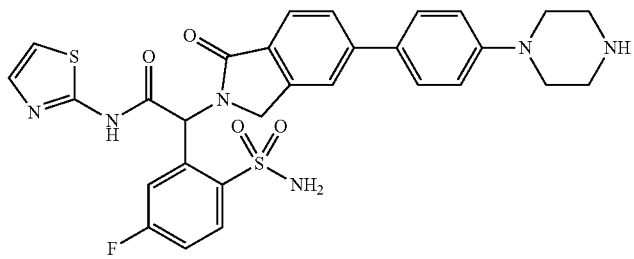 [SMILES: NS(=O)(=O)c1ccc(F)cc1C(C(=O)Nc1nccs1)N1Cc2cc(-c3ccc(N4CCNCC4)cc3)ccc2C1=O] | 2-(5-fluoro-2-sulfamoylphenyl)-2-(1-oxo-5-(4-(piperazin-1-yl)phenyl)isoindolin-2-yl)-N-(thiazol-2-yl)acetamide |
| I-158 | 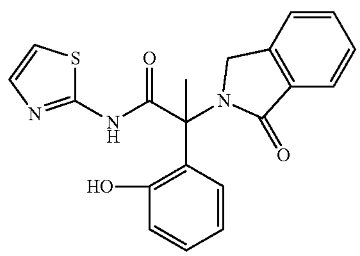 [SMILES: CC(C(=O)Nc1nccs1)(c1ccccc1O)N1Cc2ccccc2C1=O] | 2-(2-hydroxyphenyl)-2-(1-oxoisoindolin-2-yl)-N-(thiazol-2-yl)propanamide |
| I-159 | 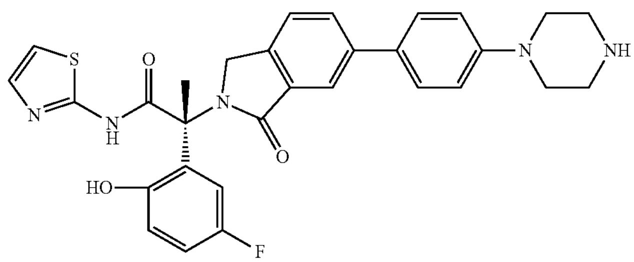 | (R)-2-(5-fluoro-2-hydroxyphenyl)-2-(1-oxo-6-(4-(piperazin-1-yl)phenyl)isoindolin-2-yl)-N-(thiazol-2-yl)propanamide |

A compound that binds to an allosteric site in EGFR or ERBB2, such as the compounds of the present disclosure (e.g., the compounds of the formulae disclosed herein), optionally in combination with a second agent wherein said second agent prevents EGFR dimer formation, are capable of modulating EGFR activity. In some embodiments, the compounds of the present disclosure are capable of inhibiting or decreasing EGFR activity, without a second agent (e.g., an antibody such as cetuximab, trastuzumab, or panitumumab). In other embodiments, the compounds of the present disclosure in combination with a second agent wherein said second agent prevents EGFR dimer formation and are capable of inhibiting or decreasing EGFR activity. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the compounds of the present disclosure are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M.

In some embodiments, the compounds of the present disclosure in combination with a second agent wherein said second agent prevents EGFR dimer formation are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the compounds of the present disclosure are capable of modulating (e.g., inhibiting or decreasing) the activity of EGFR containing one or more mutations, but do not affect the activity of a wild-type EGFR.

In other embodiments, the compounds of the present disclosure in combination with a second agent wherein said second agent prevents EGFR dimer formation are capable of modulating (e.g., inhibiting or decreasing) the activity of EGFR containing one or more mutations, but do not affect the activity of a wild-type EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

Modulation of EGFR containing one or more mutations, such as those described herein, but not a wild-type EGFR, provides a novel approach to the treatment, prevention, or amelioration of diseases including, but not limited to, cancer and metastasis, inflammation, arthritis, systemic lupus erthematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit greater inhibition of EGFR containing one or more mutations as described herein relative to a wild-type EGFR. In certain embodiments, the compounds of the disclosure exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure exhibit up to 1000-fold greater inhibition of EGFR containing one or more mutations as described herein relative to a wild-type EGFR. In various embodiments, the compounds of the disclosure exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR.

In other embodiments, the compounds of the disclosure in combination with a second agent wherein said second agent prevents EGFR dimer formation exhibit greater inhibition of EGFR containing one or more mutations as described herein relative to a wild-type EGFR. In certain embodiments, the compounds of the disclosure in combination with a second agent wherein said second agent prevents EGFR dimer formation exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure in combination with a second agent wherein said second agent prevents EGFR dimer formation exhibit up to 1000-fold greater inhibition of EGFR containing one or more mutations as described herein relative to a wild-type EGFR. In various embodiments, the compounds of the disclosure in combination with a second agent wherein said second agent prevents EGFR dimer formation exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the compounds of the disclosure exhibit from about 2-fold to about 10-fold greater inhibition of EGFR containing one or more mutations as described herein relative to a wild-type EGFR. In various embodiments, the compounds of the disclosure exhibit from about 10-fold to about 100-fold greater inhibition of EGFR containing one or more mutations as described herein relative to a wild-type EGFR. In various embodiments, the compounds of the disclosure exhibit from about 100-fold to about 1000-fold greater inhibition of EGFR containing one or more mutations as described herein relative to a wild-type EGFR. In various embodiments, the compounds of the disclosure exhibit from about 1000-fold to about 10000-fold greater inhibition of EGFR containing one or more mutations as described herein relative to a wild-type EGFR.

In other embodiments, the compounds of the disclosure in combination with a second agent wherein said second agent prevents EGFR dimer formation exhibit from about 2-fold to about 10-fold greater inhibition of EGFR containing one or more mutations as described herein relative to a wild-type EGFR. In other embodiments, the compounds of the disclosure in combination with a second agent wherein said second agent prevents EGFR dimer formation exhibit from about 10-fold to about 100-fold greater inhibition of EGFR containing one or more mutations as described herein relative to a wild-type EGFR. In other embodiments, the compounds of the disclosure in combination with a second agent wherein said second agent prevents EGFR dimer formation exhibit from about 100-fold to about 1000-fold greater inhibition of EGFR containing one or more mutations as described herein relative to a wild-type EGFR. In other embodiments, the compounds of the disclosure in combination with a second agent wherein said second agent prevents EGFR dimer formation exhibit from about 1000-fold to about 10000-fold greater inhibition of EGFR containing one or more mutations as described herein relative to a wild-type EGFR. In other embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In certain embodiments, the compounds of the disclosure exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 3-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR.

In certain embodiments, the compounds of the disclosure in combination with a second agent wherein said second agent prevents EGFR dimer formation exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent wherein said second agent prevents EGFR dimer formation exhibit at least 3-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent wherein said second agent prevents EGFR dimer formation exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent wherein said second agent prevents EGFR dimer formation exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent wherein said second agent prevents EGFR dimer formation exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent wherein said second agent prevents EGFR dimer formation exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent wherein said second agent prevents EGFR dimer formation exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the inhibition of EGFR activity is measured by $IC_{50}$.

In some embodiments, the inhibition of EGFR activity is measured by $EC_{50}$.

In some embodiments, the compounds of the disclosure bind to an allosteric site in EGFR. In some embodiments, the compounds of the disclosure interact with at least one amino acid residue of epidermal growth factor receptor (EGFR) selected from Lys745, Leu788, and Ala 743. In other embodiments, the compounds of the disclosure interact with at least one amino acid residue of epidermal growth factor receptor (EGFR) selected from Cys755, Leu777, Phe856, and Asp855. In other embodiments, the compounds of the disclosure interact with at least one amino acid residue of epidermal growth factor receptor (EGFR) selected from Met766, Ile759, Glu762, and Ala763. In other embodiments, the compounds of the disclosure interact with at least one amino acid residue of epidermal growth factor receptor (EGFR) selected from Lys745, Leu788, and Ala 743, at least one amino acid residue of epidermal growth factor receptor (EGFR) selected from Cys755, Leu777, Phe856, and Asp855, and at least one amino acid residue of epidermal growth factor receptor (EGFR) selected from Met766, Ile759, Glu762, and Ala763. In other embodiments, the compounds of the disclosure do not interact with the any of the amino acid residues of epidermal growth factor receptor (EGFR) selected from Met793, Gly796, and Cys797.

In some embodiments, the disclosure provides a compound comprising an allosteric kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002:

WZ4002:

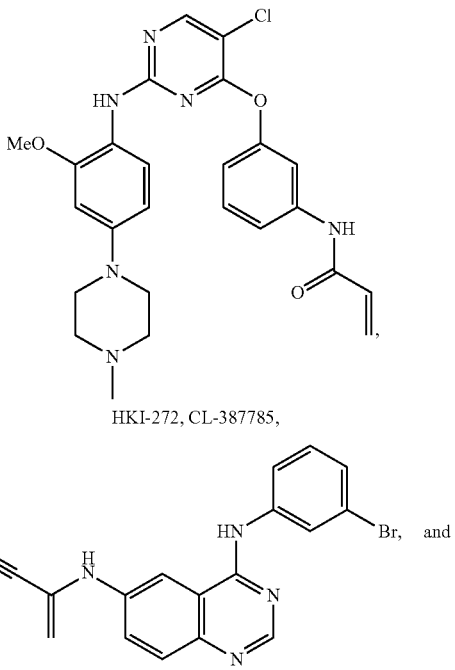

HKI-272, CL-387785,

AZD9291:

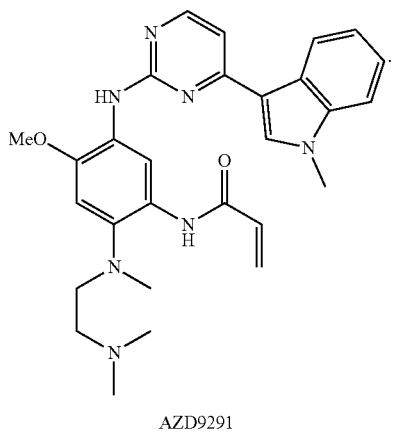

AZD9291

In some embodiments, the drug-resistant EGFR mutant comprises a sensitizing mutation, such as Del and L858R.

In some embodiments, the disclosure provides a compound comprising an allosteric kinase inhibitor in combination with a second agent wherein said second agent prevents EGFR dimer formation, wherein the compound is a more potent inhibitor of a drug-resistant EGFR mutant relative to a wild type EGFR. For example, the compound in combination with a second agent wherein said second agent prevents EGFR dimer formation can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and AZD9291. In some embodiments, the drug-resistant EGFR mutant comprises a sensitizing mutation, such as Del and L858R. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the disclosure provides a compound comprising an allosteric kinase inhibitor, wherein the compound inhibits kinase activity of a drug-resistant EGFR mutant harboring a sensitizing mutation (e.g., Del and L858R) and a drug-resistance mutation (e.g., T790M, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In other embodiments, the disclosure provides a compound comprising an allosteric kinase inhibitor in combination with a second agent wherein said second agent prevents EGFR dimer formation, wherein the compound in combination with the second agent inhibits kinase activity of a drug-resistant EGFR mutant harboring a sensitizing mutation (e.g., Del and L858R) and a drug-resistance mutation (e.g., T790M, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the disclosure provides a compound comprising an allosteric kinase inhibitor, wherein the compound is more potent than one or more known EGFR inhibitors, including but not limited to gefitinib, erlotinib, lapatinib, WZ4002, HKI-272, CL-387785, and AZD9291, at inhibiting the activity of EGFR containing one or more mutations as described herein, such as T790M, L718Q, L844V, L858R, C797S, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and AZD9291 at inhibiting the activity of the EGFR containing one or more mutations as described herein.

In other embodiments, the disclosure provides a compound comprising an allosteric kinase inhibitor in combination with a second agent wherein said second agent prevents EGFR dimer formation, wherein the compound in combination with the second agent is more potent than one or more known EGFR inhibitors, including but not limited to gefitinib, erlotinib, lapatinib, WZ4002, HKI-272, CL-387785, and AZD9291, at inhibiting the activity of EGFR containing one or more mutations as described herein, such as T790M, L718Q, L844V, L858R, C797S, and Del. For example, the compound in combination with a second agent wherein said second agent prevents EGFR dimer formation can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and AZD9291 at inhibiting the activity of the EGFR containing one or more mutations as described herein. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In some embodiments, the disclosure provides a compound comprising an allosteric kinase inhibitor, wherein the compound is less potent than one or more known EGFR inhibitors, including but not limited to gefitinib, erlotinib, lapatinib, WZ4002, HKI-272, CL-387785, and AZD9291, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and AZD9291, at inhibiting the activity of a wild-type EGFR.

In other embodiments, the disclosure provides a compound comprising an allosteric kinase inhibitor in combination with a second agent wherein said second agent prevents EGFR dimer formation, wherein the compound in combination with the second agent is less potent than one or more known EGFR inhibitors, including but not limited to gefitinib, erlotinib, lapatinib, WZ4002, HKI-272, CL-387785, and AZD9291, at inhibiting the activity of a wild-type EGFR. For example, the compound in combination with a second agent wherein said second agent prevents EGFR dimer formation can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and AZD9291, at inhibiting the activity of a wild-type EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

An EGFR sensitizing mutation comprises without limitation L858R, G719S, G719C, G719A, L861Q, a deletion in exon 19 and/or an insertion in exon 20. A drug-resistant EGFR mutant can have without limitation a drug resistance mutation comprising T790M, T854A, L718Q, C797S, or D761Y.

The selectivity between wild-type EGFR and EGFR containing one or more mutations as described herein can also be measured using cellular proliferation assays where cell proliferation is dependent on kinase activity. For example, murine Ba/F3 cells transfected with a suitable version of wild-type EGFR (such as VIII; containing a WT EGFR kinase domain), or Ba/F3 cells transfected with L858R/T790M, Del/T790M/L718Q, L858R/T790M/L718Q, L858R/T790M/C797S, Del/T790M/C797S, L858R/T790M/I941R, or Exon 19 deletion/T790M can be used. Proliferation assays are performed at a range of inhibitor concentrations (10 µM, 3 µM, 1.1 µM, 330 nM, 110 nM, 33 nM, 11 nM, 3 nM, I nM) and an $EC_{50}$ is calculated.

An alternative method to measure effects on EGFR activity is to assay EGFR phosphorylation. Wild type or mutant (L858R/T790M, Del/T790M, Del/T790M/L718Q, L858R/T790M/C797S, Del/T790M/C797S, L858R/T790M/I941R, or L858R/T790M/L718Q) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In another aspect, the present disclosure relates to a compound that binds to an allosteric site in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, L858R/T790M/C797S, Del/T790M/C797S, L858R/T790M/I941R, or L858R/T790M/L718Q) relative to a wild-type EGFR.

In other embodiments, the disclosure provides a compound that binds to an allosteric site in EGFR in combination with a second agent wherein said second agent prevents EGFR dimer formation, wherein the compound in combination with the second agent greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, Del/T790M/C797S, L858R/T790M/C797S, L858R/T790M/I941R, or L858R/T790M/L718Q) relative to a wild-type EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

Definitions

Listed below are definitions of various terms used to describe this disclosure. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals;

and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the disclosure, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the disclosure may optionally be substituted with one or more substituents, such as are illustrated generally above, or as exemplified by particular classes, subclasses, and species of the disclosure. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-

$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-Cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$— heterocycloalkyl, NHC(O)NH$_2$, —NHC(O)NH—$C_1$i-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH— $C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$i-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-SO$_2$NH$_2$, —SO$_2$NH—$C_1$-$C_{12}$-alkyl, —SO$_2$NH—$C_2$-$C_2$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

It is understood that the aryls, heteroaryls, alkyls, and the like can be substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors, spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "EGFR" herein refers to epidermal growth factor receptor kinase.

The term "HER" or "Her", herein refers to human epidermal growth factor receptor kinase.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

As used herein, the term "allosteric site" refers to a site on EGFR other than the ATP binding site, such as that characterized in a crystal structure of EGFR. An "allosteric site" can be a site that is close to the ATP binding site, such as that characterized in a crystal structure of EGFR. For example, one allosteric site includes one or more of the following amino acid residues of epidermal growth factor receptor (EGFR): Lys745, Leu788, Ala 743, Cys755, Leu777, Phe856, Asp855, Met766, Ile759, Glu762, and/or Ala763.

As used herein, the term "agent that prevents EGFR dimer formation" refers to an agent that prevents dimer formation in which the C-lobe of the "activator" subunit impinges on the N-lobe of the "receiver" subunit. Examples of agents that prevent EGFR dimer formation include, but are not limited to, cetuximab, cobimetinib, trastuzumab, panitumumab, and Mig6.

As used herein the term "GDC0973" or "Cobimetinib" refers to a compound having the chemical structure:

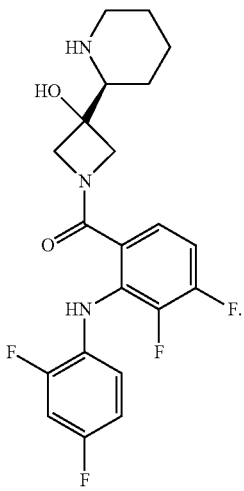 [SMILES: O=C(c1ccc(F)c(F)c1Nc1ccc(F)cc1F)N1CC(O)([C@@H]2CCCCN2)C1]

As used herein, the term "pharmaceutically acceptable salt" refers to those salts of the compounds formed by the process of the present disclosure which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J Pharmaceutical Sciences*, 66: 1-19 (1977). The salts can be prepared in situ during the final isolation and purification of the compounds of the disclosure, or separately by reacting the free base function with a suitable organic acid.

Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, gluceptate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present disclosure which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present disclosure which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present disclosure. "Prodrug", as used herein means a compound which is convertible in vivo by metabolic means (e.g., by hydrolysis) to afford any compound delineated by the formulae of the instant disclosure. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This disclosure also encompasses pharmaceutical compositions containing, and methods of treating disorders through administering, pharmaceutically acceptable prodrugs of compounds of the disclosure. For example, compounds of the disclosure having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the disclosure. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this disclosure are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The disclosure also provides for a pharmaceutical composition comprising a compound of disclosed herein, or a pharmaceutically acceptable ester, salt, or prodrug thereof, together with a pharmaceutically acceptable carrier.

In another aspect, the disclosure provides a kit comprising a compound capable of inhibiting EGFR activity selected from one or more compounds of disclosed herein, or a pharmaceutically acceptable salt, hydrate, solvate, prodrug, stereoisomer, or tautomer thereof, optionally in combination with a second agent wherein said second agent prevents EGFR dimer formation and instructions for use in treating cancer.

In another aspect, the disclosure provides a method of synthesizing a compound of disclosed herein.

The synthesis of the compounds of the disclosure can be found herein and in the Examples below.

Other embodiments are a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

A compound of the disclosure can be prepared as a pharmaceutically acceptable acid addition salt by reacting the free base form of the compound with a pharmaceutically acceptable inorganic or organic acid. Alternatively, a pharmaceutically acceptable base addition salt of a compound of the disclosure can be prepared by reacting the free acid form of the compound with a pharmaceutically acceptable inorganic or organic base.

Alternatively, the salt forms of the compounds of the disclosure can be prepared using salts of the starting materials or intermediates.

The free acid or free base forms of the compounds of the disclosure can be prepared from the corresponding base addition salt or acid addition salt from, respectively. For example a compound of the disclosure in an acid addition salt form can be converted to the corresponding free base by treating with a suitable base (e.g., ammonium hydroxide solution, sodium hydroxide, and the like). A compound of the disclosure in a base addition salt form can be converted to the corresponding free acid by treating with a suitable acid (e.g., hydrochloric acid, etc.).

Prodrugs of the compounds of the disclosure can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the disclosure with a suitable carbamylating agent (e.g., 1,1-acyloxyalkylcarbanochloridate, para-nitrophenyl carbonate, or the like).

Protected derivatives of the compounds of the disclosure can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present disclosure can be conveniently prepared, or formed during the process of the disclosure, as solvates (e.g., hydrates). Hydrates of compounds of the present disclosure can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this disclosure have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present disclosure.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

The compounds of this disclosure may also be represented in multiple tautomeric forms, in such instances, the disclosure expressly includes all tautomeric forms of the compounds described herein (e.g., alkylation of a ring system may result in alkylation at multiple sites, the disclosure expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present disclosure.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like.

Furthermore, so-called metabolite which is produced by degradation of the present compound in vivo is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present disclosure. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this disclosure may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the disclosure are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Method of Synthesizing the Compounds

The compounds of the present disclosure may be made by a variety of methods, including standard chemistry. The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5*th* edition, John Wiley & Sons: New York, 2001; and Greene, T. W., Wuts, P. G. M., *Protective Groups in Organic Synthesis*, 3*rd* edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of disclosed herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of disclosed herein.

Those skilled in the art will recognize if a stereocenter exists in the compounds of disclosed herein. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below. Compounds of the present disclosure can be synthesized by following the steps outlined in General Schemes 1-3 which comprise different sequences of assembling intermediates Ib, Ic, Id, Ie, If, Ig, Ih, Ii, Ij, Ik, and Il. Starting materials are either commercially available or made by known procedures in the reported literature or as illustrated.

General Scheme 1

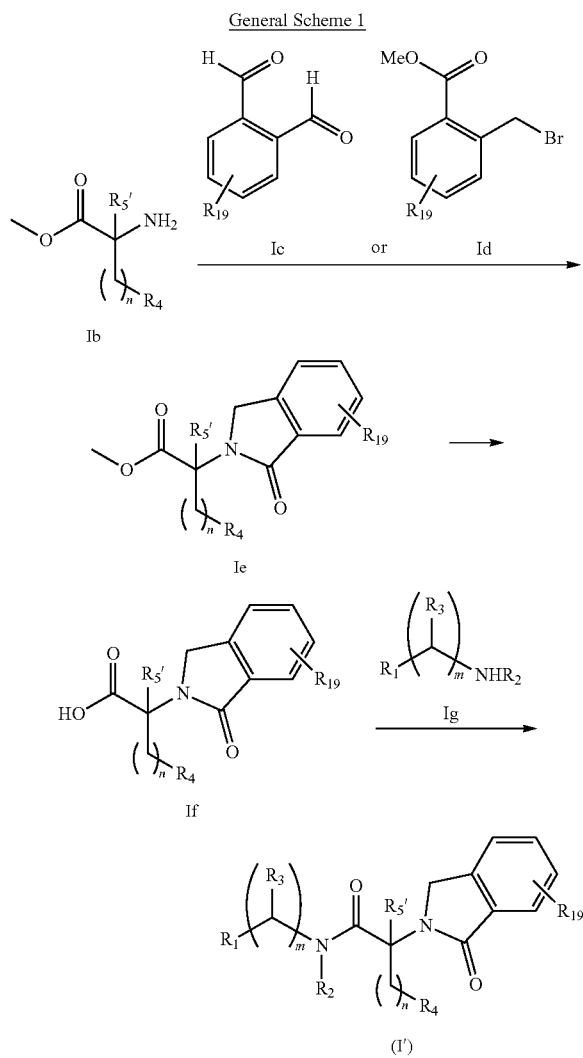

wherein R$_1$-R$_4$, R$_{22}$, m and n are defined herein.

The general way of preparing representative compounds of the present disclosure (i.e., Compound (I') shown above) using intermediates Ib, Ic, Id, Ie, If, and Ig is outlined in General Scheme 1. Cyclization of Ib and Ic using an acid, e.g., acetic acid, in solvent, e.g., CHCl$_3$, at elevated temperatures provides intermediate Ie. Alternatively, Intermediate Ie can be obtained via cyclization of Ib and Id using a base, e.g., N,N-diisopropylethylamine (DIPEA) in a solvent, e.g., dimethylformamide (DMF) at elevated temperatures. Hydrolysis of Intermediate Ie using a base, e.g., lithium hydroxide (LiOH) in a solvent, e.g., tetrahydrofuran (THF), methanol (MeOH), and/or water (H$_2$O), provides If. Coupling of acid If and amine Ig under standard coupling conditions using a coupling reagent, e.g., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF, provides Compound (I').

General Scheme 2

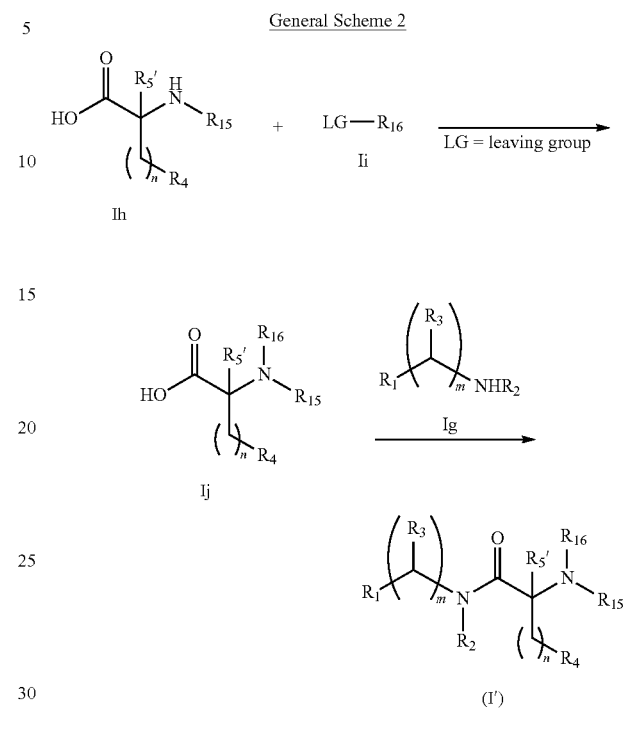

wherein R$_1$-R$_4$, R$_{15}$, R$_{16}$, m and n are defined herein.

The general way of preparing representative compounds of the present disclosure (i.e., Compound (I') shown above) using intermediates Ig, Ih, Ii, and Ij is outlined in General Scheme 2. Nucleophilic addition of Ih to Ii using a base, e.g., potassium carbonate (K$_2$CO$_3$), in solvent, e.g., DMF, at elevated temperatures provides intermediate Ij. Coupling of carboxylic acid Ij with amine Ig under standard coupling conditions using a coupling reagent, e.g., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF, provides Compound (I').

General Scheme 3

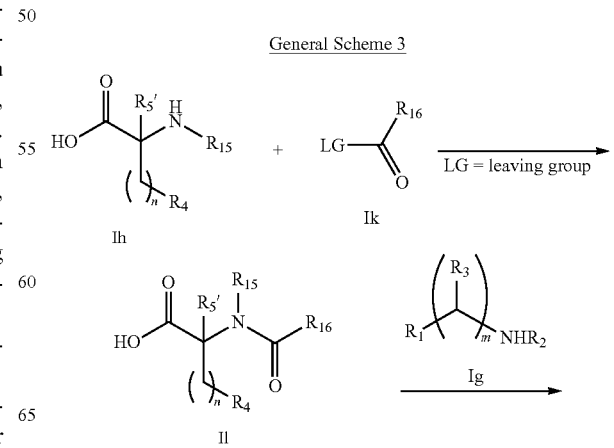

-continued

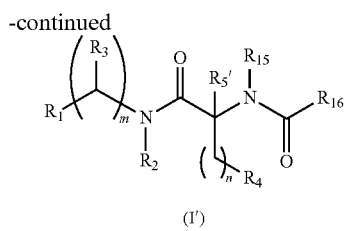

(I')

wherein $R_1$-$R_4$, $R_{15}$, $R_{16}$, m and n are defined herein.

The general way of preparing representative compounds of the present disclosure (i.e., Compound (I') shown above) using intermediates Ig, Ih, Ik, and Il is outlined in General Scheme 3. Acylation of amine Ih with Ik using a base, e.g., triethylamine or N,N-diisopropylethylamine (DIPEA), in a solvent, e.g., dichloromethane, DMF provides intermediate Il. Coupling of carboxylic acid Il with amine Ig under standard coupling conditions using a coupling reagent, e.g., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF, provides Compound (I').

A mixture of enantiomers, diastereomers, and/or cis/trans isomers resulting from the processes described above can be separated into their single components by chiral salt technique, chromatography using normal phase, or reverse phase or chiral column, depending on the nature of the separation.

It should be understood that in the description and formulae shown above, the various groups $R_1$-$R_4$, $R_{15}$, $R_{16}$, $R_{22}$, m and n and other variables are as defined herein, except where otherwise indicated. Furthermore, for synthetic purposes, the compounds of General Schemes 1-3 are mere representatives with elected radicals to illustrate the general synthetic methodology of the compounds of disclosed herein.

Biological Assays
Biochemical Assays

EGFR biochemical assays are carried out using a homogeneous time-resolved fluorescence (HTRF) assay. The reaction mixtures contain biotin-Lck-peptide substrate, wild type, or mutant EGFR enzyme in reaction buffer. Enzyme concentrations are adjusted to accommodate varying kinase activity and ATP concentrations. Compounds of the present disclosure are diluted into the assay mixture and $IC_{50}$ values are determined using 12-point inhibition curves.

Phospho-EGFR Target Modulation Assays and ELISA

Cells are lysed with lysis buffer containing protease and phosphatase inhibitors and the plates are shaken. An aliquot from each well is then transferred to prepared ELISA plates for analysis. Once harvested and plated, the cells are pre-treated with media with or without EGF. The compounds of the present disclosure are then added and $IC_{50}$ values are determined using an EGFR biochemical assay described above.

Solid high-binding ELISA plates are coated with goat anti-EGFR capture antibody. Plates are then blocked with BSA in a buffer, and then washed. Aliquots of lysed cell are added to each well of the ELISA plate and the plate is incubated. An anti-phospho-EGFR is then added and is followed by further incubation. After washing, anti-rabbit-HRP is added and the plate is again incubated. Chemiluminescent detection is carried out with SuperSignal ELISA Pico substrate. Signal is read on EnVision plate reader using built-in UltraLUM setting.

Western Blotting

Cell lysates are equalized to protein content and loaded onto a gel with running buffer. Membranes are probed with primary antibodies and are then washed. HRP-conjugated secondary antibodies are added and after washing. HRP is detected using a HRP substrate reagent and recorded with an imager.

Cell Proliferation Assays

Cell lines are plated in media. The compounds of the present disclosure are then serially diluted and transferred to the cells. Cell viability is measured via a luminescent readout. Data is analyzed by non-linear regression curve-fitting.

Methods of the Disclosure

In another aspect, the disclosure provides a method of inhibiting a kinase, comprising contacting the kinase with a compound of disclosed herein, or a pharmaceutically acceptable salt, hydrate, solvate, prodrug, stereoisomer, or tautomer thereof. In some embodiments, the kinase comprises a mutated cysteine residue. In further embodiments, the mutated cysteine residue is located in or near the position equivalent to Cys 797 in EGFR, including such position in Jak3, Blk, Bmx, Btk, HER2 (ErbB2), HER4 (ErbB4), Itk, Tec, and Txk. In other embodiments, the method further comprises a second agent wherein said second agent prevents kinase dimer formation. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In another aspect, the disclosure provides a method of inhibiting a kinase, comprising contacting the kinase with a compound of disclosed herein, or a pharmaceutically acceptable salt, hydrate, solvate, prodrug, stereoisomer, or tautomer thereof, and a second agent wherein said second agent prevents dimer formation of the kinase. In some embodiments, the kinase comprises a mutated cysteine residue. In further embodiments, the mutated cysteine residue is located in or near the position equivalent to Cys 797 in EGFR, including such position in Jak3, Blk, Bmx, Btk, HER2 (ErbB2), HER4 (ErbB4), Itk, Tec, and Txk. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In another aspect, the disclosure provides a method of inhibiting a kinase, the method comprising administering to a subject in need thereof an effective amount of a compound of disclosed herein, or a pharmaceutically acceptable salt, hydrate, solvate, prodrug, stereoisomer, or tautomer thereof. In some embodiments, the kinase is a Her-kinase. In other embodiments, the method further comprises administering a second agent wherein said second agent prevents dimer formation of the kinase. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In another aspect, the disclosure provides a method of inhibiting a kinase, the method comprising administering to a subject in need thereof an effective amount of a compound of disclosed herein, or a pharmaceutically acceptable salt, hydrate, solvate, prodrug, stereoisomer, or tautomer thereof, and a second agent wherein said second agent prevents dimer formation of the kinase. In some embodiments, the EGFR is a Her-kinase. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In still another aspect, the disclosure provides a method of inhibiting epidermal growth factor receptor (EGFR), the method comprising administering to a subject in need thereof an effective amount of a compound of disclosed herein, or a pharmaceutically acceptable salt, hydrate, solvate, prodrug, stereoisomer, or tautomer thereof. In some embodiments, the method further comprises administering a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In another aspect, the disclosure provides a method of inhibiting epidermal growth factor receptor (EGFR), the method comprising administering to a subject in need thereof an effective amount of a compound of disclosed herein, or a pharmaceutically acceptable salt, hydrate, solvate, prodrug, stereoisomer, or tautomer thereof, and a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

Another aspect of the disclosure provides a method of treating or preventing a disease, the method comprising administering to a subject in need thereof an effective amount of a compound of disclosed herein, or a pharmaceutically acceptable salt, hydrate, solvate, prodrug, stereoisomer, or tautomer thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk. In some embodiments, the method further comprises administering a second agent wherein said second agent prevents dimer formation of the kinase. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In some embodiments, the disease is mediated by EGFR (e.g., EGFR plays a role in the initiation or development of the disease). In further embodiments, the EGFR is a Her-kinase. In further embodiments, the Her-kinase is HER1, HER2, or HER4.

In another aspect, the disclosure provides a method of treating or preventing a disease, the method comprising administering to a subject in need thereof an effective amount of a compound of disclosed herein, or a pharmaceutically acceptable salt, hydrate, solvate, prodrug, stereoisomer, or tautomer thereof, and a second agent wherein said second agent prevents dimer formation of a kinase. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk.

In other embodiments, the disease is mediated by EGFR (e.g., EGFR plays a role in the initiation or development of the disease). In further embodiments, the EGFR is a Her-kinase. In further embodiments, the Her-kinase is HER1, HER2, or HER4. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In other embodiments, the disease is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In further embodiments, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

Another aspect of the disclosure provides a method of treating a kinase mediated disorder, the method comprising administering to a subject in need thereof an effective amount of a compound of disclosed herein, or a pharmaceutically acceptable salt, hydrate, solvate, prodrug, stereoisomer, or tautomer thereof. In other embodiments, the compound is an inhibitor of HER1, HER2, or HER4. In other embodiments, the subject is administered an additional therapeutic agent. In other embodiments, the compound and the additional therapeutic agent are administered simultaneously or sequentially.

In another aspect, the disclosure provides a method of treating a kinase mediated disorder, the method comprising administering to a subject in need thereof an effective amount of a compound of disclosed herein, or a pharmaceutically acceptable salt, hydrate, solvate, prodrug, stereoisomer, or tautomer thereof, and a second agent wherein said second agent prevents EGFR dimer formation. In other embodiments, the compound is an inhibitor of HER1, HER2, or HER4. In other embodiments, the subject is administered an additional therapeutic agent. In other embodiments, the compound, the second agent that prevents EGFR dimer formation, and the additional therapeutic agent are administered simultaneously or sequentially. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another aspect, the disclosure provides a method of treating or preventing cancer, wherein the cancer cell comprise activated EGFR, comprising administering to a subject in need thereof an effective amount of a compound of disclosed herein, or a pharmaceutically acceptable salt, hydrate, solvate, prodrug, stereoisomer, or tautomer thereof.

In another aspect, the disclosure provides a method of treating or preventing cancer, wherein the cancer cell comprise activated EGFR, comprising administering to a subject in need thereof an effective amount of a compound of disclosed herein, or a pharmaceutically acceptable salt, hydrate, solvate, prodrug, stereoisomer, or tautomer thereof and a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In certain embodiments, the EGFR activation is selected from mutation of EGFR, amplification of EGFR, expression of EGFR, and ligand mediated activation of EGFR.

In further embodiments, the mutation of EGFR is located at G719S, G719C, G719A, L858R, L861Q, an exon 19 deletion mutation, or an exon 20 insertion mutation.

Another aspect of the disclosure provides a method of treating or preventing cancer in a subject, wherein the subject is identified as being in need of EGFR inhibition for the treatment of cancer, comprising administering to the subject an effective amount of a compound of disclosed herein, or a pharmaceutically acceptable salt, hydrate, solvate, prodrug, stereoisomer, or tautomer thereof.

In another aspect, the disclosure provides a method of treating or preventing cancer in a subject, wherein the subject is identified as being in need of EGFR inhibition for the treatment of cancer, comprising administering to the subject an effective amount of a compound of disclosed herein, or a pharmaceutically acceptable salt, hydrate, solvate, prodrug, stereoisomer, or tautomer thereof, and optionally a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In certain embodiments, the subject identified as being in need of EGFR inhibition is resistant to a known EGFR inhibitor, including but not limited to, gefitinib or erlotinib. In certain embodiments, a diagnostic test is performed to determine if the subject has an activating mutation in EGFR. In certain embodiments, a diagnostic test is performed to determine if the subject has an EGFR harboring an activating and a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In another aspect, the disclosure provides a method of treating or preventing cancer, wherein the cancer cell comprises an activated ERBB2, comprising administering to a subject in need thereof an effective amount of a compound of disclosed herein, or a pharmaceutically acceptable salt, hydrate, solvate, prodrug, stereoisomer, or tautomer thereof. In certain embodiments, the ERBB2 activation is selected from mutation of ERBB2, expression of ERBB2 and amplification of ERBB2. In further embodiments, the mutation is a mutation in exon 20 of ERBB2.

In another aspect, the disclosure provides a method of treating or preventing cancer, wherein the cancer cell comprises an activated ERBB2, comprising administering to a subject in need thereof an effective amount of a compound of disclosed herein, or a pharmaceutically acceptable salt, hydrate, solvate, prodrug, stereoisomer, or tautomer thereof, and a second agent wherein said second agent prevents ERBB2 dimer formation. In certain embodiments, the ERBB2 activation is selected from mutation of ERBB2, expression of ERBB2 and amplification of ERBB2. In further embodiments, the mutation is a mutation in exon 20 of ERBB2. In some embodiments, the second agent that prevents ERBB2 dimer formation is an antibody. In further embodiments, the second agent that prevents ERBB2 dimer formation is cetuximab, trastuzumab, or panitumumab. In further embodiments, the second agent that prevents ERBB2 dimer formation is cetuximab.

In another aspect, the disclosure provides a method of treating cancer in a subject, wherein the subject is identified as being in need of ERBB2 inhibition for the treatment of cancer, comprising administering to the subject in need thereof an effective amount of a compound of disclosed herein, or a pharmaceutically acceptable salt, hydrate, solvate, prodrug, stereoisomer, or tautomer thereof.

In another aspect, the disclosure provides a method of treating cancer in a subject, wherein the subject is identified as being in need of ERBB2 inhibition for the treatment of cancer, comprising administering to the subject in need thereof an effective amount of a compound of disclosed herein, or a pharmaceutically acceptable salt, hydrate, solvate, prodrug, stereoisomer, or tautomer thereof, and optionally a second agent wherein said second agent prevents ERBB2 dimer formation. In some embodiments, the second agent that prevents ERBB2 dimer formation is an antibody. In further embodiments, the second agent that prevents ERBB2 dimer formation is cetuximab, trastuzumab, or panitumumab. In further embodiments, the second agent that prevents ERBB2 dimer formation is cetuximab.

Another aspect of the disclosure provides a method of preventing resistance to a known EGFR inhibitor, including but not limited to, gefitinib or erlotinib in a disease, comprising administering to a subject in need thereof an effective amount of a compound of disclosed herein, or a pharmaceutically acceptable salt, hydrate, solvate, prodrug, stereoisomer, or tautomer thereof.

Another aspect of the disclosure provides a method of preventing resistance to a known EGFR inhibitor, including but not limited to, gefitinib or erlotinib in a disease, comprising administering to a subject in need thereof an effective amount of a compound of disclosed herein, or a pharmaceutically acceptable salt, hydrate, solvate, prodrug, stereoisomer, or tautomer thereof, and a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In certain embodiments, the disclosure provides a method of treating any of the disorders described herein, wherein the subject is a human. In certain embodiments, the disclosure provides a method of preventing any of the disorders described herein, wherein the subject is a human.

In another aspect, the disclosure provides a compound of disclosed herein, or a pharmaceutically acceptable salt, hydrate, solvate, prodrug, stereoisomer, or tautomer thereof, for use in the manufacture of a medicament for treating or preventing a disease in which EGFR plays a role.

In another aspect, the disclosure provides a compound of disclosed herein, or a pharmaceutically acceptable salt, hydrate, solvate, prodrug, stereoisomer, or tautomer thereof, and a second agent wherein said second agent prevents EGFR dimer formation for use in the manufacture of a medicament for treating or preventing a disease in which EGFR plays a role. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In still another aspect, the disclosure provides the use of a compound of disclosed herein, or a pharmaceutically acceptable salt, hydrate, solvate, prodrug, stereoisomer, or tautomer thereof, in the treatment or prevention of a disease in which EGFR plays a role.

In another aspect, the disclosure provides the use of a compound of disclosed herein, or a pharmaceutically acceptable salt, hydrate, solvate, prodrug, stereoisomer, or tautomer thereof, and a second agent wherein said second agent prevents EGFR dimer formation in the treatment or prevention of a disease in which EGFR plays a role. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

As inhibitors of Her kinases, the compounds and compositions of this disclosure are particularly useful for treating or lessening the severity of a disease, condition, or disorder where a protein kinase is implicated in the disease, condition, or disorder. In one aspect, the present disclosure provides a method for treating or lessening the severity of a disease, condition, or disorder where a protein kinase is implicated in the disease state. In another aspect, the present disclosure provides a method for treating or lessening the severity of a kinase disease, condition, or disorder where inhibition of enzymatic activity is implicated in the treatment of the disease. In another aspect, this disclosure provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

This disclosure further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

Another aspect of this disclosure provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof. In other embodiments, the method further comprises administering a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

As inhibitors of Her kinases, the compounds and compositions of this disclosure are also useful in biological samples. One aspect of the disclosure relates to inhibiting protein kinase activity in a biological sample, which method comprises contacting said biological sample with a compound of the disclosure or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this disclosure relates to the study of Her kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds and compositions of the present disclosure as Her kinase inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt, hydrate, solvate, prodrug, stereoisomer, or tautomer thereof, and optionally a second agent wherein said second agent prevents EGFR dimer formation. For any of the above uses, the required dosage will vary depending on the mode of administration, the particular condition to be treated and the effect desired.

In other embodiments, the compound and the second agent that prevents EGFR dimer formation are administered simultaneously or sequentially.

Pharmaceutical Compositions

In another aspect, the disclosure provides a pharmaceutical composition comprising a compound of disclosed herein, or a pharmaceutically acceptable ester, salt, or prodrug thereof, together with a pharmaceutically acceptable carrier.

In another aspect, the disclosure provides a pharmaceutical composition comprising a compound of disclosed herein, or a pharmaceutically acceptable ester, salt, or prodrug thereof, and a second agent wherein said second agent prevents EGFR dimer formation together with a pharmaceutically acceptable carrier. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

Compounds of the disclosure can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present disclosure in free form or in a pharmaceutically acceptable salt form in association and optionally a second agent wherein said second agent prevents EGFR dimer formation with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present disclosure with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds and compositions of the disclosure can be administered in therapeutically effective amounts in a combinational therapy with one or more therapeutic agents (pharmaceutical combinations) or modalities, e.g., a second agent wherein said second agent prevents EGFR dimer formation, non-drug therapies, etc. For example, synergistic effects can occur with agents that prevents EGFR dimer formation, other anti-proliferative, anti-cancer, immunomodulatory or anti-inflammatory substances. Where the compounds of the disclosure are administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients (such as, but not limited to, a second agent wherein said second agent prevents EGFR dimer formation, a second and different antineoplastic agent) and non-drug therapies (such as, but not limited to, surgery or radiation treatment). For instance, the compounds of the disclosure can be used in combination with other pharmaceutically active compounds, preferably compounds that are able to enhance the effect of the compounds of the disclosure. The compounds of the disclosure can be administered simultaneously (as a single preparation or separate preparation) or sequentially to the other drug therapy or treatment modality. In general, a combination therapy envisions administration of two or more drugs during a single cycle or course of therapy.

In one aspect of the disclosure, the compounds may be administered in combination with one or more agents that prevent EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In another aspect of the disclosure, the compounds may be administered in combination with one or more separate pharmaceutical agents, e.g., a chemotherapeutic agent, an immunotherapeutic agent, or an adjunctive therapeutic agent. In one embodiment, the chemotherapeutic agent reduces or inhibits the binding of ATP with EGFR (e.g., gefitinib, erlotinib, AZD9291, CO-1686 or WZ4002).

The pharmaceutical compositions of the present disclosure comprise a therapeutically effective amount of a compound of the present disclosure formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this disclosure can be administered to humans and other animals orally, rectally, parenterally, intracisternally, intravaginally, intraperitoneally, topically (as by powders, ointments, or drops), buccally, or as an oral or nasal spray. In other embodiments, the composition further comprises administering a second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required.

Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combinations, e.g., a kit, comprising a) a first agent which is a compound of the disclosure as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the disclosure and a co-agent, are both administered to a patient simultaneously in the form of a single entity or dosage. The term "non-fixed combination" means that the active ingredients, e.g. a compound of the disclosure and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

In certain embodiments, these compositions optionally further comprise one or more additional therapeutic agents. For example, an agent that prevents EGFR dimer formation, chemotherapeutic agents or other antiproliferative agents may be combined with the compounds of this disclosure to treat proliferative diseases and cancer.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc;

excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

In another aspect, the disclosure provides a kit comprising a compound capable of inhibiting kinase activity selected from one or more compounds of disclosed herein, or pharmaceutically acceptable salts, hydrates, solvates, prodrugs, stereoisomers, or tautomers thereof, and instructions for use in treating cancer. In certain embodiments, the kit further comprises components for performing a test to determine whether a subject has activating and/or drug resistance mutations in EGFR.

In another aspect, the disclosure provides a kit comprising a compound capable of inhibiting EGFR activity selected from a compound of disclosed herein, or a pharmaceutically acceptable salt, hydrate, solvate, prodrug, stereoisomer, or tautomer thereof.

In another aspect, the disclosure provides a kit comprising a compound capable of inhibiting kinase activity selected from one or more compounds of disclosed herein, or pharmaceutically acceptable salts, hydrates, solvates, prodrugs, stereoisomers, or tautomers thereof, a second agent wherein said second agent prevents EGFR dimer formation, and instructions for use in treating cancer. In certain embodiments, the kit further comprises components for performing a test to determine whether a subject has activating and/or drug resistance mutations in EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In another aspect, the disclosure provides a kit comprising a compound capable of inhibiting EGFR activity selected from a compound of disclosed herein, or a pharmaceutically acceptable salt, hydrate, solvate, prodrug, stereoisomer, or tautomer thereof and second agent wherein said second agent prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Analytical Methods, Materials, and Instrumentation

All reactions were monitored by Waters LC/MS system (Waters 2998 Photodiode Array Detector, Waters SQ detector 2, Waters 515 HPLC pump, Waters 2545 Binary Gradient Module, Waters System Fluidics Organizer and Waters 2767 Sample Manager) using SunFire™ C18 column (4.6×50 mm, 5 µm particle size): solvent gradient=80% A at 0 min, 1% A at 5 min; solvent A=0.035% TFA in Water; solvent B=0.035% TFA in MeOH; flow rate: 1.5 mL/min (method A) and Waters Acquity UPLC/MS system (Waters PDA eX Detector, QDa Detector, Sample manager—FL, Binary Solvent Manager) using Acquity UPLC® BEH C18 column (2.1×50 mm, 1.7 µm particle size): solvent gradient=80% A at 0 min, 5% A at 2 min; solvent A=0.1% formic acid in Water; solvent B=0.1% formic acid in Acetonitrile; flow rate: 0.6 mL/min (method B). Reaction products were purified by flash column chromatography using CombiFlash®Rf with Teledyne Isco RediSep®Rf High Performance Gold or Silicycle SiliaSep™ High Performance columns (4 g, 12 g, 24 g, 40 g, or 80 g) and Waters HPLC system using SunFire™ Prep C18 column (19×100 mm, 5 µm particle size): solvent gradient=80% A at 0 min, 5% A at 25 min; solvent A=0.035% TFA in Water; solvent B=0.035% TFA in MeOH; flow rate: 25 mL/min. The purity of all compounds was over 95% and was analyzed with Waters LC/MS system. $^1$H NMR was obtained using a 600 MHz Varian Inova-600 or 400 MHz Varian. Chemical shifts are reported relative to chloroform ($\delta$=7.24) or dimethyl sulfoxide ($\delta$=2.50) for $^1$H NMR. Data are reported as (br=broad, s=singlet, d=doublet, t=triplet, q=quartet, m=multiplet).

Abbreviations Used in the Following Examples and Elsewhere Herein are:
atm atmosphere
br broad
DIPEA N,N-diisopropylethylamine
DMA N,N-dimethylacetamide
DMF N,N-dimethylformamide
DMSO dimethyl sulfoxide
ESI electrospray ionization
EtOAc ethyl acetate
HCl hydrochloric acid
h hour(s)
HATU bis(dimethylamino)methylene]-1H-1,2,3-triazolo[4,5-b]pyridinium 3-oxide hexafluoro-phosphate
HPLC high-performance liquid chromatography
LCMS liquid chromatography-mass spectrometry
m multiplet
MeOH methanol
MHz megahertz
min minutes
MS mass spectrometry
NMR nuclear magnetic resonance
Pd$_2$(dba)$_3$ tris(dibenzylideneacetone)dipalladium(0)
ppm parts per million
THF tetrahydrofuran
TLC thin layer chromatography Xphos 2-dicyclohexylphosphino-2',4',6'-triisopropylbiphenyl

Example 1: Synthesis of (R)-2-(1-oxoisoindolin-2-yl)-2-phenyl-N-(pyridin-2-yl)acetamide (I-8)

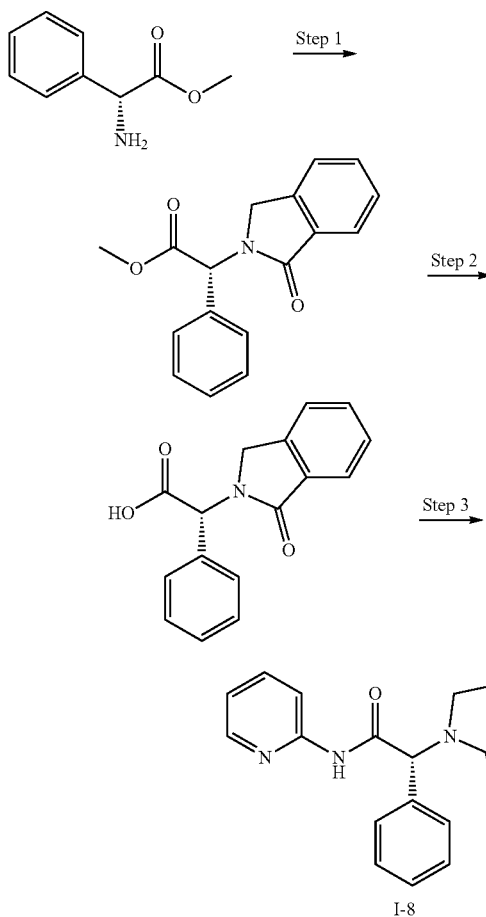

I-8

Step 1. Methyl (R)-2-(1-oxoisoindolin-2-yl)-2-phenylacetate

To a solution of methyl (R)-2-amino-2-phenylacetate (5 g, 30.3 mmol) and phthalaldehyde (4.0 g, 30.3 mmol) in CHCl$_3$ (100 mL) was added acetic acid (0.17 mL, 3.0 mmol) and the resulting mixture was heated to 80° C. After stirring for 4 hr, the reaction mixture was diluted with water (700 mL) and the resulting precipitate was filtered off. The solid was dried using a stream of nitrogen gas to provide methyl (R)-2-(1-oxoisoindolin-2-yl)-2-phenylacetate (6.5 g, 80%) as an off-white solid.

Step 2. (R)-2-(1-oxoisoindolin-2-yl)-2-phenylacetic acid

To a solution of methyl (R)-2-(1-oxoisoindolin-2-yl)-2-phenylacetate (6.5 g, 24.3 mmol) in THF/MeOH/water (150 mL, 1:1:1) was added lithium hydroxide monohydrate (5.1 g, 121.7 mmol). After stirring for 1 h, the solvent was removed under reduced pressure and the resulting residue was diluted with ice water. The aqueous mixture was acidified with concentrated HCl and the resulting suspension isolated via filtration. The solid was dried using a stream of nitrogen gas to provide (R)-2-(1-oxoisoindolin-2-yl)-2-phenylacetic acid (4.77 g, 78%) as an off-white solid.

Step 3. (R)-2-(1-oxoisoindolin-2-yl)-2-phenyl-N-(pyridin-2-yl)acetamide (I-8)

To a solution of methyl (R)-2-(1-oxoisoindolin-2-yl)-2-phenylacetic acid (50 mg, 0.20 mmol), 2-aminopyridine (36 mg, 0.38 mmol) and HATU (200 mg, 0.53 mmol) in N,N-dimethylformamide (2 mL) was added DIPEA (0.17 mL, 0.96 mmol). After stirring for 6 hr, the reaction mixture was diluted with EtOAc and washed with water five times. The organic layer was then dried over sodium sulfate, filtered, concentrated under reduced pressure and purified by preparative high performance liquid chromatography (HPLC) to obtain (R)-2-(1-oxoisoindolin-2-yl)-2-phenyl-N-(pyridin-4-yl)acetamide (I-8, 25 mg, 32%) as a white solid. HPLC method B: Rt=0.63 min; MS m/z: 344.15 [M+1].

Example 2: Synthesis of (R)-2-(1-oxo-5-phenylisoindolin-2-yl)-2-phenyl-N-(thiazol-2-yl)acetamide (I-105)

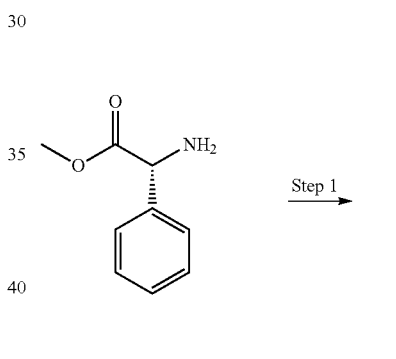

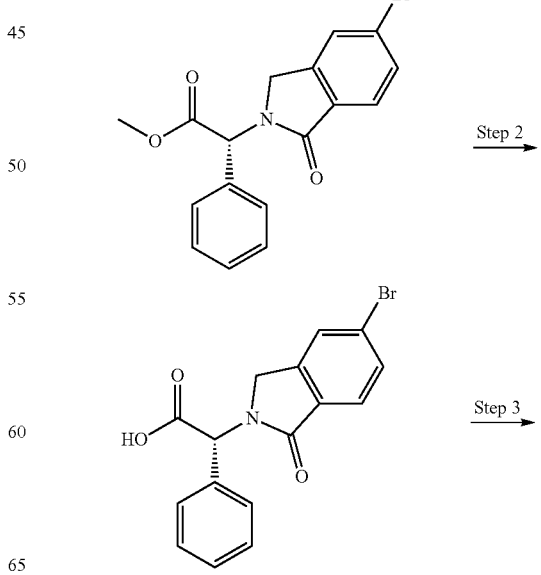

-continued

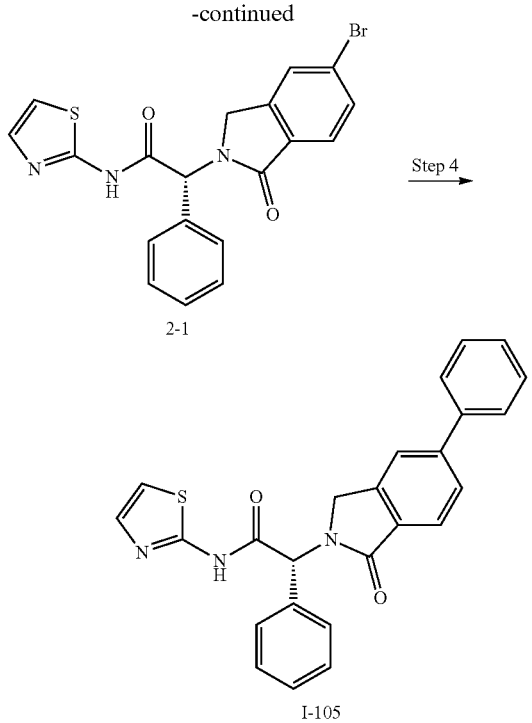

Step 1. Methyl (R)-2-(5-bromo-1-oxoisoindolin-2-yl)-2-phenylacetate

To a solution of methyl (R)-2-amino-2-phenylacetate (2.8 g, 13.9 mmol) and methyl 4-bromo-2-(bromomethyl)benzoate (3.9 g, 12.7 mmol) in N,N-dimethylformamide (120 mL) was added DIPEA (6.6 mL, 38.0 mmol) and the resulting mixture was heated to 80° C. After stirring overnight, the reaction mixture was cooled down to room temperature and diluted with water (700 mL). The precipitate was filtered off and dried using a stream of nitrogen gas to obtain methyl (R)-2-(5-bromo-1-oxoisoindolin-2-yl)-2-phenylacetate (3.2 g, 70%) as an off-white solid.

Step 2. (R)-2-(5-bromo-1-oxoisoindolin-2-yl)-2-phenylacetic acid

To a solution of methyl (R)-2-(5-bromo-1-oxoisoindolin-2-yl)-2-phenylacetate (3.2 g, 8.89 mmol) in THF/MeOH/water (150 mL, 1:1:1) was added lithium hydroxide monohydrate (2.65 g, 63.3 mmol). After stirring for 1 h, the solvent was removed under reduced pressure and the resulting residue was diluted with ice water. The aqueous mixture was acidified with concentrated HCl and the resulting suspension isolated via filtration. The solid was dried using a stream of nitrogen gas to obtain (R)-2-(5-bromo-1-oxoisoindolin-2-yl)-2-phenylacetic acid (2.8 g, 92%) as an off-white solid.

Step 3. (R)-2-(5-bromo-1-oxoisoindolin-2-yl)-2-phenyl-N-(thiazol-2-yl)acetamide (2-1)

To a solution of methyl (R)-2-(5-bromo-1-oxoisoindolin-2-yl)-2-phenylacetic acid (2.0 g, 5.78 mmol), thiazol-2-amine (1.1 g, 11.6 mmol), and HATU (4.4 g, 11.6 mmol) in N,N-dimethylformamide (30 mL) was added DIPEA (4.0 mL, 23.1 mmol). After stirring for 6 hr, the reaction mixture was diluted with EtOAc and washed with water five times. The organic layer was dried over sodium sulfate, filtered, concentrated under reduced pressure and purified by column chromatography on silica gel (DCM:EtOAc=9:1 to 4:6) to obtain (R)-2-(5-bromo-1-oxoisoindolin-2-yl)-2-phenyl-N-(thiazol-2-yl)acetamide (2-1, 1.8 g, 73%) as an off-white solid.

Step 4. (R)-2-(1-oxo-5-phenylisoindolin-2-yl)-2-phenyl-N-(thiazol-2-yl)acetamide (I-105)

A mixture of (R)-2-(5-bromo-1-oxoisoindolin-2-yl)-2-phenyl-N-(thiazol-2-yl)acetamide (50 mg, 0.117 mmol), phenyl boronic acid (21 mg, 0.175 mmol) and 2 N Sodium carbonate (0.18 mL, 0.351 mmol) in dioxane (1 mL) was degassed and heated to 100° C. PdCl$_2$(dppf)$_2$ (5 mg, 0.007 mmol) and Xphos (4.5 mg, 0.011 mmol) were then added and the resulting reaction mixture was stirred for 2 hr. The reaction mixture was then cooled down to room temperature and diluted with dichloromethane. The resulting mixture was washed with water and brine, dried over sodium sulfate, filtered, and concentrated under reduced pressure. The resulting residue was purified by preparative high performance liquid chromatography (HPLC) to provide (R)-2-(1-oxo-5-phenylisoindolin-2-yl)-2-phenyl-N-(thiazol-2-yl)acetamide (I-105, 25 mg, 50%) as a white solid. HPLC method A: Rt=4.64 min; MS m/z: 426.38 [M+1]. $^1$H NMR 400 MHz (DMSO-d$_6$) δ 12.71 (bs, NH), 7.86 (s, 1H), 7.84-7.77 (m, 2H), 7.72-7.68 (m, 2H), 7.53-7.38 (m, 10H), 7.29 (d, J=3.5 Hz, 1H), 6.36 (s, 1H), 4.83 (d, J=17.5 Hz, 1H), 4.05 (d, J=17.6 Hz, 1H).

Example 3: Synthesis of (R)-2-(1-oxo-5-(phenylamino)isoindolin-2-yl)-2-phenyl-N-(thiazol-2-yl)acetamide (I-93)

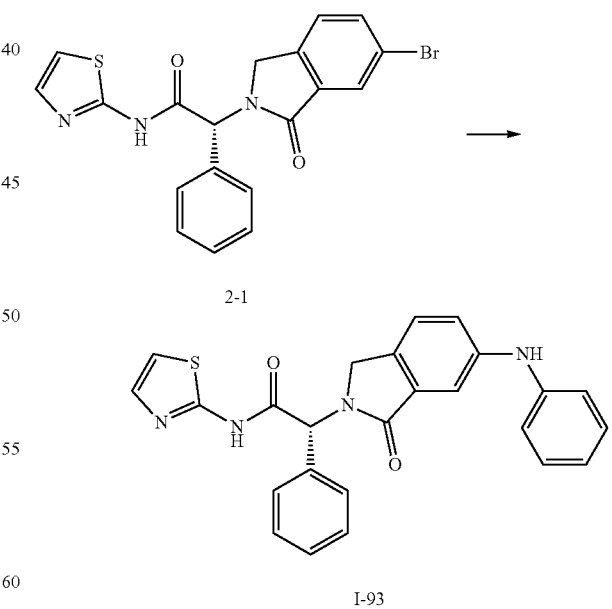

A mixture of (R)-2-(6-bromo-1-oxoisoindolin-2-yl)-2-phenyl-N-(thiazol-2-yl) acetamide (2-1, 50 mg, 0.117 mmol), aniline (22 mg, 0.234 mmol) and potassium carbonate (49 mg, 0.351 mmol) in 2-butanol (1 mL) was degassed and heated to 100° C. Pd$_2$(dba)$_3$ (110 mg, 0.012 mmol) and Xphos (84 mg, 0.176 mmol) were then added and the resulting reaction mixture was stirred for 4 hr. The reaction mixture was then cooled down to room temperature and diluted with dichloromethane. The resulting mixture was washed with water and brine, dried over sodium sulfate, filtered, and concentrated under reduced pressure. The resulting residue was purified by preparative high performance liquid chromatography (HPLC) to provide (R)-2-(1-oxo-5-(phenylamino)isoindolin-2-yl)-2-phenyl-N-(thiazol-2-yl) acetamide (I-93, 15 mg, 29%) as an off-white solid. HPLC method A: Rt=4.43 min; MS m/z: 441.38 [M+1].

Example 4: Synthesis of 5-bromo-N-(2,3-dihydroxypropyl)-2-(((R)-2-oxo-1-phenyl-2-(thiazol-2-ylamino)ethyl)amino)benzamide (I-111)

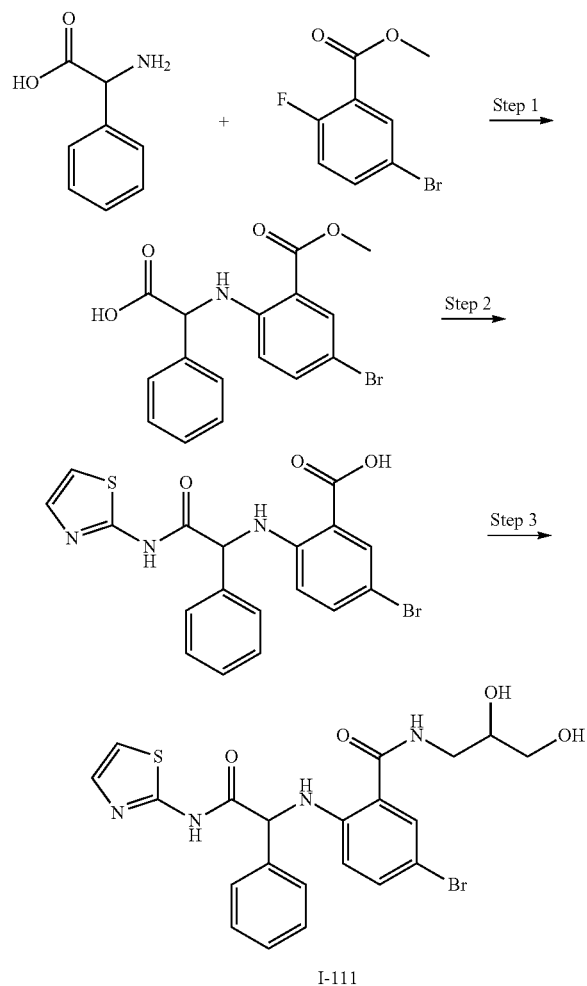

Step 1. (R)-2-((4-bromo-3-(methoxycarbonyl)phenyl)amino)-2-phenylacetic acid

To a solution of (R)-2-amino-2-phenylacetic acid (972 mg, 6.43 mmol) and methyl 2-bromo-5-fluorobenzoate (1 g, 4.29 mmol) in N,N-dimethylformamide (10 mL) was added potassium carbonate (1.8 g, 13.0 mmol) and the resulting mixture was stirred at 100° C. for 6 hr. The reaction mixture was then diluted with ice water and acidified by concentrated HCl. The resulting precipitate was isolated via filtration and dried using a stream of nitrogen gas to provide (R)-2-((4-bromo-3-(methoxycarbonyl)phenyl)amino)-2-phenylacetic acid (1.17 g, 75%) as an off-white solid.

Step 2. Methyl (R)-5-bromo-2-((2-oxo-1-phenyl-2-(thiazol-2-ylamino)ethyl)amino)benzoate To a solution of (R)-2-((4-bromo-3-(methoxycarbonyl) phenyl)amino)-2-phenylacetic acid (1.0 g, 2.75 mmol), thiazol-2-amine (860 mg, 8.58 mmol) and HATU (3.3 g, 8.58 mmol) in N,N-dimethylformamide (20 mL) was added DIPEA (3.0 mL, 17.2 mmol). After stirring for 6 hr, the reaction mixture was diluted with EtOAc and washed with water five times. The organic layer was dried over sodium sulfate, filtered, concentrated under reduced pressure and purified by column chromatography on silica gel (DCM: EtOAc=9:1 to 3:7) to provide methyl (R)-5-bromo-2-((2-oxo-1-phenyl-2-(thiazol-2-ylamino)ethyl)amino)benzoate as an off-white solid.

Step 3. (R)-5-bromo-2-((2-oxo-1-phenyl-2-(thiazol-2-ylamino)ethyl)amino)benzoic acid To a solution of methyl (R)-5-bromo-2-((2-oxo-1-phenyl-2-(thiazol-2-ylamino)ethyl)amino)benzoate (500 mg, 1.12 mmol) in THF/MeOH/water (3 mL, 1:1:1) was added lithium hydroxide monohydrate (235 mg, 5.60 mmol). After stirring for 1 h, the solvent was removed under reduced pressure and the resulting residue was diluted with ice water. The aqueous mixture was acidified with concentrated HCl and the resulting suspension isolated via filtration. The solid was dried using a stream of nitrogen gas to obtain (R)-5-bromo-2-((2-oxo-1-phenyl-2-(thiazol-2-ylamino)ethyl) amino)benzoic acid (324 mg, 67%) as an off-white solid.

Step 4. (5-bromo-N-(2,3-dihydroxypropyl)-2-(((R)-2-oxo-1-phenyl-2-(thiazol-2-ylamino)ethyl)amino) benzamide (I-111)

To a solution of (R)-5-bromo-2-((2-oxo-1-phenyl-2-(thiazol-2-ylamino)ethyl)amino)benzoic acid (50 mg, 0.116 mmol), 3-aminopropane-1,2-diol (17 mg, 0.188 mmol) and HATU (96 mg, 0.252 mmol) in N,N-dimethylformamide (1 mL) was added DIPEA (66 µL, 0.378 mmol). The resulting solution was stirred for 2 hr, diluted with EtOAc and washed with water five times. The organic layer was dried over sodium sulfate, filtered, concentrated under reduced pressure and purified by preparative high performance liquid chromatography (HPLC) to obtain 5-bromo-N-(2,3-dihydroxypropyl)-2-(((R)-2-oxo-1-phenyl-2-(thiazol-2-ylamino) ethyl)amino)benzamide (I-111, 37 mg, 64%) as an off-white solid. HPLC method A: Rt=3.74 min; MS m/z: 505.22 [M+1].

The following compounds in Table 1 were synthesized according to the procedures outlined in Examples 1-4.

TABLE 1

| Compound Number | ¹H NMR and/or MS (m/z) data |
|---|---|
| I-1 | Method B: Rt = 1.29 min, MS m/z: 371.23 [M + 1]. |
| I-2 | Method B: Rt = 1.34 min, MS m/z: 371.23 [M + 1]. |
| I-3 | Method B: Rt = 1.36 min, MS m/z: 436.22 [M + 1]. |
| I-4 | Method B: Rt = 1.32 min, MS m/z: 422.19 [M + 1]. |
| I-5 | Method B: Rt = 1.25 min, MS m/z: 364.17 [M + 1]. |
| I-6 | Method B: Rt = 1.47 min, MS m/z: 418.17 [M + 1]. |
| I-7 | Method B: Rt = 0.73 min, MS m/z: 344.15 [M + 1]. |
| I-8 | Method B: Rt = 0.63 min, MS m/z: 344.15 [M + 1]. |
| I-9 | Method B: Rt = 1.00 min, MS m/z: 407.21 [M + 1]. |
| I-10 | Method B: Rt = 0.74 min, MS m/z: 506.26 [M + 1]. |
| I-11 | Method B: Rt = 0.73 min, MS m/z: 478.28 [M + 1]. |
| I-12 | Method B: Rt = 1.15 min, MS m/z: 395.15 [M + 1]. |
| I-13 | Method B: Rt = 0.80 min, MS m/z: 365.12 [M + 1]. |
| I-14 | Method B: Rt = 0.68 min, MS m/z: 520.30 [M + 1]; ¹H NMR 600 MHz (DMSO-$d_6$) δ 12.73 (s, NH), 8.11 (t, J = 6.0 Hz, 1H), 7.83 (s, 1H), 7.72 (d, J = 7.8 Hz, 1H), 7.61 (t, J = 7.2 Hz, 1H), 7.56 (d, J = 7.8 Hz, 1H), 7.50 (t, J = 7.8 Hz, 1H), 7.45 (t, J = 7.2 Hz, 1H), 7.42 (d, J = 7.2 Hz, 1H), 7.38 (s, 1H), 7.37 (d, J = 9.0 Hz, 1H), 6.32 (s, 1H), 4.72 (d, J = 18.0 Hz, 1H), 3.98 (d, J = 17.4 Hz, 1H), 3.95 (d, J = 15.6 Hz, 2H), 3.60 (t, J = 11.4 Hz, 2H), 3.39 (d, J = 6.6 Hz, 2H), 3.10-3.07 (m, 2H), 3.05-2.99 (m, 2H), 1.89-1.83 (m, 2H). |
| I-15 | Method B: Rt = 0.64 min, MS m/z: 492.31 [M + 1]; ¹H NMR 600 MHz (DMSO-$d_6$) δ 12.75 (s, NH), 7.96 (t, J = 6.0 Hz, 1H), 7.81 (s, 1H), 7.72 (d, J = 7.8 Hz, 1H), 7.60 (t, J = 7.2 Hz, 1H), 7.56 (d, J = 7.8 Hz, 1H), 7.50 (t, J = 7.8 Hz, 1H), 7.45 (d, J = 7.8 Hz, 1H), 7.47-7.40 (m, 2H), 7.38 (s, 1H), 7.37 (d, J = 8.4 Hz, 1H), 6.31 (s, 1H), 4.72 (d, J = 17.4 Hz, 1H), 3.97 (d, J = 17.4 Hz, 1H), 3.25 (q, J = 6.6 Hz, 2H), 3.04-3.01 (m, 2H), 2.73 (s, 3H), 2.72 (s, 3H), 1.61-1.56 (m, 2H), 1.49 (quin, J = 7.2 Hz, 2H). |
| I-16 | Method B: Rt = 0.65 min, MS m/z: 464.25 [M + 1]; ¹H NMR 600 MHz (DMSO-$d_6$) δ 12.72 (s, NH), 8.20 (t, J = 6.0 Hz, 1H) 7.88 (s, 1H), 7.72 (d, J = 7.8 Hz, 1H), 7.61 (t, J = 6.6 Hz, 1H), 7.56 (d, J = 7.8 Hz, 1H), 7.50 (t, J = 7.2 Hz, 1H), 7.45 (d, J = 7.2 Hz, 1H), 7.47-7.40 (m, 2H), 7.37 (s, 1H), 7.37 (d, J = 8.4 Hz, 1H), 6.34 (s, 1H), 4.72 (d, J = 18.0 Hz, 1H), 3.98 (d, J = 17.4 Hz, 1H), 3.57 (q, J = 6.2 Hz, 2H), 3.21 (q, J = 5.4 Hz, 2H), 2.80 (s, 3H), 2.80 (s, 3H). |
| I-17 | Method B: Rt = 0.96 min, MS m/z: 393.18 [M + 1]; ¹H NMR 600 MHz (DMSO-$d_6$) δ 12.74 (s, NH), 7.82 (s, 1H) 7.60 (t, J = 7.8 Hz, 1H), 7.55 (d, J = 7.8 Hz, 1H), 7.52 (bs, 2H), 7.49 (t, J = 7.2 Hz, 1H), 7.47-7.44 (m, 1H), 7.44 (d, J = 7.8 Hz, 1H), 7.42 (d, J = 7.2 Hz, 1H), 7.37 (s, 1H), 7.37 (d, J = 8.4 Hz, 1H), 7.25 (s, 1H), 4.72 (d, J = 17.4 Hz, 1H), 3.97 (d, J = 17.4 Hz, 1H). |
| I-18 | Method B: Rt = 1.15 min, MS m/z: 395.15 [M + 1]; ¹H NMR 600 MHz (DMSO-$d_6$) δ 12.74 (s, NH), 8.26 (d, J = 8.4 Hz, 1H), 8.21 (s, 1H), 7.85 (d, J = 7.2 Hz, 1H), 7.74 (d, J = 7.8 Hz, 1H), 7.73 (d, J = 6.6 Hz, 1H), 7.62 (t, J = 7.2 Hz, 1H), 7.56 (d, J = 7.8 Hz, 1H, 7.50 (t, J = 7.2 Hz, 1H), 7.48 (d, J = 3.6 Hz, 1H), 7.28 (d, J = 3.6 Hz, 1H), 6.37 (s, 1H), 4.72 (d, J = 16.8 Hz, 1H), 4.21 (d, J = 12.0 Hz, 1H). |
| I-19 | Method B: Rt = 0.89 min, MS m/z: 334.14 [M + 1]; ¹H NMR 400 MHz (DMSO-$d_6$) δ 11.77 (s, NH), 7.88 (s, 1H), 7.74 (d, J = 7.6 Hz, 1H), 7.63-7.54 (m, 2H), 7.54-7.38 (m, 6H), 7.11 (s, 1H), 6.20 (s, 1H), 4.72 (d, J = 17.2 Hz, 1H), 3.92 (d, J = 17.6 Hz, 1H). |
| I-20 | Method B: Rt = 0.89 min, MS m/z: 334.10 [M + 1]; ¹H NMR 400 MHz (DMSO-$d_6$) δ 11.77 (s, NH), 7.88 (s, 1H), 7.75 (d, J = 8.0 Hz, 1H), 7.63-7.54 (m, 2H), 7.54-7.38 (m, 6H), 7.11 (s, 1H), 6.19 (s, 1H), 4.71 (d, J = 17.2 Hz, 1H), 3.92 (d, J = 18.0 Hz, 1H). |
| I-21 | Method B: Rt = 1.16 min, MS m/z: 350.10 [M + 1]; ¹H NMR 400 MHz (DMSO-$d_6$) δ 12.68 (s, NH), 7.74 (d, J = 8.0 Hz, 1H), 7.64-7.55 (m, 2H), 7.53-7.42 (m, 5H), 7.39 (s, 1H), 7.38 (d, J = 8.4 Hz, 1H), 7.28 (d, J = 3.6 Hz, 1H), 6.31 (s, 1H), 4.76 (d, J = 17.6 Hz, 1H), 3.98 (d, J = 17.6 Hz, 1H). |
| I-22 | Method B: Rt = 1.05 min, MS m/z: 463.22 [M + 1]; ¹H NMR 400 MHz (DMSO-$d_6$) δ 12.87 (s, NH), 7.74 (d, J = 7.6 Hz, 1H), 7.69 (s, 1H) 7.64-7.55 (m, 2H), 7.54-7.43 (m, 4H), 7.41-7.38 (m, 2H), 6.29 (s, 1H), 4.73 (d, J = 17.6 Hz, 1H), 3.99 (d, J = 17.6 Hz, 1H), 3.53 (bs, 4H), 3.32 (s, 4H). |
| I-23 | Method B: Rt = 0.70 min, MS m/z: 504.25 [M + 1]. |
| I-24 | Method B: Rt = 0.69 min, MS m/z: 546.23 [M + 1]. |
| I-25 | Method B: Rt = 0.71 min, MS m/z: 476.27 [M + 1]; ¹H NMR 400 MHz (DMSO-$d_6$) δ 12.87 (s, NH), 7.80 (s, 1H), 7.74 (d, J = 7.5 Hz, 1H), 7.62 (t, J = 7.3 Hz, 1H), 7.58 (t, J = 7.4 Hz, 1H), 7.52 (t, J = 7.4 Hz, 1H), 7.50-7.43 (m, 3H), 7.42-7.38 (m, 2H), 6.31 (s, 1H), 4.74 (d, J = 17.5 Hz, 1H), 4.60 (bs, 2H), 3.98 (d, J = 17.6 H, 1H), 3.06 (bs, 2H), 2.82 (s, 3H). |
| I-26 | Method B: Rt = 1.37 min, MS m/z: 395.23 [M + Na]. |
| I-27 | Method B: Rt = 1.36 min, MS m/z: 423.09 [M + 1]; ¹H NMR 400 MHz (DMSO-$d_6$) δ 11.56 (s, NH), 9.19 (s, 1H), 8.62 (s, 1H), 7.75 (d, J = 6.8 Hz, 1H) 7.64-7.40 (m, 8H), 6.37 (s, 1H), 4.77 (d, J = 17.3 Hz, 1H), 3.95 (d, J = 17.3 Hz, 1H). |
| I-28 | Method B: Rt = 1.49 min, MS m/z: 422.15 [M + 1]; ¹H NMR 400 MHz (DMSO-$d_6$) δ 11.29 (s, NH), 8.37 (s, 1H), 8.23 (d, J = 5.4 Hz, 1H), 7.74 (d, J = 7.5 Hz, 1H), 7.61 (t, J = 7.6 Hz, 1H), 7.57 (t, J = 7.6 Hz, 1H), 7.51 (d, J = 7.1 Hz, 1H), 7.49-7.39 (m, 6H), 6.36 (s, 1H), 4.77 (d, J = 17.6 Hz, 1H), 3.94 (d, J = 17.6 Hz, 1H). |

TABLE 1-continued

| Compound Number | ¹H NMR and/or MS (m/z) data |
|---|---|
| I-29 | Method B: Rt = 1.48 min, MS m/z: 422.11 [M + 1]; ¹H NMR 400 MHz (DMSO-d$_6$) δ 11.29 (s, NH), 8.37 (s, 1H), 8.23 (d, J = 5.4 Hz, 1H), 7.74 (d, J = 7.5 Hz, 1H), 7.61 (t, J = 7.6 Hz, 1H), 7.57 (t, J = 7.6 Hz, 1H), 7.51 (d, J = 7.1 Hz, 1H), 7.49-7.39 (m, 6H), 6.36 (s, 1H), 4.77 (d, J = 17.6 Hz, 1H), 3.94 (d, J = 17.6 Hz, 1H). |
| I-30 | Method B: Rt = 1.25 min, MS m/z: 401.18 [M + 1]. |
| I-31 | Method B: Rt = 1.12 min, MS m/z: 344.15 [M + 1]; ¹H NMR 400 MHz (DMSO-d$_6$) δ 11.03 (s, NH), 8.32 (d, J = 4.9 Hz, 1H), 8.10 (d, J = 8.1 Hz, 1H), 7.81 (t, J = 8.1 Hz, 1H), 7.74 (d, J = 7.1 Hz, 1H), 7.60 (t, J = 7.7 Hz, 1H), 7.57 (t, J = 7.2 Hz, 1H), 7.50 (t, J = 7.8 Hz, 1H), 7.49-7.38 (m, 5H), 7.13 (dd, J = 6.6, 5.0 Hz, 1H), 6.38 (s, 1H), 4.80 (d, J = 17.6 Hz, 1H), 3.94 (d, J = 17.6 Hz, 1H). |
| I-32 | Method B: Rt = 1.19 min, MS m/z: 401.18 [M + 1]. |
| I-33 | Method B: Rt = 0.92 min, MS m/z: 385.18 [M + 1]. |
| I-34 | Method B: Rt = 0.55 min, MS m/z: 333.15 [M + 1]. |
| I-35 | Method B: Rt = 0.54 min, MS m/z: 333.15 [M + 1]. |
| I-36 | Method B: Rt = 1.39 min, MS m/z: 428.10 [M + 1]; ¹H NMR 400 MHz (DMSO-d$_6$) δ 12.99 (s, NH), 7.74 (d, J = 7.5 Hz, 1H), 7.65-7.55 (m, 2H), 7.51 (t, J = 7.4 Hz, 1H), 7.49-7.42 (m, 3H), 7.39 (s, 1H), 7.38-7.35 (m, 2H), 6.23 (s, 1H), 4.70 (d, J = 17.6 Hz, 1H), 4.00 (d, J = 17.4 Hz, 1H). |
| I-37 | Method B: Rt = 0.78 min, MS m/z: 427.24 [M + 1]. |
| I-38 | Method B: Rt = 0.81 min, MS m/z: 365.12 [M + 1]. |
| I-39 | Method B: Rt = 1.19 min, MS m/z: 364.17 [M + 1]; ¹H NMR 400 MHz (DMSO-d$_6$) δ 12.61 (s, NH), 7.63 (d, J = 7.5 Hz, 1H), 7.60-7.56 (m, 2H), 7.50 (d, J = 3.6 Hz, 1H), 7.48-7.43 (m, 1H), 7.36-7.33 (m, 2H), 7.28-7.22 (m, 3H), 7.16 (t, J = 7.3 Hz, 1H), 5.47 (dd, J = 11.0, 4.9 Hz, 1H), 4.72 (d, J = 17.5 Hz, 1H), 4.57 (d, J = 17.5 Hz, 1H), 3.43 (dd, J = 14.4, 4.9 Hz, 1H), 3.26 (dd, J = 14.4, 11.1 Hz, 1H). |
| I-40 | Method B: Rt = 1.47 min, MS m/z: 428.10 [M + 1]; ¹H NMR 400 MHz (DMSO-d$_6$) δ 12.98 (s, NH), 7.74 (d, J = 7.5 Hz, 1H), 7.65-7.54 (m, 3H), 7.51 (t, J = 7.3 Hz, 1H), 7.48-7.40 (m, 3H), 7.40-7.35 (m, 2H), 6.28 (s, 1H), 4.71 (d, J = 17.5, 1H), 3.99 (d, J = 17.3 Hz, 1H). |
| I-41 | Method B: Rt = 0.98 min, MS m/z: 351.08 [M + 1]; ¹H NMR 400 MHz (DMSO-d$_6$) δ 13.17 (s, NH), 9.22 (s, 1H), 7.74 (d, J = 7.5 Hz, 1H), 7.62 (t, J = 7.6 Hz, 1H), 7.58 (t, J = 8.7 Hz, 1H), 7.51 (t, J = 7.7 Hz, 1H), 7.49-7.42 (m, 3H), 7.41-7.38 (m, 2H), 6.31 (s, 1H), 4.71 (d, J = 17.4, 1H), 4.00 (d, J = 17.5 Hz, 1H). |
| I-42 | Method B: Rt = 0.98 min, MS m/z: 351.08 [M + 1]; ¹H NMR 400 MHz (DMSO-d$_6$) δ 13.17 (s, NH), 9.22 (s, 1H), 7.74 (d, J = 7.5 Hz, 1H), 7.62 (t, J = 7.6 Hz, 1H), 7.58 (t, J = 8.7 Hz, 1H), 7.51 (t, J = 7.7 Hz, 1H), 7.49-7.42 (m, 3H), 7.41-7.38 (m, 2H), 6.31 (s, 1H), 4.71 (d, J = 17.4, 1H), 4.00 (d, J = 17.5 Hz, 1H). |
| I-43 | Method B: Rt = 0.78 min, MS m/z: 477.30 [M + 1]. |
| I-44 | Method A: Rt = 3.00 min, MS m/z: 477.39 [M + 1]. |
| I-45 | Method B: Rt = 1.19 min, MS m/z: 364.13 [M + 1]; ¹H NMR 400 MHz (DMSO-d$_6$) δ 12.61 (s, NH), 7.63 (d, J = 7.5 Hz, 1H), 7.60-7.56 (m, 2H), 7.50 (d, J = 3.6 Hz, 1H), 7.48-7.43 (m, 1H), 7.36-7.33 (m, 2H), 7.28-7.22 (m, 3H), 7.16 (t, J = 7.3 Hz, 1H), 5.47 (dd, J = 11.0, 4.9 Hz, 1H), 4.72 (d, J = 17.5 Hz, 1H), 4.57 (d, J = 17.5 Hz, 1H), 3.43 (dd, J = 14.4, 4.9 Hz, 1H), 3.26 (dd, J = 14.4, 11.1 Hz, 1H). |
| I-46 | Method B: Rt = 1.50 min, MS m/z: 432.16 [M + 1]. |
| I-47 | Method B: Rt = 1.47 min, MS m/z: 432.16 [M + 1]. |
| I-48 | Method B: Rt = 1.36 min, MS m/z: 436.22 [M + 1]; ¹H NMR 400 MHz (DMSO-d$_6$) δ 13.01 (s, NH), 8.09 (s, 1H), 7.63 (d, J = 7.5 Hz, 1H), 7.58 (td, J = 6.5, 1.1 Hz, 2H), 7.48-7.43 (m, 1H), 7.32 (d, J = 7.2 Hz, 2H), 7.24 (t, J = 7.2 Hz, 2H), 7.16 (tt, J = 7.3, 1.1 Hz, 1H), 5.36 (dd, J = 11.0, 4.9 Hz, 1H), 4.58 (s, 2H), 4.27 (q, J = 7.1 Hz, 2H), 3.49-3.42 (m, 1H), 3.32-3.24 (m, 1H), 1.28 (t, J = 7.1 Hz, 3H). |
| I-49 | Method B: Rt = 1.51 min, MS m/z: 442.63 [M + 1]; ¹H NMR 400 MHz (DMSO-d$_6$) δ 12.87 (s, NH), 7.63 (d, J = 7.5 Hz, 1H), 7.60-7.56 (m, 3H), 7.48-7.43 (m, 1H), 7.31 (d, J = 7.2 Hz, 2H), 7.24 (t, J = 7.5 Hz, 2H), 7.18-7.13 (m, 1H), 5.43 (dd, J = 10.9, 5.0 Hz, 1H), 4.60 (dd, J = 28.6, 17.5 Hz, 2H), 3.42 (dd, J = 14.4, 5.0 Hz, 1H), 3.26 (dd, J = 14.4, 10.9 Hz, 1H). |
| I-50 | Method B: Rt = 1.51 min, MS m/z: 442.63 [M + 1]; ¹H NMR 400 MHz (DMSO-d$_6$) δ 12.87 (s, NH), 7.63 (d, J = 7.5 Hz, 1H), 7.61-7.56 (m, 3H), 7.48-7.43 (m, 1H), 7.31 (d, J = 7.1 Hz, 2H), 7.24 (t, J = 7.5 Hz, 2H), 7.18-7.14 (m, 1H), 5.43 (dd, J = 10.9, 5.0 Hz, 1H), 4.60 (dd, J = 28.6, 17.5 Hz, 2H), 3.42 (dd, J = 14.5, 5.1 Hz, 1H), 3.28 (dd, J = 14.3, 10.9 Hz, 1H). |
| I-51 | Method A: Rt = 4.18 min, MS m/z: 343.48 [M + 1]; ¹H NMR 400 MHz (DMSO-d$_6$) δ 10.50 (s, NH), 7.73 (d, J = 7.5 Hz, 1H), 7.61-7.56 (m, 3H), 7.55 (t, J = 7.1 Hz, 1H), 7.49 (td, J = 7.0, 1.3 Hz, 1H), 7.46-7.36 (m, 5H), 7.30 (t, J = 7.5 Hz, 2H), 7.06 (t, J = 7.4 Hz, 1H), 6.20 (s, 1H), 4.81 (d, J = 17.7 Hz, 1H), 3.94 (d, J = 17.7 Hz, 1H). |
| I-52 | Method A: Rt = 4.15 min, MS m/z: 377.30 [M + 1]; ¹H NMR 400 MHz (DMSO-d$_6$) δ 10.13 (s, NH), 7.74 (d, J = 7.5 Hz, 1H), 7.64 (dd, J = 8.0, 1.3 Hz, 1H), 7.58 (td, J = 7.6, 1.1 Hz, 1H), 7.55 (t, J = 7.1 Hz, 1H), 7.51-7.46 (m, 2H), 7.46-7.42 (m, 4H), 7.41-7.36 (m, 1H), 7.33 (td, J = 7.6, 1.4 Hz, 1H), 7.21 (td, J = 7.8, 1.6 Hz, 1H), 6.40 (s, 1H), 4.78 (d, J = 17.7 Hz, 1H), 3.96 (d, J = 17.7 Hz, 1H). |

TABLE 1-continued

| Compound Number | $^1$H NMR and/or MS (m/z) data |
|---|---|
| I-53 | Method A: Rt = 4.15 min, MS m/z: 379.28 [M + 1]; $^1$H NMR 400 MHz (DMSO-d$_6$) δ 10.34 (s, NH), 7.79-7.71 (m, 2H), 7.58 (td, J = 7.6, 1.1 Hz, 1H), 7.54 (t, J = 7.2 Hz, 1H), 7.48 (td, J = 7.5, 1.1 Hz, 1H), 7.46-7.36 (m, 5H), 7.34-7.28 (m, 1H), 7.10-7.04 (m, 1H), 6.35 (s, 1H), 4.76 (d, J = 17.7, 1H), 3.93 (d, J = 17.7 Hz, 1H). |
| I-54 | Method A: Rt = 4.07 min, MS m/z: 371.29 [M + 1]; $^1$H NMR 400 MHz (DMSO-d$_6$) δ 9.81 (s, NH), 7.74 (d, J = 7.5 Hz, 1H), 7.60-7.39 (m, 8H), 7.08-7.01 (m, 3H), 6.23 (s, 1H), 4.76 (d, J = 17.7, 1H), 3.95 (d, J = 17.7 Hz, 1H), 2.08 (s, 6H). |
| I-55 | Method A: Rt = 4.09 min, MS m/z: 361.31 [M + 1]; $^1$H NMR 400 MHz (DMSO-d$_6$) δ 10.34 (s, NH), 7.84-7.79 (m, 1H), 7.73 (d, J = 7.5 Hz, 1H), 7.58 (td, J = 7.6, 1.1 Hz, 1H), 7.55 (t, J = 7.2 Hz, 1H), 7.48 (t, J = 7.6 Hz, 1H), 7.46-7.36 (m, 5H), 7.28-7.20 (m, 1H), 7.20-7.14 (m, 2H), 6.40 (s, 1H), 4.78 (d, J = 17.7, 1H), 3.93 (d, J = 17.7 Hz, 1H). |
| I-56 | Method A: Rt = 3.67 min, MS m/z: 362.34 [M + 1]. |
| I-57 | Method A: Rt = 3.75 min, MS m/z: 378.26 [M + 1]; $^1$H NMR 400 MHz (DMSO-d$_6$) δ 10.80 (s, NH), 8.40 (dd, J = 4.6, 1.2 Hz, 1H), 7.98 (d, J = 7.7 Hz, 1H), 7.74 (d, J = 7.5 Hz, 1H), 7.58 (d, J = 7.4 Hz, 1H), 7.55 (t, J = 7.0 Hz, 1H), 7.50-7.36 (m, 6H), 7.33 (dd, J = 7.9, 4.7 Hz, 1H), 6.38 (s, 1H), 4.79 (d, J = 17.6, 1H), 3.93 (d, J = 17.6 Hz, 1H). |
| I-58 | Method A: Rt = 4.12 min, MS m/z: 364.26 [M + 1]; $^1$H NMR 400 MHz (DMSO-d$_6$) δ 7.74 (d, J = 7.5 Hz, 1H), 7.61 (t, J = 7.6 Hz, 1H), 7.57-7.53 (m, 1H), 7.52-7.44 (m, 4H), 7.43-7.39 (m, 2H), 7.35 (d, J = 3.5 Hz, 1H), 6.70 (s, 1H), 4.66 (d, J = 17.4, 1H), 3.85 (d, J = 17.4 Hz, 1H), 3.53 (s, 3H). |
| I-59 | Method A: Rt = 4.60 min, MS m/z: 426.22 [M + 1]; $^1$H NMR 400 MHz (DMSO-d$_6$) δ 12.68 (s, NH), 7.93 (d, J = 1.8 Hz, 1H), 7.90 (dd, J = 7.9, 1.8 Hz, 1H), 7.73-7.70 (m, 2H), 7.64 (d, J = 8.0 Hz, 1H), 7.50-7.36 (m, 9H), 6.32 (s, 1H), 4.78 (d, J = 17.7, 1H), 4.01 (d, J = 17.7 Hz, 1H). |
| I-60 | Method A: Rt = 3.32 min, MS m/z: 427.31 [M + 1]; $^1$H NMR 600 MHz (DMSO-d$_6$) δ 12.70 (bs, NH), 9.11 (d, J = 2.4 Hz, 1H), 8.72 (dd, J = 1.2, 4.8 Hz, 1H), 8.49 (d, J = 6.6 Hz, 1H), 8.12 (d, J = 1.8 Hz, 1H), 8.02 (dd, J = 1.8, 7.2 Hz, 1H), 7.76 (dd, J = 5.4, 8.4 Hz, 1H), 7.72 (d, J = 7.8 Hz, 1H), 7.48-7.41 (m, 4H), 7.39 (s, 1H), 7.38 (d, J = 7.8 Hz, 1H), 7.26 (d, J = 3.6 Hz, 1H), 6.32 (s, 1H), 4.82 (d, J = 18.0 Hz, 1H), 4.04 (d, J = 18.6 Hz, 1H). |
| I-61 | Method A: Rt = 3.05 min, MS m/z: 427.24 [M + 1]; $^1$H NMR 400 MHz (DMSO-d$_6$) δ 12.70 (bs, NH), 8.85 (d, J = 4.4 Hz, 2H), 8.27 (d, J = 1.3 Hz, 1H), 8.23 (d, J = 6.1 Hz, 2H), 8.17 (dd, J = 8.0, 1.8 Hz, 1H), 7.79 (d, J = 8.0 Hz, 1H), 7.79 (d, J = 8.0 Hz, 1H), 7.50-7.42 (m, 4H), 7.41-7.36 (m, 2H), 7.27 (d, J = 3.6 Hz, 1H), 6.32 (s, 1H), 4.84 (d, J = 18.2 Hz, 1H), 4.08 (d, J = 18.2 Hz, 1H). |
| I-62 | Method A: Rt = 3.73 min, MS m/z: 428.20 [M + 1]. |
| I-63 | Method A: Rt = 4.10 min, MS m/z: 444.25 [M + 1]; $^1$H NMR 400 MHz (DMSO-d$_6$) δ 12.67 (bs, NH), 8.32 (s, 1H), 7.95 (s, 1H), 7.90 (d, J = 1.2 Hz, 1H), 7.80 (dd, J = 7.9, 6.1 Hz, 1H), 7.51 (d, J = 8.0 Hz, 1H), 7.47 (d, J = 3.5 Hz, 1H), 7.46-7.39 (m, 3H), 7.38-7.35 (m, 2H), 7.26 (d, J = 3.5 Hz, 1H), 6.30 (s, 1H), 4.72 (d, J = 17.5 Hz, 1H), 4.13 (q, J = 7.3 Hz, 2H), 3.94 (d, J = 17.6 Hz, 1H), 1.40 (t, J = 7.3 Hz, 3H). |
| I-64 | Method B: Rt = 0.98 min, MS m/z: 416.16 [M + 1]. |
| I-65 | Method A: Rt = 4.67 min, MS m/z: 484.30 [M + 1]; $^1$H NMR 600 MHz (DMSO-d$_6$) δ 12.68 (bs, NH), 7.84 (m, 1H), 7.82 (dd, J = 7.9, 1.8 Hz, 1H), 7.66 (d, J = 7.9 Hz, 1H), 7.48 (d, J = 3.6 Hz, 1H), 7.47-7.44 (m, 1H), 7.45 (d, J = 7.6 Hz, 1H), 7.43-7.39 (m, 1H), 7.38-7.36 (m, 2H), 7.26 (d, J = 3.5 Hz, 1H), 7.19 (t, J = 2.1 Hz, 1H), 7.18 (dd, J = 8.3, 2.3 Hz, 1H), 6.94 (d, J = 8.2 Hz, 1H), 6.30 (s, 1H), 4.75 (d, J = 17.6 Hz, 1H), 4.26 (s, 4H), 3.98 (d, J = 17.7 Hz, 1H). |
| I-66 | Method B: Rt = 1.41 min, MS m/z: 465.23 [M + 1]; $^1$H NMR 600 MHz (DMSO-d$_6$) δ 12.69 (s, NH), 11.16 (s, NH), 7.91 (s, 1H), 7.90 (dd, J = 7.9, 1.5 Hz, 1H), 7.86 (s, 1H), 7.60 (d, J = 7.9 Hz, 1H), 7.49-7.44 (m, 4H), 7.43-7.40 (m, 2H), 7.39-7.36 (m, 3H), 7.26 (d, J = 3.4 Hz, 1H), 6.49-6.47 (m, 1H), 6.32 (s, 1H), 4.77 (d, J = 17.4 Hz, 1H), 3.99 (d, J = 17.4 Hz, 1H). |
| I-67 | Method B: Rt = 1.47 min, MS m/z: 465.23 [M + 1]. |
| I-68 | Method B: Rt = 0.84 min, MS m/z: 510.28 [M + 1]; $^1$H NMR 600 MHz (DMSO-d$_6$) δ 12.69 (bs, NH), 7.89 (d, J = 1.3 Hz, 1H), 7.86 (dd, J = 8.0, 1.7 Hz, 1H), 7.65 (d, J = 8.9 Hz, 2H), 7.60 (d, J = 8.0 Hz, 1H), 7.49-7.45 (m, 3H), 7.44-7.40 (m, 1H), 7.39-7.36 (m, 2H), 7.27 (d, J = 3.5 Hz, 1H), 7.09 (d, J = 8.9 Hz, 2H), 6.31 (s, 1H), 4.76 (d, J = 17.5 Hz, 1H), 3.99 (d, J = 17.6 Hz, 1H), 3.42-3.39 (m, 4H), 3.25 (s, 4H). |
| I-69 | Method B: Rt = 0.84 min, MS m/z: 524.32 [M + 1]. |
| I-70 | Method A: Rt = 4.17 min, MS m/z: 477.26 [M + 1]; $^1$H NMR 400 MHz (DMSO-d$_6$) δ 12.70 (bs, NH), 9.38 (d, J = 2.3 Hz, 1H), 8.90 (d, J = 2.0 Hz, 1H), 8.24 (d, J = 1.4 Hz, 1H), 8.15 (dd, J = 8.0, 1.7 Hz, 1H), 8.11 (dd, J = 12.9, 7.6 Hz, 2H), 7.86-7.81 (m, 1H), 7.75 (d, J = 8.0 Hz, 1H), 7.73-7.68 (m, 1H), 7.50-7.38 (m, 6H), 7.27 (d, J = 3.6 Hz, 1H), 6.35 (s, 1H), 4.84 (d, J = 17.9 Hz, 1H), 4.07 (d, J = 17.9 Hz, 1H). |
| I-71 | Method A: Rt = 4.09 min, MS m/z: 477.26 [M + 1]; $^1$H NMR 400 MHz (DMSO-d$_6$) δ 12.69 (bs, NH), 8.90 (dd, J = 4.2, 1.8 Hz, 1H), 8.47 (dd, J = 8.3, 1.7 Hz, 1H), 8.04 (dd, J = 8.2, 1.3 Hz, 1H), 7.97 (d, J = 1.1 Hz, 1H), 7.86 (d, J = 7.8, 1.6 Hz, 1H), 7.83 (dd, J = 7.2, 1.4 Hz, 1H), 7.71 (t, J = 7.9 Hz, 1H), 7.65 (d, J = 7.9 Hz, 1H), 7.59 (dd, J = 8.3, 4.2 Hz, 1H), 7.50-7.38 (m, 5H), 7.27 (d, J = 3.6 Hz, 1H), 6.33 (s, 1H), 4.82 (d, J = 17.6 Hz, 1H), 4.06 (d, J = 17.7 Hz, 1H). |

TABLE 1-continued

| Compound Number | $^1$H NMR and/or MS (m/z) data |
|---|---|
| I-72 | Method A: Rt = 4.60 min, MS m/z: 484.30 [M + 1]; $^1$H NMR 400 MHz (DMSO-$d_6$) δ 12.69 (bs, NH), 8.06-8.02 (m, 3H), 7.98 (dd, J = 8.0, 1.7 Hz, 1H), 7.90 (d, J = 8.4 Hz, 2H), 7.68 (d, J = 8.0 Hz, 1H), 7.48 (d, J = 3.5 Hz, 1H), 7.47-7.36 (m, 5H), 7.27 (d, J = 3.6 Hz, 1H), 6.32 (s, 1H), 4.81 (d, J = 17.8 Hz, 1H), 4.03 (d, J = 17.9 Hz, 1H), 3.39 (s, 3H). |
| I-73 | Method B: Rt = 1.05 min, MS m/z: 441.23 [M + 1]. |
| I-74 | Method A: Rt = 4.90 min, MS m/z: 510.33 [M + 1]; $^1$H NMR 400 MHz (DMSO-$d_6$) δ 12.68 (bs, NH), 7.97 (d, J = 1.3 Hz, 1H), 7.92 (dd, J = 7.9, 1.8 Hz, 1H), 7.86 (dt, J = 8.8, 2.1 Hz, 2H), 7.66 (d, J = 7.9 Hz, 1H), 7.48 (d, J = 3.5 Hz, 1H), 7.47-7.36 (m, 7H), 7.26 (d, J = 3.5 Hz, 1H), 6.32 (s, 1H), 4.79 (d, J = 17.7 Hz, 1H), 4.01 (d, J = 17.8 Hz, 1H). |
| I-75 | Method A: Rt = 4.62 min, MS m/z: 444.32 [M + 1]; $^1$H NMR 400 MHz (DMSO-$d_6$) δ 12.76 (bs, NH), 7.91 (s, 1H), 7.85 (dt, J = 7.9, 1.5 Hz, 1H), 7.75 (d, J = 8.0 Hz, 1H), 7.66 (td, J = 7.9, 1.7 Hz, 1H), 7.56 (d, J = 3.5 Hz, 1H), 7.55-7.37 (m, 8H), 7.34 (d, J = 3.6 Hz, 1H), 6.39 (s, 1H), 4.88 (d, J = 17.7 Hz, 1H), 4.11 (d, J = 17.8 Hz, 1H). |
| I-76 | Method A: Rt = 4.67 min, MS m/z: 444.38 [M + 1]; $^1$H NMR 400 MHz (DMSO-$d_6$) δ 12.68 (bs, NH), 7.98 (d, J = 1.2 Hz, 1H), 7.94 (dd, J = 7.9, 1.7 Hz, 1H), 7.65 (d, J = 8.0 Hz, 1H), 7.61-7.58 (m, 2H), 7.54-7.36 (m, 7H), 7.27 (d, J = 3.5 Hz, 1H), 7.21 (d, J = 8.1, 1.8 Hz, 1H), 6.33 (s, 1H), 4.79 (d, J = 17.7 Hz, 1H), 4.02 (d, J = 17.8 Hz, 1H). |
| I-77 | Method A: Rt = 4.64 min, MS m/z: 444.32 [M + 1]; $^1$H NMR 400 MHz (DMSO-$d_6$) δ 12.68 (bs, NH), 7.92 (d, J = 1.3 Hz, 1H), 7.88 (dd, J = 7.9, 1.7 Hz, 1H), 7.79-7.74 (m, 2H), 7.64 (d, J = 8.0 Hz, 1H), 7.49-7.41 (m, 4H), 7.39-7.36 (m, 2H), 7.33-7.25 (m, 3H), 6.31 (s, 1H), 4.78 (d, J = 17.7 Hz, 1H), 4.01 (d, J = 17.7 Hz, 1H). |
| I-78 | Method A: Rt = 4.27 min, MS m/z: 470.35 [M + 1]; $^1$H NMR 400 MHz (DMSO-$d_6$) δ 12.95 (bs, OH), 12.69 (bs, NH), 8.04-8.00 (m, 3H), 7.97 (dd, J = 7.9, 1.7 Hz, 1H), 7.86 (d, J = 8.5 Hz, 2H), 7.68 (d, J = 8.0 Hz, 1H), 7.49-7.41 (m, 4H), 7.40-7.36 (m, 2H), 7.26 (d, J = 3.6 Hz, 1H), 6.32 (s, 1H), 4.80 (d, J = 17.7 Hz, 1H), 4.03 (d, J = 17.7 Hz, 1H). |
| I-79 | Method A: Rt = 4.67 min, MS m/z: 486.34 [M + 1]; $^1$H NMR 600 MHz (DMSO-$d_6$) δ 12.68 (bs, NH), 7.94 (s, 1H), 7.90 (d, J = 7.4 Hz, 1H), 7.62 (dd, J = 7.6, 2.6 Hz, 1H), 7.49-7.40 (m, 4H), 7.40-7.36 (m, 2H), 7.28-7.25 (m, 1H), 6.82 (s, 2H), 6.51 (s, 1H), 6.32 (s, 1H), 4.78 (d, J = 17.6 Hz, 1H), 4.01 (d, J = 17.6 Hz, 1H), 3.80 (s, 3H), 3.80 (s, 3H). |
| I-80 | Method A: Rt = 4.62 min, MS m/z: 486.34 [M + 1]; $^1$H NMR 600 MHz (DMSO-$d_6$) δ 12.68 (bs, NH), 7.72 (d, J = 1.1 Hz, 1H), 7.63 (dd, J = 7.9, 1.6 Hz, 1H), 7.55 (d, J = 7.9 Hz, 1H), 7.48 (d, J = 3.6 Hz, 1H), 7.47-7.44 (m, 2H), 7.43-7.40 (m, 1H), 7.38-7.36 (m, 2H), 7.26 (d, J = 3.5 Hz, 1H), 7.24 (d, J = 8.4 Hz, 1H), 6.29 (s, 1H), 4.74 (d, J = 17.5 Hz, 1H), 3.98 (d, J = 17.5 Hz, 1H), 3.79 (s, 3H), 3.75 (s, 3H). |
| I-81 | Method A: Rt = 3.25 min, MS m/z: 540.47 [M + 1]; $^1$H NMR 400 MHz (DMSO-$d_6$) δ 12.69 (bs, NH), 8.74 (t, J = 5.6 Hz, 1H), 8.03 (d, J = 1.2 Hz, 1H), 8.00-7.95 (m, 3H), 7.88 (d, J = 8.5 Hz, 2H), 7.68 (d, J = 8.1 Hz, 1H), 7.50-7.36 (m, 6H), 7.27 (d, J = 3.6 Hz, 1H), 6.32 (s, 1H), 4.80 (d, J = 17.8 Hz, 1H), 4.03 (d, J = 17.9 Hz, 1H), 3.61 (q, J = 5.9 Hz, 2H), 3.27 (q, J = 5.6 Hz, 2H), 2.85 (s, 3H), 2.84 (s, 2H). |
| I-82 | Method A: Rt = 3.29 min, MS m/z: 568.50 [M + 1]; $^1$H NMR 400 MHz (DMSO-$d_6$) δ 12.69 (bs, NH), 8.57 (t, J = 5.7 Hz, 1H), 8.01 (d, J = 1.3 Hz, 1H), 7.98-7.93 (m, 3H), 7.83 (d, J = 8.5 Hz, 2H), 7.67 (d, J = 8.1 Hz, 1H), 7.49-7.36 (m, 6H), 7.27 (d, J = 3.6 Hz, 1H), 6.32 (s, 1H), 4.80 (d, J = 17.9 Hz, 1H), 4.03 (d, J = 17.9 Hz, 1H), 3.30 (q, J = 6.0 Hz, 2H), 3.10-3.04 (m, 2H), 2.76 (s, 3H), 2.75 (s, 2H), 1.70-1.60 (m, 2H), 1.55 (quint, J = 6.8 Hz, 2H). |
| I-83 | Method A: Rt = 3.25 min, MS m/z: 582.45 [M + 1]; $^1$H NMR 400 MHz (DMSO-$d_6$) δ 12.69 (bs, NH), 8.78 (t, J = 5.8 Hz, 1H), 8.03 (d, J = 1.1 Hz, 1H), 8.00-7.95 (m, 3H), 7.88 (d, J = 8.5 Hz, 2H), 7.68 (d, J = 8.0 Hz, 1H), 7.49-7.36 (m, 6H), 7.27 (d, J = 3.6 Hz, 1H), 6.32 (s, 1H), 4.80 (d, J = 17.8 Hz, 1H), 4.03 (d, J = 17.9 Hz, 1H), 3.98 (bs, 2H), 3.69-3.60 (m, 4H), 3.60-3.50 (m, 2H), 3.50-3.40 (m, 2H), 3.15 (bs, 2H). |
| I-84 | Method A: Rt = 3.27 min, MS m/z: 596.46 [M + 1]; $^1$H NMR 600 MHz (DMSO-$d_6$) δ 12.69 (bs, NH), 8.70 (t, J = 5.7 Hz, 1H), 8.02 (d, J = 1.3 Hz, 1H), 7.97 (dd, J = 8.0, 1.7 Hz, 1H), 7.95 (d, J = 8.5 Hz, 2H), 7.86 (d, J = 8.4 Hz, 2H), 7.68 (d, J = 8.0 Hz, 1H), 7.49-7.41 (m, 4H), 7.39-7.36 (m, 2H), 7.27 (d, J = 3.5 Hz, 1H), 6.32 (s, 1H), 4.80 (d, J = 17.6 Hz, 1H), 4.03 (d, J = 17.6 Hz, 1H), 3.97 (d, J = 12.1 Hz, 2H), 3.62 (t, J = 12.2 Hz, 2H), 3.46-3.32 (m, 4H), 3.16 (t, J = 6.6 Hz, 2H), 3.10-3.02 (m, 2H), 1.92 (quint, J = 8.1 Hz, 2H). |
| I-85 | Method A: Rt = 4.02 min, MS m/z: 539.38 [M + 1]; $^1$H NMR 400 MHz (DMSO-$d_6$) δ 12.71 (bs, NH), 8.00 (d, J = 1.3 Hz, 1H), 7.96 (dd, J = 7.9, 1.8 Hz, 1H), 7.82 (d, J = 8.3 Hz, 2H), 7.69 (d, J = 8.0 Hz, 1H), 7.53 (d, J = 8.3 Hz, 2H), 7.50 (d, J = 3.6 Hz, 1H), 7.49-7.43 (m, 3H), 7.42-7.38 (m, 2H), 7.28 (d, J = 3.7 Hz, 1H), 6.32 (s, 1H), 4.81 (d, J = 17.8 Hz, 1H), 4.04 (d, J = 17.8 Hz, 1H), 3.70-3.50 (m, 4H). |

TABLE 1-continued

| Compound Number | $^1$H NMR and/or MS (m/z) data |
|---|---|
| I-86 | Method A: Rt = 4.97 min, MS m/z: 430.31 [M + 1]; $^1$H NMR 400 MHz (DMSO-d$_6$) δ 12.66 (bs, NH), 7.66-7.63 (m, 2H), 7.50-7.39 (m, 5H), 7.37-7.33 (m, 2H), 7.26 (d, J = 3.5 Hz, 1H), 6.28 (s, 1H), 6.25-6.21 (m, 1H), 4.71 (d, J = 17.5 Hz, 1H), 3.93 (d, J = 17.6 Hz, 1H), 2.42-2.36 (m, 2H), 2.21-2.15 (m, 2H), 1.76-1.69 (m, 2H), 1.63-1.56 (m, 2H). |
| I-87 | Method A: Rt = 4.00 min, MS m/z: 357.42 [M + 1]; $^1$H NMR 400 MHz (DMSO-d$_6$) δ 8.93 (t, J = 5.9 Hz, NH), 7.72 (d, J = 7.5 Hz, 1H), 7.59-7.51 (m, 2H), 7.47 (td, J = 7.5, 0.8 Hz, 1H), 7.42-7.26 (m, 7H), 7.25-7.19 (m, 3H), 6.08 (s, 1H), 4.78 (d, J = 17.7 Hz, 1H), 4.33 (d, J = 6.0 Hz, 2H), 3.92 (d, J = 17.7 Hz, 1H). |
| I-88 | Method A: Rt = 3.30 min, MS m/z: 540.41 [M + 1]; $^1$H NMR 400 MHz (DMSO-d$_6$) δ 12.71 (bs, NH), 8.89 (t, J = 5.6 Hz, 1H), 8.23-8.21 (m, 1H), 8.09 (d, J = 1.2 Hz, 1H), 7.99 (dd, J = 8.0, 1.7 Hz, 1H), 7.95 (d, J = 7.8 Hz, 1H), 7.90 (d, J = 7.8 Hz, 1H), 7.71 (d, J = 7.9 Hz, 1H), 7.62 (t, J = 7.5 Hz, 1H), 7.52-7.44 (m, 4H), 7.42-7.38 (m, 2H), 7.29 (d, J = 3.5 Hz, 1H), 6.34 (s, 1H), 4.83 (d, J = 17.8 Hz, 1H), 4.05 (d, J = 17.8 Hz, 1H), 3.65 (q, J = 5.9 Hz, 2H) 3.32-3.28 (m, 2H), 2.87 (s, 3H), 2.87 (s, 3H). |
| I-89 | Method B: Rt = 0.87 min, MS m/z: 568.30 [M + 1]. |
| I-90 | Method A: Rt = 3.25 min, MS m/z: 582.45 [M + 1]; $^1$H NMR 400 MHz (DMSO-d$_6$) δ 12.71 (bs, NH), 8.93 (t, J = 5.4 Hz, 1H), 8.22 (s, 1H), 8.09 (s, 1H), 7.99 (dd, J = 7.9, 1.4 Hz, 1H), 7.96 (d, J = 7.8 Hz, 1H), 7.91 (d, J = 7.8 Hz, 1H), 7.71 (d, J = 8.1 Hz, 1H), 7.63 (t, J = 7.7 Hz, 1H), 7.53-7.44 (m, 4H), 7.42-7.38 (m, 2H), 7.29 (d, J = 3.5 Hz, 1H), 6.34 (s, 1H), 4.83 (d, J = 17.7 Hz, 1H), 4.05 (d, J = 17.8 Hz, 1H), 4.00 (bs, 2H), 3.73-3.65 (m, 4H), 3.57 (bs, 2H), 3.38 (bs, 2H), 3.17 (bs, 2H). |
| I-91 | Method A: Rt = 3.25 min, MS m/z: 596.46 [M + 1]; $^1$H NMR 400 MHz (DMSO-d$_6$) δ 12.71 (bs, NH), 8.84 (t, J = 5.7 Hz, 1H), 8.21-8.19 (m, 1H), 8.10 (d, J = 1.4 Hz, 1H), 7.99 (dd, J = 8.0, 1.7 Hz, 1H), 7.93 (d, J = 7.9 Hz, 1H), 7.89 (d, J = 7.9 Hz, 1H), 7.70 (d, J = 8.0 Hz, 1H), 7.60 (t, J = 7.8 Hz, 1H), 7.52-7.44 (m, 4H), 7.42-7.38 (m, 2H), 7.29 (d, J = 3.6 Hz, 1H), 6.34 (s, 1H), 4.82 (d, J = 17.8 Hz, 1H), 4.05 (d, J = 17.8 Hz, 1H), 3.98 (d, J = 12.8 Hz, 2H), 3.64 (t, J = 12.1 Hz, 2H), 3.49-3.35 (m, 4H), 3.22-3.14 (m, 2H), 3.14-3.00 (m, 2H), 2.00-1.90 (m, 2H). |
| I-92 | Method A: Rt = 4.02 min, MS m/z: 539.38 [M + 1]; $^1$H NMR 400 MHz (DMSO-d$_6$) δ 12.71 (bs, NH), 8.00 (s, 1H), 7.96 (dd, J = 7.9, 1.4 Hz, 1H), 7.83 (d, J = 7.9 Hz, 1H), 7.75 (s, 1H), 7.68 (d, J = 7.9 Hz, 1H), 7.57 (t, J = 7.7 Hz, 1H), 7.52-7.38 (m, 7H), 7.28 (d, J = 3.5 Hz, 1H), 6.34 (s, 1H), 4.81 (d, J = 17.8 Hz, 1H), 4.04 (d, J = 17.8 Hz, 1H), 3.70-3.35 (m, 4H). |
| I-93 | Method A: Rt = 4.43 min, MS m/z: 441.38 [M + 1]. |
| I-94 | Method A: Rt = 3.80 min, MS m/z: 526.39 [M + 1]. |
| I-95 | Method A: Rt = 3.07 min, MS m/z: 524.41 [M + 1]; $^1$H NMR 400 MHz (DMSO-d$_6$) δ 12.66 (bs, NH), 8.83 (s, NH), 7.59 (d, J = 8.3 Hz, 1H), 7.49 (d, J = 3.6 Hz, 1H), 7.48-7.40 (m, 3H), 7.37-7.33 (m, 4H), 7.28 (d, J = 3.5 Hz, 1H), 7.23 (d, J = 1.3 Hz, 1H), 7.17 (dd, J = 8.0, 1.4 Hz, 1H), 7.13 (dd, J = 8.4, 1.9 Hz, 1H), 7.04 (d, J = 7.6 Hz, 1H), 6.29 (s, 1H), 4.72 (d, J = 17.3 Hz, 1H), 4.30 (d, J = 5.7 Hz, 2H), 3.89 (d, J = 17.4 Hz, 1H), 3.40-3.36 (m, 2H), 3.13-3.03 (m, 2H), 2.07-1.96 (m, 2H), 1.90-1.80 (m, 2H). |
| I-96 | Method A: Rt = 4.85 min, MS m/z: 547.38 [M + 1]; $^1$H NMR 400 MHz (DMSO-d$_6$) δ 12.62 (bs, NH), 8.42 (bs, NH), 7.51-7.36 (m, 9H), 7.35-7.30 (m, 3H), 7.27 (d, J = 3.5 Hz, 1H), 7.11 (d, J = 8.9 Hz, 2H), 6.99-6.95 (m, 3H), 6.92 (dd, J = 8.4, 1.7 Hz, 1H), 6.25 (s, 1H), 5.07 (s, 2H), 4.64 (d, J = 17.3 Hz, 1H), 3.84 (d, J = 17.3 Hz, 1H). |
| I-97 | Method A: Rt = 4.52 min, MS m/z: 459.35 [M + 1]; $^1$H NMR 400 MHz (DMSO-d$_6$) δ 12.65 (bs, NH), 8.88 (bs, NH), 7.59 (d, J = 8.3 Hz, 1H), 7.49 (d, J = 3.6 Hz, 1H), 7.47-7.40 (m, 3H), 7.37-7.34 (m, 2H), 7.14-7.08 (m, 1H), 6.99-6.91 (m, 2H), 6.69 (td, J = 8.5, 2.2 Hz, 1H), 6.27 (s, 1H), 4.70 (d, J = 17.5 Hz, 1H), 3.91 (d, J = 17.4 Hz, 1H). |
| I-98 | Method A: Rt = 4.45 min, MS m/z: 441.31 [M + 1]; $^1$H NMR 600 MHz (DMSO-d$_6$) δ 12.65 (bs, NH), 8.37 (bs, NH), 7.47 (d, J = 3.5 Hz, 1H), 7.46-7.32 (m, 7H), 7.27-7.23 (m, 4H), 7.08 (d, J = 7.6 Hz, 2H), 6.86 (t, J = 7.3 Hz, 1H), 6.25 (s, 1H), 4.63 (d, J = 17.0 Hz, 1H), 3.85 (d, J = 17.0 Hz, 1H). |
| I-99 | Method A: Rt = 4.55 min, MS m/z: 459.35 [M + 1]; $^1$H NMR 400 MHz (DMSO-d$_6$) δ 12.68 (bs, NH), 8.63 (bs, NH), 7.49 (d, J = 3.5 Hz, 1H), 7.48-7.42 (m, 4H), 7.40-7.36 (m, 3H), 7.32 (dd, J = 8.2, 2.2 Hz, 1H), 7.30-7.23 (m, 2H), 6.90 (dd, J = 8.1, 1.7 Hz, 1H), 6.82 (dt, J = 11.8, 2.0 Hz, 1H), 6.34 (td, J = 8.4, 2.8 Hz, 1H), 6.29 (s, 1H), 4.68 (d, J = 17.1 Hz, 1H), 3.90 (d, J = 17.2 Hz, 1H). |
| I-100 | Method A: Rt = 3.22 min, MS m/z: 524.41 [M + 1]. |
| I-101 | Method A: Rt = 4.65 min, MS m/z: 444.32 [M + 1]; $^1$H NMR 400 MHz (DMSO-d$_6$) δ 12.71 (bs, NH), 7.84 (d, J = 8.0 Hz, 1H), 7.75 (s, 1H), 7.68 (d, J = 7.9 Hz, 1H), 7.55 (td, J = 7.8, 1.7 Hz, 1H), 7.50 (d, J = 3.5 Hz, 1H), 7.49-7.31 (m, 7H), 7.29 (d, J = 3.6 Hz, 1H), 6.34 (s, 1H), 4.82 (d, J = 17.6 Hz, 1H), 4.05 (d, J = 17.6 Hz, 1H). |
| I-102 | Method A: Rt = 3.09 min, MS m/z: 524.41 [M + 1]; $^1$H NMR 400 MHz (DMSO-d$_6$) δ 12.71 (bs, NH), 7.81 (s, 1H), 7.76 (s, 2H), 7.64 (d, J = 8.8 Hz, 2H), 7.50 (d, J = 3.5 Hz, 1H), 7.47 (d, J = 7.4 Hz, 2H), 7.46-7.41 (m, 1H), 7.41-7.37 (m, 2H), 7.28 (d, J = 3.6 Hz, 1H), 7.12 (d, J = 8.9 Hz, 1H), 6.33 (s, 1H), 4.80 (d, J = 17.6 Hz, 1H), 4.01 (d, J = 17.7 Hz, 1H), 3.96 (d, J = 13.9 Hz, 2H), 3.60-3.50 (m, 2H), 3.22-3.10 (m, 2H), 3.03 (t, J = 12.5 Hz, 2H), 2.87 (s, 3H). |

TABLE 1-continued

| Compound Number | $^1$H NMR and/or MS (m/z) data |
|---|---|
| I-103 | Method A: Rt = 4.62 min, MS m/z: 484.36 [M + 1]; $^1$H NMR 400 MHz (DMSO-d$_6$) δ 12.69 (bs, NH), 7.79-7.70 (m, 3H), 7.50 (d, J = 3.4 Hz, 1H), 7.47 (d, J = 7.4 Hz, 2H), 7.46-7.42 (m, 1H), 7.40-7.36 (m, 2H), 7.28 (d, J = 3.4 Hz, 1H), 7.21-7.16 (m, 2H), 6.96 (d, J = 8.2 Hz, 1H), 6.32 (s, 1H), 4.79 (d, J = 17.5 Hz, 1H), 4.28 (s, 4H), 4.01 (d, J = 17.5 Hz, 1H). |
| I-104 | Method A: Rt = 4.37 min, MS m/z: 465.30 [M + 1]; $^1$H NMR 400 MHz (DMSO-d$_6$) δ 12.70 (bs, NH), 11.20 (bs, NH), 7.86 (d, J = 10.8 Hz, 2H), 7.82-7.76 (m, 2H), 7.56-7.37 (m, 9H), 7.29 (d, J = 3.5 Hz, 1H), 6.50 (t, J = 2.0 Hz, 1H), 6.34 (s, 1H), 4.82 (d, J = 17.4 Hz, 1H), 4.04 (d, J = 17.5 Hz, 1H). |
| I-105 | Method A: Rt = 4.64 min, MS m/z: 426.38 [M + 1]; $^1$H NMR 400 MHz (DMSO-d$_6$) δ 12.71 (bs, NH), 7.86 (s, 1H), 7.84-7.77 (m, 2H), 7.72-7.68 (m, 2H), 7.53-7.38 (m, 10H), 7.29 (d, J = 3.5 Hz, 1H), 6.36 (s, 1H), 4.83 (d, J = 17.5 Hz, 1H), 4.05 (d, J = 17.6 Hz, 1H). |
| I-106 | Method A: Rt = 4.74 min, MS m/z: 446.17 [M + 1]. |
| I-107 | Method A: Rt = 4.74 min, MS m/z: 446.15 [M + 1]. |
| I-108 | Method A: Rt = 3.65 min, MS m/z: 427.31 [M + 1]. |
| I-109 | Method A: Rt = 4.45 min, MS m/z: 510.33 [M + 1]. |
| I-110 | Method A: Rt = 3.13 min, MS m/z: 472.27 [M + 1]. |
| I-111 | Method A: Rt = 3.74 min, MS m/z: 505.22 [M + 1]. |
| I-112 | Method A: Rt = 4.47 min, MS m/z: 465.30 [M + 1]; $^1$H NMR 400 MHz (DMSO-d$_6$) δ 12.68 (s, NH), 11.16 (s, NH), 7.91 (s, 1H), 7.93-7.88 (m, 2H), 7.86 (s, 1H), 7.60 (d, J = 7.8 Hz, 1H), 7.49-7.36 (m, 9H), 7.27 (d, J = 3.5 Hz, 1H), 6.50-6.44 (m, 1H), 6.32 (s, 1H), 4.78 (d, J = 17.5 Hz, 1H), 4.00 (d, J = 17.5 Hz, 1H). |
| I-113 | Method A: Rt = 4.60 min, MS m/z: 444.32 [M + 1]; $^1$H NMR 400 MHz (DMSO-d$_6$) δ 12.68 (bs, NH), 7.83 (s, 1H), 7.78 (dt, J = 7.9, 1.5 Hz, 1H), 7.67 (d, J = 8.0 Hz, 1H), 7.58 (td, J = 7.8, 1.7 Hz, 1H), 7.48 (d, J = 3.6 Hz, 1H), 7.48-7.29 (m, 8H), 7.27 (d, J = 3.6 Hz, 1H), 6.31 (s, 1H), 4.80 (d, J = 17.8 Hz, 1H), 4.03 (d, J = 17.8 Hz, 1H). |
| I-114 | Method A: Rt = 4.37 min, MS m/z: 469.33 [M + 1]; $^1$H NMR 400 MHz (DMSO-d$_6$) δ 12.69 (bs, NH), 8.11 (s, 1H), 8.05-7.98 (m, 3H), 7.83 (dd, J = 8.2, 1.2 Hz, 1H), 7.70 (d, J = 8.0 Hz, 1H), 7.49-7.40 (m, 4H), 7.38 (d, J = 7.2 Hz, 2H), 7.27 (d, J = 3.2 Hz, 1H), 6.32 (s, 1H), 4.81 (d, J = 17.9 Hz, 1H), 4.04 (d, J = 18.0 Hz, 1H). |
| I-115 | Method A: Rt = 3.32 min, MS m/z: 510.46 [M + 1]. |
| I-116 | Method A: Rt = 3.98 min, MS m/z: 403.32 [M + 1]; $^1$H NMR 400 MHz (DMSO-d$_6$) δ 12.42 (bs, NH), 11.54 (bs, NH), 7.93 (dd, J = 7.9, 1.8 Hz, 1H), 7.87 (dd, J = 4.5, 1.3 Hz, 2H), 7.68 (d, J = 8.0 Hz, 1H), 7.50-7.46 (m, 2H), 7.42 (dd, J = 8.5, 1.7 Hz, 1H), 7.37 (t, J = 7.4 Hz, 1H), 7.22 (d, J = 3.6 Hz, 1H), 6.49 (t, J = 2.1 Hz, 1H), 5.08 (q, J = 7.3 Hz, 1H), 4.69 (dd, J = 39.1, 17.4 Hz, 2H), 1.59 (d, J = 7.3 Hz, 3H). |
| I-117 | Method A: Rt = 4.57 min, MS m/z: 548.40 [M + 1]; $^1$H NMR 400 MHz (DMSO-d$_6$) δ 12.41 (bs, NH), 7.87 (dd, J = 7.9, 1.86 Hz, 1H), 7.83 (s, 2H), 7.65 (d, J = 8.0 Hz, 1H), 7.60 (d, J = 8.8 Hz, 2H), 7.47 (d, J = 3.5 Hz, 1H), 7.22 (d, J = 3.5 Hz, 1H), 7.04 (d, J = 8.8 Hz, 2H), 5.07 (q, J = 7.3 Hz, 1H), 4.67 (dd, J = 39.1, 17.5 Hz, 2H), 3.49-3.43 (m, 4H), 3.18-3.14 (m, 4H), 1.58 (d, J = 7.3 Hz, 3H), 1.41 (s, 9H). |
| I-118 | Method A: Rt = 2.87 min, MS m/z: 448.41 [M + 1]; $^1$H NMR 400 MHz (DMSO-d$_6$) δ 12.41 (bs, NH), 7.88 (d, J = 8.1 Hz, 1H), 7.85 (s, 2H), 7.69-7.63 (m, 3H), 7.47 (d, J = 3.5 Hz, 1H), 7.22 (d, J = 3.5 Hz, 1H), 7.09 (d, J = 8.7 Hz, 2H), 5.06 (q, J = 7.3 Hz, 1H), 4.68 (dd, J = 38.9, 17.5 Hz, 2H), 3.45-3.38 (m, 4H), 3.24 (bs, 4H), 1.59 (d, J = 7.3 Hz, 3H). |
| I-119 | Method A: Rt = 4.97 min, MS m/z: 628.46 [M + 1]; $^1$H NMR 400 MHz (DMSO-d$_6$) δ 12.67 (bs, NH), 7.77 (s, 1H), 7.71 (d, J = 8.0 Hz, 1H), 7.60 (d, J = 8.1 Hz, 1H), 7.48 (d, J = 3.6 Hz, 1H), 7.47-7.36 (m, 6H), 7.26 (d, J = 3.6 Hz, 1H), 6.90-6.87 (m, 1H), 6.87-6.85 (m, 1H), 6.30 (s, 1H), 4.77 (d, J = 17.7 Hz, 1H), 4.00 (d, J = 17.7 Hz, 1H), 3.47-3.42 (m, 4H), 3.23-3.19 (m, 4H), 1.41 (s, 9H). |
| I-120 | Method A: Rt = 3.37 min, MS m/z: 528.44 [M + 1]; $^1$H NMR 400 MHz (DMSO-d$_6$) δ 12.68 (bs, NH), 7.78 (s, 1H), 7.72 (dt, J = 8.0, 1.3 Hz, 1H), 7.62 (d, J = 8.0 Hz, 1H), 7.50-7.35 (m, 7H), 7.26 (d, J = 3.6 Hz, 1H), 6.99-6.90 (m, 2H), 6.30 (s, 1H), 4.77 (d, J = 17.7 Hz, 1H), 4.00 (d, J = 17.8 Hz, 1H), 3.49-3.43 (m, 4H), 3.23 (bs, 4H). |
| I-121 | Method A: Rt = 3.13 min, MS m/z: 524.47 [M + 1]; $^1$H NMR 400 MHz (DMSO-d$_6$) δ 12.69 (bs, NH), 7.97 (s, 1H), 7.92 (dd, J = 8.0, 1.7 Hz, 1H), 7.79 (d, J = 8.2 Hz, 2H), 7.66 (d, J = 8.0 Hz, 1H), 7.51 (d, J = 8.1 Hz, 2H), 7.49-7.40 (m, 4H), 7.39-7.36 (m, 2H), 6.31 (s, 1H), 4.79 (d, J = 17.8 Hz, 1H), 4.01 (d, J = 17.8 Hz, 1H), 3.22 (bs, 4H), 2.94 (bs, 4H). |
| I-122 | Method A: Rt = 4.55 min, MS m/z: 483.34 [M + 1]; $^1$H NMR 600 MHz (DMSO-d$_6$) δ 12.72 (bs, NH), 11.17 (bs, NH), 7.93-7.86 (s, 3H), 7.62 (d, J = 8.0 Hz, 1H), 7.55-7.46 (m, 3H), 7.43 (d, J = 8.0 Hz, 1H), 7.38 (s, 1H), 7.31-7.20 (m, 4H), 6.49 (s, 1H), 6.30 (s, 1H), 4.76 (d, J = 17.1 Hz, 1H), 4.12 (d, J = 17.3 Hz, 1H). |
| I-123 | Method B: Rt = 1.18 min, MS m/z: 466.26 [M + 1]; $^1$H NMR 600 MHz (DMSO-d$_6$) δ 12.72 (bs, NH), 11.17 (bs, NH), 7.93-7.86 (s, 3H), 7.62 (d, J = 8.0 Hz, 1H), 7.55-7.46 (m, 3H), 7.43 (d, J = 8.0 Hz, 1H), 7.38 (s, 1H), 7.31-7.20 (m, 4H), 6.49 (s, 1H), 6.30 (s, 1H), 4.76 (d, J = 17.1 Hz, 1H), 4.12 (d, J = 17.3 Hz, 1H). |

TABLE 1-continued

| Compound Number | $^1$H NMR and/or MS (m/z) data |
|---|---|
| I-124 | Method B: Rt = 0.67 min, MS m/z: 511.27 [M + 1], $^1$H NMR 600 MHz (DMSO-$d_6$) δ 12.72 (bs, NH), 11.17 (bs, NH), 7.93-7.86 (s, 3H), 7.62 (d, J = 8.0 Hz, 1H), 7.55-7.46 (m, 3H), 7.43 (d, J = 8.0 Hz, 1H), 7.38 (s, 1H), 7.31-7.20 (m, 4H), 6.49 (s, 1H), 6.30 (s, 1H), 4.76 (d, J = 17.1 Hz, 1H), 4.12 (d, J = 17.3 Hz, 1H). |
| I-125 | Method B: Rt = 0.73 min, MS m/z: 542.27 [M + 1]; $^1$H NMR 600 MHz (DMSO-$d_6$) δ 12.72 (bs, NH), 11.17 (bs, NH), 7.93-7.86 (s, 3H), 7.62 (d, J = 8.0 Hz, 1H), 7.55-7.46 (m, 3H), 7.43 (d, J = 8.0 Hz, 1H), 7.38 (s, 1H), 7.31-7.20 (m, 4H), 6.49 (s, 1H), 6.30 (s, 1H), 4.76 (d, J = 17.1 Hz, 1H), 4.12 (d, J = 17.3 Hz, 1H). |
| I-126 | Method B: Rt = 0.63 min, MS m/z: 543.89 [M + 1]. $^1$H NMR 500 MHz (DMSO-$d_6$) δ 12.62 (bs, NH), 10.00 (bs, OH), 7.90-7.86 (m, 3H), 7.69-7.65 (m, 2H), 7.62 (d, J = 7.9 Hz, 1H), 7.49 (d, J = 3.4 Hz, 1H), 7.28 (d, J = 3.4 Hz, 1H), 7.15-7.09 (m, 3H), 6.94 (dd, J = 4.9, 8.9 Hz, 1H), 6.87 (dd, J = 3.1, 9.2 Hz, 1H), 6.34 (s, 1H), 4.64 (d, J = 17.7 Hz, 1H), 4.02 (d, J = 17.7 Hz, 1H), 3.46-3.42 (m, 4H), 3.27-3.23 (m, 4H), 2.56 (bs, NH). |
| I-127 | Method B: Rt = 1.02 min, MS m/z: 465.97 [M + 1]. $^1$H NMR 500 MHz (DMSO-$d_6$) δ 13.20 (s, NH), 11.19 (s, NH), 9.23 (s, 1H), 7.95-7.91 (m, 3H), 7.63 (d, J = 7.9 Hz, 1H), 7.52-7.39 (m, 8H), 6.52-6.50 (m, 1H), 6.35 (s, 1H), 4.95 (d, J = 17.4 Hz, 1H), 4.05 (d, J = 17.4 Hz, 1H). |
| I-128 | Method B: Rt = 1.16 min, MS m/z: 464.99 [M + 1]. $^1$H NMR 500 MHz (DMSO-$d_6$) δ 11.25 (bs, NH), 11.19 (bs, NH), 8.98 (s, 1H), 8.64 (s, 1H), 7.96-7.88 (m, 3H), 7.63 (d, J = 7.9 Hz, 1H), 7.52-7.41 (m, 7H), 7.40 (t, J = 2.6 Hz, 1H), 6.52-6.50 (m, 1H), 6.23 (s, 1H), 4.83 (d, J = 17.7 Hz, 1H), 4.03 (d, J = 17.7 Hz, 1H) |
| I-129 | Method B: Rt = 0.96 min, MS m/z: 449.03 [M + 1]. $^1$H NMR 500 MHz (DMSO-$d_6$) δ 11.80 (s, NH), 11.19 (s, NH), 7.97-7.88 (m, 3H), 7.62 (d, J = 7.9 Hz, 1H), 7.57-7.41 (m, 7H), 7.40 (t, J = 2.6 Hz, 1H), 6.52-6.50 (m, 1H), 6.23 (bs, 1H), 4.75 (d, J = 17.4 Hz, 1H), 3.97 (d, J = 17.4 Hz, 1H). |
| I-130 | Method B: Rt = 1.11 min, MS m/z: 449.03 [M + 1]. $^1$H NMR 500 MHz (DMSO-$d_6$) δ 11.19 (s, NH), 10.88 (s, NH), 9.20 (s, 1H), 8.67 (s, 1H), 7.96-7.88 (m, 3H), 7.63 (d, J = 7.9 Hz, 1H), 7.52-7.39 (m, 8H), 6.52-6.50 (m, 1H), 6.22 (s, 1H), 4.79 (d, J = 17.4 Hz, 1H), 4.02 (d, J = 17.4 Hz, 1H). |
| I-131 | Method B: Rt = 1.24 min, MS m/z: 478.98 [M + 1]. $^1$H NMR 500 MHz (DMSO-$d_6$) δ 12.62 (s, NH), 11.19 (s, NH), 7.95-7.88 (m, 3H), 7.63 (d, J = 7.9 Hz, 1H), 7.52-7.38 (m, 8H), 6.83 (s, 1H), 6.52-6.50 (m, 1H), 6.31 (s, 1H), 4.79 (d, J = 17.4 Hz, 1H), 4.02 (d, J = 17.4 Hz, 1H), 2.26 (s, 3H). |
| I-132 | Method B: Rt = 1.41 min, MS m/z: 532.89 [M + 1]. $^1$H NMR 500 MHz (DMSO-$d_6$) δ 13.20 (s, NH), 11.19 (s, NH), 8.04 (s, 1H), 7.95-7.88 (m, 3H), 7.63 (d, J = 8.5 Hz, 1H), 7.52-7.41 (m, 7H), 7.40 (t, J = 2.8 Hz, 1H), 6.52-6.50 (m, 1H), 6.27 (s, 1H), 4.74 (d, J = 17.4 Hz, 1H), 4.06 (d, J = 17.4 Hz, 1H). |
| I-133 | Method B: Rt = 0.65 min, MS m/z: 448.04 [M + 1]. $^1$H NMR 500 MHz (DMSO-$d_6$) δ 11.79 (bs, 2NH), 11.27 (s, NH), 8.03-7.95 (m, 3H), 7.71 (d, J = 7.9 Hz, 1H), 7.60-7.47 (m, 8H), 6.85 (bs, 2H), 6.60-6.58 (m, 1H), 6.33 (s, 1H), 4.93 (d, J = 17.7 Hz, 1H), 4.09 (d, J = 17.7 Hz, 1H). |
| I-134 | Method B: Rt = 0.97 min, MS m/z: 460.06 [M + 1]. $^1$H NMR 500 MHz (DMSO-$d_6$) δ 11.19 (bs, NH), 10.99 (s, NH), 9.06 (s, 2H), 8.94 (s, 1H), 7.96-7.88 (m, 3H), 7.63 (d, J = 7.9 Hz, 1H), 7.52-7.42 (m, 7H), 7.40 (t, J = 2.8 Hz, 1H), 6.52-6.50 (m, 1H), 6.29 (s, 1H), 4.82 (d, J = 17.4 Hz, 1H), 4.03 (d, J = 17.7 Hz, 1H). |
| I-135 | Method B: Rt = 0.89 min, MS m/z: 561.90 [M + 1]; $^1$H NMR 500 MHz (DMSO-$d_6$) δ 12.61 (s, NH), 10.01 (s, OH), 7.78 (s, 1H), 7.74 (d, J = 7.9 Hz, 1H), 7.64 (d, J = 7.9 Hz, 1H), 7.53-7.47 (m, 2H), 7.27 (d, J = 3.7 Hz, 1H), 7.12 (td, J = 8.5, 3.1 Hz, 1H), 7.01-6.90 (m, 3H), 6.87 (dd, J = 9.5, 3.4 Hz, 1H), 6.32 (s, 1H), 4.65 (d, J = 17.7 Hz, 1H), 4.02 (d, J = 17.7 Hz, 1H), 3.51-3.44 (m, 4H), 3.27-3.20 (m, 4H). |
| I-136 | Method B: Rt = 1.11 min, MS m/z: 49.90 [M + 1]. |
| I-137 | Method B: Rt = 1.05 min, MS m/z: 499.94 [M + 1]; $^1$H NMR 500 MHz (DMSO-$d_6$) δ 12.62 (s, NH), 11.75 (s, NH), 9.97 (s, OH), 8.56 (d, J = 2.1 Hz, 1H), 8.29 (d, J = 2.1 Hz, 1H), 8.00-7.95 (m, 2H), 7.67 (d, J = 7.9 Hz, 1H), 7.53 (t, J = 2.9 Hz, 1H), 7.49 (d, J = 3.7 Hz, 1H), 7.27 (d, J = 3.7 Hz, 1H), 7.12 (td, J = 8.5, 3.1 Hz, 1H), 6.92 (dd, J = 8.9, 4.9 Hz, 1H), 6.88 (dd, J = 9.2, 3.1 Hz, 1H), 6.52 (dd, J = 3.4, 1.8 Hz, 1H), 6.35 (s, 1H), 4.67 (d, J = 17.4 Hz, 1H), 4.04 (d, J = 17.7 Hz, 1H). |
| I-138 | Method B: Rt = 0.94 min, MS m/z: 545.94 [M + 1]; $^1$H NMR 500 MHz (DMSO-$d_6$) δ 7.90-7.86 (m, 2H), 7.63-7.59 (m, 3H), 7.49 (d, J = 3.7 Hz, 1H), 7.44-7.35 (m, 2H), 7.27 (d, J = 3.4 Hz, 1H), 7.21-7.16 (m, 1H), 7.03 (d, J = 8.9 Hz, 1H), 6.45 (s, 1H), 4.75 (d, J = 17.1 Hz, 1H), 4.15 (d, J = 17.4 Hz, 1H), 3.16-3.12 (m, 4H), 2.92-2.86 (m, 4H). |
| I-139 | Method B: Rt = 0.98 min, MS m/z: 563.95 [M + 1]; $^1$H NMR 500 MHz (DMSO-$d_6$) δ 7.79 (s, 1H), 7.75 (dt, J = 7.9, 1.5 Hz, 1H), 7.64 (d, J = 7.9 Hz, 1H), 7.49 (d, J = 3.7 Hz, 1H), 7.46-7.34 (m, 3H), 7.28 (d, J = 3.7 Hz, 1H), 7.21-7.16 (m, 1H), 6.88-6.83 (m, 2H), 6.44 (s, 1H), 4.76 (d, J = 17.4 Hz, 1H), 4.17 (d, J = 17.4 Hz, 1H), 3.20-3.14 (m, 4H), 2.90-2.83 (m, 4H). |
| I-140 | Method B: Rt = 1.37 min, MS m/z: 500.89 [M + 1]; $^1$H NMR 500 MHz (DMSO-$d_6$) δ 12.76 (s, NH), 11.18 (s, NH), 7.96-7.92 (m, 2H), 7.89 (s, 1H), 7.64 (d, J = 8.5 Hz, 1H), 7.64-7.48 (m, 2H), 7.47-7.36 (m, 4H), 7.31 (s, 1H), 7.22-7.17 (m, 1H), 6.50 (bs, 1H), 6.47 (s, 1H), 4.76 (d, J = 17.1 Hz, 1H), 4.17 (d, J = 17.1 Hz, 1H). |

TABLE 1-continued

| Compound Number | ¹H NMR and/or MS (m/z) data |
|---|---|
| I-141 | Method B: Rt = 1.21 min, MS m/z: 501.91 [M + 1]; ¹H NMR 500 MHz (DMSO-$d_6$) δ 13.15 (s, NH), 12.77 (bs, NH), 8.00-7.96 (m, 2H), 7.73 (dd, J = 8.9, 1.5 Hz, 1H), 7.69-7.63 (m, 2H), 7.50 (d, J = 3.1 Hz, 1H), 7.45-7.36 (m, 2H), 7.29 (bs, 1H), 7.22-7.16 (m, 1H), 6.47 (s, 1H), 4.79 (d, J = 17.4 Hz, 1H), 4.18 (d, J = 17.4 Hz, 1H). |
| I-142 | Method B: Rt = 1.17 min, MS m/z: 501.87 [M + 1]; ¹H NMR 500 MHz (DMSO-$d_6$) δ 12.70 (s, NH), 11.68 (s, NH), 8.50 (d, J = 2.1 Hz, 1H), 8.23 (d, J = 2.1 Hz, 1H), 7.94 (s, 1H), 7.92 (d, J = 7.9 Hz, 1H), 7.62 (d, J = 7.6 Hz, 1H), 7.47 (t, J = 2.9 Hz, 1H), 7.44 (d, J = 3.7 Hz, 1H), 7.39-7.31 (m, 2H), 7.24 (d, J = 3.1 Hz, 1H), 7.16-7.11 (m, 1H), 6.45 (bs, 1H), 6.41 (s, 1H), 4.71 (d, J = 17.4 Hz, 1H), 4.13 (d, J = 17.1 Hz, 1H). |

Example 5: Synthesis of (R)-2-(5-fluoro-2-hydroxyphenyl)-2-(1-oxo-6-(4-(piperazin-1-yl)phenyl)isoindolin-2-yl)-N-(thiazol-2-yl)acetamide

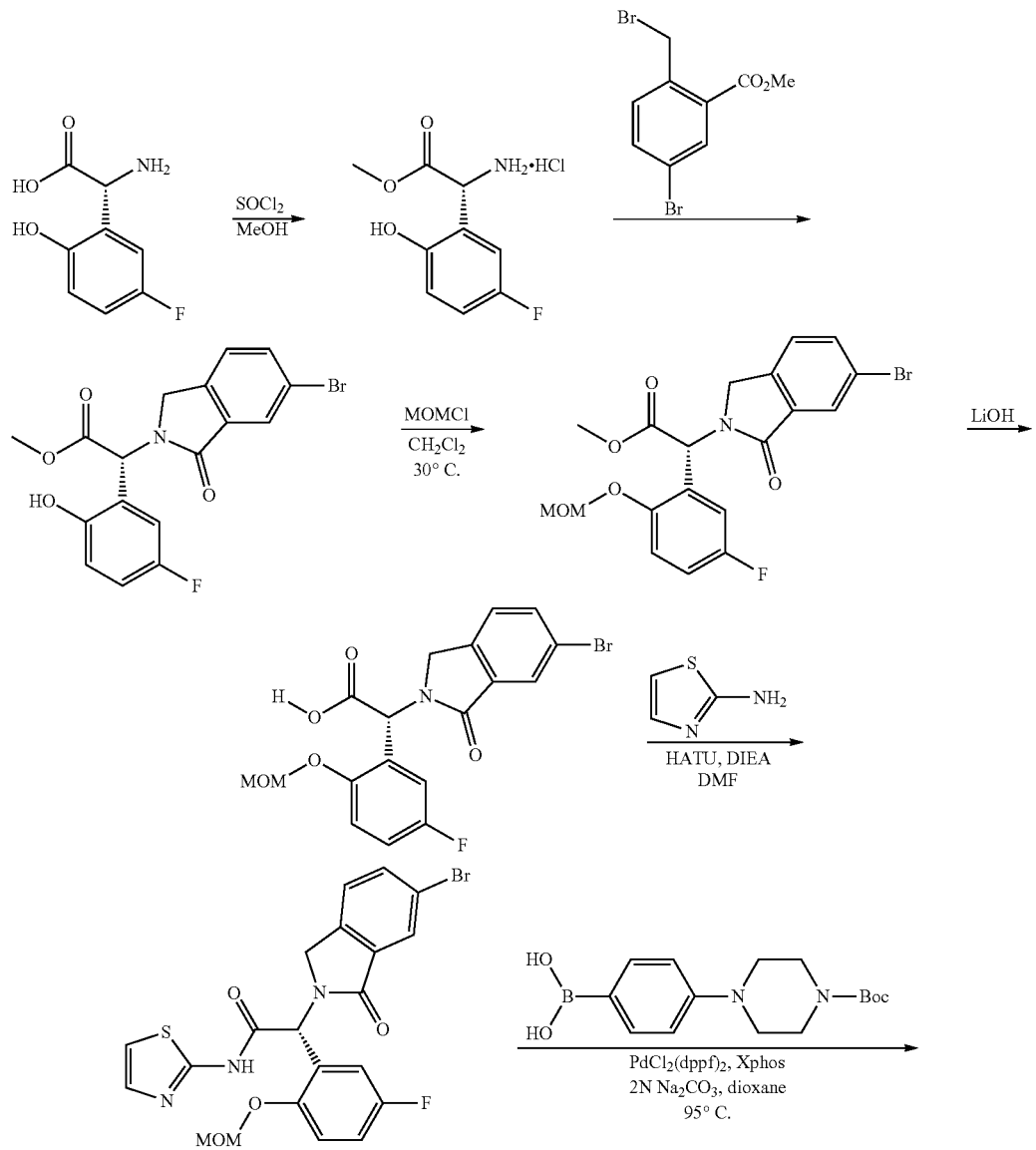

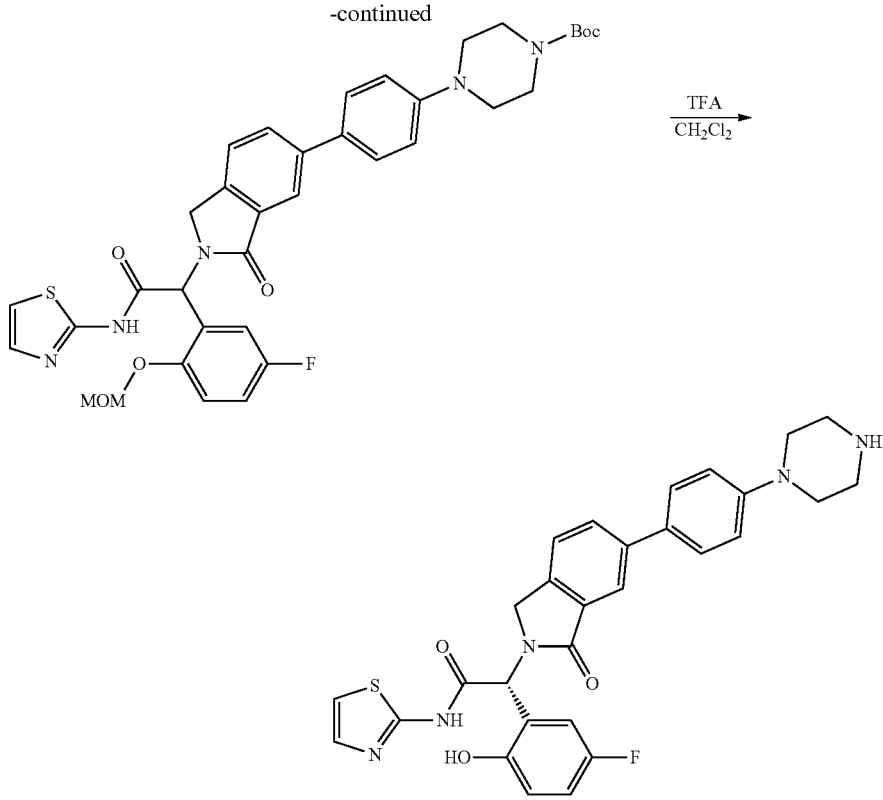

Step 1: Synthesis of methyl (R)-2-amino-2-(5-fluoro-2-hydroxyphenyl)acetate hydrochloride

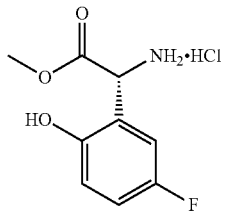

To a solution of (R)-2-amino-2-(5-fluoro-2-hydroxyphenyl)acetic acid (500 mg, 2.26 mmol) in methanol (10 mL) was added thionyl chloride (0.33 mL, 4.51 mmol) dropwise at 0° C. The resulting mixture was stirred for 1 hr. After completion, the reaction mixture was concentrated under reduced pressure. The crude product was used in next step without further purification.

Step 2: Synthesis of methyl (R)-2-(6-bromo-1-oxoisoindolin-2-yl)-2-(5-fluoro-2-hydroxyphenyl)acetate

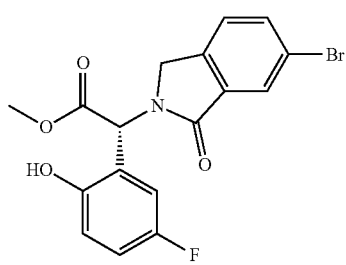 [SMILES: COC(=O)[C@@H](c1cc(F)ccc1O)N1Cc2ccc(Br)cc2C1=O]

Methyl (R)-2-(6-bromo-1-oxoisoindolin-2-yl)-2-(5-fluoro-2-hydroxyphenyl)acetate was synthesized by following the reaction scheme described above in Examples 1-4.

Step 3: Synthesis of methyl (R)-2-(6-bromo-1-oxoisoindolin-2-yl)-2-(5-fluoro-2-(methoxymethoxy)phenyl)acetate

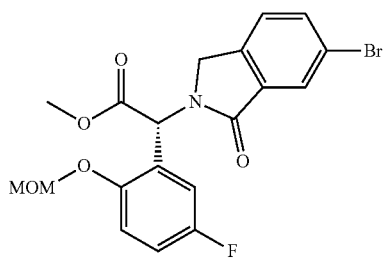

To a solution of methyl (R)-2-(6-bromo-1-oxoisoindolin-2-yl)-2-(5-fluoro-2-hydroxyphenyl)acetate (350 mg, 0.89 mmol) in dichloromethane (5 mL) were added methoxymethyl chloride (0.17 mL, 2.25 mmol) and DIEA (0.47 mL, 2.70 mmol). The reaction mixture was warmed to 30° C. and stirred for 4 hr. The resulting mixture was diluted with dichloromethane and washed with water and brine. The organic layer was dried over sodium sulfate, filtered, and concentrated under reduced pressure. The residue was purified by flash column chromatography (Hex:EtOAc=80:20 to 20:80) to obtain methyl (R)-2-(6-bromo-1-oxoisoindolin-2-yl)-2-(5-fluoro-2-(methoxymethoxy)phenyl)acetate (403 mg, 92%).

Step 4: Synthesis of tert-butyl (R)-4-(4-(2-(1-(5-fluoro-2-(methoxymethoxy)phenyl)-2-oxo-2-(thiazol-2-ylamino)ethyl)-3-oxoisoindolin-5-yl)phenyl)piperazine-1-carboxylate

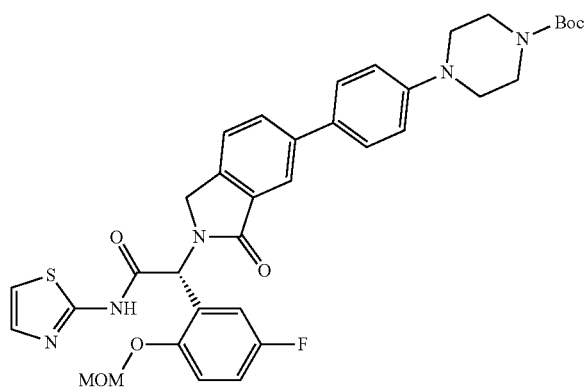

tert-Butyl (R)-4-(4-(2-(1-(5-fluoro-2-(methoxymethoxy)phenyl)-2-oxo-2-(thiazol-2-ylamino)ethyl)-3-oxoisoindolin-5-yl)phenyl)piperazine-1-carboxylate was synthesized by following the reaction scheme described above in Examples 1-4.

Step 5: Synthesis of (R)-2-(5-fluoro-2-hydroxyphenyl)-2-(1-oxo-6-(4-(piperazin-1-yl)phenyl)isoindolin-2-yl)-N-(thiazol-2-yl)acetamide

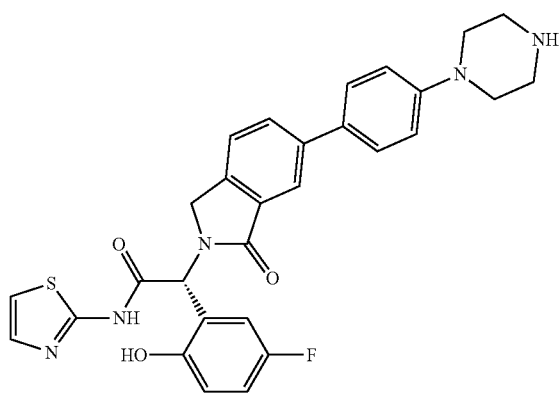 [SMILES: O=C(Nc1nccs1)[C@@H](c1cc(F)ccc1O)N1Cc2ccc(-c3ccc(N4CCNCC4)cc3)cc2C1=O]

To a solution of tert-butyl (R)-4-(4-(2-(1-(5-fluoro-2-(methoxymethoxy)phenyl)-2-oxo-2-(thiazol-2-ylamino)ethyl)-3-oxoisoindolin-5-yl)phenyl)piperazine-1-carboxylate (42 mg, 0.061 mmol) in dichloromethane (1.6 mL) was added trifluoroacetic acid (0.4 mL). The reaction mixture was stirred for 3 hr. The resulting mixture was concentrated and trifluoroacetic acid was removed under reduced pressure. The residue was purified by preparative high performance liquid chromatography (HPCL) to obtain (R)-2-(5-fluoro-2-hydroxyphenyl)-2-(1-oxo-6-(4-(piperazin-1-yl)phenyl)isoindolin-2-yl)-N-(thiazol-2-yl)acetamide (23 mg, 70%) as an off-white solid. Method B: Rt=0.63 min, MS m/z: 543.89 [M+1]. $^{1}$H NMR 500 MHz (DMSO-$d_{6}$) δ 12.62 (bs, NH), 10.00 (bs, OH), 7.90-7.86 (m, 3H), 7.69-7.65 (m, 2H), 7.62 (d, J=7.9 Hz, 1H), 7.49 (d, J=3.4 Hz, 1H), 7.28 (d, J=3.4 Hz, 1H), 7.15-7.09 (m, 3H), 6.94 (dd, J=4.9, 8.9 Hz, 1H), 6.87 (dd, J=3.1, 9.2 Hz, 1H), 6.34 (s, 1H), 4.64 (d, J=17.7 Hz, 1H), 4.02 (d, J=17.7 Hz, 1H), 3.46-3.42 (m, 4H), 3.27-3.23 (m, 4H), 2.56 (bs, NH).

Example 6: Synthesis of 2-(1-oxoisoindolin-2-yl)-3-(pyridin-3-yl)-N-(thiazol-2-yl)propanamide (I-143)

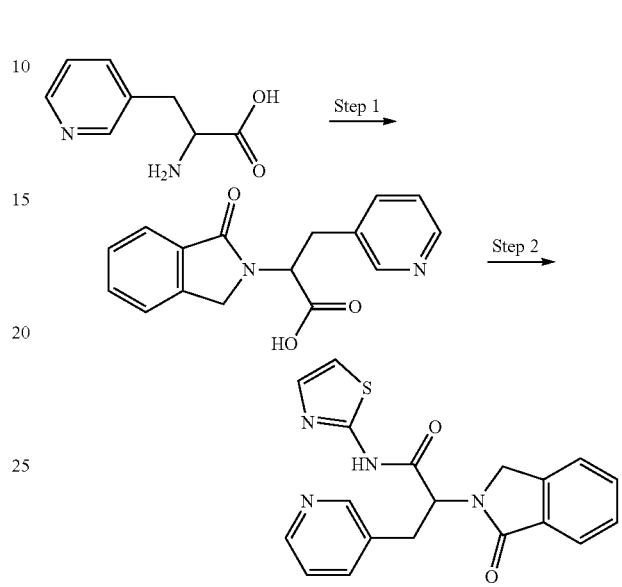

Step 1: 2-(1-oxoisoindolin-2-yl)-3-(pyridin-3-yl)propanoic Acid

To a solution of 2-Amino-3-(pyridin-3-yl)propanoic acid (83 mg, 0.5 mmol) and phthalaldehyde (67 mg, 0.5 mmol) in CHCl3 (3 mL) was added acetic acid (0.03 mL, 0.5 mmol) and the resulting mixture was heated to 80° C. for 8 hrs. The reaction mixture was concentrated under reduced pressure and purified by preparative high performance liquid chromatography (HPLC) to obtain 2-(1-oxoisoindolin-2-yl)-3-(pyridin-3-yl)propanoic acid (100 mg, 71%) as a yellow solid. Rt=0.38 min; MS m/z: 283.25 [M+1].

Step 2: 2-(1-oxoisoindolin-2-yl)-3-(pyridin-3-yl)-N-(thiazol-2-yl)propanamide (I-143)

To a solution of 2-(1-oxoisoindolin-2-yl)-3-(pyridin-3-yl)propanoic acid (35 mg, 0.12 mmol) in DCM (2 mL) was added 2-aminothiazole (15 mg, 0.15 mmol). After stirring for 1 hr at room temperature, the reaction mixture was diluted with DCM and washed with water. The organic layer was then dried over sodium sulfate, filtered, concentrated under reduced pressure. The crude product was purified by preparative high performance liquid chromatography (HPLC) to obtain 2-(1-oxoisoindolin-2-yl)-3-(pyridin-3-yl)-N-(thiazol-2-yl)propanamide (I-143, 20 mg, 46%) as an white solid. Rt=0.61 min; MS m/z: 365.36 [M+1].

Example 7: Biochemical Studies

EGFR Protein Expression and Purification

Constructs spanning residues 696-1022 of the human EGFR (including wild type and L858R, L858R/T790M, T790M, and T790M/V948R mutant sequences) were prepared in a GST-fusion format using the pTriEX system (Novagen) for expression in Sf9 insect cells essentially as described. (Yun, C. H. et al. The T790M mutation in EGFR kinase causes drug resistance by increasing the affinity for ATP. *Proc Natl Acad Sci USA* 105, 2070-2075 (2008); Yun, C. H. et al. Structures of lung cancer-derived EGFR mutants and inhibitor complexes: mechanism of activation and insights into differential inhibitor sensitivity. *Cancer Cell* 11, 217-227 (2007)) EGFR kinase proteins were purified by glutathione-affinity chromatography followed by size-exclusion chromatography after cleavage with TEV or thrombin to remove the GST fusion partner following established procedures. (Yun, C. H. et al. *Proc Natl Acad Sci USA* 105, 2070-2075 (2008); Yun, C. H. et al. *Cancer Cell* 11, 217-227 (2007)

High-Throughput Screening

Purified EGFR-L858R/T790M enzyme was screened against compounds of the present disclosure using HTRF-based biochemical assay format. The screening was performed at 1 µM ATP using a single compound concentration (12.5 µM). 1322 top hits were picked for follow-up $IC_{50}$ confirmation. $IC_{50}$ values were determined at both 1 µM and 1 mM ATP to identify both ATP competitive and non-competitive compounds. Hits were also counter-screened against wild type EGFR to evaluate the mutant selectivity.

The HTRF-based screen was carried out using 1 µM ATP, and active compounds were counter-screened at 1 mM ATP and against wild type EGFR to identify those that were potentially non-ATP-competitive and mutant selective. This strategy identified several compounds of distinct chemical classes that were both selective for the L858R/T790M mutant over WT EGFR and relatively insensitive to ATP concentrations, suggesting an allosteric mechanism of action. Among the compounds identified in the screen, EGFR allosteric inhibitor-1 (FIG. 1A) was of particular interest due to its potency and selectivity for mutant EGFR ($IC_{50}$=0.033 LM for L858R/T790M at 1 mM ATP, $IC_{50}$>50 µM for wild type EGFR). Further characterization of the mutant-selectivity of Compound A1 revealed similar activity against L858R/T790M and T790M mutants, with approximately 2-fold decreased potency against L858R mutant EGFR.

HTRF-Based EGFR Biochemical Assays

EGFR biochemical assays were carried out using a homogeneous time-resolved fluorescence (HTRF) assay as described previously. The reaction mixtures contained 1 µM biotin-Lck-peptide substrate, wild type or mutant EGFR enzyme in reaction buffer (50 mM HEPES pH 7.1, 10 mM $MgCl_2$, 0.01% BSA, 1 mM TCEP and 0.1 mM $Na_3VO_4$) at a final volume of 10 µL. Enzyme concentrations were adjusted to accommodate varying kinase activity and ATP concentrations (0.2-0.4 nM L858R/T790M; or 2-4 nM L858R, or 2-4 nM T790M, or 40 nM WT). All reactions were carried out at room temperature in white ProxiPlate™ 384-well Plus plates (PerkinElmer) and were quenched with 5 µL of 0.2 M EDTA at 60 min. Five µL per well of the detection reagent containing 2.5 ng PT66K (Cis-bio) and 0.05 µg SAXL (Prozyme) were added, and the plates were then incubated at room temperature for 1 hour and read with an EnVision plate reader. For $IC_{50}$ determinations, compounds of the present disclosure were diluted into assay mixture (final DMSO 0.5%), and $IC_{50}$ values were determined by 12-point inhibition curves (from 50 to 0.000282 µM) in duplicate under the assay conditions as described above.

Structure Determination Using Compound A1

Prior to crystallization, 0.1 mM of EGFR-T790M/V943R was incubated for 1 hour with 0.5 mM Compound A1, 1 mM Adenosine 5'-(β,γ-imido)triphosphate (AMP-PNP) and 10 mM $MgCl_2$ at room temperature. Crystals of T790MV943R EGFR in complex with Compound A1 were prepared by hanging-drop vapor diffusion method over a reservoir solution containing 0.1M Bis-Tris pH 5.5, 25% PEG 3350, 5 mM tris (2-carboxyethyl)-phosphine (TCEP). Crystals were flash-frozen in liquid nitrogen after rapid immersion in a cryoprotectant solution containing 0.1 M Bis-Tris 5.5, 25% PEG3350, 10% ethylene glycol and 5 mM TCEP. Diffraction data were recorded using a Mar343 image plate detector on a rotating anode source at 100 K. Data were processed and merged with HKL2000, as described previously. The structure was determined by molecular replacement with the program PHASER using an inactive EGFR kinase structure (PDB 2GS7) as the search model. Repeated rounds of manual refitting and crystallographic refinement were performed using COOT and REFMAC. The inhibitor was modeled into the closely fitting positive Fo-Fc electron density and then included in following refinement cycles. Topology and parameter files for the inhibitors were generated using PRODRG.

To better understand the mechanism of inhibition and mutant-selectivity of the compounds of the present disclosure, the crystal structure of Compound A1, and known EGFR inhibitors, lapatinib and neratinib, bound to T790M-mutant EGFR, were determined. The structure reveals that the compound binds in an allosteric pocket that is created in part by the outward displacement of the C-helix in the inactive conformation of the kinase (FIGS. 1B and 1C). The compound binds as a "three-bladed propeller" with the aminothiazole moiety inserted between the mutant gatekeeper methionine and active site residue Lys745. The phenyl substituent extends into a hydrophobic cleft at the back of the pocket and is in contact with Leu777 and Phe856. Finally, the oxaindole group extends along the C-helix toward the solvent exposed exterior. It packs between Ile759 and Met766 in the C-helix, and is also in van der Waals contact with Leu788. The compound also forms a hydrogen bond with Asp855 in the DFG motif. In further support of a non-ATP competitive mechanism, the ATP-analog AMP-PNP is bound in the expected manner in the active site cleft (FIG. 1C).

Figure 3:
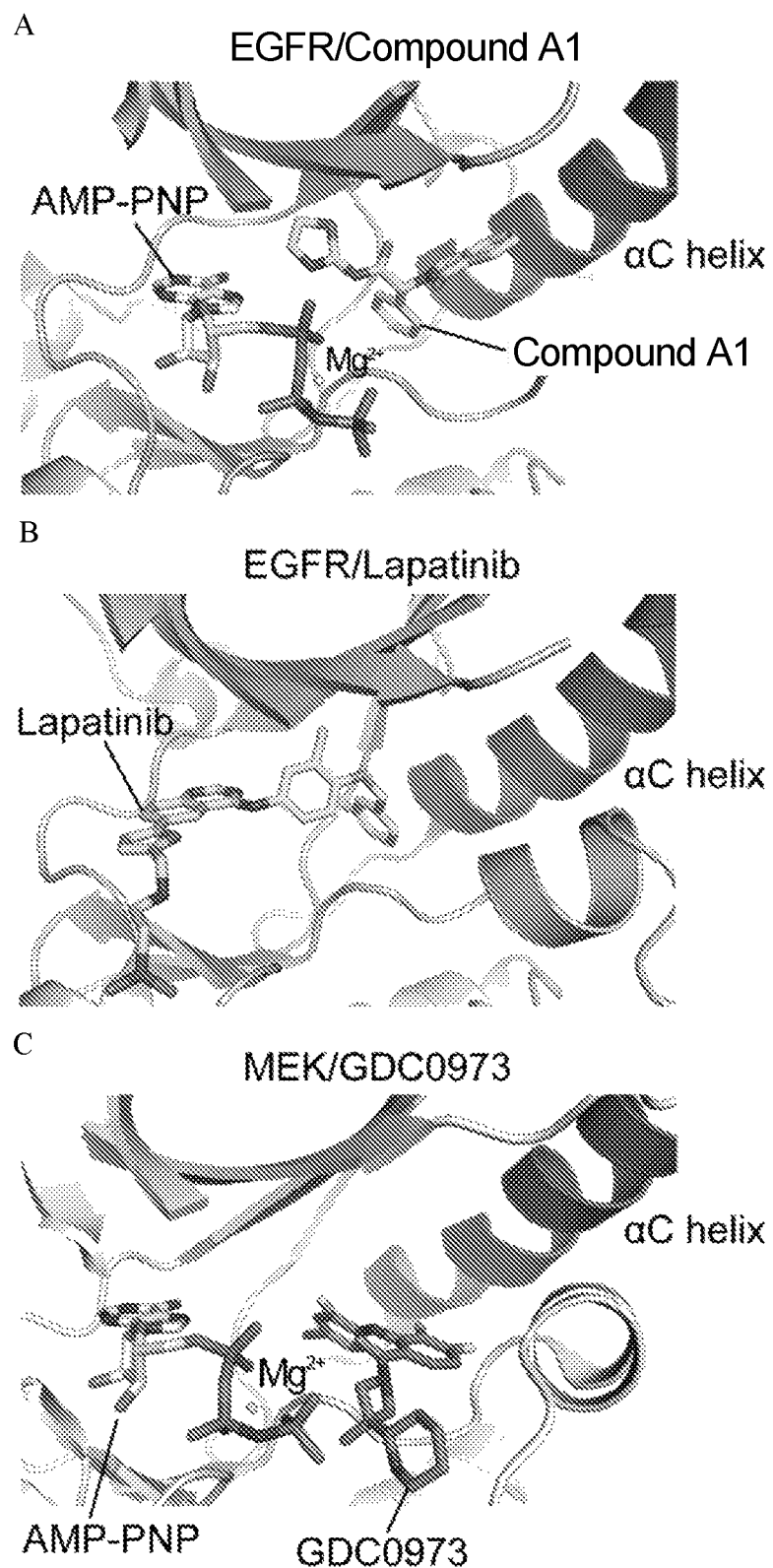
FIG. 3A shows structure of Compound A1 in complex with EGFR.
FIG. 3B shows structure of lapatinib bound to EGFR (PDB ID 1XKK). Lapatinib also binds an inactive conformation of the kinase. Like other anilinoquinazoline inhibitors it occupies the ATP site, but it also extends into the allosteric pocket occupied by Compound A1. Note that it places phenyl groups in positions similar to those occupied by the aminothiazole and phenyl substituents of Compound A1.
FIG. 3C shows structure of MEK1 kinase bound to allosteric MEK1 inhibitor GDC0973 (Cobimetinib). GDC0973 and other allosteric MEK inhibitors occupy a pocket created by displacement of the C-helix in the inactive conformation of the kinase. Most allosteric MEK inhibitors make hydrogen bond interactions with the γ-phosphate group of ATP that are important for their potency. The allosteric EGFR inhibitors described herein bind in a generally analogous location in EGFR, but lack any clear structural similarity to MEK inhibitors and do not contact the γ-phosphate group of ATP.
Figure 4:
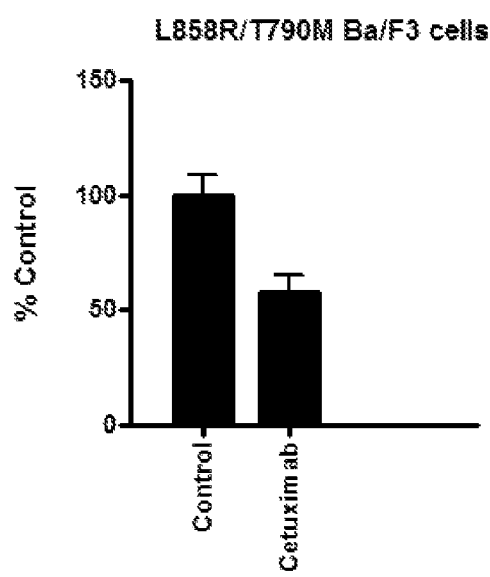
FIG. 4 is a graph showing EGFR activity in cells expressing EGFR T790M/L858R treated with 1 μg/mL cetuximab.
Figure 5:
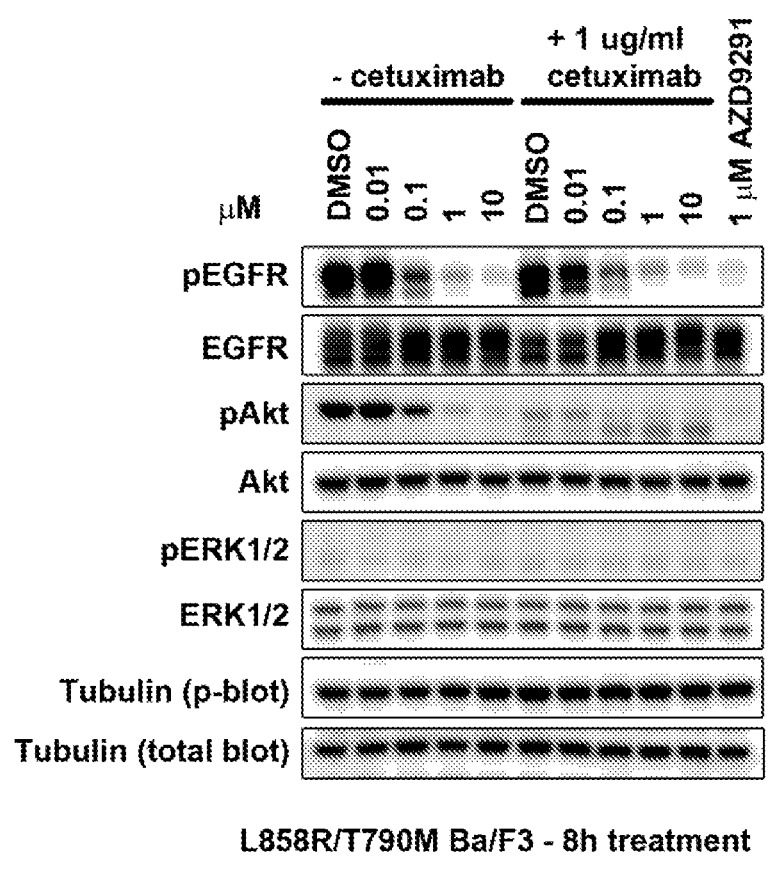
FIG. 5 is a western blot showing the levels of pEGFR, EGFR, pAkt, Akt, pErk, Erk, and tubulin in cells expressing EGFR T790M/L858R after a 8-hour treatment with Compound I-126, in the absence or presence of cetuximab.

EGFR inhibitors lapatinib and neratinib extend into the allosteric site and make interactions that resemble those of two of the three blades of the allosteric agents (FIGS. 3A and 3B). (Wood, E. R. et al. A unique structure for epidermal growth factor receptor bound to GW572016 (Lapatinib): relationships among protein conformation, inhibitor off-rate, and receptor activity in tumor cells. *Cancer Res* 64, 6652-6659 (2004); Tsou, H. R. et al. Optimization of 6,7-disubstituted-4-(arylamino)quinoline-3-carbonitriles as orally active, irreversible inhibitors of human epidermal growth factor receptor-2 kinase activity. *Journal of medicinal chemistry* 48, 1107-1131 (2005)) These ATP-competitive inhibitors are not mutant selective, and they span both the ATP and allosteric sites. Notably, the EGFR allosteric pocket is roughly analogous to a site in MEK1 that is targeted by a number of allosteric inhibitors that are now in clinical trials. (Zhao, Y. & Adjei, A. A. The clinical development of MEK inhibitors, *Nature reviews. Clinical oncology* 11, 385-400, doi: 10.1038/nrclinonc.2014.83 (2014)) Despite the similar location of the MEK allosteric site, there is not structural correspondence in the binding modes of the respective allosteric inhibitors (FIGS. 3B and 3C).

The mutant-specificity of the EGFR allosteric inhibitors arises from at least two effects. Most obviously, the direct contact of the aminothiazole group with the mutant gatekeeper methionine residue can explain the selectivity for the T790M mutant. Secondly, selectivity for L858R (and by extension the lack of activity on wild type EGFR) is likely attributable to the fact that the compound cannot bind the fully inactive conformation of the kinase, in which the N-terminal portion of the activation loop forms a short helix that includes Leu858. Simple modeling reveals that Compound A1 binding will be precluded by steric clashes of the oxindole group with Leu858 and Leu861 in this region in the fully inactive conformation of the wild type receptor. Prior structural analysis of the L858R mutant revealed that it destabilizes this inactive conformation to promote kinase activation. (Yun, C. H. et al. Structures of lung cancer-derived EGFR mutants and inhibitor complexes: mechanism of activation and insights into differential inhibitor sensitivity. *Cancer Cell* 11, 217-227 (2007)) In the present structure, Leu858 assumes an alternate position and the remainder of the activation loop is disordered. Thus, binding of the allosteric inhibitor is favored in the L858R mutant where this constraint is released. The compounds may also inhibit other mutants with a similar mechanism of activation, such as L861Q. By contrast, it is not expected the compounds to bind most exon19 deletion variants. Although no structure is available for any of the exon19 deletions, these mutations shorten the loop leading into the C-helix and likely lock it in the inward active position, thereby precluding binding of the allosteric agents, irrespective of the presence of the T790M mutation.

H1975, H3255 & HaCaT Target Modulation Assays
Tissue Culture

Cells were maintained in 10% FBS/RPMI supplemented with 100 µg/mL Penicillin/Streptomycin (Hyclone #SH30236.01). The cells were harvested with 0.25% Trypsin/EDTA (Hyclone #SH30042.1), re-suspended in 5% FBS/RPMI Pen/Strep and plated at 7,500 cells per well in 50 µL of media in a 384-well black plate with clear bottoms (Greiner #789068G). The cells were allowed to incubate overnight in a 37° C., 5% $CO_2$ humidified tissue culture incubator. The 12-point serial diluted test compounds were transferred to the plate containing cells by using a 50 nL Pin Head device (Perkin Elmer) and the cells were placed back in the incubator for 3 hours.

Phospho-EGFR (Y1173) Target Modulation Assay

HaCaT cells were stimulated with 10 ng/mL EGF (Peprotech # AF-100-15) for 5 minutes at room temperature. Constitutively activated EGFR mutant cell lines (H1975 and H3255) were not stimulated with EGF. The media was reduced to 20 µL using a Bio-Tek ELx 405 Select™ plate washer. Cells were lysed with 20 µL of 2× Lysis buffer containing protease and phosphatase inhibitors (2% Triton X-100, 40 mM Tris, pH 7.5, 2 mM EDTA, 2 mM EGTA, 300 mM NaCl, 2× complete cocktail inhibitor (Roche #11 697 498 001), 2× Phosphatase Inhibitor Cocktail Set II and Set III (Sigma #P5726 and #P0044)). The plates were shaken for 20 minutes. An aliquot of 25 µL from each well was transferred to prepared ELISA plates for analysis.

For the experiment studying the effect of EGF pretreatment on compound (e.g., compounds of the present disclosure) target modulation, H1975 cells were harvested and plated in 0.5% FBS/RPMI Pen/Strep. On the following day, cells were pre-treated with 0.5% FBS/RPMI media with or without 10 ng EGF/mL for 5 minutes. Compound (i.e., compounds of the present disclosure) was added and assay was carried out as described above.

Phospho-EGFR (Y1173) ELISA

Solid white 384-well high-binding ELISA plates (Greiner #781074) were coated with 5 µg/mL goat anti-EGFR capture antibody overnight in 50 mM carbonate/bicarbonate pH 9.5 buffer. Plates were blocked with 1% BSA (Sigma #A7030) in PBS for 1 hour at room temperature, and washes were carried out with a Bio-Tek ELx405 Select™ using 4 cycles of 100 µL TBS-T (20 mM Tris, 137 mM NaCl, 0.05% Tween-20) per well. A 25 µL aliquot of lysed cell was added to each well of the ELISA plate and incubated overnight at 4° C. with gentle shaking. A 1:1,000 anti-phospho-EGFR in 0.2% BSA/TBS-T was added and incubated for 2 hours at room temperature. After washing, 1:2,000 anti-rabbit-HRP in 0.2% BSA/TBS-T was added and incubated for 1 hour at room temperature. Chemiluminescent detection was carried out with SuperSignal ELISA Pico substrate. Signal was read on EnVision plate reader using built-in UltraLUM setting.

Western Blotting

Cell lysates were equalized to protein content determined by Coomassie Plus™ Protein Assay Reagent (ThermoScientific #1856210) and loaded onto 4-12% NuPAGE Bis-Tris gels with MOPS running buffer with LDS Sample buffer (supplemented with DTT. Gel proteins were transferred to PVDF membranes with an iBlot® Gel Transfer Device. 1× Casein-blocked membranes were probed with primary antibodies overnight at 4° C. on an end-over-end rotisserie. Membranes were washed with TBS-T and HRP-conjugated secondary antibodies were added for 1 hour at room temperature. After washing, HRP was detected using Luminata™ Forte Western HRP Substrate reagent and recorded with a Bio-Rad VersaDoc imager.

Proliferation Assay

H1975, H3255 and HaCaT cell lines were plated in solid white 384-well plates (Greiner) at 500 cells per well in 10% FBS RPMI P/S media. Using a Pin Tool, 50 nL of serial diluted compounds of the present disclosure were transferred to the cells. After 3 days, cell viability was measured by CellTiter-Glo (Promega) according to manufacturer's instructions. Luminescent readout was normalized to 0.1% DMSO-treated cells and empty wells. Data was analyzed by non-linear regression curve-fitting and $EC_{50}$ values were reported. Inhibition data of an EGFR T790M/L858R cell line for exemplary compounds of the present disclosure combined with cetuximab (% cetuximab, 1.0 µM drug concentration with 1.0 µg/mL cetuximab) can be found in Table 2 below.

Ba/F3 Cell Proliferation Models

The EGFR mutant L858R, Del E746_A750, L858R/T790M, DelE746_A750/T790M, L858R/T790M/C797S and Del/T790M/C797S Ba/F3 cells have been previously described (Zhou, W., Ercan, D., Chen, L., Yun, C. H., Li, D., Capelletti, M., Cortot, A. B., Chirieac, L., Iacob, R. E., Padera, R., et al. "Novel mutant-selective EGFR kinase inhibitors against EGFR T790M," *Nature* 462, (2009), 1070-1074). All cell lines were maintained in RPMI 1640 (Cellgro; Mediatech Inc., Herndon, Calif.) supplemented with 10% FBS 100 units/mL penicillin, 100 units/mL streptomycin, and 2 mM glutamine. L858R cells were maintained in ACL-4 media (Invitrogen, Carlsbad, Calif.) supplemented with 5% FBS, 100 units/mL penicillin, 100 units/mL streptomycin, and 2 mM glutamine. The EGFR I941R mutation was introduced via site directed mutagenesis using the Quick Change Site-Directed Mutagenesis kit (Stratagene; La Jolla, Calif.) according to the manufacturer's instructions. All constructs were confirmed by DNA sequencing. The constructs were shuttled into the retroviral vector JP 1540 using the BD Creator™ System (BD Biosciences).

Ba/F3 cells were infected with retrovirus and according to standard protocols, as described previously (Zhou et al, Nature 2009). Stable clones were obtained by selection in puromycin (2 µg/ml).

Growth and inhibition of growth was assessed by MTS assay and was performed according to previously established methods (Zhou et al., *Nature* 2009). The MTS assay is a colorimetric method for determining the number of viable cells that is based on the bioreduction of MTS by cells to a formazan product that is soluble in cell culture medium and can be detected spectrophotometrically. Ba/F3 cells of different EGFR genotypes were exposed to treatment for 72 hours and the number of cells used per experiment determined empirically and has been previously established (Zhou et al., *Nature* 2009). All experimental points were set up in six wells and all experiments were repeated at least three times. The data was graphically displayed using GraphPad Prism version 5.0 for Windows, (GraphPad Software; www.graphpad.com). The curves were fitted using a non-linear regression model with a sigmoidal dose response.

Inhibition data of an EGFR T790M/L858R Ba/F3 cell line. A indicates a % inhibition of about 75%; B indicates a % inhibition of between about 50% to about 75%; C indicates a % inhibition of between about 25% to about 50%; and D indicates a % inhibition of between about 0% to about 25%.

TABLE 2

| Compound Number | Activity (% inhibition) |
|---|---|
| I-1 | A |
| I-2 | A |
| I-3 | A |
| I-4 | A |
| I-5 | A |
| I-6 | A |
| I-7 | A |
| I-8 | A |
| I-9 | A |
| I-10 | A |
| I-11 | A |
| I-12 | A |
| I-13 | A |
| I-14 | A |
| I-15 | A |
| I-16 | A |
| I-17 | A |
| I-18 | A |
| I-19 | A |
| I-20 | A |
| I-21 | B |
| I-22 | A |
| I-23 | A |
| I-24 | A |
| I-25 | A |
| I-26 | A |
| I-27 | A |
| I-28 | A |
| I-29 | A |
| I-30 | A |
| I-31 | A |
| I-32 | A |
| I-33 | A |
| I-34 | A |
| I-35 | A |
| I-36 | A |
| I-37 | A |
| I-38 | A |
| I-39 | A |
| I-40 | A |
| I-41 | A |
| I-42 | A |
| I-43 | A |
| I-44 | A |
| I-45 | A |
| I-46 | B |
| I-47 | B |
| I-48 | A |
| I-49 | A |
| I-50 | A |
| I-51 | A |
| I-52 | A |
| I-53 | A |
| I-54 | A |
| I-55 | B |
| I-56 | B |
| I-57 | A |
| I-58 | B |
| I-59 | C |
| I-60 | C |
| I-61 | C |
| I-62 | B |
| I-63 | C |
| I-64 | B |
| I-65 | D |
| I-66 | D |
| I-67 | C |
| I-68 | D |
| I-69 | D |
| I-70 | D |
| I-71 | C |
| I-72 | B |
| I-73 | C |
| I-74 | B |
| I-75 | D |
| I-76 | B |
| I-77 | B |
| I-78 | A |
| I-79 | D |
| I-80 | C |
| I-81 | D |
| I-82 | C |
| I-83 | D |
| I-84 | D |
| I-85 | D |
| I-86 | B |
| I-87 | A |
| I-88 | C |
| I-89 | B |
| I-90 | C |
| I-91 | D |
| I-92 | C |
| I-93 | A |
| I-94 | C |
| I-95 | B |
| I-96 | A |
| I-97 | A |
| I-98 | C |
| I-99 | C |
| I-100 | D |
| I-101 | B |
| I-102 | B |
| I-103 | C |
| I-104 | C |
| I-105 | B |
| I-106 | B |
| I-107 | B |
| I-108 | C |
| I-109 | B |
| I-110 | A |
| I-111 | A |
| I-112 | D |
| I-113 | C |
| I-114 | B |
| I-115 | D |
| I-116 | A |
| I-117 | A |
| I-118 | A |
| I-119 | D |
| I-120 | D |

TABLE 2-continued

| Compound Number | Activity (% inhibition) |
|---|---|
| I-121 | D |
| I-122 | D |
| I-123 | D |
| I-124 | D |
| I-125 | D |
| I-126 | D |
| I-127 | A |
| I-128 | A |
| I-129 | B |
| I-130 | C |
| I-131 | A |
| I-132 | A |
| I-133 | D |
| I-134 | A |

Considering the allosteric mechanism of action the compounds of the present disclosure, the extent to which ligand stimulation would affect potency of inhibition of the mutant receptor was studied. To this end, inhibition of EGFR phosphorylation in H1975 cells in the presence and absence of EGF using the quantitative ELISA-based assay was examined. In both the presence and absence of exogenous EGF (10 ng/ml), representative compounds of the present disclosure inhibited EGFR phosphorylation with a similar $EC_{50}$, but strikingly, inhibition plateaued at 50% in the presence of ligand. This phenomenon suggests two populations of receptor, one that remains sensitive to the allosteric inhibitor upon ligand stimulation, and another, equal in number, that is rendered insensitive. Ligand-induced dimerization of the EGF receptor is known to induce an asymmetric interaction of the kinase domains, and is an obvious potential source of two receptor populations with differential inhibitor sensitivity. (Zhang, X., Gureasko, J., Shen, K., Cole, P. A. & Kuriyan, J. "An allosteric mechanism for activation of the kinase domain of epidermal growth factor receptor," Cell 125, 1137-1149 (2006)).

In the EGFR asymmetric dimer, the C-lobe of the "activator" subunit impinges on the N-lobe of the "receiver" subunit, inducing an active conformation in the receiver by reorienting the regulatory C-helix to its inward, catalytically functional position. In wild-type EGFR, only the receiver subunit is activated. Oncogenic mutations in the EGFR kinase domain induce an active conformation even in the absence of ligand stimulation, thus both subunits of a ligand-bound mutant receptor are expected to be catalytically active. In the receiver subunit but not the activator, outward displacement of the C-helix is impeded by the asymmetric dimer interaction. Because the mutant receptor favors dimer formation and could promote dimerization even in the absence of ligand, this effect could explain the apparent disconnect in biochemical and cellular potencies of the allosteric inhibitor. (Red Brewer, M. et al. Mechanism for activation of mutated epidermal growth factor receptors in lung cancer. Proc Natl Acad Sci USA 110, E3595-3604, doi:10.1073/pnas.1220050110 (2013); Shan, Y. et al. Oncogenic mutations counteract intrinsic disorder in the EGFR kinase and promote receptor dimerization. Cell 149, 860-870, doi:10.1016/j.cell.2012.02.063 (2012)). To test this notion, an I941R point mutation in the C-lobe of the kinase, which is known to block the asymmetric dimer interaction, was exploited. (Zhang, X., Gureasko, J., Shen, K., Cole, P. A. & Kuriyan, J., "An allosteric mechanism for activation of the kinase domain of epidermal growth factor receptor," Cell 125, 1137-1149 (2006); Cho, J. et al., "Cetuximab response of lung cancer-derived EGF receptor mutants is associated with asymmetric dimerization," Cancer Res 73, 6770-6779, doi:10.1158/0008-5472.CAN-13-1145 (2013)). The activity of the L858R/T790M mutant is dimerization-independent, and as expected Ba/F3 cells bearing the L858R/T790M/I941R triple mutant EGFR proliferated in the absence of IL-3. In support of our hypothesis, the dimerization-defective mutant was dramatically more sensitive to the allosteric inhibitor.

One therapeutic antibody, cetuximab, targets the extracellular portion of the EGF receptor, blocking ligand binding and preventing dimer formation. (Goldstein, N. I., Prewett, M., Zuklys, K., Rockwell, P. & Mendelsohn, J., "Biological efficacy of a chimeric antibody to the epidermal growth factor receptor in a human tumor xenograft model," Clin Cancer Res 1, 1311-1318 (1995); Li, S. et al., "Structural basis for inhibition of the epidermal growth factor receptor by cetuximab," Cancer Cell 7, 301-311, doi: 10.1016/j.ccr.2005.03.003 (2005)) The antibody is not effective clinically in EGFR-mutant NSCLC, and in cell-based studies cetuximab alone does not inhibit L858R/T790M or Del/T790M mutant EGFR, because their activity is dimerization independent. (Cho, J. et al. Cancer Res 73, 6770-6779, doi:10.1158/0008-5472.CAN-13-1145 (2013)).

Table 3 shows the inhibition data of an EGFR Parental Ba/F3 cell line, EGFR L858R/T790M Ba/F3 cell line, EGFR L858R/T790M Ba/F3 cell line, EGFR Del/T790M, and Del/T790M Ba/F3 cell line treated with compounds of the present disclosure or in combination with Cetuximab. A indicates an $IC_{50}$ of <0.5 µM; B indicates an $IC_{50}$ between about 0.5 µM to about 1 µM; C indicates an $IC_{50}$ between about 1 µM to about 10 µM; and D indicates an $IC_{50}$>10 µM.

TABLE 3

| Compound Number | Parental | L858R/T790M | L858R/T790M Cetuximab | Del/T790M | Del/T790M Cetuximab |
|---|---|---|---|---|---|
| I-65 | D | D | A | D | D |
| I-66 | D | C | A | D | C |
| I-68 | C | C | A | C | C |
| I-69 | C | C | A | C | C |
| I-70 | D | D | A | D | D |
| I-75 | D | D | A | C | C |
| I-79 | D | D | A | D | D |
| I-81 | C | C | A | C | C |
| I-112 | D | C | A | D | D |
| I-113 | D | D | A | D | D |
| I-115 | C | C | A | C | C |
| I-119 | D | D | A | D | D |
| I-120 | C | C | A | C | C |
| I-121 | C | C | A | C | C |
| I-122 | C | C | A | D | D |
| I-126 | — | B | A | — | — |

Mouse Efficacy Studies

EGFR-TL (T790M/L858R) and EGFR-TD (exon 19 deletion-T790M) mice were generated as previously described (Li, D., Shimamura, T., Ji, H., Chen, L., Haringsma, H. J., McNamara, K., Liang, M. C., Perera, S. A., Zaghlul, S., Borgman, C. L., et al., "Bronchial and peripheral murine lung carcinomas induced by T790M-L858R mutant EGFR respond to HKI-272 and rapamycin combination therapy," Cancer Cell 12, (2007), 81-93; Zhou et al., Nature 2009). The EGFR-L858R;T790M;C797S ("TLCS") mutant mouse cohort was established briefly as follows: The full-length HuTLCS cDNA was generated by site-directed mutagenesis using the Quickchange site directed mutagenesis kit (Agilent Technologies) and further verified by DNA sequencing. Sequence-verified targeting vectors were co-electroporated with an FLPe recombinase plasmid into v6.5 C57BL/6J (female)×129/sv (male) embryonic stem cells (Open Biosystems) as described elsewhere (Beard, C., Hochedlinger, K., Plath, K., Wutz, A., and Jaenisch, R., "Efficient method to generate single-copy transgenic mice by site-specific integration in embryonic stem cells," Genesis 44, (2006), 23-28). Resulting hygromycin-resistant embryonic stem clones were evaluated for transgene integration via PCR. Then, transgene-positive embryonic stem clones were injected into C57BL/6 blastocysts, and the resulting chimeras were mated with BALB/c WT mice to determine germline transmission of the TLCS transgene. Progeny of TL, TD and TLCS mice were genotyped by PCR of tail DNA.

The TL and TD mice were fed a doxycycline diet at 6 weeks of age to induce EGFR TL or TD expression, respectively. The TLCS mice were intranasally instilled with Ad-Cre (University of Iowa viral vector core) at 6 weeks of age to excise the loxP sites, activating EGFR TLCS expression.

All care of experimental animals was in accordance with Harvard Medical School/Dana-Farber Cancer Institute (DFCI) institutional animal care and use committee (IACUC) guidelines. All mice were housed in a pathogen-free environment at a DFCI animal facility and handled in strict accordance with Good Animal Practice as defined by the Office of Laboratory Animal Welfare.

In Vivo Treatment and MRI Tumor Volume Quantification

The TL, TD and TLCS mice were monitored by MRI to quantify lung tumor burden before being assigned to various treatment study cohorts. All the treatment mice had equal amount initial tumor burden. A compound of the present disclosure was dissolved in 10% NMP (10% 1-methyl-2-pyrrolidinone: 90% PEG-300), and was dosed at 60 mg/kg daily by oral gavage. Cetuximab was administered at 1 mg/mouse every three days by intraperitoneal in injection. MRI evaluation was repeated every 2 weeks during the treatment. The animals were imaged with a rapid acquisition with relaxation enhancement sequence (TR=2000 ms, TE effect=25 ms) in the coronal and axial planes with a 1-mm slice thickness gating with respiratory rates. The detailed procedure for MRI scanning has been previously described (Li et al., 2007). The tumor burden volumes were quantified using 3-dimensional Slicer software.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I'):

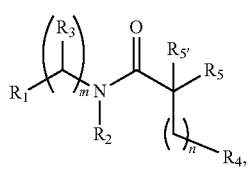

(I')

or pharmaceutically acceptable salts, hydrates, solvates, stereoisomers, or tautomers thereof, wherein:
$R_1$ is $(C_6-C_{10})$ aryl, or heteroaryl comprising one or two 5- to 7-membered rings and 1-4 heteroatoms selected from N, O, and S, wherein the aryl and heteroaryl are each optionally substituted with one or more $R_{11}$;
each $R_{11}$ is independently selected from $(C_1-C_4)$ haloalkyl, $(C_1-C_4)$ alkoxy, $(C_1-C_4)$ haloalkoxy, halogen, $NO_2$, OH, CN, $C(O)R_{13}$, $C(O)OR_{13}$, $C(O)NR_{13}R_{14}$, $NR_{13}R_{14}$, $(C_3-C_7)$ cycloalkyl, heterocyclyl comprising a 5- to 7-membered ring and 1-3 heteroatoms selected from N, O, and S, $(C_6-C_{10})$ aryl, and heteroaryl comprising one or two 5- to 7-membered rings and 1-4 heteroatoms selected from N, O, and S, wherein the cycloalkyl, heterocyclyl, aryl, and heteroaryl are each optionally substituted with one or more $R_{12}$;
each $R_{12}$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, OH, CN, $(C_3-C_7)$ cycloalkyl, heterocyclyl comprising a 5- to 7-membered ring and 1-3 heteroatoms selected from N, O, and S, $(C_6-C_{10})$ aryl, and heteroaryl comprising one or two 5- to 7-membered rings and 1-4 heteroatoms selected from N, O, and S, wherein the aryl and heteroaryl are each optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, halogen, $NH_2$, $NH(C_1-C_4)$ alkyl, $N((C_1-C_4)$ alkyl$)_2$, $(C_3-C_7)$ cycloalkyl, and heterocyclyl comprising a 5- to 7-membered ring and 1-3 heteroatoms selected from N, O, and S;
each $R_{13}$ is independently selected from H, $(C_1-C_4)$ alkyl, $(C_3-C_7)$ cycloalkyl, and heterocyclyl comprising a 5- to 7-membered ring and 1-3 heteroatoms selected from N, O, and S, wherein the alkyl, cycloalkyl, and heterocyclyl are each optionally substituted with one or more substituents independently selected from $(C_1-C_4)$ alkyl, halogen, OH, $NH_2$, $NH(C_1-C_4)$ alkyl, $N((C_1-C_4)$ alkyl$)_2$, and heterocyclyl comprising a 5- to 7-membered ring and 1-3 heteroatoms selected from N, O, and S;
each $R_{14}$ is independently H or $(C_1-C_3)$ alkyl;
$R_2$ is H or $(C_1-C_3)$ alkyl;
$R_3$ is H or $(C_1-C_3)$ alkyl;
$R_4$ is

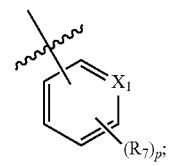

$X_1$ is N or $CR_6$;
$R_6$ is H, $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, $(CH_2)_qOH$, $S(O)_rR_{23}$, or CN;
each $R_7$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, $(CH_2)_qOH$, $S(O)_rR_{23}$, and CN;
$R_5$ is $NR_{15}R_{16}$;
$R_{5'}$ is H or $(C_1-C_4)$ alkyl;
$R_{15}$ is H or $(C_1-C_3)$ alkyl;
$R_{16}$ is $(C_6-C_{10})$ aryl, or heteroaryl comprising a 5- to 7-membered ring and 1-3 heteroatoms selected from N, O, and S, wherein the aryl and heteroaryl are each optionally substituted with one or more $R_{18}$; or
$R_{15}$ and $R_{16}$ together with the nitrogen atom to which they are attached form a 5- or 6-membered heterocyclyl optionally comprising 1 or 2 additional heteroatoms selected from N, O, and S and optionally substituted with one or more oxo groups, wherein the heterocyclyl is fused with a phenyl ring which is optionally substituted with one or more $R_{19}$;

each $R_{18}$ is independently selected from $(C_1-C_4)$ alkyl, $(C_1-C_4)$ alkoxy, $(C_1-C_4)$ haloalkyl, $(C_1-C_4)$ haloalkoxy, halogen, $C(O)O(C_1-C_4)$ alkyl, $NO_2$, $C(O)NH(C_1-C_4)$ alkyl, $NH_2$, $NH(C_1-C_4)$ alkyl, and $N((C_1-C_4)$ alkyl$)_2$, wherein the alkyl is optionally substituted with one or more substituents independently selected from halogen, OH, $NH_2$, $NH(C_1-C_4)$ alkyl, and $N((C_1-C_4)$ alkyl$)_2$;

each $R_{19}$ is independently selected from halogen, $O(CH_2)_{1-3}$—OH, $(C_3-C_7)$ cycloalkyl, $(C_4-C_7)$ cycloalkenyl, $(C_6-C_{10})$ aryl, NH—$(C_6-C_{10})$ aryl, and heteroaryl comprising one or two 5- to 7-membered ring and 1-4 heteroatoms selected from N, O, and S, wherein the aryl and heteroaryl are each optionally substituted with one or more $R_{20}$; or two $R_{19}$ together with the atoms to which they are attached form a $(C_6-C_{10})$ aryl optionally substituted with one or more $R_{20}$;

each $R_{20}$ is independently selected from $(C_1-C_4)$ alkyl, $(C_1-C_4)$ alkoxy, $(C_1-C_4)$ haloalkyl, $(C_1-C_4)$ haloalkoxy, halogen, C(O)OH, $C(O)O(C_1-C_4)$ alkyl, $C(O)NR_{21}R_{22}$, $O(CH_2)_{1-3}$—OH, $NH_2$, OH, CN, $O(CH_2)_{0-3}$—$(C_6-C_{10})$ aryl, and $(CH_2)_{0-3}$-heterocyclyl which comprises a 5- to 7-membered ring and 1-3 heteroatoms selected from N, O, and S, wherein the heterocyclyl is optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, halogen, $NH_2$, $NH(C_1-C_4)$ alkyl, $N((C_1-C_4)$ alkyl$)_2$, $S(O)_2NH_2$, $(CH_2)_sOH$, $C(O)(CH_2)_sOH$, and $C(O)O(C_1-C_4)$ alkyl);

$R_{21}$ is H or $(C_1-C_3)$ alkyl;

$R_{22}$ is H or $(C_1-C_4)$ alkyl optionally substituted with one or more substituents independently selected from $NH_2$, $NH(C_1-C_4)$ alkyl, $N((C_1-C_4)alkyl)_2$, and heterocyclyl comprising a 5- to 7-membered ring and 1-3 heteroatoms selected from N, O, and S; or $R_{21}$ and $R_{22}$ together with the nitrogen atom to which they are attached form a 5- or 6-membered heterocyclyl optionally containing 1-2 additional heteroatoms selected from N, O, and S;

$R_{23}$ is H or $NH_2$;

m and n are each independently 0 or 1;

each r and each q are independently 0, 1, or 2;

each s is 1 or 2; and p is 0, 2, 3 or 4;

provided that when m is 0, n is 0, p is 0, $R_{15}$ and $R_{16}$ together with the nitrogen atom to which they are attached form an unsubstituted isoindolinone, and $R_6$ is H, then $R_1$ is not

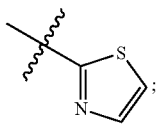 [SMILES: *c1nccs1]

and provided that $R_4$ is not 4-fluoro-2-hydroxyphenyl.

2. The compound of claim 1, wherein m is 0.

3. The compound of claim 1, wherein $R_5$ is

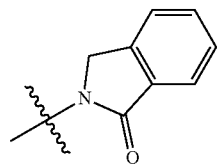 [SMILES: *N1Cc2ccccc2C1=O]

optionally substituted with one to three $R_{19}$.

4. The compound of claim 1, wherein one $R_{19}$ is phenyl or heteroaryl comprising one or two 5- to 7-membered ring and 1-4 heteroatoms selected from N, O, and S, wherein the phenyl and heteroaryl are each optionally substituted with one or more $R_{20}$.

5. The compound of claim 1, wherein $R_{20}$ is halogen, $O(CH_2)_{1-3}$—OH, or optionally substituted $(CH_2)_{0-3}$-heterocyclyl which comprises a 5- to 7-membered ring and 1-3 heteroatoms selected from N, O, and S.

6. The compound of claim 1, wherein $R_{20}$ is piperazinyl or piperazinyl substituted with one or more substituents independently selected from $(C_1-C_4)$ alkyl, $S(O)_2NH_2$, $(CH_2)_sOH$, and $C(O)(CH_2)_sOH$.

7. The compound of claim 1, wherein $R_1$ is

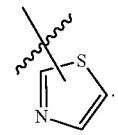

8. The compound of claim 1, wherein $R_4$ is phenyl substituted with two or more $R_7$.

9. The compound of claim 1, wherein at least one $R_7$ is halogen or at least one $R_7$ is halogen and at least one $R_7$ is OH.

10. The compound of claim 1, wherein n is 0.

11. The compound of claim 1, wherein n is 1.

12. A compound of the following structure

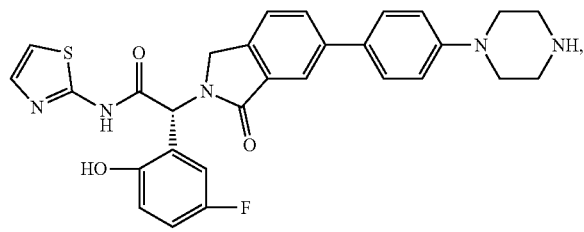 [SMILES: O=C(Nc1nccs1)[C@@H](c1cc(F)ccc1O)N1Cc2ccc(-c3ccc(N4CCNCC4)cc3)cc2C1=O]

or pharmaceutically acceptable salts, hydrates, solvates, stereoisomers, or tautomers thereof.

13. A pharmaceutical composition comprising a compound of claim 12, and a pharmaceutically acceptable carrier.

14. A pharmaceutical composition comprising a compound of claim 1, and a pharmaceutically acceptable carrier.

15. The compound of claim 1, of Formula (I):

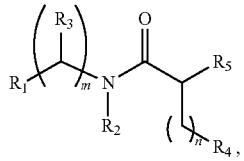

(I)

or pharmaceutically acceptable salts, hydrates, solvates, stereoisomers, or tautomers thereof, wherein $R_6$ is H, $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, OH, or CN; and each $R_7$ is independently selected from $(C_1-C_4)$ alkyl, $(C_1-C_4)$ haloalkyl, $(C_1-C_4)$ alkoxy, $(C_1-C_4)$ haloalkoxy, halogen, $NO_2$, $NH_2$, OH, and CN.

16. The compound of claim 1, wherein $R_5$ is

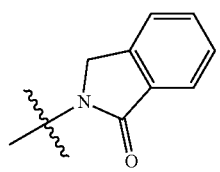

17. The compound of claim 1, wherein $R_1$ is

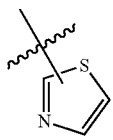

substituted with one or more substituents independently selected from $(C_1-C_4)$ haloalkyl, halogen, $C(O)R_{13}$, $C(O)OR_{13}$, $C(O)NR_{13}R_{14}$, and heteroaryl.

18. The compound of claim 1, wherein $R_4$ is unsubstituted phenyl.

19. The compound of claim 1, wherein p is 0 or 2.

20. The compound of claim 12, of the following structure

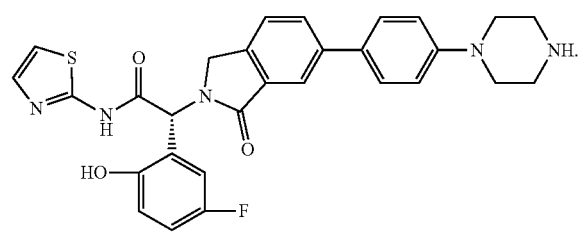 [SMILES: O=C(Nc1nccs1)[C@@H](c1cc(F)ccc1O)N1Cc2ccc(-c3ccc(N4CCNCC4)cc3)cc2C1=O]

21. A compound selected from:

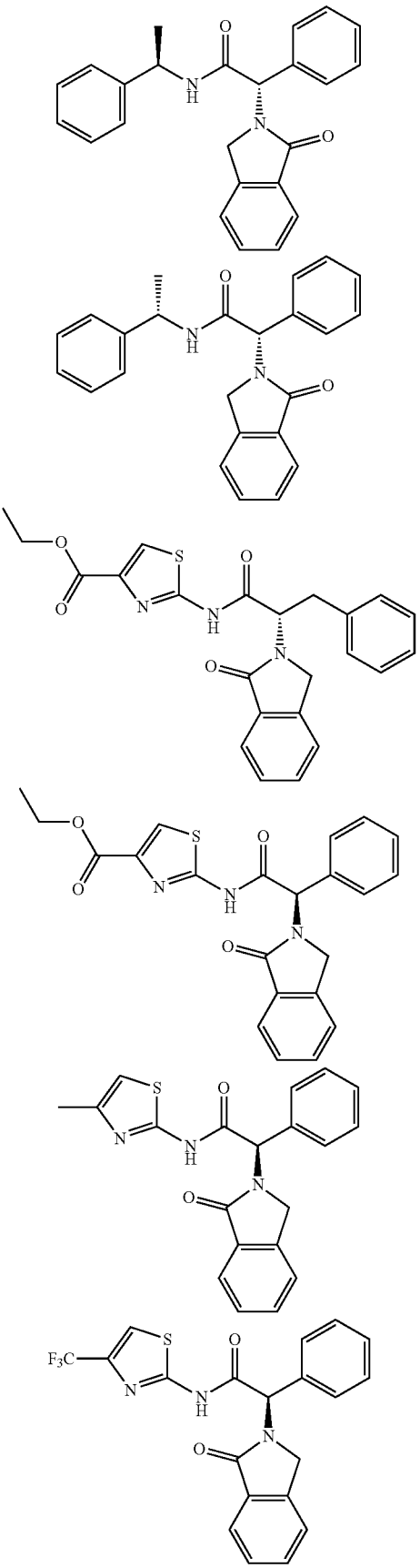

201
-continued
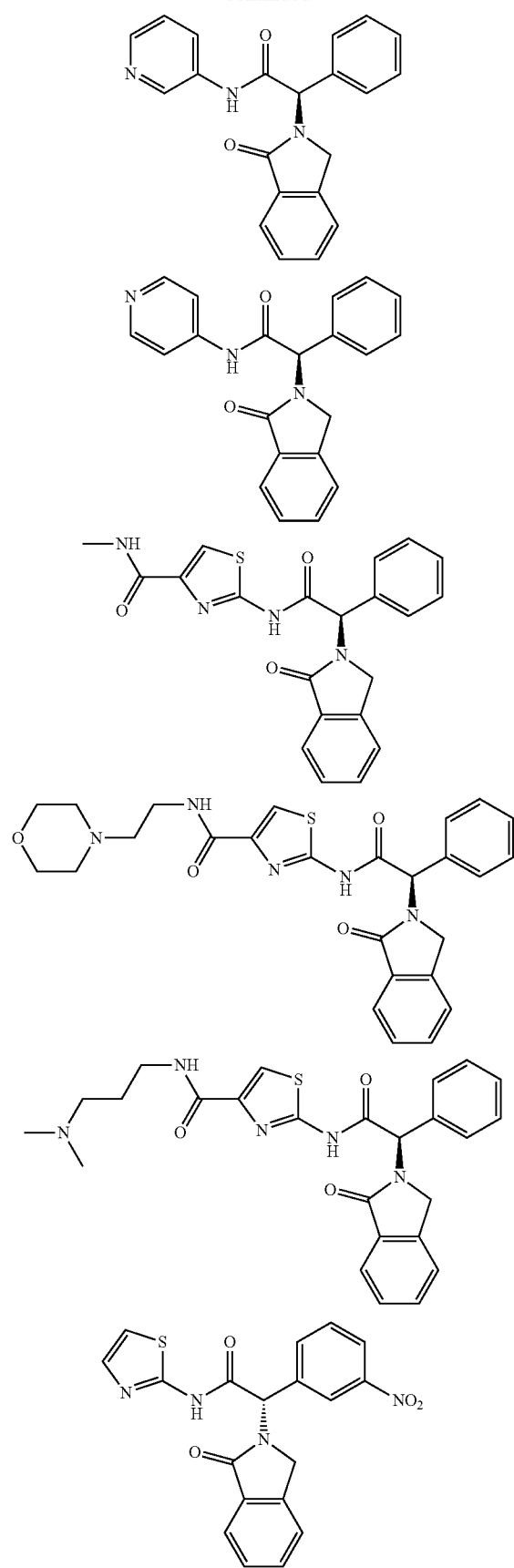
202
-continued
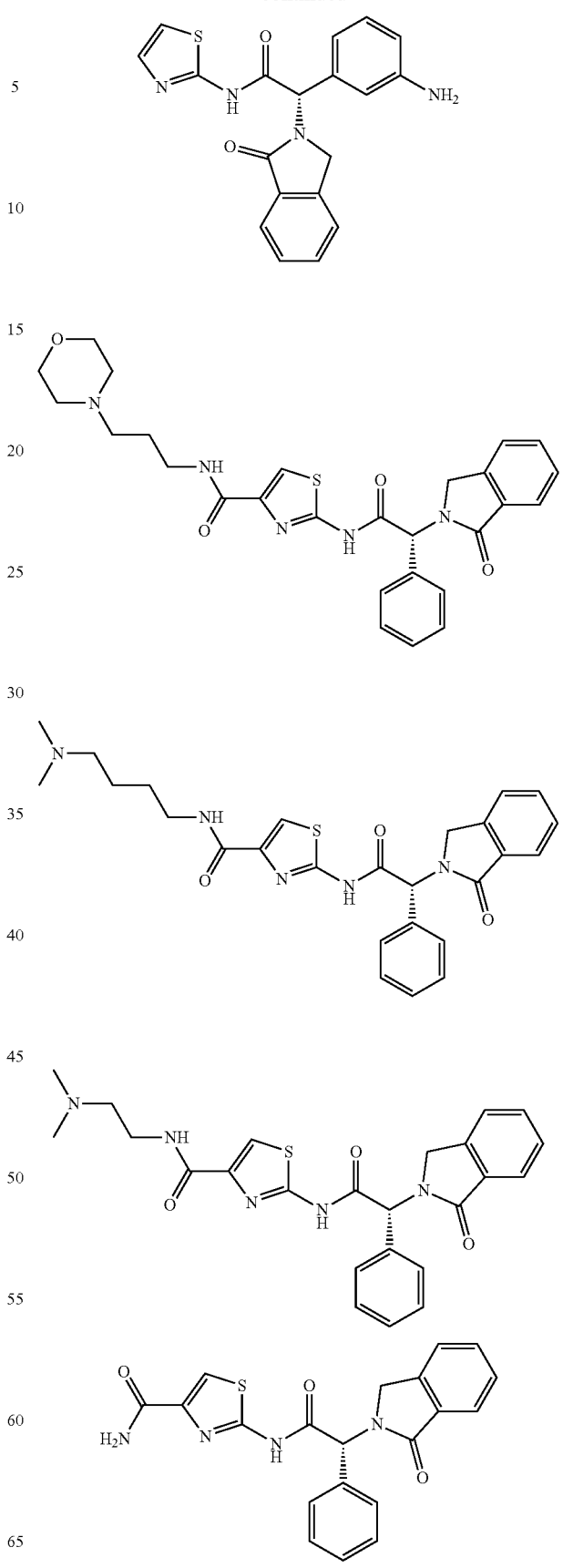

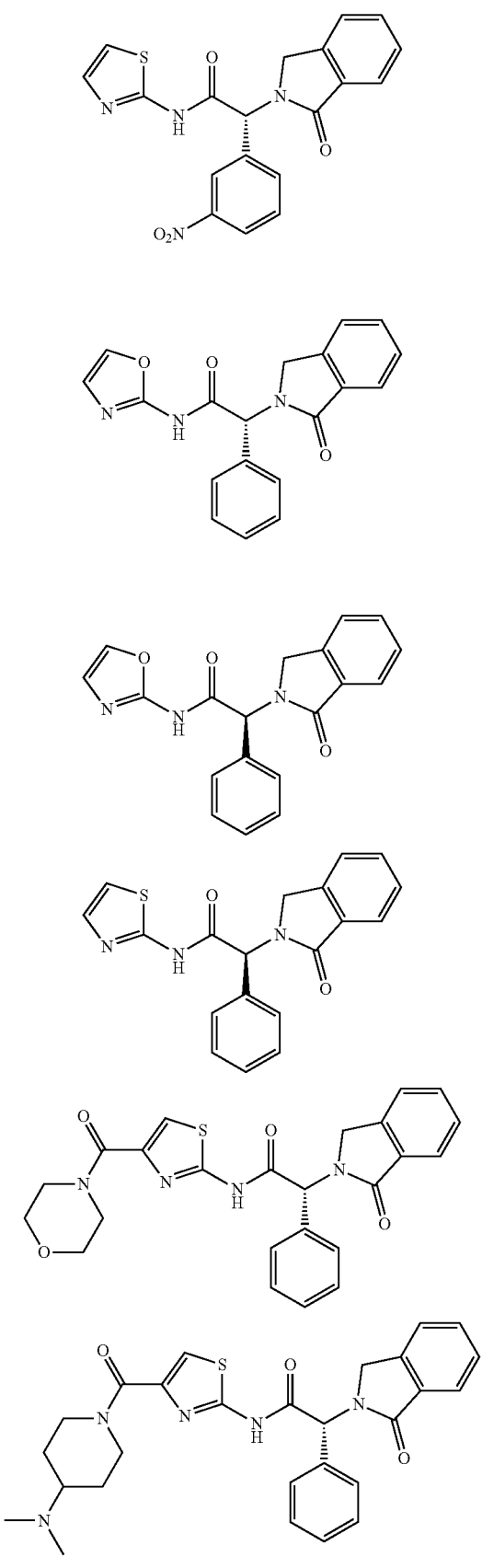

205
-continued
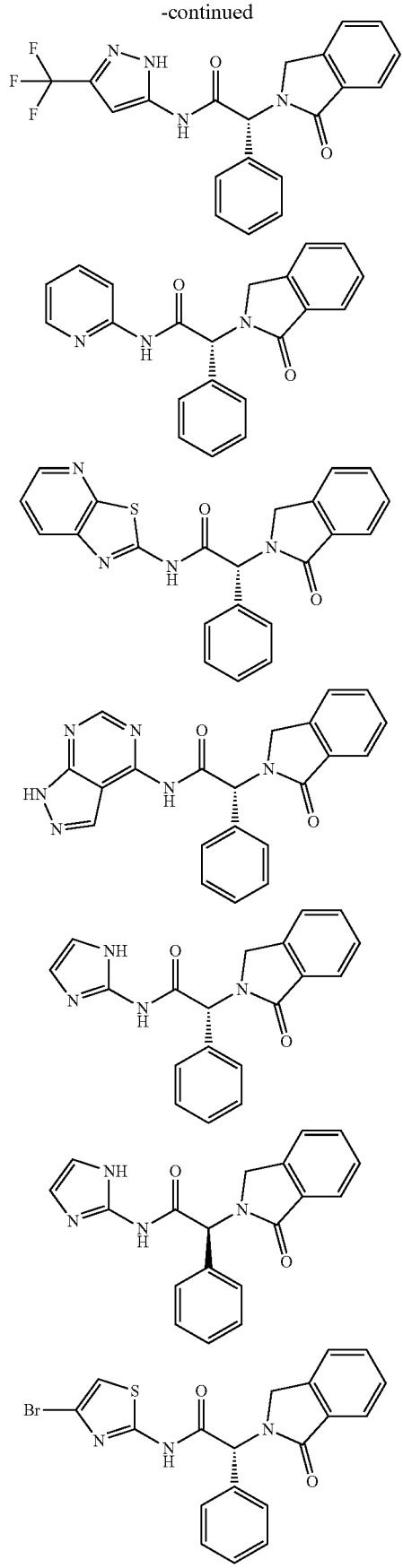
206
-continued
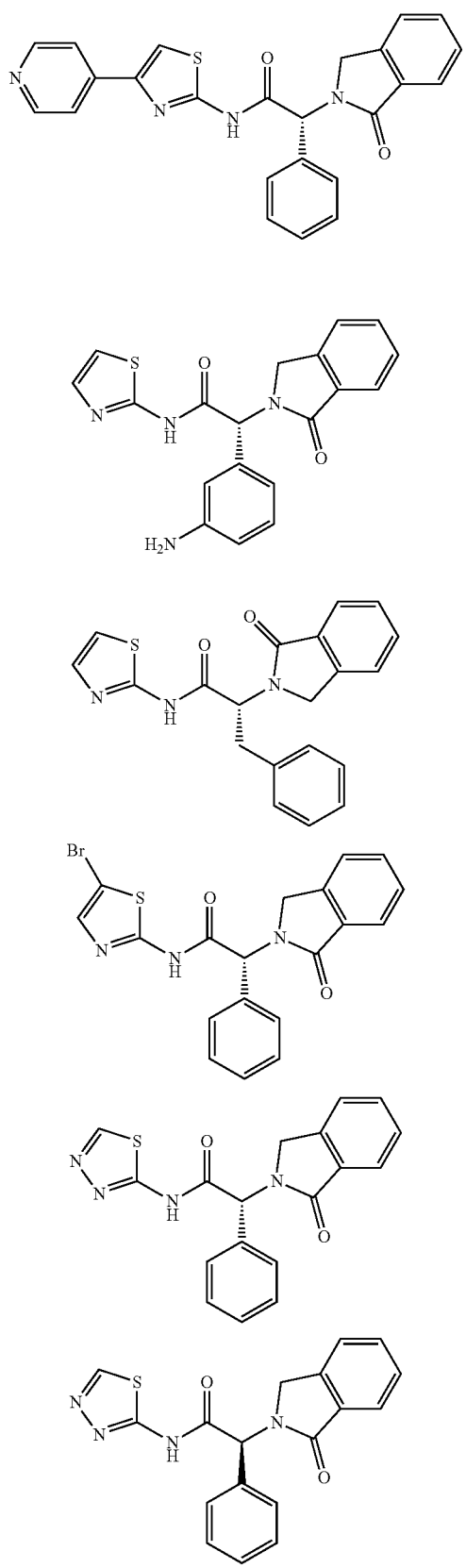

207
-continued
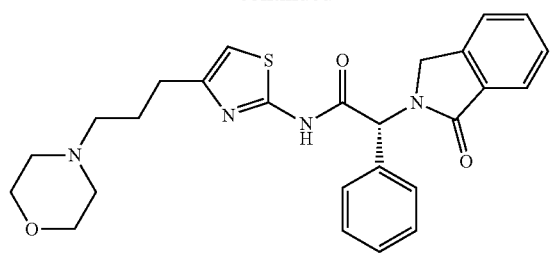
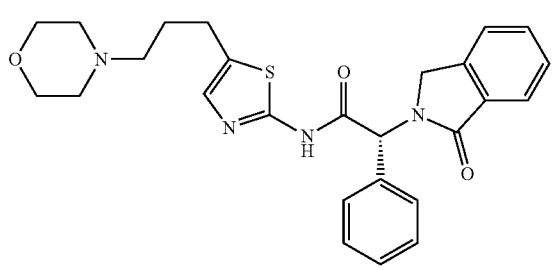
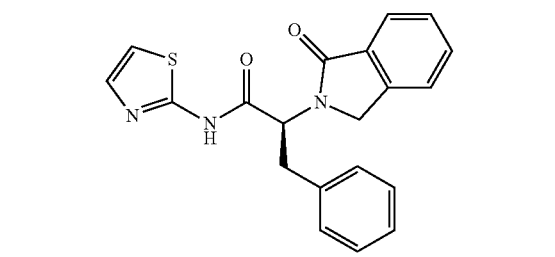
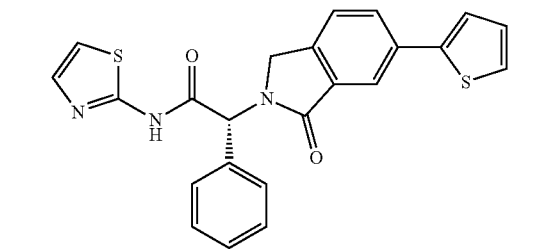
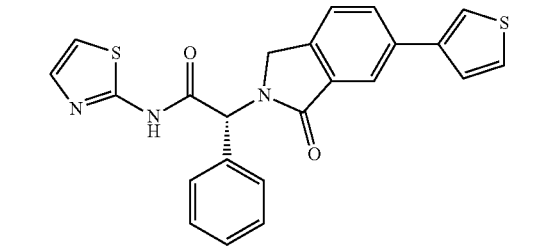
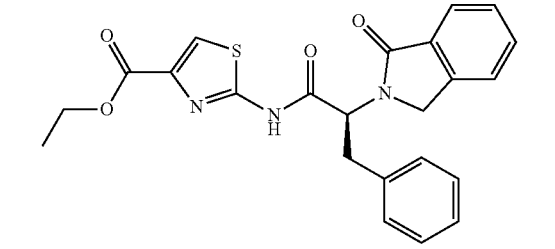
208
-continued
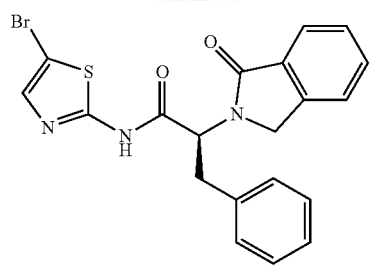
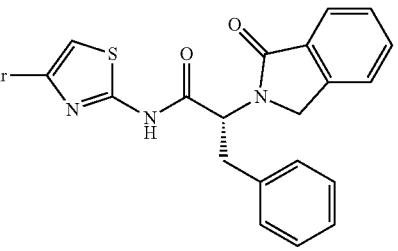
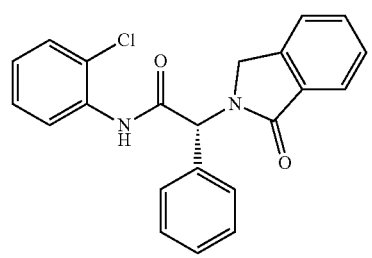
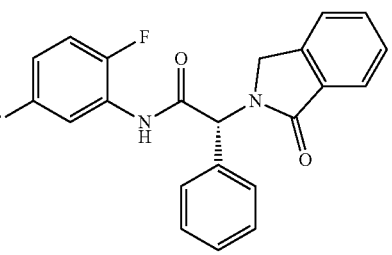
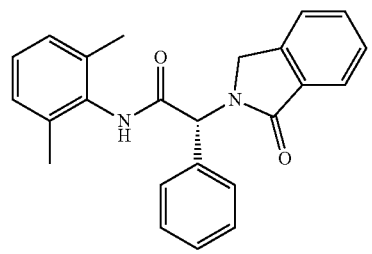

209
-continued
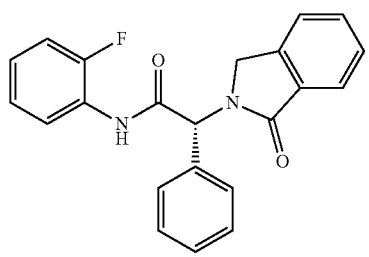
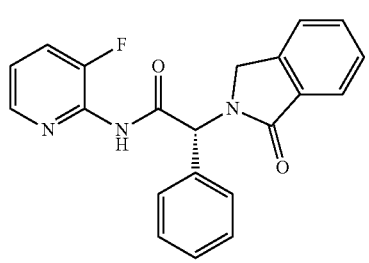
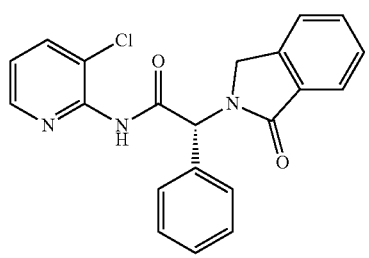
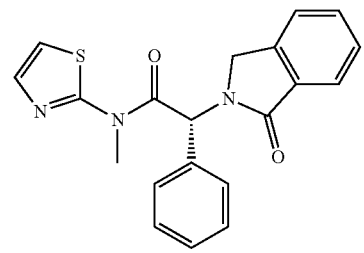
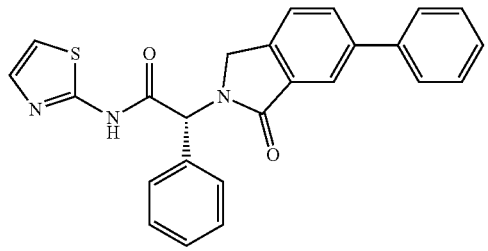
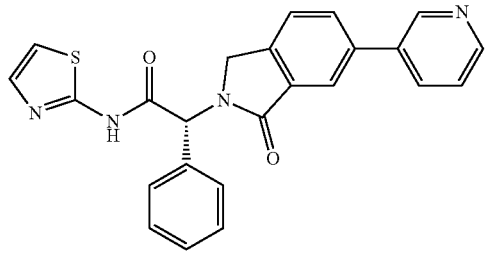
210
-continued
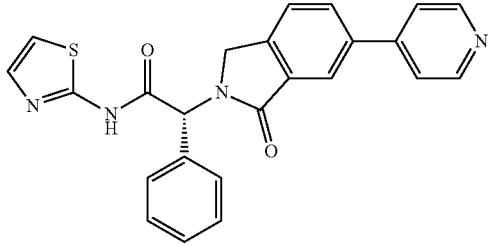
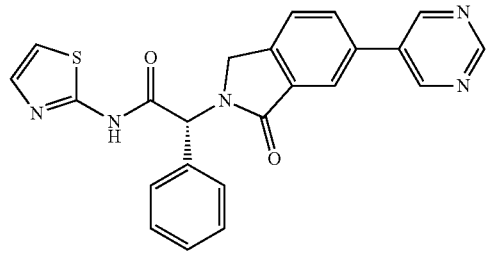
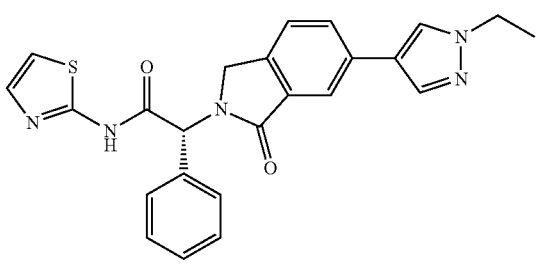
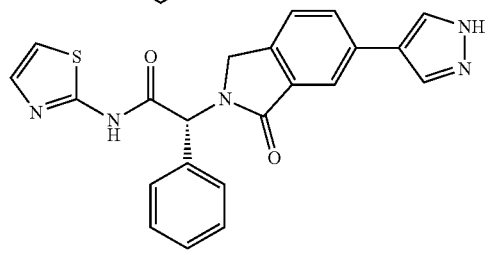
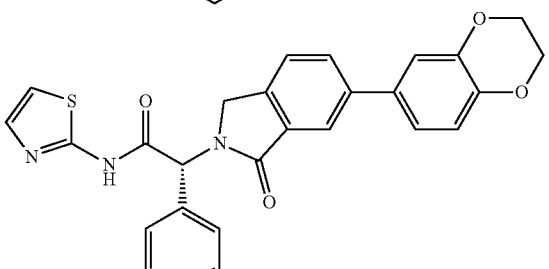
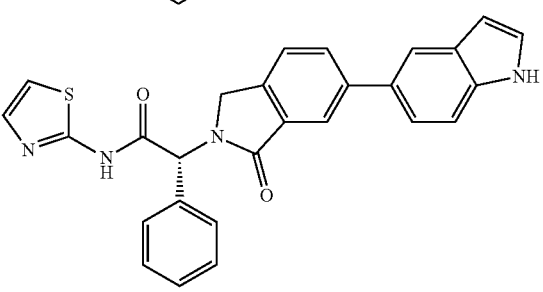

211
-continued
212
-continued
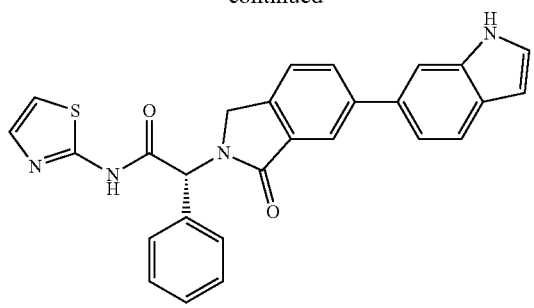
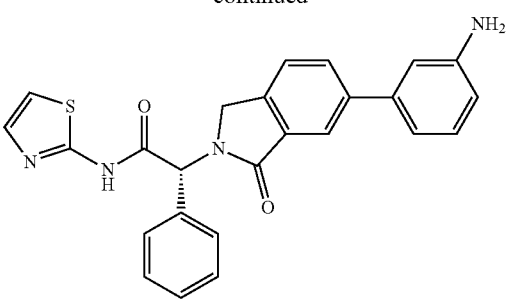

213
-continued
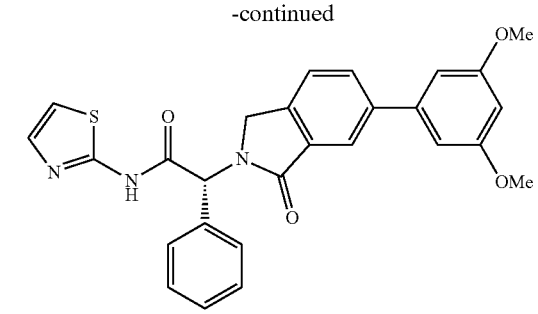
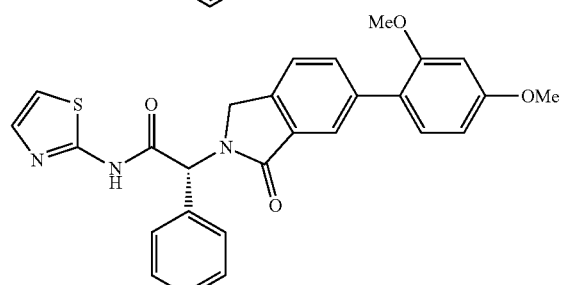
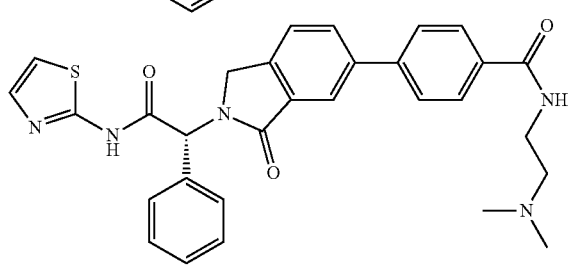
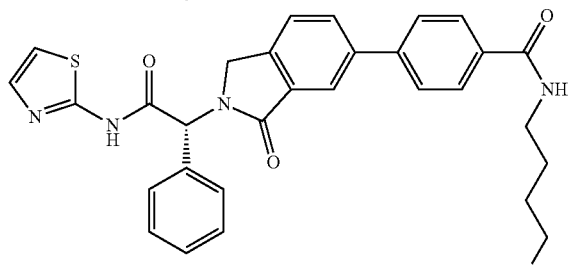
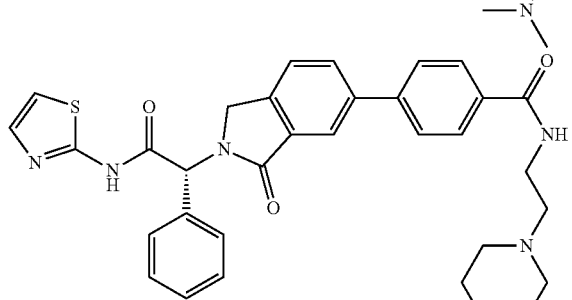
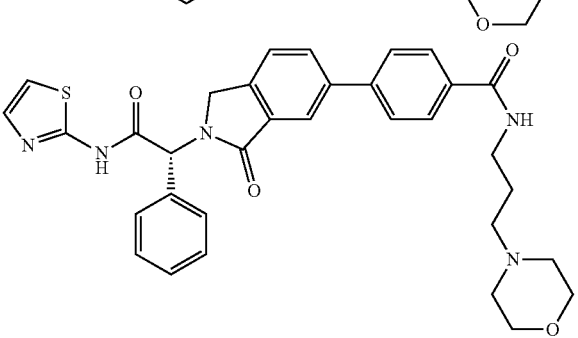
214
-continued
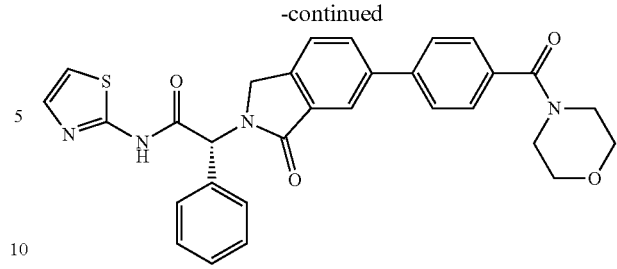
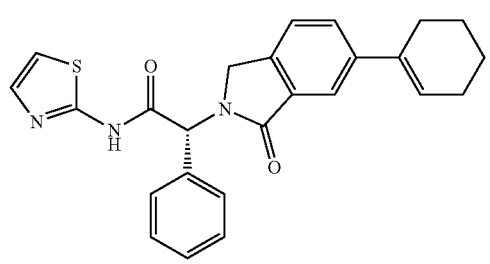
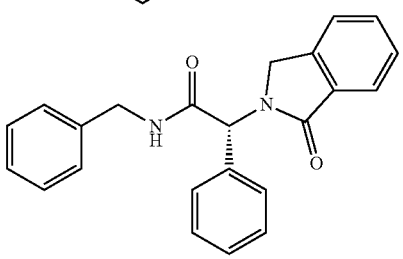
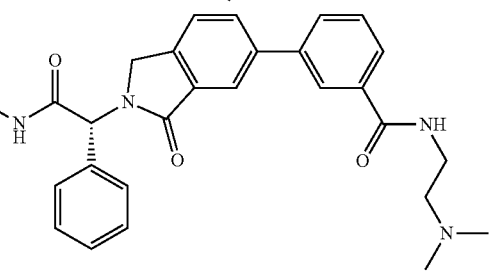
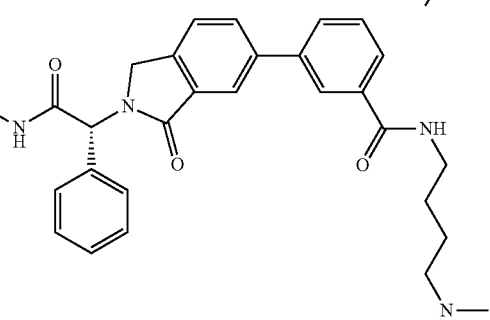
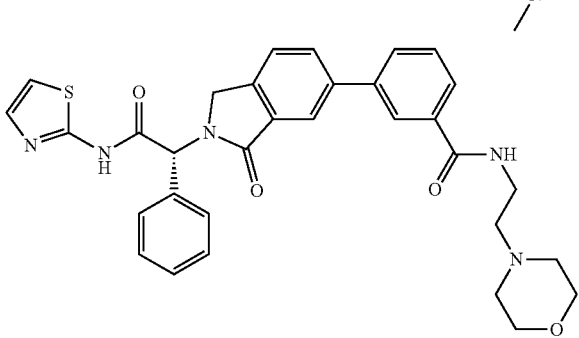

215
-continued
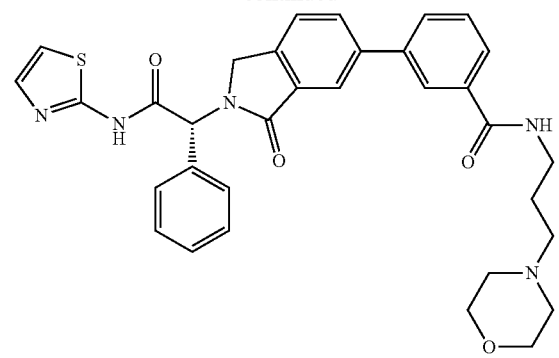
216
-continued
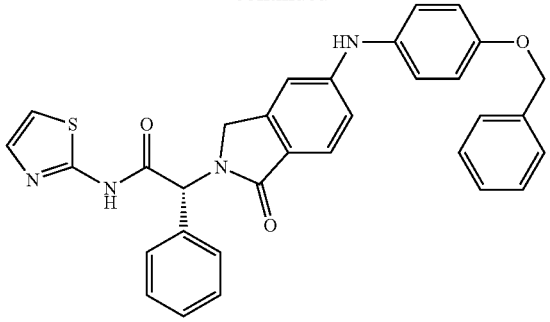
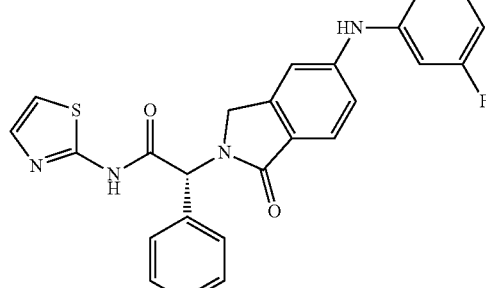
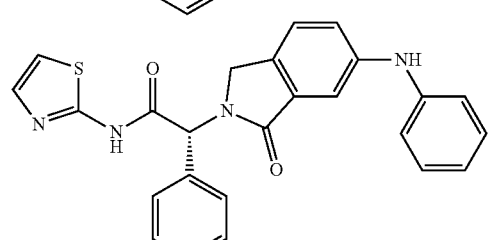
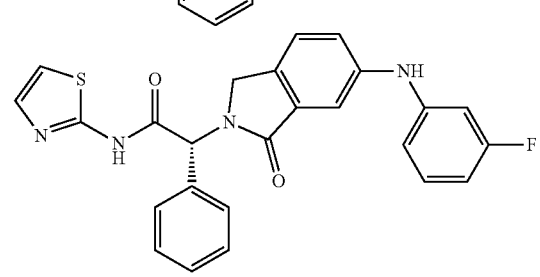
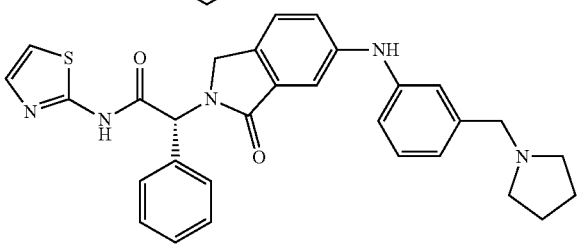
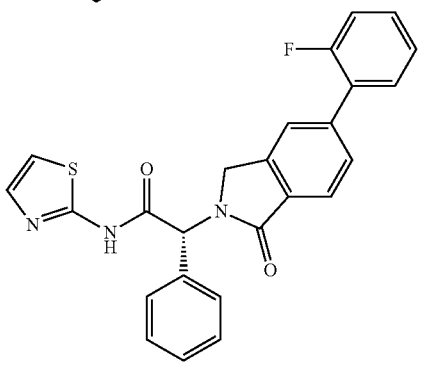

217
-continued
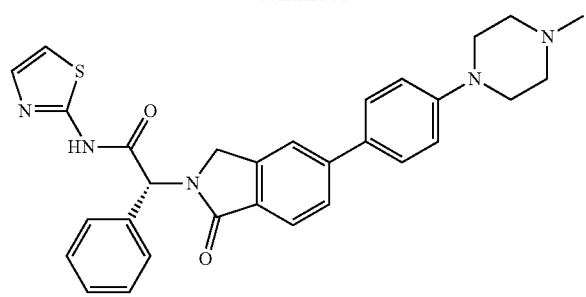
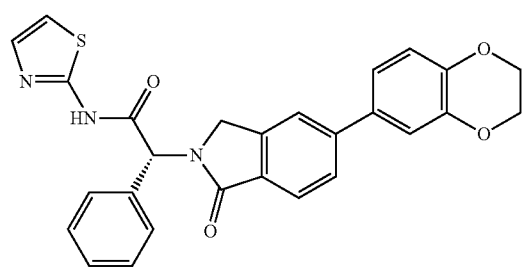
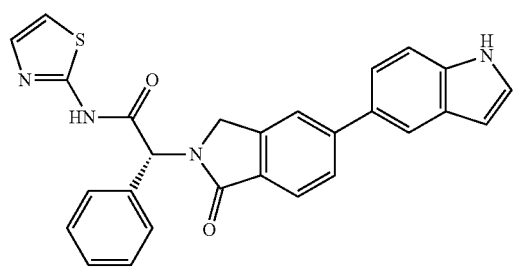
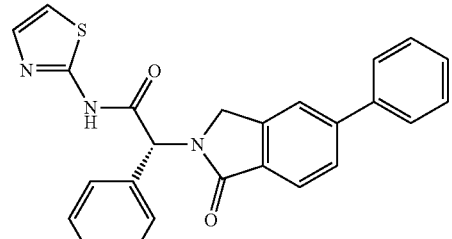
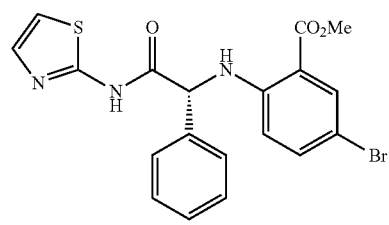
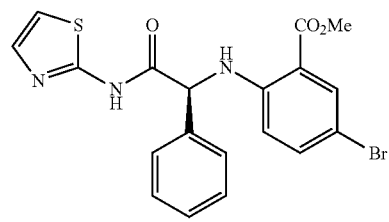
218
-continued
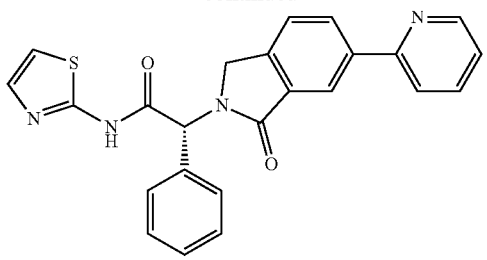
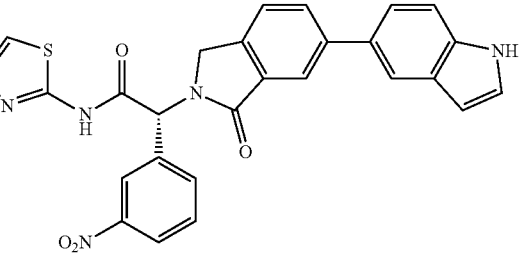
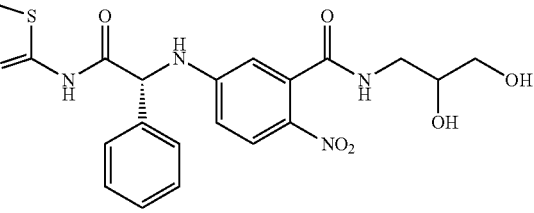
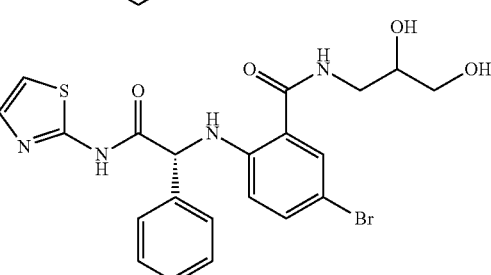
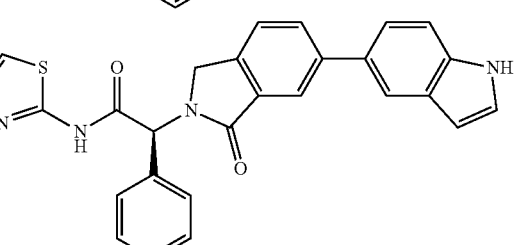
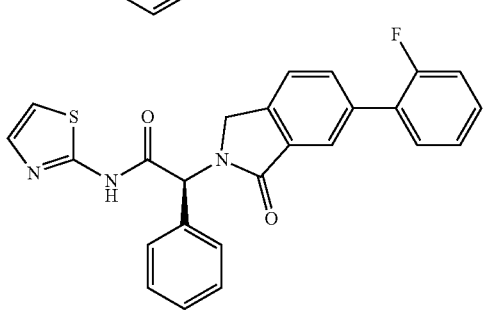

-continued
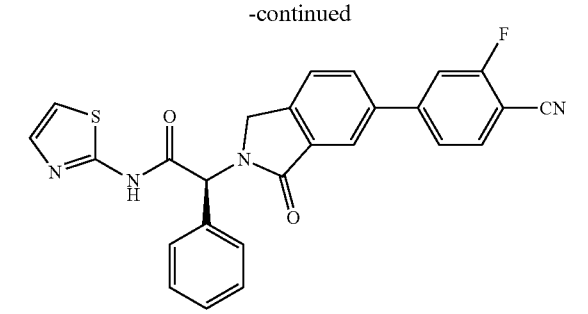
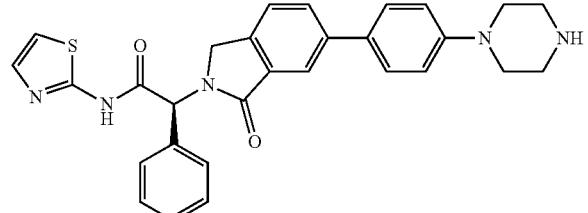
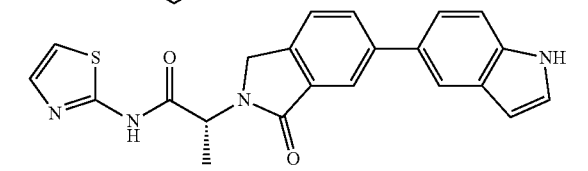
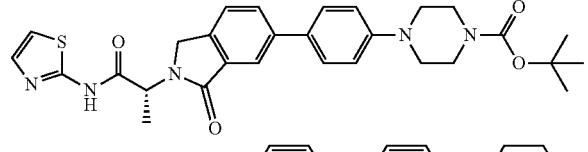
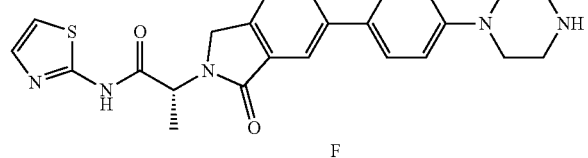
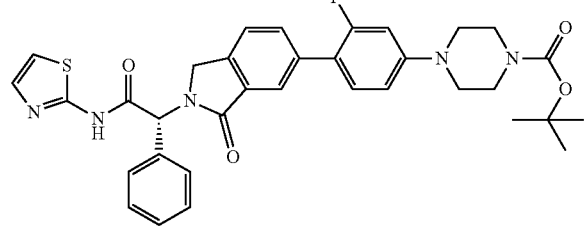
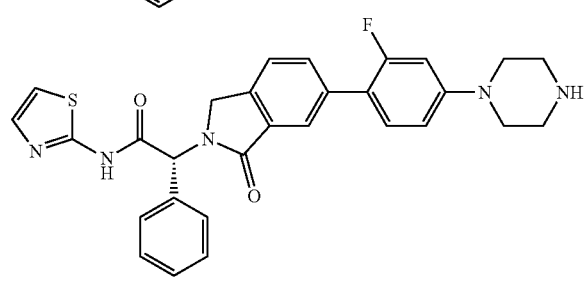
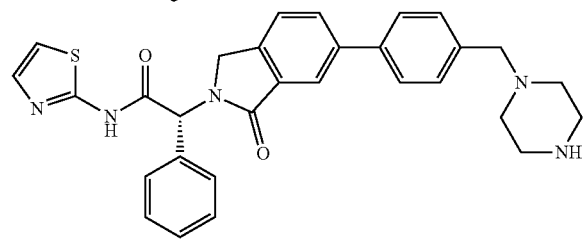
-continued
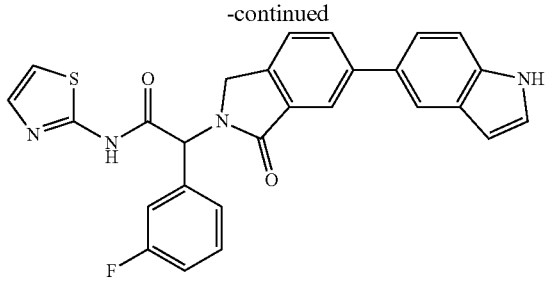
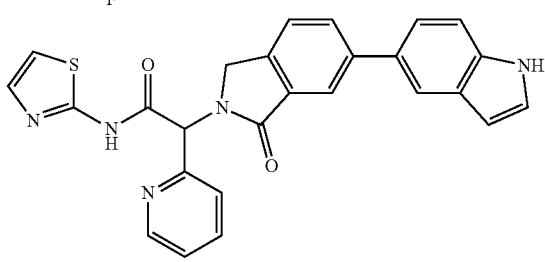
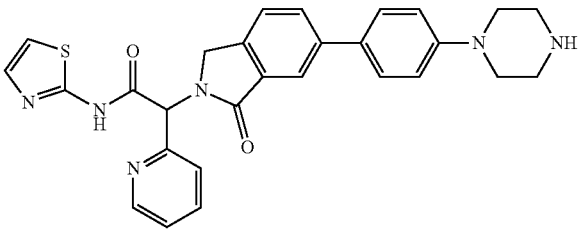
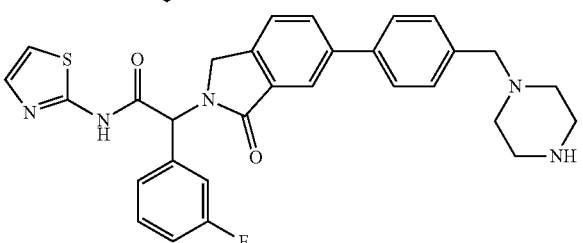
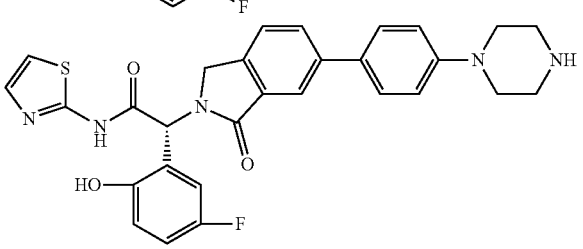
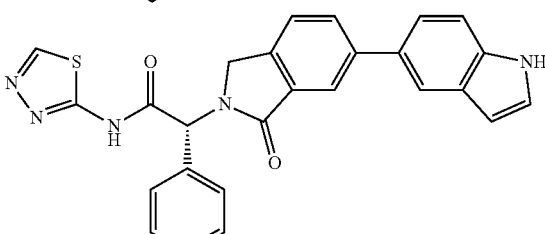
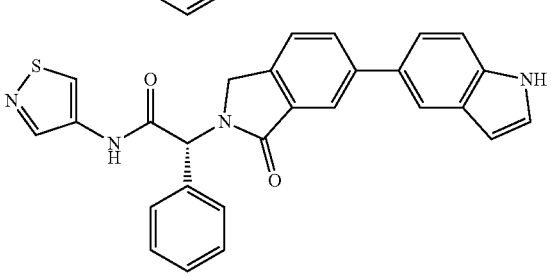

221
-continued
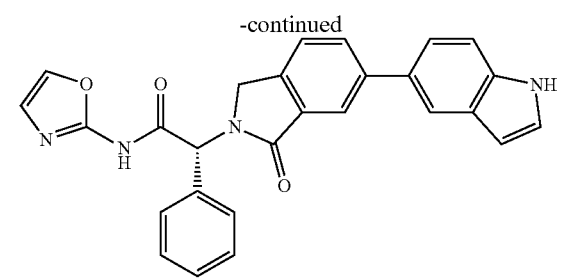
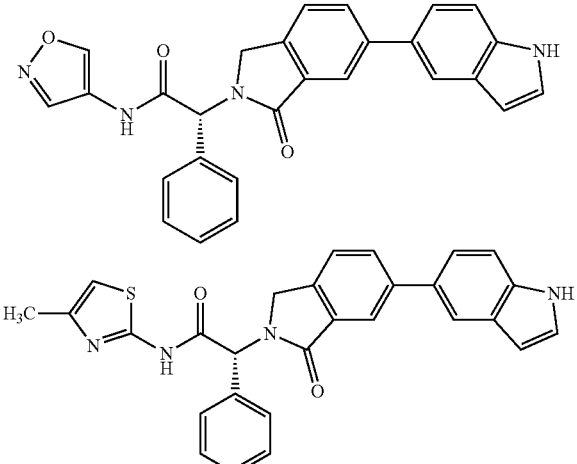
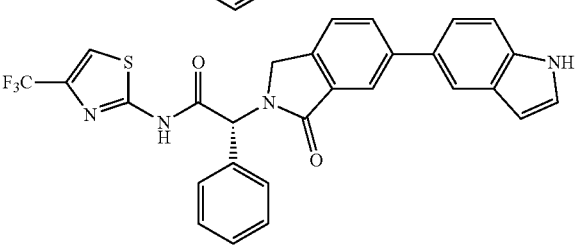
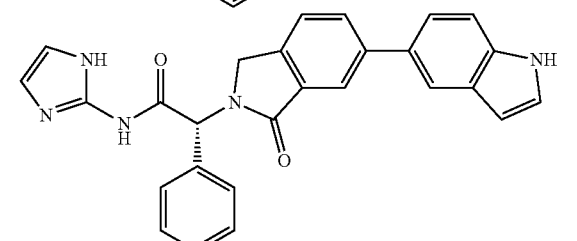
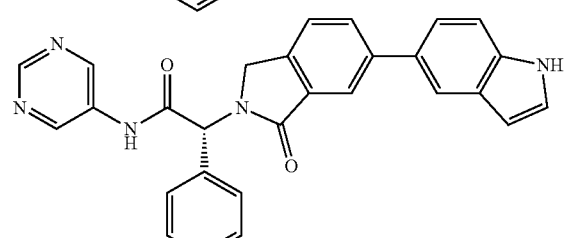
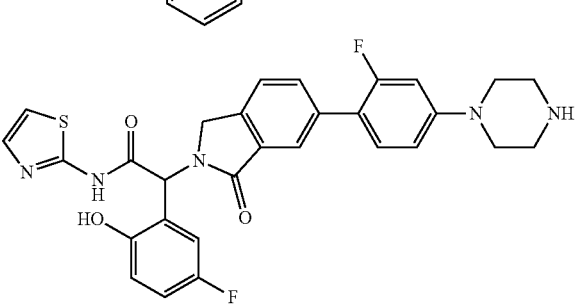
222
-continued
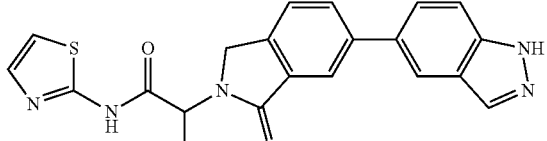
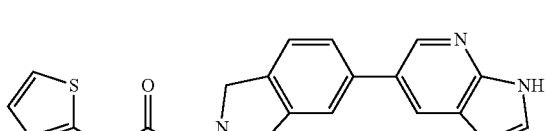
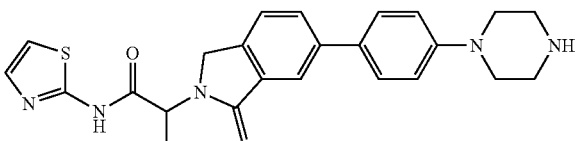
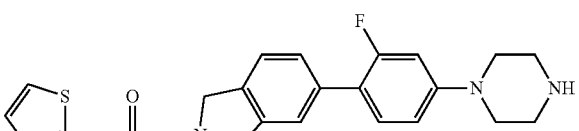
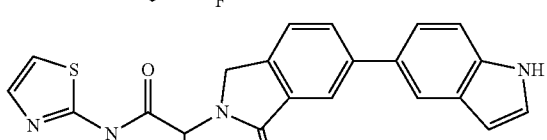
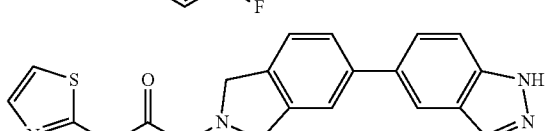

223
-continued
224
-continued
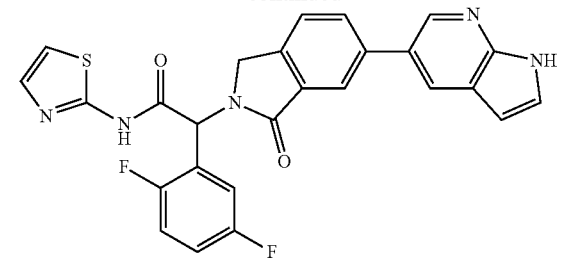
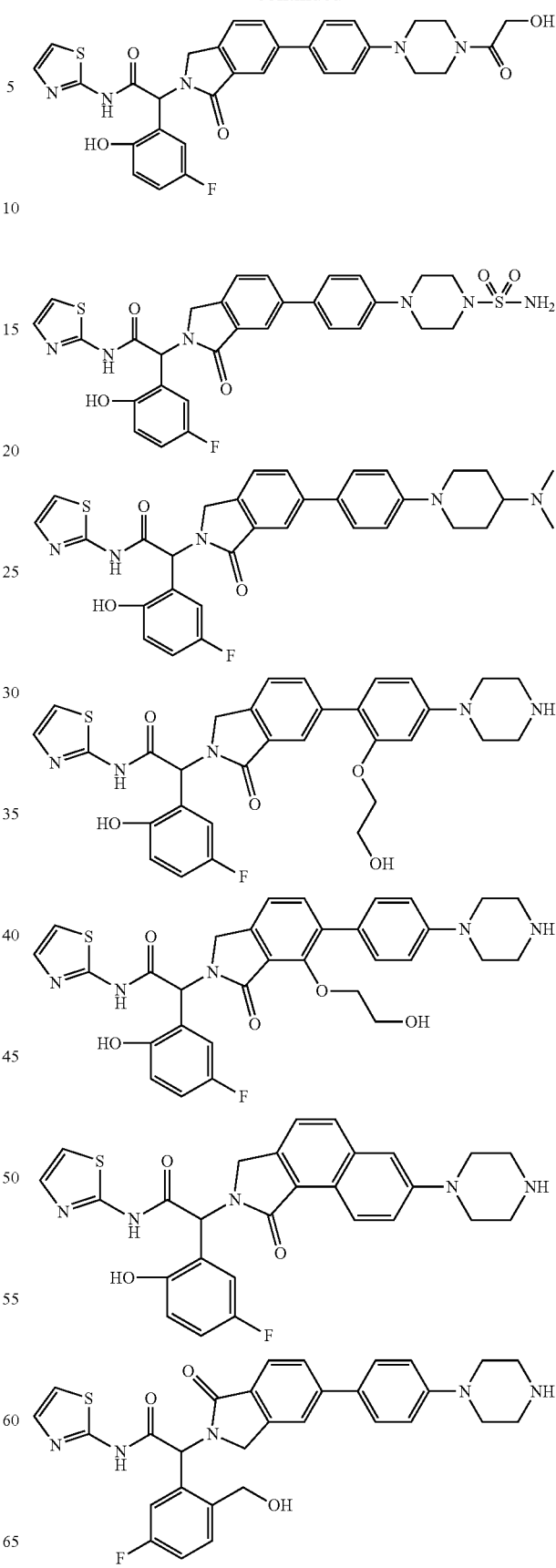

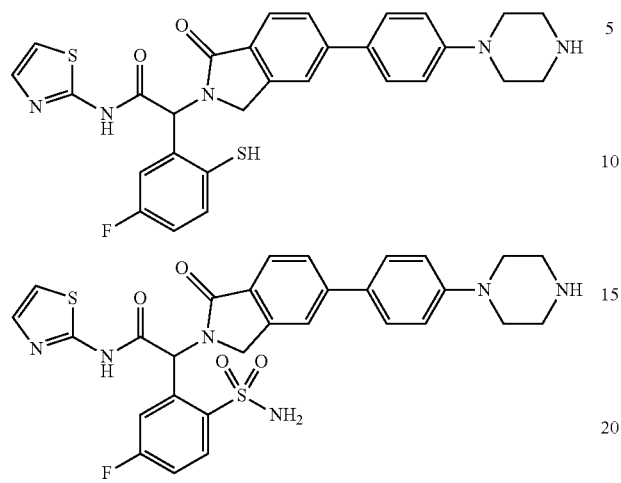
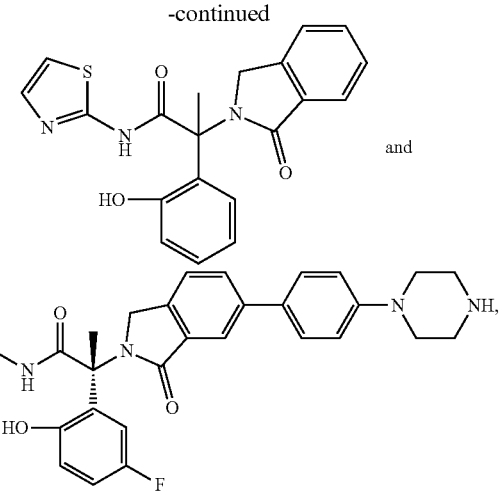
or pharmaceutically acceptable salts, hydrates, solvates, stereoisomers, or tautomers thereof.
* * * * *

UNITED STATES PATENT AND TRADEMARK OFFICE
CERTIFICATE OF CORRECTION

PATENT NO. : 10,385,019 B2
APPLICATION NO. : 15/580088
DATED : August 20, 2019
INVENTOR(S) : Nathanael S. Gray et al.

Page 1 of 1

It is certified that error appears in the above-identified patent and that said Letters Patent is hereby corrected as shown below:

In the Specification

At Column 1, Line number 16:
"The work described herein was supported by the National Institutes of Health, NIH Grant No. P01 CA154303. The U.S. Government has certain rights to the claimed invention."

Should read:
--This invention was made with government support under grant number CA154303 awarded by The National Institutes of Health. The government has certain rights in the invention.--

Signed and Sealed this
Seventeenth Day of September, 2019

Andrei Iancu
*Director of the United States Patent and Trademark Office*